(12) United States Patent
Han et al.

(10) Patent No.: US 10,174,024 B2
(45) Date of Patent: Jan. 8, 2019

(54) 5H-PYRIDO[3,2-B]INDOLE COMPOUNDS AS ANTICANCER AGENTS

(71) Applicant: BRISTOL-MYERS SQUIBB COMPANY, Princeton, NJ (US)

(72) Inventors: Wen-Ching Han, Newtown, PA (US); Andrew P. Degnan, Jamison, PA (US); Jeffrey A. Deskus, Marlborough, CT (US); Ashvinikumar V. Gavai, Princeton Junction, NJ (US); Patrice Gill, Levittown, PA (US); William D. Schmitz, Cheshire, CT (US); John E. Starrett, Jr., Waterford, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 15/573,151

(22) PCT Filed: May 11, 2016

(86) PCT No.: PCT/US2016/031702
§ 371 (c)(1),
(2) Date: Nov. 10, 2017

(87) PCT Pub. No.: WO2016/183115
PCT Pub. Date: Nov. 17, 2016

(65) Prior Publication Data
US 2018/0093983 A1    Apr. 5, 2018

Related U.S. Application Data

(60) Provisional application No. 62/159,996, filed on May 12, 2015.

(51) Int. Cl.
*C07D 471/04* (2006.01)
(52) U.S. Cl.
CPC .................. *C07D 471/04* (2013.01)
(58) Field of Classification Search
CPC .................................................. C07D 471/04
USPC ........................................................ 544/58.1
See application file for complete search history.

(56) References Cited

FOREIGN PATENT DOCUMENTS

| WO | PCT/US2014/018820 | 2/2014 |
| WO | PCT/US2014/018914 | 2/2014 |
| WO | WO 2014/134232 A1 | 9/2014 |
| WO | WO 2014/134267 A1 | 9/2014 |
| WO | WO 2014/164596 A1 | 10/2014 |
| WO | PCT/US2014/072031 | 12/2014 |
| WO | WO 2015/100282 A1 | 7/2015 |
| WO | PCT/US2016/031701 | 5/2016 |
| WO | PCT/US2016/031707 | 5/2016 |

OTHER PUBLICATIONS

U.S. Appl. No. 15/150,492, filed May 10, 2016, Granted U.S. Pat. No. 9,725,449.
U.S. Appl. No. 14/770,230, filed Aug. 25, 2015, Published US20160009701A1.
U.S. Appl. No. 15/430,883, filed Feb. 13, 2017, Published US20170152248A1.
U.S. Appl. No. 14/190,477, filed Feb. 26, 2014, Granted U.S. Pat. No. 9,492,460.
U.S. Appl. No. 15/107,652, filed Jun. 23, 2016, Abandoned.
U.S. Appl. No. 14/580,355, filed Dec. 23, 2014, Granted U.S. Pat. No. 9,458,156.
U.S. Appl. No. 15/219,611, filed Jul. 26, 2016, Granted U.S. Pat. No. 9,751,879.
U.S. Appl. No. 15/661,373, filed Jul. 27, 2017, Published US20170327498A1.
U.S. Appl. No. 15/573,141, filed Nov. 10, 2017, Filed.

*Primary Examiner* — Kahsay Habte
(74) *Attorney, Agent, or Firm* — Elliot Korsen

(57) ABSTRACT

The present invention is directed to tricyclic compounds of formula (I), pharmaceutically acceptable compositions comprising compounds of the invention and said compositions for use in methods for the treatment of various disorders in particular cancer.

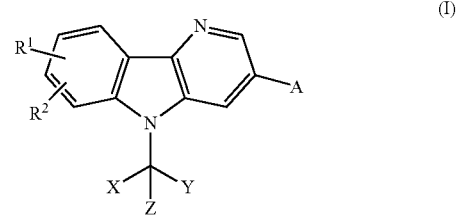

(I)

13 Claims, No Drawings
Specification includes a Sequence Listing.

5H-PYRIDO[3,2-B]INDOLE COMPOUNDS AS ANTICANCER AGENTS

CROSS-REFERENCE TO RELATED APPLICATIONS

This application claims priority from U.S. Provisional Application No. 62/159,996 filed May 12, 2015, the disclosures of which are incorporated herein by reference in their entirety.

FIELD OF THE INVENTION

The invention provides novel tricyclic compounds, pharmaceutical compositions comprising the compounds, and methods of using them, for example, for the treatment or prophylaxis of certain cancers and to their use in therapy.

BACKGROUND OF THE INVENTION

The genomes of eukaryotic organisms are highly organized within the nucleus of the cell. The long strands of duplex DNA are wrapped around an octomer of histone proteins to form a nucleosome. This basic unit is then further compressed by the aggregation and folding of nucleosomes to form a highly condensed chromatin structure. A range of different states of condensation are possible, and the tightness of this structure varies during the cell cycle, being most compact during the process of cell division. There has been appreciation recently that chromatin templates form a fundamentally important set of gene control mechanisms referred to as epigenetic regulation. By conferring a wide range of specific chemical modifications to histones and DNA (such as acetylation, methylation, phosphorylation, ubiquitinylation and SUMOylation) epigenetic regulators modulate the structure, function and accessibility of our genome, thereby exerting a huge impact in gene expression.

Histone acetylation is most usually associated with the activation of gene transcription, as the modification loosens the interaction of the DNA and the histone octomer by changing the electrostatics. In addition to this physical change, specific proteins bind to acetylated lysine residues within histones to read the epigenetic code. Bromodomains are small (~110 amino acid) distinct domains within proteins that bind to acetylated lysine residues commonly but not exclusively in the context of histones. There is a family of around 50 proteins known to contain bromodomains, and they have a range of functions within the cell. The BET family of bromodomain containing proteins comprises 4 proteins (BRD2, BRD3, BRD4 and BRD-T) which contain tandem bromodomains capable of binding to two acetylated lysine residues in close proximity, increasing the specificity of the interaction.

BRD2 and BRD3 are reported to associate with histones along actively transcribed genes and may be involved in facilitating transcriptional elongation (Leroy et al., Mol. Cell. 2008 30(1):51-60), while BRD4 appears to be involved in the recruitment of the pTEF-I3 complex to inducible genes, resulting in phosphorylation of RNA polymerase and increased transcriptional output (Hargreaves et al., Cell, 2009 138(1): 1294145). All family members have been reported to have some function in controlling or executing aspects of the cell cycle, and have been shown to remain in complex with chromosomes during cell division—suggesting a role in the maintenance of epigenetic memory. In addition some viruses make use of these proteins to tether their genomes to the host cell chromatin, as part of the process of viral replication (You et al., Cell, 2004 117(3): 349-60).

Recent articles relating to this target include Prinjha et al., Trends in Pharmacological Sciences, March 2012, Vol. 33, No. 3, pp. 146-153; Conway, ACS Med. Chem. Lett., 2012, 3, 691-694 and Hewings et al., J. Med. Chem., 2012, 55, 9393-9413.

Small molecule BET inhibitors that are reported to be in clinical development include GSK-525762, OTX-015, TEN-010, CPI-0610, BAY-1238097, and ABBV-075.

Hundreds of epigenetic effectors have been identified, many of which are chromatin-binding proteins or chromatin-modifying enzymes. These proteins have been associated with a variety of disorders such as neurodegenerative disorders, metabolic diseases, inflammation and cancer. Thus, these compounds which inhibit the binding of a bromodomain with its cognate acetylated proteins, promise new approaches in the treatment of a range of autoimmune and inflammatory diseases or conditions and in the treatment of various types of cancer.

SUMMARY OF THE INVENTION

There is provided a compound of formula (I)

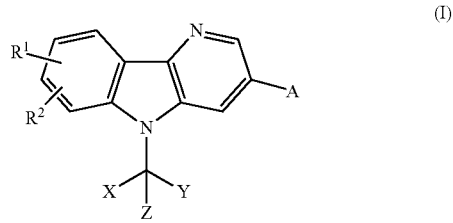

wherein:

A is optionally substituted heterocyclo or optionally substituted heteroaryl, wherein the substituents are one or more R;

R is independently one or more hydrogen, $CD_3$, halogen, haloalkyl, hydroxyalkyl, CN, $CF_3$, $CH_2F$, $CHF_2$, optionally substituted $(C_1-C_6)$alkyl, optionally substituted $(C_1-C_6)$ alkoxy, optionally substituted $(C_3-C_6)$cycloalkyl, —$OR^4$, —$NR^3R^4$, $NR^3R^4(C_1-C_6)$alkyl-, —$NR^6OCOR^3$, —$NR^6COR^3$ or $NR^6CONR^3R^4$;

X and Y are independently selected from hydrogen, optionally substituted $(C_1-C_6)$alkyl, optionally substituted $(C_3-C_8)$cycloalkyl, optionally substituted aryl, optionally substituted heteroaryl or optionally substituted heterocyclo;

Z is hydrogen, halogen, —OH, $(C_1-C_6)$alkyl or $(C_1-C_6)$ alkoxy;

$R^1$ is optionally substituted heteroaryl or optionally substituted 5-8 membered heterocyclyl;

$R^2$ is hydrogen, halogen, optionally substituted $(C_1-C_6)$ alkyl, optionally substituted $(C_1-C_6)$ alkoxy, optionally substituted aryl, optionally substituted $(C_1-C_6)$alkyl, —$SO_2$ optionally substituted 5-8 membered heteroaryl or optionally substituted 5-8 membered heterocyclo;

$R^3$ is hydrogen, optionally substituted $(C_1-C_6)$alkyl, optionally substituted $(C_3-C_8)$cycloalkyl, optionally substituted $(C_2-C_6)$alkenyl, optionally substituted $(C_2-C_6)$alkynyl, cyano$(C_1-C_6)$alkyl, hydroxy$(C_1-C_6)$alkyl, optionally substituted aryl, optionally substituted aryl$(C_1-C_6)$alkyl, optionally substituted aryloxy$(C_1-C_6)$alkyl, optionally substituted $(C_1-C_6)$alkyl-$SO_2$—, optionally substituted heterocyclyl, optionally substituted heterocyclyl$(C_1-C_6)$alkyl, optionally substituted heteroaryl or optionally substituted heteroaryl $(C_1-C_6)$alkyl;

$R^4$ is hydrogen, optionally substituted $(C_1-C_6)$alkyl or optionally substituted $(C_3-C_8)$cycloalkyl;

$R^6$ is hydrogen, optionally substituted $(C_1-C_6)$alkyl or optionally substituted $(C_3-C_8)$cycloalkyl;

and/or a pharmaceutically acceptable salt, tautomer or stereoisomer thereof.

In another aspect, there is provided a pharmaceutical composition comprising a compound of the invention or a pharmaceutically acceptable salt thereof and one or more pharmaceutically acceptable carriers, diluents or excipients.

In another aspect, there is provided a compound of the invention or a pharmaceutically acceptable salt thereof for use in therapy. In particular, the use is for the treatment of a disease or condition for which a bromodomain inhibitor is indicated.

In another aspect, there is provided a method of treating autoimmune and inflammatory diseases or conditions which comprises administering to a subject in need thereof a therapeutically effective amount of a bromodomain inhibitor.

In another aspect, there is provided a method of treating cancer which comprises administering to a subject in need thereof a therapeutically effective amount of a bromodomain inhibitor.

In another aspect of the present invention, there is provided a method for treating a bromodomain-containing protein mediated disorder in a patient in need thereof, comprising the step of administering to said patient a compound of the invention.

DETAILED DESCRIPTION OF THE INVENTION

In a first aspect of the present invention, there is provided a compound of formula (I)

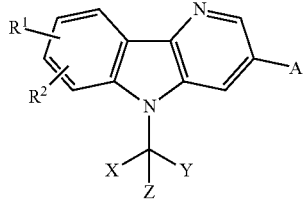

(I)

wherein:

A is optionally substituted heterocyclo or optionally substituted heteroaryl, wherein the substituents are one or more R;

R is independently one or more hydrogen, $CD_3$, halogen, haloalkyl, hydroxyalkyl, CN, $CF_3$, $CH_2F$, $CHF_2$, optionally substituted $(C_1-C_6)$alkyl, optionally substituted $(C_1-C_6)$alkoxy, optionally substituted $(C_3-C_6)$cycloalkyl, —$OR^4$, —$NR^3R^4$, $NR^3R^4(C_1-C_6)$alkyl-, —$NR^6OCOR^3$, —$NR^6COR^3$ or $NR^6CONR^3R^4$;

X and Y are independently selected from hydrogen, optionally substituted $(C_1-C_6)$alkyl, optionally substituted $(C_3-C_8)$cycloalkyl, optionally substituted aryl, optionally substituted heteroaryl or optionally substituted heterocyclo;

Z is hydrogen, halogen, —OH, $(C_1-C_6)$alkyl or $(C_1-C_6)$alkoxy;

$R^1$ is optionally substituted heteroaryl or optionally substituted 5-8 membered heterocyclyl;

$R^2$ is hydrogen, halogen, optionally substituted $(C_1-C_6)$alkyl, optionally substituted $(C_1-C_6)$ alkoxy, optionally substituted aryl, optionally substituted $(C_1-C_6)$alkyl, —$SO_2$ optionally substituted 5-8 membered heteroaryl or optionally substituted 5-8 membered heterocyclo;

$R^3$ is hydrogen, optionally substituted $(C_1-C_6)$alkyl, optionally substituted $(C_3-C_8)$cycloalkyl, optionally substituted $(C_2-C_6)$alkenyl, optionally substituted $(C_2-C_6)$alkynyl, cyano$(C_1-C_6)$alkyl, hydroxy$(C_1-C_6)$alkyl, optionally substituted aryl, optionally substituted aryl$(C_1-C_6)$alkyl, optionally substituted aryloxy$(C_1-C_6)$alkyl, optionally substituted $(C_1-C_6)$alkyl-$SO_2$—, optionally substituted heterocyclyl, optionally substituted heterocyclyl$(C_1-C_6)$alkyl, optionally substituted heteroaryl or optionally substituted heteroaryl$(C_1-C_6)$alkyl;

$R^4$ is hydrogen, optionally substituted $(C_1-C_6)$alkyl or optionally substituted $(C_3-C_8)$cycloalkyl;

$R^6$ is hydrogen, optionally substituted $(C_1-C_6)$alkyl or optionally substituted $(C_3-C_8)$cycloalkyl;

and/or a pharmaceutically acceptable salt, tautomer or stereoisomer thereof.

In a second aspect of the invention, there is provided a compound according to claim 1 of formula (I) wherein:

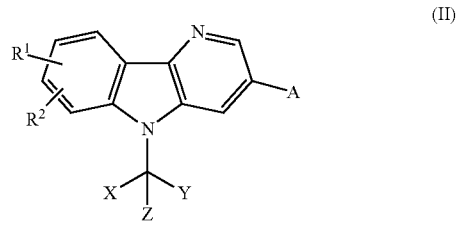

(II)

wherein:

A is

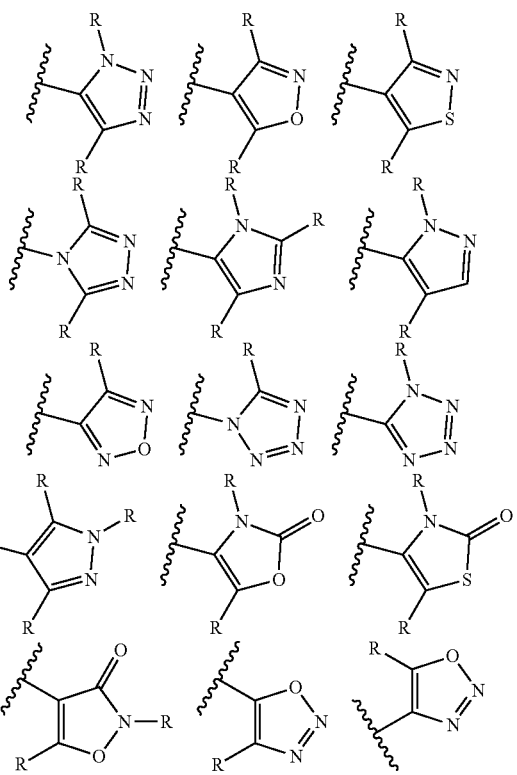

-continued

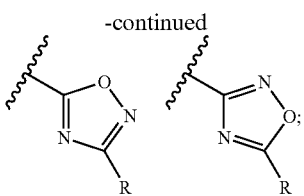

R is independently one or more hydrogen, CD$_3$, halogen, haloalkyl, hydroxyalkyl, CN, CF$_3$, CH$_2$F, CHF$_2$, optionally substituted (C$_1$-C$_6$)alkyl, optionally substituted (C$_1$-C$_6$) alkoxy, optionally substituted (C$_3$-C$_6$)cycloalkyl, —OR$^4$, —NR$^3$R$^4$, NR$^3$R$^4$(C$_1$-C$_6$)alkyl-, —NR$^6$OCOR$^3$, —NR$^6$COR$^3$ or NR$^6$CONR$^3$R$^4$;

X and Y are independently selected from hydrogen, optionally substituted (C$_1$-C$_6$)alkyl, optionally substituted (C$_3$-C$_8$)cycloalkyl, optionally substituted aryl, optionally substituted heteroaryl or optionally substituted heterocyclo;

Z is hydrogen, halogen, —OH, (C$_1$-C$_6$)alkyl or (C$_1$-C$_6$) alkoxy;

R$^1$ is optionally substituted heteroaryl or optionally substituted 5-8 membered heterocyclyl;

R$^2$ is hydrogen, halogen, optionally substituted (C$_1$-C$_6$) alkyl, optionally substituted (C$_1$-C$_6$) alkoxy, optionally substituted aryl, optionally substituted (C$_1$-C$_6$)alkyl, —SO$_2$ optionally substituted 5-8 membered heteroaryl or optionally substituted 5-8 membered heterocyclo;

R$^3$ is hydrogen, optionally substituted (C$_1$-C$_6$)alkyl, optionally substituted (C$_3$-C$_8$)cycloalkyl, optionally substituted (C$_2$-C$_6$)alkenyl, optionally substituted (C$_2$-C$_6$)alkynyl, cyano(C$_1$-C$_6$)alkyl, hydroxy(C$_1$-C$_6$)alkyl, optionally substituted aryl, optionally substituted aryl(C$_1$-C$_6$)alkyl, optionally substituted aryloxy(C$_1$-C$_6$)alkyl, optionally substituted (C$_1$-C$_6$)alkyl-SO$_2$—, optionally substituted heterocyclyl, optionally substituted heterocyclyl(C$_1$-C$_6$)alkyl, optionally substituted heteroaryl or optionally substituted heteroaryl (C$_1$-C$_6$)alkyl;

R$^4$ is hydrogen, optionally substituted (C$_1$-C$_6$)alkyl or optionally substituted (C$_3$-C$_8$)cycloalkyl;

R$^6$ is hydrogen, optionally substituted (C$_1$-C$_6$)alkyl or optionally substituted (C$_3$-C$_8$)cycloalkyl;

and/or a pharmaceutically acceptable salt, tautomer or stereoisomer thereof.

In a third aspect of the invention within the scope of the first two aspects, there is provided a compound of formula (II)

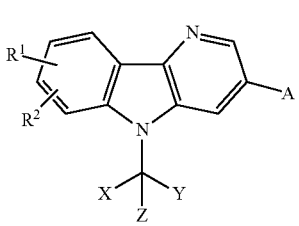

(II)

wherein:
A is

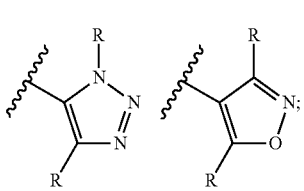

R is independently one or more hydrogen, CD$_3$, halogen, haloalkyl, hydroxyalkyl, CN, CF$_3$, CH$_2$F, CHF$_2$, optionally substituted (C$_1$-C$_6$)alkyl, optionally substituted (C$_1$-C$_6$) alkoxy, optionally substituted (C$_3$-C$_6$)cycloalkyl, —OR$^4$, —NR$^3$R$^4$, NR$^3$R$^4$(C$_1$-C$_6$)alkyl-, —NR$^6$OCOR$^3$, —NR$^6$COR$^3$, —NR$^6$CONR$^3$R$^4$;

X and Y are independently selected from hydrogen, optionally substituted (C$_1$-C$_6$)alkyl, optionally substituted (C$_3$-C$_8$)cycloalkyl, optionally substituted aryl, optionally substituted heteroaryl or optionally substituted heterocyclo;

Z is hydrogen, halogen, —OH, (C$_1$-C$_6$)alkyl or (C$_1$-C$_6$) alkoxy;

R$^1$ is optionally substituted heteroaryl or optionally substituted 5-8 membered heterocyclyl;

R$^2$ is hydrogen, halogen, optionally substituted (C$_1$-C$_6$) alkyl, optionally substituted (C$_1$-C$_6$) alkoxy, optionally substituted aryl, optionally substituted (C$_1$-C$_6$)alkyl, —SO$_2$ optionally substituted 5-8 membered heteroaryl or optionally substituted 5-8 membered heterocyclo;

R$^3$ is hydrogen, optionally substituted (C$_1$-C$_6$)alkyl, optionally substituted (C$_3$-C$_8$)cycloalkyl, optionally substituted (C$_2$-C$_6$)alkenyl, optionally substituted (C$_2$-C$_6$)alkynyl, cyano(C$_1$-C$_6$)alkyl, hydroxy(C$_1$-C$_6$)alkyl, optionally substituted aryl, optionally substituted aryl(C$_1$-C$_6$)alkyl, optionally substituted aryloxy(C$_1$-C$_6$)alkyl, optionally substituted (C$_1$-C$_6$)alkyl-SO$_2$—, optionally substituted heterocyclyl, optionally substituted heterocyclyl(C$_1$-C$_6$)alkyl, optionally substituted heteroaryl or optionally substituted heteroaryl (C$_1$-C$_6$)alkyl;

R$^4$ is hydrogen, optionally substituted (C$_1$-C$_6$)alkyl or optionally substituted (C$_3$-C$_8$)cycloalkyl;

R$^6$ is hydrogen, optionally substituted (C$_1$-C$_6$)alkyl or optionally substituted (C$_3$-C$_8$)cycloalkyl;

and/or a pharmaceutically acceptable salt, tautomer or stereoisomer thereof.

In a 4$^{th}$ aspect within the scope of the prior aspects, there is provided a compound of the formula

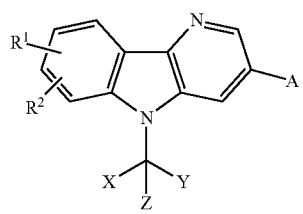

wherein
A is

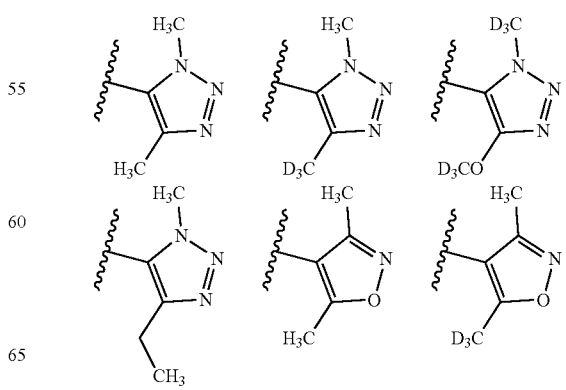

-continued

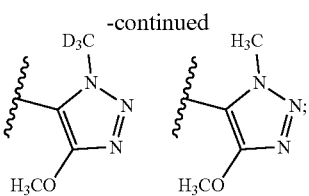

X and Y are independently selected from hydrogen, optionally substituted (C$_1$-C$_6$)alkyl, optionally substituted (C$_3$-C$_8$)cycloalkyl, optionally substituted aryl, optionally substituted heteroaryl or optionally substituted heterocyclo;

Z is hydrogen, halogen, —OH, (C$_1$-C$_6$)alkyl or (C$_1$-C$_6$) alkoxy;

R$^1$ is optionally substituted heteroaryl or optionally substituted 5-8 membered heterocyclyl;

R$^2$ is hydrogen, halogen, optionally substituted (C$_1$-C$_6$) alkyl, optionally substituted (C$_1$-C$_6$) alkoxy, optionally substituted aryl, optionally substituted (C$_1$-C$_6$)alkyl, —SO$_2$ optionally substituted 5-8 membered heteroaryl or optionally substituted 5-8 membered heterocyclo;

R$^3$ is hydrogen, optionally substituted (C$_1$-C$_6$)alkyl, optionally substituted (C$_3$-C$_8$)cycloalkyl, optionally substituted (C$_2$-C$_6$)alkenyl, optionally substituted (C$_2$-C$_6$)alkynyl, cyano(C$_1$-C$_6$)alkyl, hydroxy(C$_1$-C$_6$)alkyl, optionally substituted aryl, optionally substituted aryl(C$_1$-C$_6$)alkyl, optionally substituted aryloxy(C$_1$-C$_6$)alkyl, optionally substituted (C$_1$-C$_6$)alkyl-SO$_2$—, optionally substituted heterocyclyl, optionally substituted heterocyclyl(C$_1$-C$_6$)alkyl, optionally substituted heteroaryl or optionally substituted heteroaryl (C$_1$-C$_6$)alkyl;

R$^4$ is hydrogen, optionally substituted (C$_1$-C$_6$)alkyl or optionally substituted (C$_3$-C$_8$)cycloalkyl;

R$^6$ is hydrogen, optionally substituted (C$_1$-C$_6$)alkyl or optionally substituted (C$_3$-C$_8$)cycloalkyl;

and/or a pharmaceutically acceptable salt, tautomer or stereoisomer thereof.

In a 5$^{th}$ aspect of the invention within the scope of the prior aspects, there is provided a compound of the formula

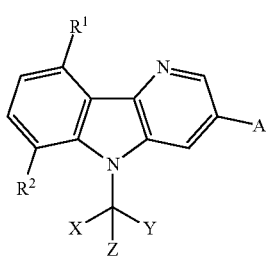

wherein:

A is

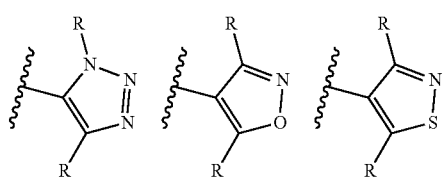

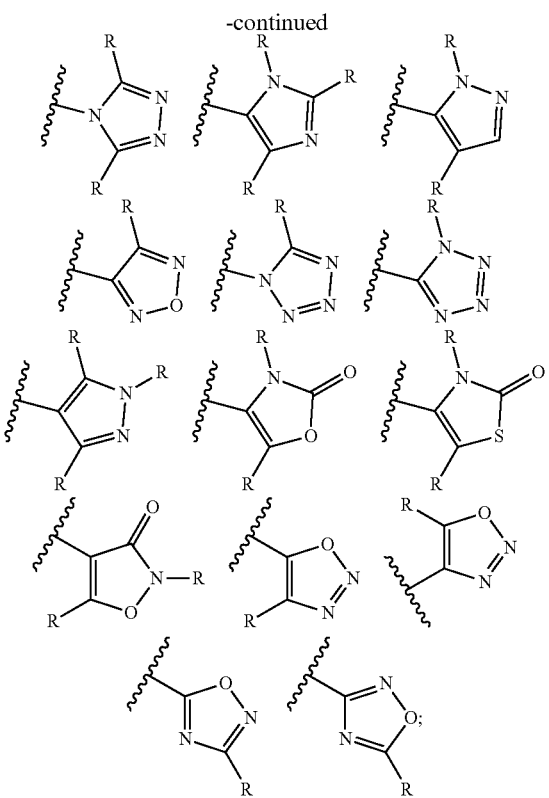

R is independently one or more hydrogen, CD$_3$, halogen, haloalkyl, hydroxyalkyl, CN, CF$_3$, CH$_2$F, CHF$_2$, optionally substituted (C$_1$-C$_6$)alkyl, optionally substituted (C$_1$-C$_6$) alkoxy, optionally substituted (C$_3$-C$_6$)cycloalkyl, —OR$^4$, —NR$^3$R$^4$, NR$^3$R$^4$(C$_1$-C$_6$)alkyl-, —NR$^6$OCOR$^3$, —NR$^6$COR$^3$ or NR$^6$CONR$^3$R$^4$;

X and Y are independently selected from hydrogen, optionally substituted (C$_1$-C$_6$)alkyl, optionally substituted (C$_3$-C$_8$)cycloalkyl, optionally substituted aryl, optionally substituted heteroaryl or optionally substituted heterocyclo;

Z is hydrogen, halogen, —OH, (C$_1$-C$_6$)alkyl or (C$_1$-C$_6$) alkoxy;

R$^1$ is optionally substituted heteroaryl or optionally substituted 5-8 membered heterocyclyl;

R$^2$ is hydrogen, halogen, optionally substituted (C$_1$-C$_6$) alkyl, optionally substituted (C$_1$-C$_6$) alkoxy, optionally substituted aryl, optionally substituted (C$_1$-C$_6$)alkyl, —SO$_2$ optionally substituted 5-8 membered heteroaryl or optionally substituted 5-8 membered heterocyclo;

R$^3$ is hydrogen, optionally substituted (C$_1$-C$_6$)alkyl, optionally substituted (C$_3$-C$_8$)cycloalkyl, optionally substituted (C$_2$-C$_6$)alkenyl, optionally substituted (C$_2$-C$_6$)alkynyl, cyano(C$_1$-C$_6$)alkyl, hydroxy(C$_1$-C$_6$)alkyl, optionally substituted aryl, optionally substituted aryl(C$_1$-C$_6$)alkyl, optionally substituted aryloxy(C$_1$-C$_6$)alkyl, optionally substituted (C$_1$-C$_6$)alkyl-SO$_2$—, optionally substituted heterocyclyl, optionally substituted heterocyclyl(C$_1$-C$_6$)alkyl, optionally substituted heteroaryl or optionally substituted heteroaryl (C$_1$-C$_6$)alkyl;

R$^4$ is hydrogen, optionally substituted (C$_1$-C$_6$)alkyl or optionally substituted (C$_3$-C$_8$)cycloalkyl;

R$^6$ is hydrogen, optionally substituted (C$_1$-C$_6$)alkyl or optionally substituted (C$_3$-C$_8$)cycloalkyl;

and/or a pharmaceutically acceptable salt, tautomer or stereoisomer thereof.

In a 6th aspect of the invention within the scope of the prior aspects, there is provided a compound of the formula

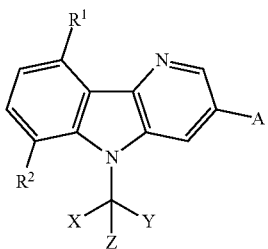

wherein
A is

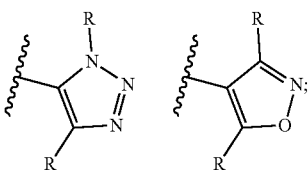

R is independently one or more hydrogen, CD$_3$, halogen, haloalkyl, hydroxyalkyl, CN, CF$_3$, CH$_2$F, CHF$_2$, optionally substituted (C$_1$-C$_6$)alkyl, optionally substituted (C$_1$-C$_6$) alkoxy, optionally substituted (C$_3$-C$_6$)cycloalkyl, —OR$^4$, —NR$^3$R$^4$, NR$^3$R$^4$(C$_1$-C$_6$)alkyl-, —NR$^6$OCOR$^3$, —NR$^6$COR$^3$ or NR$^6$CONR$^3$R$^4$;

X and Y are independently selected from hydrogen, optionally substituted (C$_1$-C$_6$)alkyl, optionally substituted (C$_3$-C$_8$)cycloalkyl, optionally substituted aryl, optionally substituted heteroaryl or optionally substituted heterocyclo;

Z is hydrogen, halogen, —OH, (C$_1$-C$_6$)alkyl or (C$_1$-C$_6$) alkoxy;

R$^1$ is optionally substituted heteroaryl or optionally substituted 5-8 membered heterocyclyl;

R$^2$ is hydrogen, halogen, optionally substituted (C$_1$-C$_6$) alkyl, optionally substituted (C$_1$-C$_6$) alkoxy, optionally substituted aryl, optionally substituted (C$_1$-C$_6$)alkyl, —SO$_2$ optionally substituted 5-8 membered heteroaryl or optionally substituted 5-8 membered heterocyclo;

R$^3$ is hydrogen, optionally substituted (C$_1$-C$_6$)alkyl, optionally substituted (C$_3$-C$_8$)cycloalkyl, optionally substituted (C$_2$-C$_6$)alkenyl, optionally substituted (C$_2$-C$_6$)alkynyl, cyano(C$_1$-C$_6$)alkyl, hydroxy(C$_1$-C$_6$)alkyl, optionally substituted aryl, optionally substituted aryl(C$_1$-C$_6$)alkyl, optionally substituted aryloxy(C$_1$-C$_6$)alkyl, optionally substituted (C$_1$-C$_6$)alkyl-SO$_2$—, optionally substituted heterocyclyl, optionally substituted heterocyclyl(C$_1$-C$_6$)alkyl, optionally substituted heteroaryl or optionally substituted heteroaryl (C$_1$-C$_6$)alkyl;

R$^4$ is hydrogen, optionally substituted (C$_1$-C$_6$)alkyl or optionally substituted (C$_3$-C$_8$)cycloalkyl;

R$^6$ is hydrogen, optionally substituted (C$_1$-C$_6$)alkyl or optionally substituted (C$_3$-C$_8$)cycloalkyl;

and/or a pharmaceutically acceptable salt, tautomer or stereoisomer thereof.

In a 7th aspect of the invention within the scope of the prior aspects, there is provided a compound of the formula

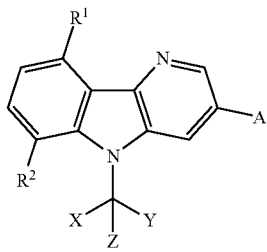

wherein
A is

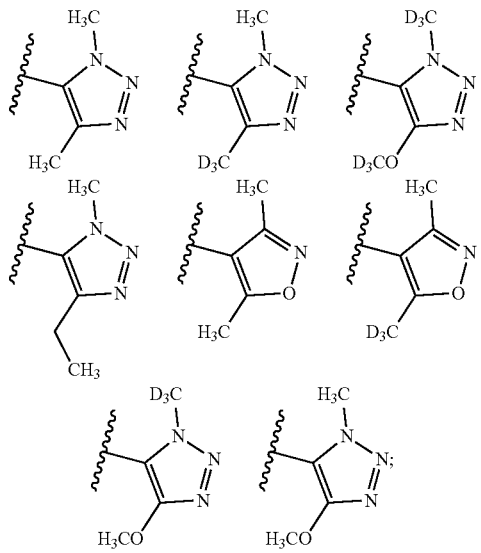

X and Y are independently selected from hydrogen, optionally substituted (C$_1$-C$_6$)alkyl, optionally substituted (C$_3$-C$_8$)cycloalkyl, optionally substituted aryl, optionally substituted heteroaryl or optionally substituted heterocyclo;

Z is hydrogen, halogen, —OH, (C$_1$-C$_6$)alkyl, (C$_1$-C$_6$) alkoxy, —NR$^3$R$^4$, —CONR$^3$R$^4$, —OCONR$^3$R$^4$, —NR$^6$OCOR$^3$, —NR$^6$CONR$^3$R$^4$, —NR$^6$SO$_2$NR$^3$R$^4$ or —NR$^6$SO$_2$R$^4$;

R$^1$ is optionally substituted heteroaryl or optionally substituted 5-8 membered heterocyclyl;

R$^2$ is hydrogen, halogen, —CN, OH, optionally substituted (C$_1$-C$_6$)alkyl, optionally substituted (C$_3$-C$_8$)cycloalkyl, optionally substituted (C$_1$-C$_6$) alkoxy, optionally substituted aryl, optionally substituted heteroaryl or optionally substituted heterocyclo;

R$^3$ is hydrogen, optionally substituted (C$_1$-C$_6$)alkyl, optionally substituted (C$_3$-C$_8$)cycloalkyl, optionally substituted (C$_2$-C$_6$)alkenyl, optionally substituted (C$_2$-C$_6$)alkynyl, cyano(C$_1$-C$_6$)alkyl, hydroxy(C$_1$-C$_6$)alkyl, optionally substituted aryl, optionally substituted aryl(C$_1$-C$_6$)alkyl, optionally substituted aryloxy(C$_1$-C$_6$)alkyl, optionally substituted (C$_1$-C$_6$)alkyl-SO$_2$—, optionally substituted heterocyclyl, optionally substituted heterocyclyl(C$_1$-C$_6$)alkyl, optionally substituted heteroaryl or optionally substituted heteroaryl (C$_1$-C$_6$)alkyl;

R$^4$ is hydrogen, optionally substituted (C$_1$-C$_6$)alkyl or optionally substituted (C$_3$-C$_8$)cycloalkyl;

or R$^3$ and R$^4$ may be taken together with the nitrogen atom to which they are attached to form an optionally substituted (C$_4$-C$_8$) heteroaryl or (C$_4$-C$_8$) heterocyclic ring;

R⁶ is hydrogen, optionally substituted (C₁-C₆)alkyl or optionally substituted (C₃-C₈)cycloalkyl;
and/or a pharmaceutically acceptable salt, tautomer or stereoisomer thereof.

In an 8th aspect of the invention within the scope of the prior aspects, there is provided a compound of the formula

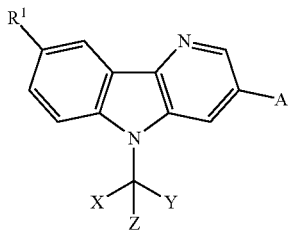

and/or a pharmaceutically acceptable salt, tautomer or stereoisomer thereof.

In a 9th aspect of the invention within the scope of the prior aspects, there is provided a compound of the formula

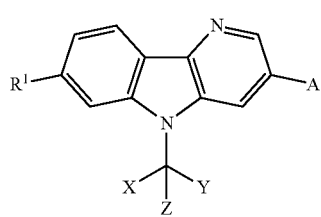

(IV)

and/or a pharmaceutically acceptable salt, tautomer or stereoisomer thereof.

In another aspect, there is provided a compound selected from the exemplified examples within the scope of the first aspect, or a pharmaceutically acceptable salt, tautomer or stereoisomer thereof.

In another aspect, there is provided a compound selected from any subset list of compounds within the scope of any of the above aspects.

In another aspect, there is provided a compound selected from the following 1,4-dimethyl-5-[7-(1-methyl-1H-pyrazol-5-yl)-5-[(S)-oxan-4-yl(phenyl)methyl]-5H-pyrido[3,2-b]indol-3-yl]-1H-1,2,3-triazole, 1,4-dimethyl-5-{5-[(S)-oxan-4-yl(phenyl)methyl]-7-(1,2-oxazol-3-yl)-5H-pyrido[3,2-b]indol-3-yl}-1H-1,2,3-triazole, (2R,6S)-4-[3-(dimethyl-1H-1,2,3-triazol-5-yl)-5-[(R)-oxan-4-yl(phenyl)methyl]-5H-pyrido[3,2-b]indol-8-yl]-2,6-dimethylmorpholine, 4-[3-(dimethyl-1H-1,2,3-triazol-5-yl)-5-[(S)-oxan-4-yl(phenyl)methyl]-5H-pyrido[3,2-b]indol-8-yl]piperidine, tert-butyl 4-[3-(dimethyl-1H-1,2,3-triazol-5-yl)-5-[(S)-oxan-4-yl(phenyl)methyl]-5H-pyrido[3,2-b]indol-8-yl]piperidine-1-carboxylate, 1-{4-[3-(dimethyl-1,2-oxazol-4-yl)-5-[(S)-oxan-4-yl(phenyl)methyl]-5H-pyrido[3,2-b]indol-8-yl]piperidin-1-yl}-2-hydroxyethan-1-one, 1-{4-[3-(dimethyl-1,2-oxazol-4-yl)-5-[(S)-oxan-4-yl(phenyl)methyl]-5H-pyrido[3,2-b]indol-8-yl]piperidin-1-yl}ethan-1-one, 2-{4-[3-(dimethyl-1H-1,2,3-triazol-5-yl)-5-[(S)-oxan-4-yl(phenyl)methyl]-5H-pyrido[3,2-b]indol-8-yl]piperidin-1-yl}-2-oxoethyl acetate, (5 S)-5-[3-(dimethyl-1H-1,2,3-triazol-5-yl)-5-[(S)-oxan-4-yl(phenyl)methyl]-5H-pyrido[3,2-b]indol-7-yl]-5-methyl-1,3-oxazolidin-2-one, (5R)-5-[3-(dimethyl-1H-1,2,3-triazol-5-yl)-5-[(S)-oxan-4-yl(phenyl)methyl]-5H-pyrido[3,2-b]indol-7-yl]-5-methyl-1,3-oxazolidin-2-one, 5-[3-(dimethyl-1H-1,2,3-triazol-5-yl)-5-[(S)-oxan-4-yl(phenyl)methyl]-5H-pyrido[3,2-b]indol-7-yl]-1H-1,2,3,4-tetrazole, 3-[3-(dimethyl-1H-1,2,3-triazol-5-yl)-5-[(S)-oxan-4-yl(phenyl)methyl]-5H-pyrido[3,2-b]indol-7-yl]-1,3-oxazinan-2-one, 1-[3-(dimethyl-1H-1,2,3-triazol-5-yl)-5-[(S)-oxan-4-yl(phenyl)methyl]-5H-pyrido[3,2-b]indol-8-yl]piperazine, 2-{4-[3-(dimethyl-1H-1,2,3-triazol-5-yl)-5-[(S)-oxan-4-yl(phenyl)methyl]-5H-pyrido[3,2-b]indol-8-yl]piperazin-1-yl}-2-oxoethyl acetate, 1-[3-(dimethyl-1H-1,2,3-triazol-5-yl)-5-[(S)-oxan-4-yl(phenyl)methyl]-5H-pyrido[3,2-b]indol-8-yl]-4-(oxetan-3-yl)piperazine, 1,4-dimethyl-5-{5-[(S)-oxan-4-yl(phenyl)methyl]-7-[1-(propan-2-yl)-1H-pyrazol-4-yl]-5H-pyrido[3,2-b]indol-3-yl}-1H-1,2,3-triazole, 5-[7-(3,5-dimethyl-1H-pyrazol-4-yl)-5-[(S)-oxan-4-yl(phenyl)methyl]-5H-pyrido[3,2-b]indol-3-yl]-1,4-dimethyl-1H-1,2,3-triazole, 5-[3-(dimethyl-1H-1,2,3-triazol-5-yl)-5-[(S)-oxan-4-yl(phenyl)methyl]-5H-pyrido[3,2-b]indol-7-yl]-4-($^{2}H_{3}$)methyl-1-methyl-1H-1,2,3-triazole, 2-[3-(dimethyl-1H-1,2,3-triazol-5-yl)-6-methanesulfonyl-5-[(S)-oxan-4-yl(phenyl)methyl]-5H-pyrido[3,2-b]indol-9-yl]-1λ⁶,2-thiazolidine-1,1-dione, 2-[3-(dimethyl-1H-1,2,3-triazol-5-yl)-6-methanesulfonyl-5-[(S)-oxan-4-yl(phenyl)methyl]-5H-pyrido[3,2-b]indol-9-yl]-1λ⁶,2-thiazinane-1,1-dione, 1-[3-(dimethyl-1H-1,2,3-triazol-5-yl)-6-methanesulfonyl-5-[(S)-oxan-4-yl(phenyl)methyl]-5H-pyrido[3,2-b]indol-9-yl]piperazine, 2-{4-[3-(dimethyl-1H-1,2,3-triazol-5-yl)-6-methanesulfonyl-5-[(S)-oxan-4-yl(phenyl)methyl]-5H-pyrido[3,2-b]indol-9-yl]piperazin-1-yl}acetamide, 1-[3-(dimethyl-1H-1,2,3-triazol-5-yl)-6-methanesulfonyl-5-[(S)-oxan-4-yl(phenyl)methyl]-5H-pyrido[3,2-b]indol-9-yl]-4-(oxetan-3-yl)piperazine, 4-{6-methanesulfonyl-3-[4-($^{2}H_{3}$)methyl-1-methyl-1H-1,2,3-triazol-5-yl]-5-[(S)-oxan-4-yl(phenyl)methyl]-5H-pyrido[3,2-b]indol-9-yl}-1λ⁶,4-thiomorpholine-1,1-dione, tert-butyl 4-[3-(dimethyl-1H-1,2,3-triazol-5-yl)-6-methanesulfonyl-5-[(S)-oxan-4-yl(phenyl)methyl]-5H-pyrido[3,2-b]indol-9-yl]piperazine-1-carboxylate, 2-{6-methanesulfonyl-3-[4-($^{2}H_{3}$)methyl-1-methyl-1H-1,2,3-triazol-5-yl]-5-[(S)-oxan-4-yl(phenyl)methyl]-5H-pyrido[3,2-b]indol-9-yl}-1λ⁶,2-thiazolidine-1,1-dione, 2-({3,7-bis[4-($^{2}H_{3}$)methyl-1-methyl-1H-1,2,3-triazol-5-yl]-5H-pyrido[3,2-b]indol-5-yl}(oxan-4-yl)methyl)-3-fluoropyridine, 2-({3,7-bis[4-($^{2}H_{3}$)methyl-1-methyl-1H-1,2,3-triazol-5-yl]-5H-pyrido[3,2-b]indol-5-yl}(oxan-4-yl)methyl)-3-fluoropyridine, 4-($^{2}H_{3}$)methoxy-5-{7-[4-($^{2}H_{3}$)methoxy-1-methyl-1H-1,2,3-triazol-5-yl]-5-[(S)-oxan-4-yl(phenyl)methyl]-5H-pyrido[3,2-b]indol-3-yl}-1-methyl-1H-1,2,3-triazole, 4-methoxy-5-{7-[4-methoxy-1-($^{2}H_{3}$)methyl-1H-1,2,3-triazol-5-yl]-5-[(S)-oxan-4-yl(phenyl)methyl]-5H-pyrido[3,2-b]indol-3-yl}-1-($^{2}H_{3}$)methyl-1H-1,2,3-triazole, 4-($^2$H$_3$)methyl-1-methyl-5-{7-[4-($^2$H$_3$)methyl-1-methyl-1H-1,2,3-triazol-5-yl]-5-[(S)-oxan-4-yl(phenyl)methyl]-5H-pyrido[3,2-b]indol-3-yl}-1H-1,2,3-triazole, 4-methoxy-5-[7-(4-methoxy-1-methyl-1H-1,2,3-triazol-5-yl)-5-[(S)-oxan-4-yl(phenyl)methyl]-5H-pyrido[3,2-b]indol-3-yl]-1-methyl-1H-1,2,3-triazole, 2-{5-[(S)-(4-fluorophenyl)(oxan-4-yl)methyl]-6-methanesulfonyl-3-[4-($^2$H$_3$)methyl-1-methyl-1H-1,2,3-triazol-5-yl]-5H-pyrido[3,2-b]indol-9-yl}-1λ$^6$,2-thiazolidine-1,1-dione, 2-{5-[(S)-(2-fluorophenyl)(oxan-4-yl)methyl]-6-methanesulfonyl-3-[4-($^2$H$_3$)methyl-1-methyl-1H-1,2,3-triazol-5-yl]-5H-pyrido[3,2-b]indol-9-yl}-1λ$^6$,2-thiazolidine-1,1-dione, 2-{5-[(3-fluoropyridin-2-yl)(oxan-4-yl)methyl]-6-methanesulfonyl-3-[4-($^2$H$_3$)methyl-1-methyl-1H-1,2,3-triazol-5-yl]-5H-pyrido[3,2-b]indol-9-yl}-1λ$^6$,2-thiazolidine-1,1-dione, 2-{5-[(3-fluoropyridin-2-yl)(oxan-4-yl)methyl]-6-methanesulfonyl-3-[4-($^2$H$_3$)methyl-1-methyl-1H-1,2,3-triazol-5-yl]-5H-pyrido[3,2-b]indol-9-yl}-1λ$^6$,2-thiazolidine-1,1-dione, 2-{5-[(S)-(2-fluorophenyl)(oxan-4-yl)($^2$H)methyl]-6-methanesulfonyl-3-[4-($^2$H$_3$)methyl-1-methyl-1H-1,2,3-triazol-5-yl]-5H-pyrido[3,2-b]indol-9-yl}-1λ$^6$,2-thiazolidine-1,1-dione, 2-{6-methanesulfonyl-3-[4-($^2$H$_3$)methyl-1-methyl-1H-1,2,3-triazol-5-yl]-5-[(S)-oxan-4-yl(phenyl)(2H)methyl]-5H-pyrido[3,2-b]indol-9-yl}-1λ$^6$,2-thiazolidine-1,1-dione, 4-{5-[(S)-(4-fluorophenyl)(oxan-4-yl)methyl]-3-[4-($^2$H$_3$)methyl-1-methyl-1H-1,2,3-triazol-5-yl]-5H-pyrido[3,2-b]indol-8-yl}-1λ$^6$,4-thiomorpholine-1,1-dione, 1-{5-[(S)-(4-fluorophenyl)(oxan-4-yl)methyl]-3-[4-($^2$H$_3$)methyl-1-methyl-1H-1,2,3-triazol-5-yl]-5H-pyrido[3,2-b]indol-8-yl}-4-methanesulfonylpiperazine, 4-{5-[(S)-(2-fluorophenyl)(oxan-4-yl)methyl]-3-[4-($^2$H$_3$)methyl-1-methyl-1H-1,2,3-triazol-5-yl]-5H-pyrido[3,2-b]indol-8-yl}-1λ$^6$,4-thiomorpholine-1,1-dione, 1-{5-[(S)-(2-fluorophenyl)(oxan-4-yl)methyl]-3-[4-($^2$H$_3$)methyl-1-methyl-1H-1,2,3-triazol-5-yl]-5H-pyrido[3,2-b]indol-8-yl}-4-methanesulfonylpiperazine, 2-{5-[(S)-(4-fluorophenyl)(oxan-4-yl)methyl]-3-[4-($^2$H$_3$)methyl-1-methyl-1H-1,2,3-triazol-5-yl]-5H-pyrido[3,2-b]indol-8-yl}-1,2,3,4-tetrahydroisoquinoline, 4-[3-(dimethyl-1H-1,2,3-triazol-5-yl)-5-[(S)-oxan-4-yl(phenyl)methyl]-5H-pyrido[3,2-b]indol-7-yl]-1λ$^6$,4-thiomorpholine-1,1-dione, 4-{3-[4-($^2$H$_3$)methyl-1-methyl-1H-1,2,3-triazol-5-yl]-5-[(S)-oxan-4-yl(phenyl)methyl]-5H-pyrido[3,2-b]indol-7-yl}-1λ$^6$,4-thiomorpholine-1,1-dione, 1-methanesulfonyl-4-{3-[4-($^2$H$_3$)methyl-1-methyl-1H-1,2,3-triazol-5-yl]-5-[(S)-oxan-4-yl(phenyl)methyl]-5H-pyrido[3,2-b]indol-7-yl}piperazine, 1-[3-(dimethyl-1H-1,2,3-triazol-5-yl)-5-[(S)-oxan-4-yl(phenyl)methyl]-5H-pyrido[3,2-b]indol-7-yl]-4-methylpiperazine, 1-[3-(dimethyl-1H-1,2,3-triazol-5-yl)-5-[(S)-oxan-4-yl(phenyl)methyl]-5H-pyrido[3,2-b]indol-7-yl]-4-(1-methylpiperidin-4-yl)piperazine, 4-[3-(dimethyl-1H-1,2,3-triazol-5-yl)-5-[(S)-oxan-4-yl(phenyl)methyl]-5H-pyrido[3,2-b]indol-7-yl]-N,N-dimethylpiperazine-1-carboxamide, 4-[3-(dimethyl-1H-1,2,3-triazol-5-yl)-5-[(S)-oxan-4-yl(phenyl)methyl]-5H-pyrido[3,2-b]indol-7-yl]-N,N-dimethylpiperazine-1-sulfonamide, (2R)-4-{5-[(S)-(2-fluorophenyl)(oxan-4-yl)methyl]-3-[4-($^2$H$_3$)methyl-1-methyl-1H-1,2,3-triazol-5-yl]-5H-pyrido[3,2-b]indol-8-yl}-2-methyl-1λ$^6$,4-thiomorpholine-1,1-dione, (2S)-4-{5-[(S)-(2-fluorophenyl)(oxan-4-yl)methyl]-3-[4-($^2$H$_3$)methyl-1-methyl-1H-1,2,3-triazol-5-yl]-5H-pyrido[3,2-b]indol-8-yl}-2-methyl-1λ$^6$,4-thiomorpholine-1,1-dione, 4-{6-Fluoro-3-[4-($^2$H$_3$)methyl-1-methyl-1H-1,2,3-triazol-5-yl]-5-[(S)-oxan-4-yl(phenyl)methyl]-5H-pyrido[3,2-b]indol-7-yl}piperidin-4-ol, 4-{6-Fluoro-3-[4-($^2$H$_3$)methyl-1-methyl-1H-1,2,3-triazol-5-yl]-5-[(S)-oxan-4-yl(phenyl)methyl]-5H-pyrido[3,2-b]indol-7-yl}-1-methylpiperidin-4-ol, 4-{6-Fluoro-3-[4-($^2$H$_3$)methyl-1-methyl-1H-1,2,3-triazol-5-yl]-5-[(S)-oxan-4-yl(phenyl)methyl]-5H-pyrido[3,2-b]indol-7-yl}-4-methyl-1,3-oxazolidin-2-one, Diastereomer A, 4-{6-Fluoro-3-[4-($^2$H$_3$)methyl-1-methyl-1H-1,2,3-triazol-5-yl]-5-[(S)-oxan-4-yl(phenyl)methyl]-5H-pyrido[3,2-b]indol-7-yl}-4-methyl-1,3-oxazolidin-2-one, Diastereomer B, 1-{6-Fluoro-3-[4-($^2$H$_3$)methyl-1-methyl-1H-1,2,3-triazol-5-yl]-5-[(S)-oxan-4-yl(phenyl)methyl]-5H-pyrido[3,2-b]indol-7-yl}pyrrolidin-2-one, 2-{6-Fluoro-3-[4-($^2$H$_3$)methyl-1-methyl-1H-1,2,3-triazol-5-yl]-5-[(S)-oxan-4-yl(phenyl)methyl]-5H-pyrido[3,2-b]indol-7-yl}-1λ$^6$,2-thiazolidine-1,1-dione, 1-{6-Fluoro-3-[4-($^2$H$_3$)methyl-1-methyl-1H-1,2,3-triazol-5-yl]-5-[(S)-oxan-4-yl(phenyl)methyl]-5H-pyrido[3,2-b]indol-7-yl}imidazolidin-2-one, 3-{6-Fluoro-3-[4-($^2$H$_3$)methyl-1-methyl-1H-1,2,3-triazol-5-yl]-5-[(S)-oxan-4-yl(phenyl)methyl]-5H-pyrido[3,2-b]indol-7-yl}-1,3-oxazolidin-2-one, 2-{6-Fluoro-5-[(S)-(3-fluoropyridin-2-yl)(oxan-4-yl)methyl]-3-[4-($^2$H$_3$)methyl-1-methyl-1H-1,2,3-triazol-5-yl]-5H-pyrido[3,2-b]indol-7-yl}-1λ$^6$,2-thiazolidine-1,1-dione, 4-{6-Fluoro-3-[4-($^2$H$_3$)methyl-1-methyl-1H-1,2,3-triazol-5-yl]-5-[(S)-oxan-4-yl(phenyl)methyl]-5H-pyrido[3,2-b]indol-7-yl}oxan-4-ol, 3-{6-Fluoro-3-[4-($^2$H$_3$)methyl-1-methyl-1H-1,2,3-triazol-5-yl]-5-[(S)-oxan-4-yl(phenyl)methyl]-5H-pyrido[3,2-b]indol-7-yl}oxolan-3-ol, Diastereomer 1, 3-{6-Fluoro-3-[4-($^2$H$_3$)methyl-1-methyl-1H-1,2,3-triazol-5-yl]-5-[(S)-oxan-4-yl(phenyl)methyl]-5H-pyrido[3,2-b]indol-7-yl}oxolan-3-ol, Diastereomer 2, 2-{[7-(4,4-Difluoropiperidin-1-yl)-3-[4-($^2$H$_3$)methyl-1-methyl-1H-1,2,3-triazol-5-yl]-5H-pyrido[3,2-b]indol-5-yl](oxan-4-yl)methyl}-3-fluoropyridine, Enantiomer A, 2-{[7-(4,4-Difluoropiperidin-1-yl)-3-[4-($^2$H$_3$)methyl-1-methyl-1H-1,2,3-triazol-5-yl]-5H-pyrido[3,2-b]indol-5-yl](oxan-4-yl)methyl}-3-fluoropyridine, Enantiomer B, 4-{5-[(3-Fluoropyridin-2-yl)(oxan-4-yl)methyl]-3-[4-($^2$H$_3$)methyl-1-methyl-1H-1,2,3-triazol-5-yl]-5H-pyrido[3,2-b]indol-7-yl}-1λ$^6$,4-thiomorpholine-1,1-dione, Enantiomer A, 4-{5-[(3-Fluoropyridin-2-yl)(oxan-4-yl)methyl]-3-[4-($^2$H$_3$)methyl-1-methyl-1H-1,2,3-triazol-5-yl]-5H-pyrido[3,2-b]indol-7-yl}-1λ$^6$,4-thiomorpholine-1,1-dione, Enantiomer B, 3-Fluoro-2-{[7-(4-methanesulfonylpiperidin-1-yl)-3-[4-($^2$H$_3$)methyl-1-methyl-1H-1,2,3-triazol-5-yl]-5H-pyrido[3,2-b]indol-5-yl](oxan-4-yl)methyl}pyridine, Enantiomer A, 3-Fluoro-2-{[7-(4-methanesulfonylpiperidin-1-yl)-3-[4-(²H₃)methyl-1-methyl-1H-1,2,3-triazol-5-yl]-5H-pyrido[3,2-b]indol-5-yl](oxan-4-yl)methyl}pyridine, Enantiomer B, 1-[3-(Dimethyl-1H-1,2,3-triazol-5-yl)-5-[(S)-oxan-4-yl(phenyl)methyl]-5H-pyrido[3,2-b]indol-7-yl]-4,4-difluoropiperidine, 1-[3-(Dimethyl-1H-1,2,3-triazol-5-yl)-5-[(S)-oxan-4-yl(phenyl)methyl]-5H-pyrido[3,2-b]indol-7-yl]-4-(trifluoromethyl)piperidine, 1-{5-[(4,4-Difluorocyclohexyl)(phenyl)methyl]-6-methanesulfonyl-3-[4-(²H₃)methyl-1-methyl-1H-1,2,3-triazol-5-yl]-5H-pyrido[3,2-b]indol-9-yl}-4,4-difluoropiperidine, Enantiomer A, 1-{5-[(4,4-Difluorocyclohexyl)(phenyl)methyl]-6-methanesulfonyl-3-[4-(²H₃)methyl-1-methyl-1H-1,2,3-triazol-5-yl]-5H-pyrido[3,2-b]indol-9-yl}-4,4-difluoropiperidine, Enantiomer B, 1-{5-[(4,4-Difluorocyclohexyl)(phenyl)methyl]-3-(dimethyl-1H-1,2,3-triazol-5-yl)-5H-pyrido[3,2-b]indol-7-yl}-4,4-difluoropiperidine, Enantiomer A, 1-{5-[(4,4-Difluorocyclohexyl)(phenyl)methyl]-3-(dimethyl-1H-1,2,3-triazol-5-yl)-5H-pyrido[3,2-b]indol-7-yl}-4,4-difluoropiperidine, Enantiomer B, 1-{5-[(4,4-Difluorocyclohexyl)(phenyl)methyl]-3-(dimethyl-1H-1,2,3-triazol-5-yl)-5H-pyrido[3,2-b]indol-7-yl}-4-(trifluoromethyl)piperidine, Enantiomer A, or 1-{5-[(4,4-Difluorocyclohexyl)(phenyl)methyl]-3-(dimethyl-1H-1,2,3-triazol-5-yl)-5H-pyrido[3,2-b]indol-7-yl}-4-(trifluoromethyl)piperidine, Enantiomer B, and/or a pharmaceutically acceptable salt, tautomer or stereoisomer thereof.

One embodiment of the invention provides compounds wherein A is optionally substituted heterocyclo or optionally substituted heteroaryl, wherein the substituents are one or more R;

Another embodiment of the invention provides compounds wherein A is

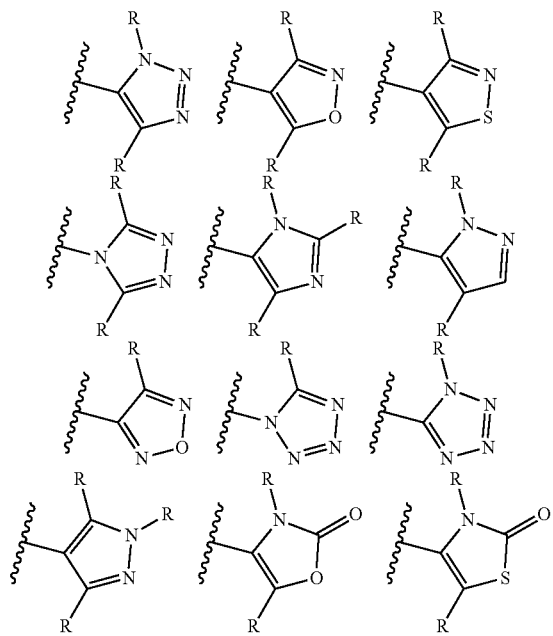

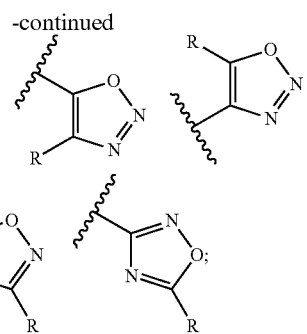

and R is independently one or more hydrogen, CD₃, OCD₃, CF₃, CHF₂ or (C₁-C₃)alkyl.

Another embodiment of the invention provides compounds wherein A is

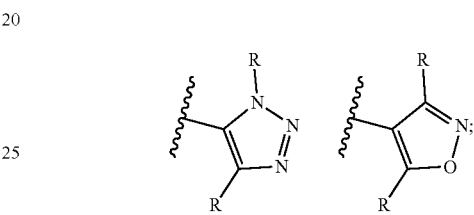

and R is independently one or more hydrogen, CD₃, OCD₃, CF₃, CHF₂ or (C₁-C₃)alkyl.

Another embodiment of the invention provides compounds wherein A is

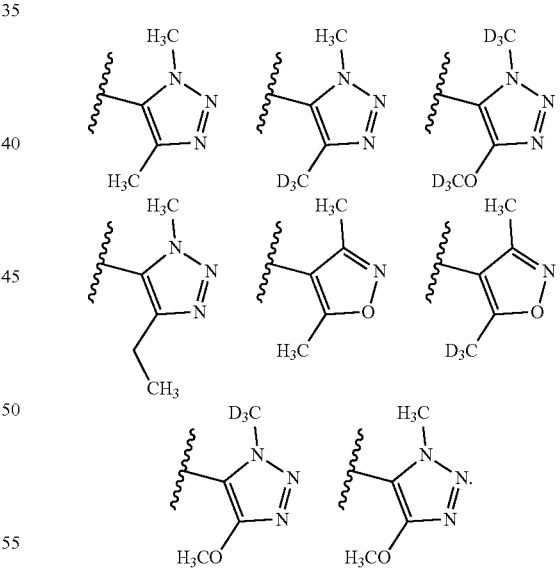

Other Embodiments of the Invention

In another embodiment, the invention provides a pharmaceutical composition, comprising a pharmaceutically acceptable carrier and a therapeutically effective amount of at least one of the compounds of the invention or a stereoisomer, a tautomer, a pharmaceutically acceptable salt, or a solvate thereof.

In another embodiment, the invention provides a process for making a compound of the invention or a stereoisomer, a tautomer, a pharmaceutically acceptable salt, or a solvate thereof.

In another embodiment, the invention provides a method for inhibiting activity of a bromodomain-containing protein mediated disorder in a patient in need thereof comprising the step of administering to said patient at least one compound of the invention.

In another embodiment, the invention provides a method for the treatment and/or prophylaxis of various types of cancer, comprising administering to a patient in need of such treatment and/or prophylaxis a therapeutically effective amount of one or more compounds of the invention, alone, or, optionally, in combination with another compound of the invention and/or at least one other type of therapeutic agent.

In another embodiment, the invention provides a method for the treatment and/or prophylaxis of various types of cancer, including without limitation, small cell lung cancer, non-small cell lung cancer, colorectal cancer, multiple myeloma, acute myeloid leukemia (AML), acute lymphoblastic leukemia (ALL), pancreatic cancer, liver cancer, hepatocellular cancer, neuroblastoma, other solid tumors or other hematological cancers.

In another embodiment, the invention provides a method for the treatment and/or prophylaxis of various types of cancer, including without limitation, small cell lung cancer, non-small cell lung cancer, colorectal cancer, multiple myeloma or AML.

In another embodiment, the invention provides a compound of the present invention for use in therapy.

In another embodiment, the invention provides a combined preparation of a compound of the present invention and additional therapeutic agent(s) for simultaneous, separate or sequential use in therapy.

In another embodiment, the invention provides a method of inhibiting a bromodomain-containing protein comprising contacting said protein with any exemplified compound or a pharmaceutically acceptable salt or composition thereof.

Therapeutic Applications

The compounds of formula (I) of the invention are bromodomain inhibitors and have potential utility in the treatment of diseases and conditions for which a bromodomain inhibitor is indicated.

In one embodiment there is provided a method for the treatment of a disease or condition, for which a bromodomain inhibitor is indicated, in a subject in need thereof which comprises administering a therapeutically effective amount of compound of formula (I) or a pharmaceutically acceptable salt thereof.

In another embodiment there is provided a method for treatment of a chronic autoimmune and/or inflammatory condition, in a subject in need thereof which comprises administering a therapeutically effective amount of one or more compounds of formula (I) or a pharmaceutically acceptable salt thereof.

In a further embodiment there is provided a method for treatment of cancer in a subject in need thereof which comprises administering a therapeutically effective amount of one or more compounds of formula (I) or a pharmaceutically acceptable salt thereof.

In one embodiment the subject in need thereof is a mammal, particularly a human.

Bromodomain inhibitors are believed to be useful in the treatment of a variety of diseases or conditions related to systemic or tissue inflammation, inflammatory responses to infection or hypoxia, cellular activation and proliferation, lipid metabolism, fibrosis and in the prevention and treatment of viral infections.

Bromodomain inhibitors may be useful in the treatment of a wide variety of chronic autoimmune and inflammatory conditions such as rheumatoid arthritis, osteoarthritis, acute gout, psoriasis, systemic lupus erythematosus, multiple sclerosis, inflammatory bowel disease (Crohn's disease and Ulcerative colitis), asthma, chronic obstructive airways disease, pneumonitis, myocarditis, pericarditis, myositis, eczema, dermatitis, alopecia, vitiligo, bullous skin diseases, nephritis, vasculitis, atherosclerosis, Alzheimer's disease, depression, retinitis, uveitis, scleritis, hepatitis, pancreatitis, primary biliary cirrhosis, sclerosing cholangitis, Addison's disease, hypophysitis, thyroiditis, type I diabetes and acute rejection of transplanted organs.

Bromodomain inhibitors may be useful in the treatment of a wide variety of acute inflammatory conditions such as acute gout, giant cell arteritis, nephritis including lupus nephritis, vasculitis with organ involvement such as glomerulonephritis, vasculitis including giant cell arteritis, Wegener's granulomatosis, Polyarteritis nodosa, Behcet's disease, Kawasaki disease, Takayasu's Arteritis and acute rejection of transplanted organs.

Bromodomain inhibitors may be useful in the prevention or treatment of diseases or conditions which involve inflammatory responses to infections with bacteria, viruses, fungi, parasites or their toxins, such as sepsis, sepsis syndrome, septic shock, endotoxaemia, systemic inflammatory response syndrome (SIRS), multi-organ dysfunction syndrome, toxic shock syndrome, acute lung injury, ARDS (adult respiratory distress syndrome), acute renal failure, fulminant hepatitis, burns, acute pancreatitis, post-surgical syndromes, sarcoidosis, Herxheimer reactions, encephalitis, myelitis, meningitis, malaria, SIRS associated with viral infections such as influenza, herpes zoster, herpes simplex and coronavirus.

Bromodomain inhibitors may be useful in the prevention or treatment of conditions associated with ischaemia-reperfusion injury such as myocardial infarction, cerebrovascular ischaemia (stroke), acute coronary syndromes, renal reperfusion injury, organ transplantation, coronary artery bypass grafting, cardio-pulmonary bypass procedures and pulmonary, renal, hepatic, gastro-intestinal or peripheral limb embolism.

Bromodomain inhibitors may be useful in the treatment of disorders of lipid metabolism via the regulation of APO-A1 such as hypercholesterolemia, atherosclerosis and Alzheimer's disease.

Bromodomain inhibitors may be useful in the treatment of fibrotic conditions such as idiopathic pulmonary fibrosis, renal fibrosis, post-operative stricture, keloid formation, scleroderma and cardiac fibrosis.

Bromodomain inhibitors may be useful in the prevention and treatment of viral infections such as herpes virus, human papilloma virus, adenovirus, poxvirus and other DNA viruses.

Bromodomain inhibitors may also be useful in the treatment of cancer, including hematological, epithelial including lung, breast and colon carcinomas, midline carcinomas, mesenchymal, hepatic, renal and neurological tumours.

In one embodiment the disease or condition for which a bromodomain inhibitor is indicated is selected from diseases associated with systemic inflammatory response syndrome, such as sepsis, burns, pancreatitis, major trauma, hemorrhage and ischemia. In this embodiment, the bromodomain inhibitor would be administered at the point of diagnosis to reduce the incidence of SIRS, the onset of shock, multi-organ dysfunction syndrome, which includes the onset of acute lung injury, ARDS, acute renal, hepatic, cardiac and gastro-intestinal injury and mortality. In another embodiment the bromodomain inhibitor would be administered prior to surgical or other procedures associated with a high risk of sepsis, hemorrhage, extensive tissue damage, SIRS or MODS (multiple organ dysfunction syndrome). In a particular embodiment the disease or condition for which a bromodomain inhibitor is indicated is sepsis, sepsis syndrome, septic shock and endotoxemia. In another embodiment, the bromodomain inhibitor is indicated for the treatment of acute or acute on chronic pancreatitis. In another embodiment the bromodomain inhibitor is indicated for the treatment of burns.

In one embodiment the disease or condition for which a bromodomain inhibitor is indicated is selected from herpes simplex infections and reactivations, cold sores, herpes zoster infections and reactivations, chickenpox, shingles, human papilloma virus, cervical neoplasia, adenovirus infections, including acute respiratory disease, and poxvirus infections such as cowpox and smallpox and African swine fever virus.

The term "diseases or conditions for which a bromodomain inhibitor is indicated" is intended to include any of or all of the above disease states.

In one embodiment, there is provided a method for inhibiting a bromodomain which comprises contacting the bromodomain with a compound of formula (1) or a pharmaceutically acceptable salt thereof.

While it is possible that for use in therapy, a compound of formula (I) as well as pharmaceutically acceptable salts thereof may be administered as the compound itself, it is more commonly presented as a pharmaceutical composition.

Pharmaceutical compositions may be presented in unit dose forms containing a predetermined amount of active ingredient pep unit dose. Preferred unit dosage compositions are those containing a daily dose or sub-dose, or an appropriate fraction thereof, of an active ingredient. Such unit doses may therefore be administered more than once a day. Preferred unit dosage compositions are those containing a daily dose or sub-dose (for administration more than once a day), as herein above recited, or an appropriate fraction thereof, of an active ingredient.

Types of cancers that may be treated with the compounds of this invention include, but are not limited to, brain cancers, skin cancers, bladder cancers, ovarian cancers, breast cancers, gastric cancers, pancreatic cancers, prostate cancers, colon cancers, blood cancers, lung cancers and bone cancers. Examples of such cancer types include neuroblastoma, intestine carcinoma such as rectum carcinoma, colon carcinoma, familiar adenomatous polyposis carcinoma and hereditary non-polyposis colorectal cancer, esophageal carcinoma, labial carcinoma, larynx carcinoma, hypopharynx carcinoma, tong carcinoma, salivary gland carcinoma, gastric carcinoma, adenocarcinoma, medullary thyroid carcinoma, papillary thyroid carcinoma, renal carcinoma, kidney parenchymal carcinoma, ovarian carcinoma, cervix carcinoma, uterine corpus carcinoma, endometrium carcinoma, chorion carcinoma, pancreatic carcinoma, prostate carcinoma, testis carcinoma, breast carcinoma, urinary carcinoma, melanoma, brain tumors such as glioblastoma, astrocytoma, meningioma, medulloblastoma and peripheral neuroectodermal tumors, Hodgkin lymphoma, non-Hodgkin lymphoma, Burkitt lymphoma, acute lymphatic leukemia (ALL), chronic lymphatic leukemia (CLL), acute myeloid leukemia (AML), chronic myeloid leukemia (CML), adult T-cell leukemia lymphoma, diffuse large B-cell lymphoma (DLBCL), hepatocellular carcinoma, gall bladder carcinoma, bronchial carcinoma, small cell lung carcinoma, non-small cell lung carcinoma, multiple myeloma, basalioma, teratoma, retinoblastoma, choroid melanoma, seminoma, rhabdomyosarcoma, craniopharyngioma, osteosarcoma, chondrosarcoma, myosarcoma, liposarcoma, fibrosarcoma, Ewing sarcoma and plasmocytoma.

In addition to apoptosis defects found in tumors, defects in the ability to eliminate self-reactive cells of the immune system due to apoptosis resistance are considered to play a key role in the pathogenesis of autoimmune diseases. Autoimmune diseases are characterized in that the cells of the immune system produce antibodies against its own organs and molecules or directly attack tissues resulting in the destruction of the latter. A failure of those self-reactive cells to undergo apoptosis leads to the manifestation of the disease. Defects in apoptosis regulation have been identified in autoimmune diseases such as systemic lupus erythematosus or rheumatoid arthritis.

Thus, according to another embodiment, the invention provides a method of treating an autoimmune disease by providing to a patient in need thereof a compound or composition of the present invention. Examples of such autoimmune diseases include, but are not limited to, collagen diseases such as rheumatoid arthritis, systemic lupus erythematosus. Sharp's syndrome, CREST syndrome (calcinosis, Raynaud's syndrome, esophageal dysmotility, telangiectasia), dermatomyositis, vasculitis (Morbus Wegener's) and Sjogren's syndrome, renal diseases such as Goodpasture's syndrome, rapidly-progressing glomerulonephritis and membrano-proliferative glomerulonephritis type II, endocrine diseases such as type-I diabetes, autoimmune polyendocrinopathy-candidiasis-ectodermal dystrophy (APECED), autoimmune parathyroidism, pernicious anemia, gonad insufficiency, idiopathic Morbus Addison's, hyperthyreosis, Hashimoto's thyroiditis and primary myxedema, skin diseases such as pemphigus vulgaris, bullous pemphigoid, herpes gestationis, epidermolysis bullosa and erythema multiforme major, liver diseases such as primary biliary cirrhosis, autoimmune cholangitis, autoimmune hepatitis type-1, autoimmune hepatitis type-2, primary sclerosing cholangitis, neuronal diseases such as multiple sclerosis, myasthenia gravis, myasthenic Lambert-Eaton syndrome, acquired neuromyotomy, Guillain-Barre syndrome (Muller-Fischer syndrome), stiff-man syndrome, cerebellar degeneration, ataxia, opsoclonus, sensoric neuropathy and achalasia, blood diseases such as autoimmune hemolytic anemia, idiopathic thrombocytopenic purpura (Morbus Werlhof), infectious diseases with associated autoimmune reactions such as AIDS, malaria and Chagas disease.

Compounds of the invention are useful for the treatment of certain types of cancer by themselves or in combination or co-administration with other therapeutic agents or radiation therapy. Thus, in one embodiment, the compounds of the invention are co-administered with radiation therapy or a second therapeutic agent with cytostatic or antineoplastic activity. Suitable cytostatic chemotherapy compounds include, but are not limited to (i) antimetabolites; (ii) DNA-fragmenting agents, (iii) DNA-crosslinking agents, (iv) intercalating agents (v) protein synthesis inhibitors, (vi) topoisomerase I poisons, such as camptothecin or topotecan; (vii) topoisomerase II poisons, (viii) microtubule-directed agents, (ix) kinase inhibitors (x) miscellaneous investigational agents (xi) hormones and (xii) hormone antagonists. It is contemplated that compounds of the invention may be useful in combination with any known agents falling into the above 12 classes as well as any future agents that are currently in development. In particular, it is contemplated that compounds of the invention may be useful in combination with current Standards of Care as well as any that evolve over the foreseeable future. Specific dosages and dosing regimens would be based on physicians' evolving knowledge and the general skill in the art.

Further provided herein are methods of treatment wherein compounds of the invention are administered with one or more immuno-oncology agents. The immuno-oncology agents used herein, also known as cancer immunotherapies, are effective to enhance, stimulate, and/or up-regulate immune responses in a subject. In one aspect, the administration of a compound of the invention with an immuno-oncology agent has a synergic effect in inhibiting tumor growth.

In one aspect, the compound(s) of the invention are sequentially administered prior to administration of the immuno-oncology agent. In another aspect, compound(s) of the invention are administered concurrently with the immunology-oncology agent. In yet another aspect, compound(s) of the invention are sequentially administered after administration of the immuno-oncology agent.

In another aspect, compounds of the invention may be co-formulated with an immuno-oncology agent.

Immuno-oncology agents include, for example, a small molecule drug, antibody, or other biologic or small molecule. Examples of biologic immuno-oncology agents include, but are not limited to, cancer vaccines, antibodies, and cytokines. In one aspect, the antibody is a monoclonal antibody. In another aspect, the monoclonal antibody is humanized or human.

In one aspect, the immuno-oncology agent is (i) an agonist of a stimulatory (including a co-stimulatory) receptor or (ii) an antagonist of an inhibitory (including a co-inhibitory) signal on T cells, both of which result in amplifying antigen-specific T cell responses (often referred to as immune checkpoint regulators).

Certain of the stimulatory and inhibitory molecules are members of the immunoglobulin super family (IgSF). One important family of membrane-bound ligands that bind to co-stimulatory or co-inhibitory receptors is the B7 family, which includes B7-1, B7-2, B7-H1 (PD-L1), B7-DC (PD-L2), B7-H2 (ICOS-L), B7-H3, B7-H4, B7-H5 (VISTA), and B7-H6. Another family of membrane bound ligands that bind to co-stimulatory or co-inhibitory receptors is the TNF family of molecules that bind to cognate TNF receptor family members, which includes CD40 and CD40L, OX-40, OX-40L, CD70, CD27L, CD30, CD30L, 4-1BBL, CD137 (4-1BB), TRAIL/Apo2-L, TRAILR1/DR4, TRAILR2/DR5, TRAILR3, TRAILR4, OPG, RANK, RANKL, TWEAKR/Fn14, TWEAK, BAFFR, EDAR, XEDAR, TACI, APRIL, BCMA, LTβR, LIGHT, DcR3, HVEM, VEGI/TL1A, TRAMP/DR3, EDAR, EDA1, XEDAR, EDA2, TNFR1, Lymphotoxin α/TNFβ, TNFR2, TNFα, LTβR, Lymphotoxin α 1β2, FAS, FASL, RELT, DR6, TROY, NGFR.

In another aspect, the immuno-oncology agent is a cytokine that inhibits T cell activation (e.g., IL-6, IL-10, TGF-β, VEGF, and other immunosuppressive cytokines) or a cytokine that stimulates T cell activation, for stimulating an immune response.

In one aspect, T cell responses can be stimulated by a combination of a compound of the invention and one or more of (i) an antagonist of a protein that inhibits T cell activation (e.g., immune checkpoint inhibitors) such as CTLA-4, PD-1, PD-L1, PD-L2, LAG-3, TIM-3, Galectin 9, CEACAM-1, BTLA, CD69, Galectin-1, TIGIT, CD113, GPR56, VISTA, 2B4, CD48, GARP, PD1H, LAIR1, TIM-1, and TIM-4, and (ii) an agonist of a protein that stimulates T cell activation such as B7-1, B7-2, CD28, 4-1BB (CD137), 4-1BBL, ICOS, ICOS-L, OX40, OX40L, GITR, GITRL, CD70, CD27, CD40, DR3 and CD28H.

Other agents that can be combined with compounds of the invention for the treatment of cancer include antagonists of inhibitory receptors on NK cells or agonists of activating receptors on NK cells. For example, compounds of the invention can be combined with antagonists of KIR, such as lirilumab.

Yet other agents for combination therapies include agents that inhibit or deplete macrophages or monocytes, including but not limited to CSF-1R antagonists such as CSF-1R antagonist antibodies including RG7155 (WO11/70024, WO11/107553, WO11/131407, WO13/87699, WO13/119716, WO13/132044) or FPA-008 (WO11/140249; WO13169264; WO14/036357).

In another aspect, compounds of the invention can be used with one or more of agonistic agents that ligate positive costimulatory receptors, blocking agents that attenuate signaling through inhibitory receptors, antagonists, and one or more agents that increase systemically the frequency of anti-tumor T cells, agents that overcome distinct immune suppressive pathways within the tumor microenvironment (e.g., block inhibitory receptor engagement (e.g., PD-L1/PD-1 interactions), deplete or inhibit Tregs (e.g., using an anti-CD25 monoclonal antibody (e.g., daclizumab) or by ex vivo anti-CD25 bead depletion), inhibit metabolic enzymes such as IDO, or reverse/prevent T cell anergy or exhaustion) and agents that trigger innate immune activation and/or inflammation at tumor sites.

In one aspect, the immuno-oncology agent is a CTLA-4 antagonist, such as an antagonistic CTLA-4 antibody. Suitable CTLA-4 antibodies include, for example, YERVOY (ipilimumab) or tremelimumab.

In another aspect, the immuno-oncology agent is a PD-1 antagonist, such as an antagonistic PD-1 antibody. Suitable PD-1 antibodies include, for example, OPDIVO (nivolumab), KEYTRUDA (pembrolizumab), or MEDI-0680 (AMP-514; WO2012/145493). The immuno-oncology agent may also include pidilizumab (CT-011), though its specificity for PD-1 binding has been questioned. Another approach to target the PD-1 receptor is the recombinant protein composed of the extracellular domain of PD-L2 (B7-DC) fused to the Fc portion of IgG1, called AMP-224

In another aspect, the immuno-oncology agent is a PD-L1 antagonist, such as an antagonistic PD-L1 antibody. Suitable PD-L1 antibodies include, for example, MPDL3280A (RG7446; WO2010/077634), durvalumab (MEDI4736), BMS-936559 (WO2007/005874), and MSB0010718C (WO2013/79174).

In another aspect, the immuno-oncology agent is a LAG-3 antagonist, such as an antagonistic LAG-3 antibody. Suitable LAG3 antibodies include, for example, BMS-986016 (WO10/19570, WO14/08218), or IMP-731 or IMP-321 (WO08/132601, WO09/44273).

In another aspect, the immuno-oncology agent is a CD137 (4-1BB) agonist, such as an agonistic CD137 antibody. Suitable CD137 antibodies include, for example, urelumab and PF-05082566 (WO12/32433).

In another aspect, the immuno-oncology agent is a GITR agonist, such as an agonistic GITR antibody. Suitable GITR antibodies include, for example, BMS-986153, BMS-986156, TRX-518 (WO06/105021, WO009/009116) and MK-4166 (WO11/028683).

In another aspect, the immuno-oncology agent is an IDO antagonist. Suitable IDO antagonists include, for example, INCB-024360 (WO2006/122150, WO07/75598, WO08/36653, WO08/36642), indoximod, or NLG-919 (WO09/73620, WO009/1156652, WO11/56652, WO12/142237).

In another aspect, the immuno-oncology agent is an OX40 agonist, such as an agonistic OX40 antibody. Suitable OX40 antibodies include, for example, MEDI-6383 or MEDI-6469.

In another aspect, the immuno-oncology agent is an OX40L antagonist, such as an antagonistic OX40 antibody. Suitable OX40L antagonists include, for example, RG-7888 (WO06/029879).

In another aspect, the immuno-oncology agent is a CD40 agonist, such as an agonistic CD40 antibody. In yet another embodiment, the immuno-oncology agent is a CD40 antagonist, such as an antagonistic CD40 antibody. Suitable CD40 antibodies include, for example, lucatumumab or dacetuzumab.

In another aspect, the immuno-oncology agent is a CD27 agonist, such as an agonistic CD27 antibody. Suitable CD27 antibodies include, for example, varlilumab.

In another aspect, the immuno-oncology agent is MGA271 (to B7H3) (WO11/109400).

The combination therapy is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single dosage form having a fixed ratio of each therapeutic agent or in multiple, single dosage forms for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. Combination therapy also can embrace the administration of the therapeutic agents as described above in further combination with other biologically active ingredients and non-drug therapies (e.g., surgery or radiation treatment.) Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional embodiments. It is also understood that each individual element of the embodiments is its own independent embodiment. Furthermore, any element of an embodiment is meant to be combined with any and all other elements from any embodiment to describe an additional embodiment.

Pharmaceutical Compositions and Dosing

The invention also provides pharmaceutically acceptable compositions which comprise a therapeutically effective amount of one or more of the compounds of Formula I, formulated together with one or more pharmaceutically acceptable carriers (additives) and/or diluents, and optionally, one or more additional therapeutic agents described above. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained release formulation; (3) topical application, for example, as a cream, ointment, or a controlled release patch or spray applied to the skin; (4) intravaginally or intrarectally, for example, as a pessary, cream or foam; (5) sublingually; (6) ocularly; (7) transdermally; or (8) nasally.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the patient being treated and the particular mode of administration. The amount of active ingredient which can be combined with a carrier material to produce a single dosage form will generally be that amount of the compound which produces a therapeutic effect. Generally, out of one hundred percent, this amount will range from about 0.1 percent to about ninety-nine percent of active ingredient, preferably from about 5 percent to about 70 percent, most preferably from about 10 percent to about 30 percent.

In certain embodiments, a formulation of the present invention comprises an excipient selected from the group consisting of cyclodextrins, celluloses, liposomes, micelle forming agents, e.g., bile acids, and polymeric carriers, e.g., polyesters and polyanhydrides; and a compound of the present invention. In certain embodiments, an aforementioned formulation renders orally bioavailable a compound of the present invention.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules, troches and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds and surfactants, such as poloxamer and sodium lauryl sulfate; (7) wetting agents, such as, for example, cetyl alcohol, glycerol monostearate, and non-ionic surfactants; (8) absorbents, such as kaolin and bentonite clay; (9) lubricants, such as talc, calcium stearate, magnesium stearate, solid polyethylene glycols, sodium lauryl sulfate, zinc stearate, sodium stearate, stearic acid, and mixtures thereof; (10) coloring agents; and (11) controlled release agents such as crospovidone or ethyl cellulose. In the case of capsules, tablets and pills, the pharmaceutical compositions may also comprise buffering agents. Solid compositions of a similar type may also be employed as fillers in soft and hard shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically acceptable sterile isotonic aqueous or non-aqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and non-aqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsuled matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the compounds of the present invention are administered as pharmaceuticals, to humans and animals, they can be given per se or as a pharmaceutical composition containing, for example, 0.1 to 99% (more preferably, 10 to 30%) of active ingredient in combination with a pharmaceutically acceptable carrier.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, oral, intravenous, intracerebroventricular and subcutaneous doses of the compounds of this invention for a patient will range from about 0.01 to about 50 mg per kilogram of body weight per day.

If desired, the effective daily dose of the active compound may be administered as two, three, four, five, six or more sub-doses administered separately at appropriate intervals throughout the day, optionally, in unit dosage forms. In certain aspects of the invention, dosing is one administration per day.

While it is possible for a compound of the present invention to be administered alone, it is preferable to administer the compound as a pharmaceutical formulation (composition).

Definitions

Unless specifically stated otherwise herein, references made in the singular may also include the plural. For example, "a" and "an" may refer to either one, or one or more.

Unless otherwise indicated, any heteroatom with unsatisfied valences is assumed to have hydrogen atoms sufficient to satisfy the valences.

Throughout the specification and the appended claims, a given chemical formula or name shall encompass all stereo and optical isomers and racemates thereof where such isomers exist. Unless otherwise indicated, all chiral (enantiomeric and diastereomeric) and racemic forms are within the scope of the invention. Many geometric isomers of C=C double bonds, C=N double bonds, ring systems, and the like can also be present in the compounds, and all such stable isomers are contemplated in the present invention. Cis- and trans- (or E- and Z-) geometric isomers of the compounds of the present invention are described and may be isolated as a mixture of isomers or as separated isomeric forms. The present compounds can be isolated in optically active or racemic forms. Optically active forms may be prepared by resolution of racemic forms or by synthesis from optically active starting materials. All processes used to prepare compounds of the present invention and intermediates made therein are considered to be part of the present invention. When enantiomeric or diastereomeric products are prepared, they may be separated by conventional methods, for example, by chromatography or fractional crystallization. Depending on the process conditions the end products of the present invention are obtained either in free (neutral) or salt form. Both the free form and the salts of these end products are within the scope of the invention. If so desired, one form of a compound may be converted into another form. A free base or acid may be converted into a salt; a salt may be converted into the free compound or another salt; a mixture of isomeric compounds of the present invention may be separated into the individual isomers. Compounds of the present invention, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

When a substituent is noted as "optionally substituted", the substituents are selected from, for example, substituents such as alkyl, cycloalkyl, aryl, heterocyclo, halo, hydroxy, alkoxy, oxo, alkanoyl, aryloxy, alkanoyloxy, amino, alkylamino, arylamino, arylalkylamino, disubstituted amines in which the 2 amino substituents are selected from alkyl, aryl or arylalkyl; alkanoylamino, aroylamino, aralkanoylamino, substituted alkanoylamino, substituted arylamino, substituted aralkanoylamino, thiol, alkylthio, arylthio, arylalkylthio, alkylthiono, arylthiono, arylalkylthiono, alkylsulfonyl, arylsulfonyl, arylalkylsulfonyl, sulfonamido, e.g. —SO$_2$NH$_2$, substituted sulfonamido, nitro, cyano, carboxy, carbamyl, e.g. —CONH$_2$, substituted carbamyl e.g. —CONHalkyl, —CONHaryl, —CONHarylalkyl or cases where there are two substituents on the nitrogen selected from alkyl, aryl or arylalkyl; alkoxycarbonyl, aryl, substituted aryl, guanidino, heterocyclyl, e.g., indolyl, imidazolyl, furyl, thienyl, thiazolyl, pyrrolidyl, pyridyl, pyrimidyl, pyrrolidinyl, piperidinyl, morpholinyl, piperazinyl, homopiperazinyl and the like, and substituted heterocyclyl, unless otherwise defined.

For purposes of clarity and in accordance with standard convention in the art, the symbol

is used in formulas and tables to show the bond that is the point of attachment of the moiety or substituent to the core/nucleus of the structure.

Additionally, for purposes of clarity, where a substituent has a dash (-) that is not between two letters or symbols; this is used to indicate a point of attachment for a substituent. For example, —CONH$_2$ is attached through the carbon atom.

Additionally, for purposes of clarity, when there is no substituent shown at the end of a solid line, this indicates that there is a methyl (CH$_3$) group connected to the bond.

As used herein, the term "alkyl" or "alkylene" is intended to include both branched and straight-chain saturated aliphatic hydrocarbon groups having the specified number of carbon atoms. For example, "C$_1$-C$_6$ alkyl" denotes alkyl having 1 to 6 carbon atoms. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl).

The term "alkenyl" denotes a straight- or branch-chained hydrocarbon radical containing one or more double bonds and typically from 2 to 20 carbon atoms in length. For example, "C$_2$-C$_8$ alkenyl" contains from two to eight carbon atoms. Alkenyl groups include, but are not limited to, for example, ethenyl, propenyl, butenyl, 1-methyl-2-buten-1-yl, heptenyl, octenyl and the like.

The term "alkynyl" denotes a straight- or branch-chained hydrocarbon radical containing one or more triple bonds and typically from 2 to 20 carbon atoms in length. For example, "C$_2$-C$_8$ alkenyl" contains from two to eight carbon atoms. Representative alkynyl groups include, but are not limited to, for example, ethynyl, 1-propynyl, 1-butynyl, heptynyl, octynyl and the like.

The term "alkoxy" or "alkyloxy" refers to an —O-alkyl group. "$C_{1-6}$ alkoxy" (or alkyloxy), is intended to include $C_1$, $C_2$, $C_3$, $C_4$, $C_5$, and $C_6$ alkoxy groups. Example alkoxy groups include, but are not limited to, methoxy, ethoxy, propoxy (e.g., n-propoxy and isopropoxy), and t-butoxy. Similarly, "alkylthio" or "thioalkoxy" represents an alkyl group as defined above with the indicated number of carbon atoms attached through a sulphur bridge; for example methyl-S— and ethyl-S—.

The term "aryl", either alone or as part of a larger moiety such as "aralkyl", "aralkoxy", or aryloxyalkyl", refers to monocyclic, bicyclic and tricyclic ring systems having a total of five to 15 ring members, wherein at least one ring in the system is aromatic and wherein each ring in the system contains three to seven ring members. In certain embodiments of the invention, "aryl" refers to an aromatic ring system which includes, but not limited to phenyl, biphenyl, indanyl, 1-naphthyl, 2-naphthyl and terahydronaphthyl. The term "aralkyl" or "arylalkyl" refers to an alkyl residue attached to an aryl ring. Non-limiting examples include benzyl, phenethyl and the like. The fused aryls may be connected to another group either at a suitable position on the cycloalkyl ring or the aromatic ring. For example:

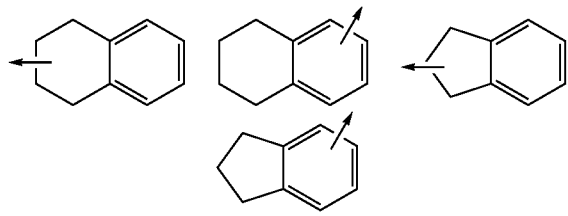

Arrowed lines drawn from the ring system indicate that the bond may be attached to any of the suitable ring atoms.

The term "cycloalkyl" refers to cyclized alkyl groups. $C_{3-6}$ cycloalkyl is intended to include $C_3$, $C_4$, $C_5$, and $C_6$ cycloalkyl groups. Example cycloalkyl groups include, but are not limited to, cyclopropyl, cyclobutyl, cyclopentyl, cyclohexyl, and norbornyl. Branched cycloalkyl groups such as 1-methylcyclopropyl and 2-methylcyclopropyl are included in the definition of "cycloalkyl". The term "cycloalkenyl" refers to cyclized alkenyl groups. $C_{4-6}$ cycloalkenyl is intended to include $C_4$, $C_5$, and $C_6$ cycloalkenyl groups. Example cycloalkenyl groups include, but are not limited to, cyclobutenyl, cyclopentenyl, and cyclohexenyl.

The term "cycloalkylalkyl" refers to a cycloalkyl or substituted cycloalkyl bonded to an alkyl group connected to the core of the compound.

"Halo" or "halogen" includes fluoro, chloro, bromo, and iodo. "Haloalkyl" is intended to include both branched and straight-chain saturated aliphatic hydrocarbon groups having the specified number of carbon atoms, substituted with 1 or more halogens. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with 1 or more fluorine atoms.

"Haloalkoxy" or "haloalkyloxy" represents a haloalkyl group as defined above with the indicated number of carbon atoms attached through an oxygen bridge. For example, "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, and pentafluorothoxy. Similarly, "haloalkylthio" or "thiohaloalkoxy" represents a haloalkyl group as defined above with the indicated number of carbon atoms attached through a sulphur bridge; for example trifluoromethyl-S—, and pentafluoroethyl-S—.

The term "benzyl," as used herein, refers to a methyl group on which one of the hydrogen atoms is replaced by a phenyl group.

As used herein, the term "heterocycle," "heterocyclyl," or "heterocyclic group" is intended to mean a stable 3-, 4-, 5-, 6-, or 7-membered monocyclic or bicyclic or 7-, 8-, 9-, 10-, 11-, 12-, 13-, or 14-membered polycyclic heterocyclic ring that is saturated, partially unsaturated, or fully unsaturated, and that contains carbon atoms and 1, 2, 3 or 4 heteroatoms independently selected from the group consisting of N, O and S; and including any polycyclic group in which any of the above-defined heterocyclic rings is fused to a benzene ring. The nitrogen and sulfur heteroatoms may optionally be oxidized (i.e., N→O and $S(O)_p$, wherein p is 0, 1 or 2). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. When the term "heterocycle" is used, it is intended to include heteroaryl.

Examples of heterocycles include, but are not limited to, acridinyl, azetidinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, imidazolopyridinyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolopyridinyl, pyrazolyl, pyridazinyl, pyridooxazolyl, pyridoimidazolyl, pyridothiazolyl, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrazolyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thiazolopyridinyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

As used herein, the term "bicyclic heterocycle" or "bicyclic heterocyclic group" is intended to mean a stable 9- or 10-membered heterocyclic ring system which contains two fused rings and consists of carbon atoms and 1, 2, 3, or 4 heteroatoms independently selected from the group consisting of N, O and S. Of the two fused rings, one ring is a 5- or 6-membered monocyclic aromatic ring comprising a 5-membered heteroaryl ring, a 6-membered heteroaryl ring or a benzo ring, each fused to a second ring. The second ring is a 5- or 6-membered monocyclic ring which is saturated, partially unsaturated, or unsaturated, and comprises a 5-membered heterocycle, a 6-membered heterocycle or a carbocycle (provided the first ring is not benzo when the second ring is a carbocycle).

The bicyclic heterocyclic group may be attached to its pendant group at any heteroatom or carbon atom which results in a stable structure. The bicyclic heterocyclic group described herein may be substituted on carbon or on a nitrogen atom if the resulting compound is stable. It is preferred that when the total number of S and O atoms in the heterocycle exceeds 1, then these heteroatoms are not adjacent to one another. It is preferred that the total number of S and O atoms in the heterocycle is not more than 1.

Examples of a bicyclic heterocyclic group are, but not limited to, quinolinyl, isoquinolinyl, phthalazinyl, quinazolinyl, indolyl, isoindolyl, indolinyl, 1H-indazolyl, benzimidazolyl, 1,2,3,4-tetrahydroquinolinyl, 1,2,3,4-tetrahydroisoquinolinyl, 5,6,7,8-tetrahydro-quinolinyl, 2,3-dihydrobenzofuranyl, chromanyl, 1,2,3,4-tetrahydro-quinoxalinyl and 1,2,3,4-tetrahydro-quinazolinyl.

As used herein, the term "aromatic heterocyclic group" or "heteroaryl" is intended to mean stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl and benzodioxane. Heteroaryl groups are substituted or unsubstituted. The nitrogen atom is substituted or unsubstituted (i.e., N or NR wherein R is H or another substituent, if defined). The nitrogen and sulfur heteroatoms may optionally be oxidized (i.e., N→O and $S(O)_p$, wherein p is 0, 1 or 2).

Bridged rings are also included in the definition of heterocycle. A bridged ring occurs when one or more, preferably one to three, atoms (i.e., C, O, N, or S) link two non-adjacent carbon or nitrogen atoms. Examples of bridged rings include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

The term "heterocyclylalkyl" refers to a heterocyclyl or substituted heterocyclyl bonded to an alkyl group connected to the core of the compound.

The term "counter ion" is used to represent a negatively charged species such as chloride, bromide, hydroxide, acetate, and sulfate or a positively charged species such as sodium (Na+), potassium (K+), ammonium ($R_nNH_m$+ where n=0-4 and m=0-4) and the like.

The term "electron withdrawing group" (EWG) refers to a substituent which polarizes a bond, drawing electron density towards itself and away from other bonded atoms. Examples of EWGs include, but are not limited to, $CF_3$, $CF_2CF_3$, CN, halogen, haloalkyl, $NO_2$, sulfone, sulfoxide, ester, sulfonamide, carboxamide, alkoxy, alkoxyether, alkenyl, alkynyl, OH, C(O)alkyl, $CO_2H$, phenyl, heteroaryl, —O-phenyl, and —O— heteroaryl. Preferred examples of EWG include, but are not limited to, $CF_3$, $CF_2CF_3$, CN, halogen, $SO_2(C_{1-4}$ alkyl), $CONH(C_{1-4}$ alkyl), $CON(C_{1-4}$ alkyl)$_2$, and heteroaryl. More preferred examples of EWG include, but are not limited to, $CF_3$ and CN.

As used herein, the term "amine protecting group" means any group known in the art of organic synthesis for the protection of amine groups which is stable to an ester reducing agent, a disubstituted hydrazine, R4-M and R7-M, a nucleophile, a hydrazine reducing agent, an activator, a strong base, a hindered amine base and a cyclizing agent. Such amine protecting groups fitting these criteria include those listed in Wuts, P. G. M. and Greene, T. W. *Protecting Groups in Organic Synthesis,* 4th Edition, Wiley (2007) and *The Peptides: Analysis, Synthesis, Biology,* Vol. 3, Academic Press, New York (1981), the disclosure of which is hereby incorporated by reference. Examples of amine protecting groups include, but are not limited to, the following: (1) acyl types such as formyl, trifluoroacetyl, phthalyl, and p-toluenesulfonyl; (2) aromatic carbamate types such as benzyloxycarbonyl (Cbz) and substituted benzyloxycarbonyls, 1-(p-biphenyl)-1-methylethoxycarbonyl, and 9-fluorenylmethyloxycarbonyl (Fmoc); (3) aliphatic carbamate types such as tert-butyloxycarbonyl (Boc), ethoxycarbonyl, diisopropylmethoxycarbonyl, and allyloxycarbonyl; (4) cyclic alkyl carbamate types such as cyclopentyloxycarbonyl and adamantyloxycarbonyl; (5) alkyl types such as triphenylmethyl and benzyl; (6) trialkylsilane such as trimethylsilane; (7) thiol containing types such as phenylthiocarbonyl and dithiasuccinoyl; and (8) alkyl types such as triphenylmethyl, methyl, and benzyl; and substituted alkyl types such as 2,2,2-trichloroethyl, 2-phenylethyl, and t-butyl; and trialkylsilane types such as trimethylsilane.

As referred to herein, the term "substituted" means that at least one hydrogen atom is replaced with a non-hydrogen group, provided that normal valencies are maintained and that the substitution results in a stable compound. Ring double bonds, as used herein, are double bonds that are formed between two adjacent ring atoms (e.g., C=C, C=N, or N=N).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative.

When any variable occurs more than one time in any constituent or formula for a compound, its definition at each occurrence is independent of its definition at every other occurrence. Thus, for example, if a group is shown to be substituted with 0-3 R, then said group may optionally be substituted with up to three R groups, and at each occurrence R is selected independently from the definition of R. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent. Combinations of substituents and/or variables are permissible only if such combinations result in stable compounds.

The present invention is intended to include all isotopes of atoms occurring in the present compounds. Isotopes include those atoms having the same atomic number but different mass numbers. By way of general example and without limitation, isotopes of hydrogen include deuterium and tritium. The isotopes of hydrogen can be denoted as $^1$H (hydrogen), $^2$H (deuterium) and $^3$H (tritium). They are also commonly denoted as D for deuterium and T for tritium. In the application, $CD_3$ denotes a methyl group wherein all of the hydrogen atoms are deuterium. Isotopes of carbon include $^{13}$C and $^{14}$C. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington: The Science and Practice of Pharmacy*, 22$^{nd}$ Edition, Allen, L. V. Jr., Ed.; Pharmaceutical Press, London, UK (2012), the disclosure of which is hereby incorporated by reference.

In addition, compounds of formula I may have prodrug forms. Any compound that will be converted in vivo to provide the bioactive agent (i.e., a compound of formula I) is a prodrug within the scope and spirit of the invention. Various forms of prodrugs are well known in the art. For examples of such prodrug derivatives, see:

a) Bundgaard, H., ed., *Design of Prodrugs*, Elsevier (1985), and Widder, K. et al., eds., *Methods in Enzymology*, 112:309-396, Academic Press (1985);

b) Bundgaard, H., Chapter 5, "Design and Application of Prodrugs," *A Textbook of Drug Design and Development*, pp. 113-191, Krosgaard-Larsen, P. et al., eds., Harwood Academic Publishers (1991);

c) Bundgaard, H., *Adv. Drug Deliv. Rev.*, 8:1-38 (1992);

d) Bundgaard, H. et al., *J. Pharm. Sci.*, 77:285 (1988);

e) Kakeya, N. et al., *Chem. Pharm. Bull.*, 32:692 (1984); and f) Rautio, J (Editor). *Prodrugs and Targeted Delivery (Methods and Principles in Medicinal Chemistry)*, Vol 47, Wiley-VCH, 2011.

Compounds containing a carboxy group can form physiologically hydrolyzable esters that serve as prodrugs by being hydrolyzed in the body to yield formula I compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I include $C_{1-6}$alkyl, $C_{1-6}$alkylbenzyl, 4-methoxybenzyl, indanyl, phthalyl, methoxymethyl, $C_{1-6}$ alkanoyloxy-$C_{1-6}$alkyl (e.g., acetoxymethyl, pivaloyloxymethyl or propionyloxymethyl), $C_{1-6}$alkoxycarbonyloxy-$C_{1-6}$alkyl (e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl), and other well known physiologically hydrolyzable esters used, for example, in the penicillin and cephalosporin arts. Such esters may be prepared by conventional techniques known in the art. Preparation of prodrugs is well known in the art and described in, for example, King, F. D., ed., *Medicinal Chemistry: Principles and Practice*, The Royal Society of Chemistry, Cambridge, UK (2$^{nd}$ edition, reproduced, 2006); Testa, B. et al., *Hydrolysis in Drug and Prodrug Metabolism. Chemistry, Biochemistry and Enzymology*, VCHA and Wiley-VCH, Zurich, Switzerland (2003); Wermuth, C. G., ed., *The Practice of Medicinal Chemistry*, 3$^{rd}$ edition, Academic Press, San Diego, Calif. (2008).

The term "solvate" means a physical association of a compound of this invention with one or more solvent molecules, whether organic or inorganic. This physical association includes hydrogen bonding. In certain instances the solvate will be capable of isolation, for example when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. "Solvate" encompasses both solution-phase and isolable solvates. Exemplary solvates include, but are not limited to, hydrates, ethanolates, methanolates, and isopropanolates. Methods of solvation are generally known in the art.

As used herein, the term "patient" refers to organisms to be treated by the methods of the present invention. Such organisms preferably include, but are not limited to, mammals (e.g., murines, simians, equines, bovines, porcines, canines, felines, and the like), and most preferably refers to humans.

As used herein, the term "effective amount" means that amount of a drug or pharmaceutical agent, i.e., a compound of the invention, that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. An effective amount can be administered in one or more administrations, applications or dosages and is not intended to be limited to a particular formulation or administration route. The term also includes within its scope amounts effective to enhance normal physiological function As used herein, the term "treating" includes any effect, e.g., lessening, reducing, modulating, ameliorating or eliminating, that results in the improvement of the condition, disease, disorder, and the like, or ameliorating a symptom thereof.

As used herein, the term "pharmaceutical composition" refers to the combination of an active agent with a carrier, inert or active, making the composition especially suitable for diagnostic or therapeutic use in vivo or ex vivo.

Examples of bases include, but are not limited to, alkali metals (e.g., sodium) hydroxides, alkaline earth metals (e.g., magnesium), hydroxides, ammonia, and compounds of formula $NW_4^+$, wherein W is $C_{1-4}$ alkyl, and the like.

For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

Methods of Preparation

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated by reference in their entirety.

The compounds of this invention may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and work up procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents that are compatible with the reaction conditions will be readily apparent to one skilled in the art and alternate methods must then be used. This will sometimes require a judgment to modify the order of the synthetic steps or to select one particular process scheme over another in order to obtain a desired compound of the invention. It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene and Wuts (*Protective Groups In Organic Synthesis*, Third Edition, Wiley and Sons, 1999).

Compounds of Formula (I) may be prepared by reference to the methods illustrated in the following Schemes. As shown therein the end product is a compound having the same structural formula as Formula (I). It will be understood that any compound of Formula (I) may be produced by the schemes by the suitable selection of reagents with appropriate substitution. Solvents, temperatures, pressures, and other reaction conditions may readily be selected by one of ordinary skill in the art. Starting materials are commercially available or readily prepared by one of ordinary skill in the art. Constituents of compounds are as defined herein or elsewhere in the specification.

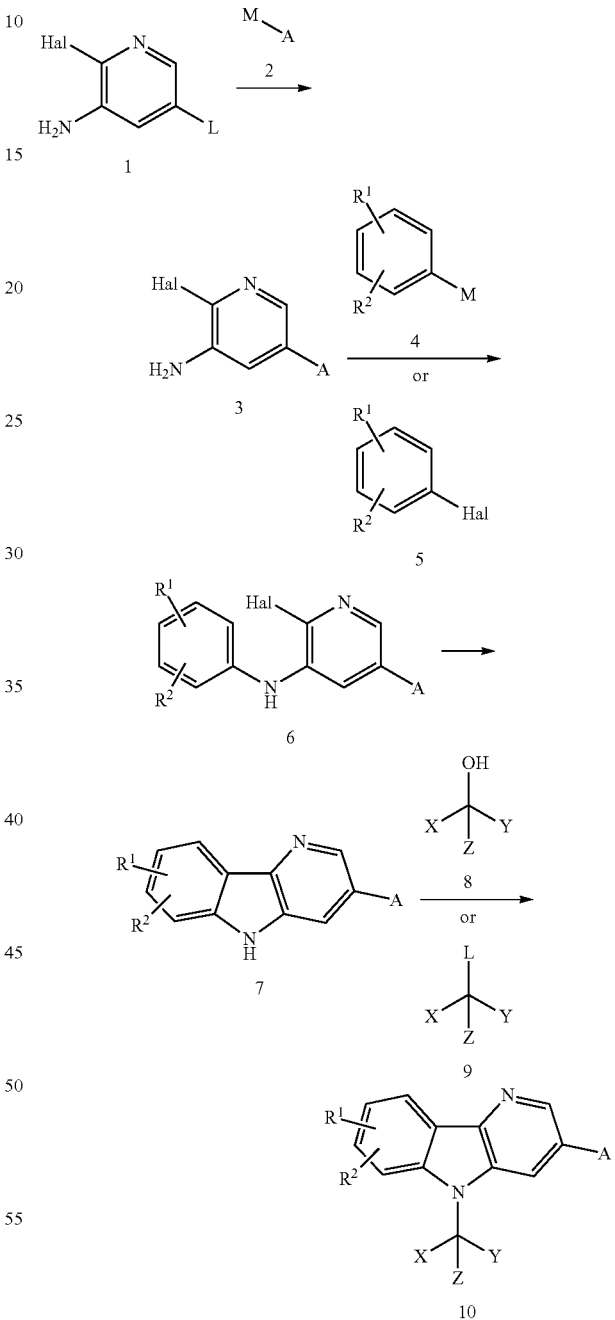

General routes to compounds described in the invention are illustrated in Schemes 1-13, where the $R^1$, $R^2$, X, Y, Z and A substituents are defined previously in the text or a functional group that can be converted to the desired final substituent. The substituent Hal is a halide. L is a leaving group such as a halide or OH that can be easily converted to a leaving group such as a triflate. As shown in Scheme 1, a general procedure for the preparation of compounds of the invention involves starting with the substituted aminopyridine 1. Coupling of 1 with the aromatic heterocycle A (2, where M is a suitable coupling partner, such as boronic acid, boronic ester or stannane) using a suitable catalyst can yield functionalized aminopyridines 3. For example, 3 could arise from a Suzuki coupling reaction between 5-bromo-2-chloropyridin-3-amine and a heteroaromatic boronic acid using Pd(dppf)Cl$_2$ as a catalyst. Subsequent coupling to give the functionalized aniline 6 can be achieved using a variety of conditions known in the literature. For example, aminopyridine 3 can undergo copper-mediated coupling with a suitably substituted arene 4 (where M is a boronic acid, boronic ester or stannane) to give aniline 6. Alternatively, 6 could arise from a Buchwald N-arylation reaction of 3 with an aromatic halide 5 (where Hal is a halide). Ring closure to generate carboline 7 can be achieved using a Pd catalyst in the presence of a base, such as sodium acetate. In the final step, the carboline nitrogen can be substituted under Mitsunobu conditions using triphenylphosphine and diisopropyl azodicarboxylate (DIAD) with an alkylating agent 8. Alternatively, functionalized carboline 10 can be generated from a displacement reaction between the carboline 7 and an alkylating agent 9, where L is a leaving group such as a halide, mesylate or triflate, in the presence of a base, such as potassium carbonate. In cases where 10 is a racemate, chiral separation can provide enantiomerically pure products. Further derivatization of R$^1$ can provide additional compounds of the invention. For example, when R$^1$ is an ester, addition of a Grignard reagent or alkyl lithium can generate tertiary alcohols. The same R$^1$ ester could instead be hydrolyzed using, for example, sodium hydroxide to give a carboxylic acid (R$^1$=CO$_2$H) as the final substituent.

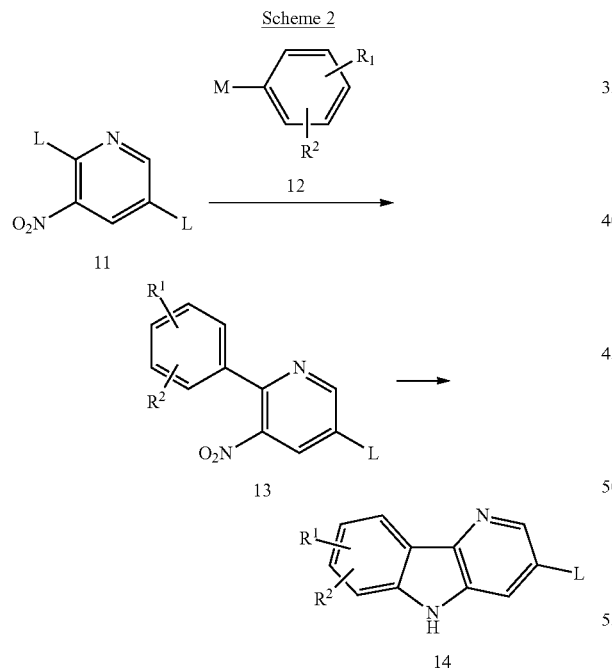

An alternative synthesis of the carbolines 7 and 10 starts from nitropyridine 11 as shown in Schemes 2 to 4. A Suzuki reaction between, for example, 2,5-dibromo-3-nitropyridine and an appropriately substituted arene (12, where M is a suitable coupling partner, such as boronic acid or boronic ester) can give the functionalized pyridine 13. Reductive cyclization mediated by a phosphine reagent, such as 1,2-bis(diphenylphosphino)ethane (dppe), can provide carboline 14. Coupling of 14 with the aromatic heterocycle A (2, where M is a suitable coupling partner, such as boronic acid, boronic ester or stannane) using a suitable catalyst then generates carboline 7 as shown in Scheme 3.

Alternately, the carboline nitrogen of intermediate 14 can be first substituted under Mitsunobu conditions with an alkylating agent 8 or with alkylating agent 9, where L is a leaving group such as a halide, mesylate or triflate, in the presence of a base, such as potassium carbonate as previously described in Scheme 1 to give intermediate 15. Then coupling of 15 with the aromatic heterocycle A (2, where M is a suitable coupling partner, such as boronic acid, boronic ester or stannane) using a suitable catalyst then generates the final carboline 10 as shown in Scheme 4.

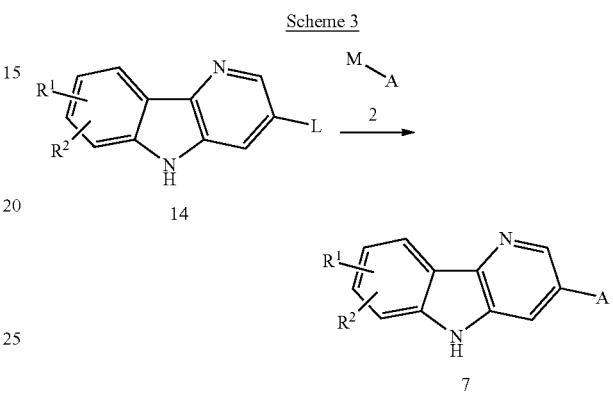

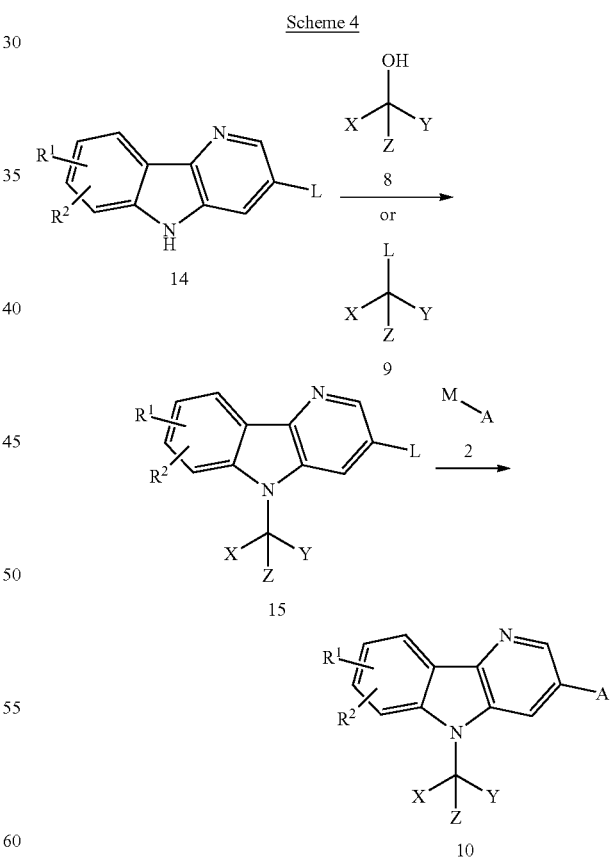

An alternate synthesis of carbolines 10 can be achieved as outlined in Scheme 5. The leaving group, L, of 15 (prepared as in Scheme 4) can be converted to a suitable coupling partner, M (preferably a boronic ester or boronic acid) by the action of a palladium catalyst, affording 16. Coupling of 16 with the aromatic heterocycle A (17, where L is a suitable leaving group, such as a halogen or triflate) using a suitable catalyst can give carbolines 10.

Scheme 5

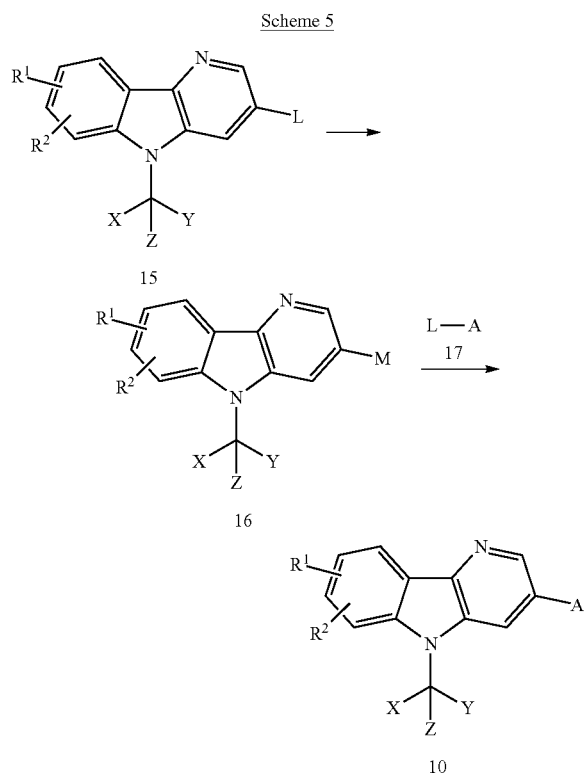

Hydroxymethyl pyrazole derivatives such as 20 can be accessed according to Scheme 6. Intermediate 16 (where M is a suitable coupling partner such as a boronic acid or boronic ester; prepared as in Scheme 5) can be coupled to an appropriately protected triazole 18 by the action of a suitable catalyst. Triazole 18 is available in one step from a copper-mediated cycloaddition reaction of (azidomethyl)trimethyl-silane with a protected propargyl alcohol. Intermediate 19 can then be deprotected using a variety of conditions. For example, when PG is tert-butyldimethylsilyl, treatment with tetrabutylammonium fluoride can give the final compound 20. Further derivatization of the hydroxyl group (for example: alkylation, conversion to a leaving group and displacement, oxidation to either an aldehyde or carboxylic acid and subsequent elaboration) can provide additional compounds of the invention by application of methods which will be readily apparent to one of ordinary skill in the art.

Scheme 6

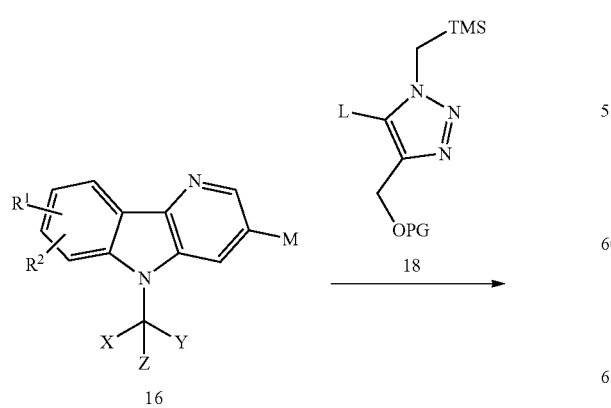

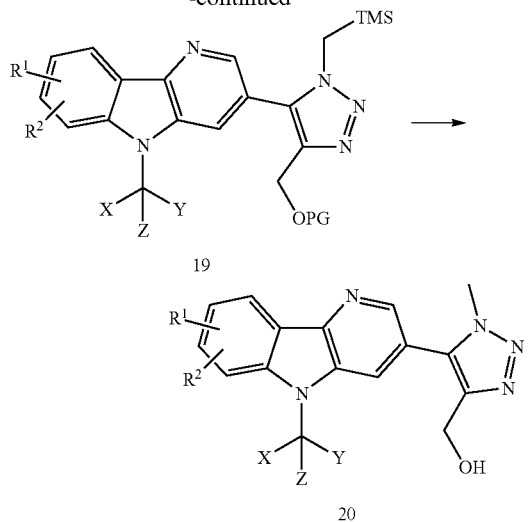

Alternately, intermediate 15 (prepared as in Scheme 4) can be directly coupled with a suitable aromatic heterocycle, 21, via palladium-mediated C—H activation to afford compounds 10. This is illustrated in Scheme 7.

Scheme 7

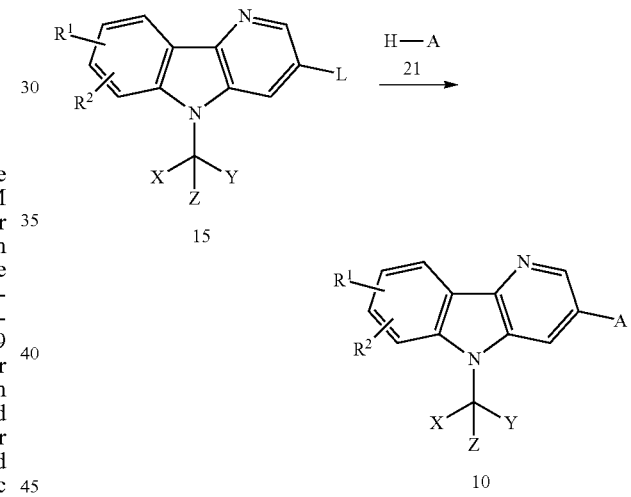

Alternately, aromatic heterocycle 21 can be deprotonated with a strong base such as n-BuLi and transmetallated to zinc, tin, or boron to afford compounds 2. Compounds 2 can then be coupled in a Negishi, Stille, or Suzuki coupling to intermediate 15 (prepared as in Scheme 4) by the action of a suitable palladium catalyst to afford compounds 10. This is illustrated in Scheme 8.

Scheme 8

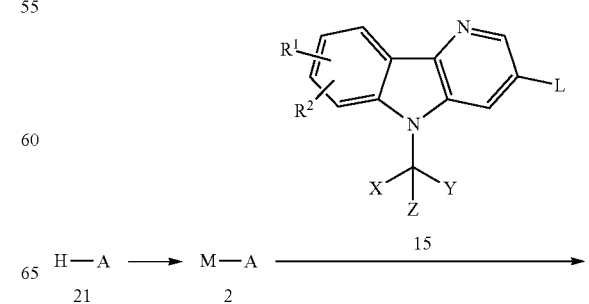

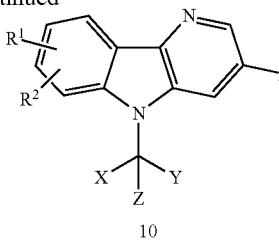

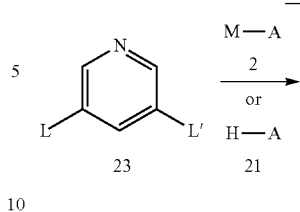

Scheme 10

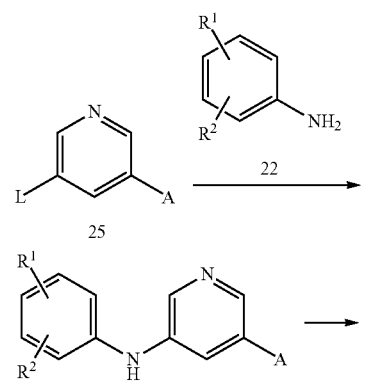

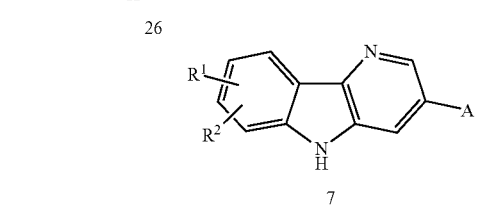

An alternate synthesis of carbolines 14 can be achieved as outlined in Scheme 9. Aniline 22 can be coupled to pyridine 23, where L and L' are two leaving groups such as halide or triflate, using a Buchwald N-arylation reaction to give intermediate 24. For example, 24 could arise from a Buchwald N-arylation reaction between 3,5-dibromopyridine and a suitable aniline. Oxidative ring closure, using an appropriate catalyst such as Pd(OAc)$_2$ in an acidic media such as trifluoroacetic acid, can afford carbolines 14. This is illustrated in Scheme 9.

Scheme 9

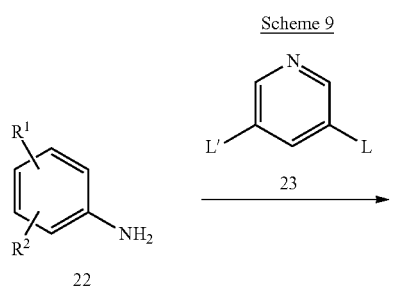

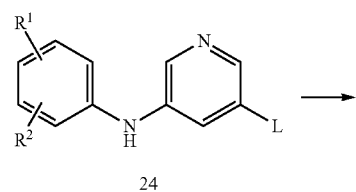

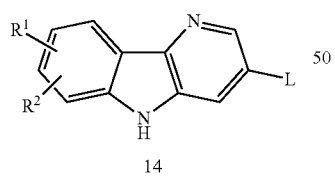

Pyridines 23 (where L and L' are suitable leaving groups such as halides or triflates) can also be coupled to aromatic heterocycles 2 (where M is a suitable coupling partner such as a boronic ester, boronic acid, or stannane) or 21 by methods analogous to those illustrated in Schemes 1, 3, 4, 7, and 8. Pyridines 25 can be coupled to anilines 22, using a Buchwald N-arylation reaction to give intermediate 26. Oxidative ring closure, using an appropriate catalyst such as Pd(OAc)$_2$ in an acidic media such as trifluoroacetic acid, can afford carbolines 7. This is illustrated in Scheme 10.

Alkoxy-substituted triazoles 32 can be prepared as illustrated in Scheme 11. Aldehyde 27 can be converted to acetal 29 by treatment with alcohol 28 (where Alk is a C$_1$-C$_6$ alkyl or C$_3$-C$_6$ cycloalkyl optionally substituted with deuterium) in the presence of acid or a dehydrating agent such as CaCl$_2$. Acetal 29 can be converted to alkoxy-substituted alkynes 30 by treatment with a strong base such as lithium diethylamide or sodium amide. Compounds 30 can be converted to triazoles 32 through a copper-catalyzed 3+2 cycloaddition reaction with azide 31. Triazoles 32 can be directly coupled to carbolines as illustrated in Scheme 7. In most cases, said coupling results in loss of the trimethylsilyl group. In cases where the trimethylsilyl group is not lost, it can be removed by treatment with tetrabutylammonium fluoride.

Scheme 11

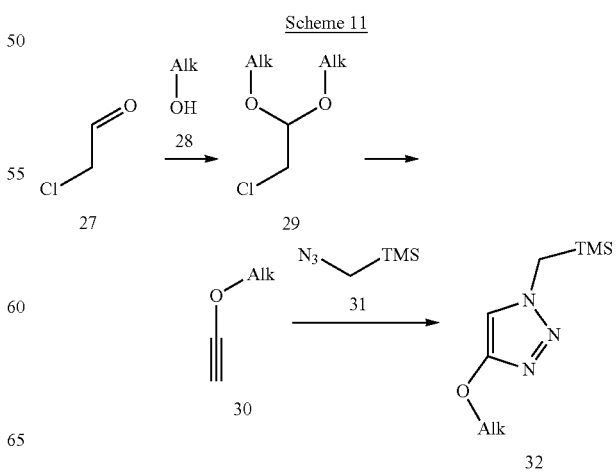

Alkyl-substituted triazoles 39 can be prepared as illustrated in Scheme 12. Acetylene 33 can be alkylated with 34 (where Alk is a $C_1$-$C_6$ alkyl or $C_3$-$C_6$ cycloalkyl optionally substituted with deuterium and where L is an appropriate leaving group such as iodide, bromide, chloride, or sulfonate) by the action of a strong base such as n-BuLi. Alkyne 35 can be converted to triazoles 36 through a copper-catalyzed 3+2 cycloaddition reaction with 31. Triazoles 36 can be directly coupled to carbolines as illustrated in Scheme 7. Alternately, the trimethylsilyl group of 36 can be removed directly by the action of tetrabutyl ammonium fluoride to give N-methyl-triazole 37. Deprotonation of 37 with a strong base such as n-BuLi, followed by reaction with an appropriate electrophile 38 (where L is a leaving group such as a halide or alkoxide and M is an appropriate group to facilitate metal-mediated couplings such as tributyltin or a boronic ester; e.g. M-L=$Bu_3SnCl$ or $B(OMe)_3$) can afford triazoles 39 which can readily be coupled as illustrated in Schemes 1, 3, 4, 8, and 10.

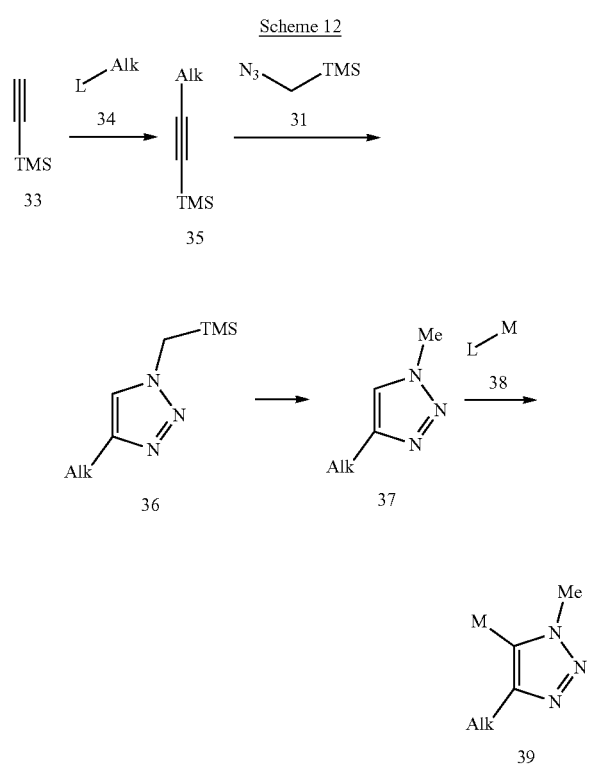

One can vary the substituents of the triazole as shown in Scheme 13. The leaving group of 34 (where Alk is a $C_1$-$C_6$ alkyl or $C_3$-$C_6$ cycloalkyl optionally substituted with deuterium and where L is an appropriate leaving group such as iodide, bromide, chloride, or sulfonate) can be displaced by treatment with sodium azide to afford 40. Alkynes 41 or 42 can be coupled to azides 40 to give triazoles 43 through a copper-catalyzed 3+2 cycoaddition reaction. Triazoles 43 can be directly coupled to carbolines as illustrated in Scheme 7. Alternately, deprotonation of 43 with a strong base such as n-BuLi, followed by reaction with an appropriate electrophile 38 (where L is a leaving group such as a halide or alkoxide and M is an appropriate group to facilitate metal-mediated couplings such as tributyltin or a boronic ester; e.g. M-L=$Bu_3SnCl$ or $B(OMe)_3$) can afford triazoles 44 which can readily be coupled as illustrated in Schemes 1, 3, 4, 8, and 10.

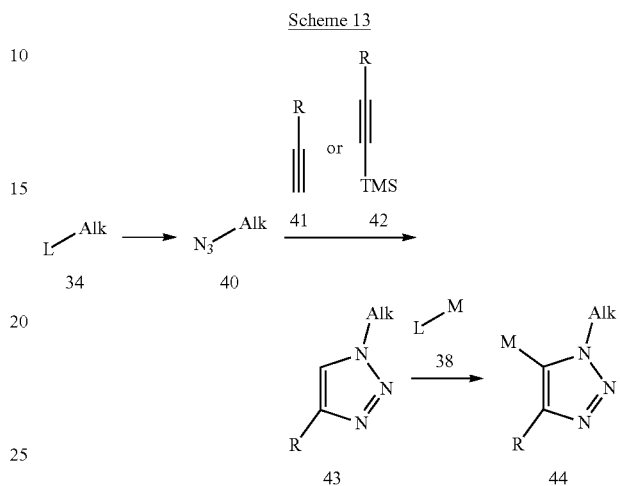

In some cases, it may be advantageous to install the $R^1$ substituent later in the synthetic sequence. An alternative synthesis of carbolines 10 is depicted in Scheme 14. Installation of a leaving group, L, can be accomplished by treatment of 45 with a suitable halogenating reagent (such as NBS, NCS, Selectfluor®, or elemental bromine) to give 46. Carboline 46 can be alkylated using conditions previously described in Scheme 1 to give intermediate 47. The leaving group, L, of 47 can be exchanged with a variety of $R^1$ substituents using methods which will be obvious to one of ordinary skill in the art to give 10. For instance, when L=Br or Cl, 47 can undergo a Stille or Suzuki coupling in the presence of a a palladium catalyst and a boronic acid, boronic ester, or stannane to afford 10. Alternately, in cases where $R^1$ is attached through nitrogen, a Buchwald N-arylation reaction can afford additional compounds of the invention. In some cases, especially where $R^2$ is an electron-withdrawing substituent, $R^1$ substituents linked through nitrogen can be installed using an $S_NAr$ reaction by deprotonation of the heterocycle (to give 48) with a suitable base such as potassium t-butoxide at elevated temperatures to give 10. Further derivatization of $R^1$ and $R^2$ can provide additional compounds of the invention by application of methods which will be readily apparent to one of ordinary skill in the art.

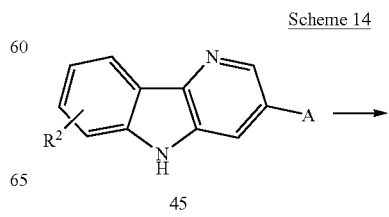

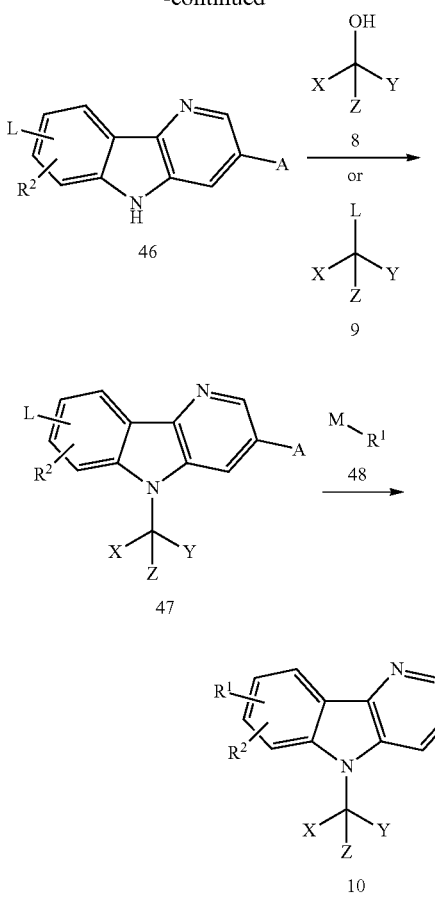

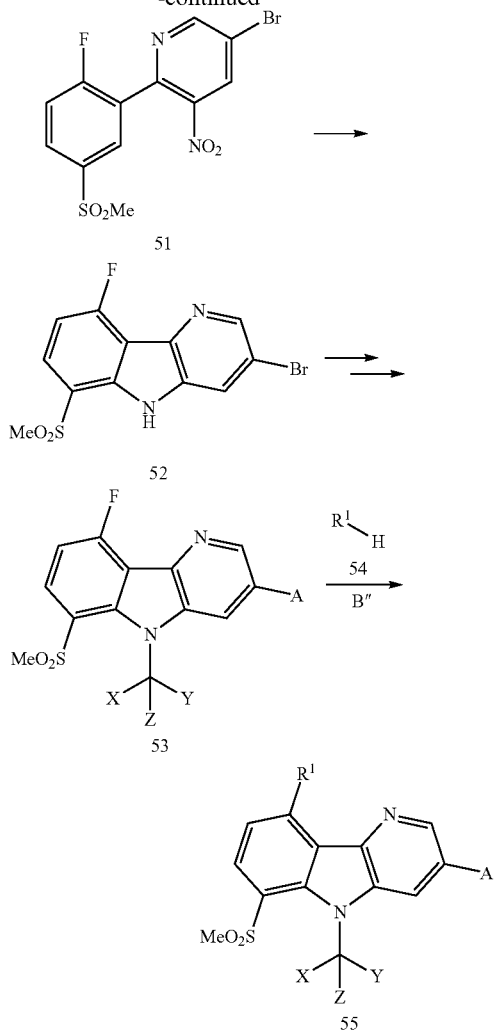

In some cases, it may be advantageous to install the leaving group, L, earlier in the synthesis. A specific example of this is depicted in Scheme 15. For instance, boronate ester 49 can be coupled to dibromide 50 in a Suzuki coupling reaction to furnish 51. The ring closure to carboline 52 can be accomplished using DPPE at elevated temperatures. 52 can be transformed to 53 by methods previously described herein. N-linked $R^1$ substituents can be installed using an $S_NAr$ reaction by deprotonation of heterocycle 54 with a suitable base (B—) such as potassium t-butoxide at elevated temperatures to give 55. Further derivatization of $R^1$ and $R^2$ can provide additional compounds of the invention by application of methods which will be readily apparent to one of ordinary skill in the art.

Scheme 15

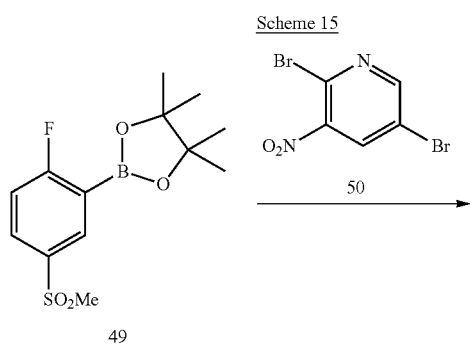

EXAMPLES

The invention is further defined in the following Examples. It should be understood that the Examples are given by way of illustration only. From the above discussion and the Examples, one skilled in the art can ascertain the essential characteristics of the invention, and without departing from the spirit and scope thereof, can make various changes and modifications to adapt the invention to various uses and conditions. As a result, the invention is not limited by the illustrative examples set forth herein below, but rather is defined by the claims appended hereto.

ABBREVIATIONS

| | |
|---|---|
| MeCN | acetonitrile |
| AcOH | acetic acid |
| AlMe₃ | trimethyl aluminum |
| Aq | aqueous |
| Bn | benzyl |
| Boc | tert-butoxycarbonyl |
| Boc₂O | di-tert-butyl dicarbonate |
| CBz | benzyloxycarbonyl |

-continued

| | |
|---|---|
| DCC | 1,3-dicyclohexylcarbodiimide |
| DCM | dichloromethane |
| DDQ | 2,3-dichloro-5,6-dicyano-1,4-benzoquinone |
| DIAD | diisopropyl azodicarboxylate |
| DIEA | diisopropylethylamine |
| DMAP | 4-dimethylaminopyridine |
| DMA | dimethylacetamide |
| DME | dimethoxyethane |
| DMF | dimethylformamide |
| DMSO | dimethyl sulfoxide |
| EDC | 1-(3-dimethylaminopropyl)-3-ethylcarbodiimide hydrochloride |
| $Et_2AlCl$ | diethyl aluminum chloride |
| $Et_3N$ | triethyl amine |
| $Et_2O$ | diethyl ether |
| EtOH | ethanol |
| EtOAc | ethyl acetate |
| equiv. | equivalent(s) |
| g | gram(s) |
| h or hr | hour(s) |
| HOBt | hydroxybenzotriazole |
| HPLC | high pressure liquid chromatography |
| iPrOH | isopropyl alcohol |
| KOtBu | potassium tert-butoxide |
| LCMS | Liquid Chromatography-Mass Spectroscopy |
| LDA | lithium diisopropylamide |
| LiHMDS | lithium bis(trimethylsilyl)amide |
| Me | methyl |
| MeI | methyl iodide |
| MeOH | methanol |
| min | minute(s) |
| mL | milliliter(s) |
| mmol | millimole |
| MTBE | methyl t-butyl ether |
| NaHMDS | sodium bis(trimethylsilyl)amide |
| n-BuLi | n-butyl lithium |
| $NH_4OAc$ | ammonium acetate |
| NMP | N-methylpyrrolidinone |
| $Pd(OAc)_2$ | palladium acetate |
| $Pd(dppf)Cl_2$ | [1,1'-bis(diphenylphosphino)ferrocene]dichloropalladium(II) |
| RT or Rt or $T_R$ | retention time |
| sat | saturated |
| SFC | Supercritical fluid chromatography |
| t-Bu | tertiary butyl |
| t-BuLi | t-butyl lithium |
| t-BuOH | tertiary butyl alcohol |
| t-BuOMe | tert-butyl methyl ether |
| TBTU | O-(1H-benzotriazol-1-yl)-N,N,N',N'-tetramethyluronium tetrafluoroborate |
| TCTU | O-(1H-6-chlorobenzotriazol-1-yl)-N,N,N',N'-tetramethyluronium tetrafluoroborate |
| TEA | triethylamine |
| tetrakis | tetrakis(triphenylphosphine) palladium (0) |
| TFA | trifluoroacetic acid |
| $Tf_2O$ | trifluoromethylsulfonic anhydride |
| THF | tetrahydrofuran |
| UPLC | Ultra Performance Liquid Chromatography |

HPLC Methods

LC/MS Method 3: Waters BEH C18, 2.0×50 mm, 1.7-μm particles; Mobile Phase A: 5:95 ACN:water with 10 mM $NH_4OAc$; Mobile Phase B: 95:5 ACN:water with 10 mM $NH_4OAc$; Temperature: 50° C.; Gradient: 0% B, 0-100% B over 3 min, then a 0.5-min hold at 100% B; Flow: 1 mL/min; Detection: UV at 220 nm.

LC/MS Method 4: Waters BEH C18, 2.0×50 mm, 1.7-μm particles; Mobile Phase A: 5:95 MeOH:water with 10 mM $NH_4OAc$; Mobile Phase B: 95:5 MeOH:water with 10 mM $NH_4OAc$; Temperature: 50° C.; Gradient: 0%-100% B over 3 min, then a 0.5-min hold at 100% B; Flow: 0.5 mL/min; Detection: UV at 220 nm.

LC/MS Method 5: Acquity UPLC BEH C18, 1.7 μm particles; Mobile Phase A: 100% water with 0.05% TFA; Mobile Phase B: 100% acetonitrile with 0.05% TFA; Temperature 50° C.; Gradient 2% B to 98% B over 1 min, 98% B for 0.6 min, then 98% A for 0.6 min; Detection 220 nm.

LC/MS Method 6: Phenomenex Luna C18, 30×2 mm, 3-μm particles; Mobile Phase A: 5:95 ACN:water with 10 mM $NH_4OAc$; Mobile Phase B: 95:5 ACN:water with 10 mM $NH_4OAc$; Temperature: 40° C.; Gradient: 0% B, 0-100% B over 2 min, then a 1-min hold at 100% B; Flow: 1 mL/min; Detection: UV at 220 nm.

Preparative HPLC Method 1: XBridge C18, 19×200 mm, 5-μm particles; Mobile Phase A: 5:95 ACN: water with 10 mM $NH_4OAc$; Mobile Phase B: 95:5 ACN: water with 10 mM $NH_4OAc$; Gradient: 30-70% B over 20 min, then a 5-min hold at 100% B; Flow: 20 mL/min.

Preparative HPLC Method 2: XBridge C18, 19×200 mm, 5-μm particles; Mobile Phase A: 5:95 MeOH: water with 10 mM $NH_4OAc$; Mobile Phase B: 95:5 MeOH: water with 10 mM $NH_4OAc$; Gradient: 40-80% B over 20 min, then a 5-min hold at 100% B; Flow: 20 mL/min.

Preparative HPLC Method 3: XBridge C18, 19×200 mm, 5-μm particles; Mobile Phase A: 5:95 ACN: water with 0.1% trifluoroacetic acid; Mobile Phase B: 95:5 ACN: water with 0.1% trifluoroacetic acid; Gradient: 15-55% B over 20 min, then a 5-min hold at 100% B; Flow: 20 mL/min.

Example 1

1,4-Dimethyl-5-[7-(1-methyl-1H-pyrazol-5-yl)-5-[(S)-oxan-4-yl(phenyl)methyl]-5H-pyrido[3,2-b]indol-3-yl]-1H-1,2,3-triazole

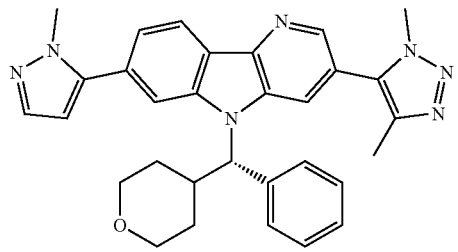 [SMILES: Cc1nnn(C)c1-c1cnc2c3ccc(-c4ccnn4C)cc3n([C@H](c3ccccc3)C3CCOCC3)c2c1]

Step 1: 3-(1,4-Dimethyl-1H-1,2,3-triazol-5-yl)-7-(1-methyl-1H-pyrazol-5-yl)-5H-pyrido[3,2-b]indole A solution of 5-{7-chloro-5H-pyrido[3,2-b]indol-3-yl}-1,4-dimethyl-1H-1,2,3-triazole, 1-methyl-5-(4,4,5,5-tetramethyl-1,3,2-dioxaborolan-2-yl)-1H-pyrazole (52.6 mg, 0.253 mmol), $Pd_2dba_3$ (30.9 mg, 0.0340 mmol), tricyclohexylphosphine (20% solution in toluene, 105 μL, 0.0670 mmol), and cesium carbonate (110 mg, 0.337 mmol) in dioxane (2 mL) was degassed by bubbling through argon while sonicating for several min, then the vial was sealed and heated to 100° C., and held at that temperature overnight. The reaction was cooled, filtered, and concentrated. This material was purified on $SiO_2$ (4 g) eluting with 10 to 30% acetone/DCM to give the title compound (37.4 mg, 62%) as a yellow film. $^1$H NMR (400 MHz, $CDCl_3$) δ 9.62 (br. s, 1H), 8.56 (d, J=1.5 Hz, 1H), 8.48 (d, J=8.3 Hz, 1H), 7.74 (d, J=1.8 Hz, 1H), 7.60 (d, J=1.8 Hz, 1H), 7.58 (d, J=0.5 Hz, 1H), 7.44 (d, J=8.3 Hz, 1H), 6.45 (d, J=1.8 Hz, 1H), 4.05 (s, 3H), 3.99 (s, 3H), 2.41 (s, 3H); LC/MS (344, [M+H]$^+$).

Step 2: 1,4-Dimethyl-5-[7-(1-methyl-1H-pyrazol-5-yl)-5-[(S)-oxan-4-yl(phenyl)methyl]-5H-pyrido[3,2-b]indol-3-yl]-1H-1,2,3-triazole A solution of 3-(1,4-dimethyl-1H-1,2,3-triazol-5-yl)-7-(1-methyl-1H-pyrazol-5-yl)-5H-pyrido[3,2-b]indole (37.4 mg, 0.109 mmol), (R)-phenyl(tetrahydro-2H-pyran-4-yl)methanol (25.1 mg, 0.131 mmol) and triphenylphosphine (42.9 mg, 0.163 mmol) in 1.0 mL THF was cooled in an ice water bath and diisopropylazodicarboxylate (0.0260 mL, 0.136 mmol) in 0.5 mL THF was added dropwise over about 10 min. The cooling bath was removed. The mixture was stirred overnight, concentrated, and purified on $SiO_2$ eluting with 10-50% acetone/DCM. The recovered material was further purified via preparative LC/MS with the following conditions: Column: XBridge C18, 19×200 mm, 5-μm particles; Mobile Phase A: 5:95 ACN: water with 10 mM $NH_4OAc$; Mobile Phase B: 95:5 ACN: water with 10 mM $NH_4OAc$; Gradient: 35-75% B over 20 min, then a 5-min hold at 100% B; Flow: 20 mL/min. Fractions containing the desired product were combined and dried via centrifugal evaporation to give the title compound (8.6 mg, 15%). $^1$H NMR (500 MHz, DMSO-$d_6$) δ 8.59 (s, 1H), 8.33 (d, J=7.7 Hz, 1H), 7.72 (d, J=7.7 Hz, 3H), 7.57 (s, 1H), 7.46 (d, J=7.7 Hz, 1H), 7.34 (t, J=7.3 Hz, 2H), 7.30-7.21 (m, 1H), 6.58 (br. s., 1H), 5.95 (d, J=11.0 Hz, 1H), 4.04 (br. s., 3H), 3.96 (br. s., 3H), 3.92-3.85 (m, 2H), 3.73 (d, J=10.3 Hz, 1H), 3.48 (br. s., 2H), 3.26 (t, J=11.7 Hz, 1H), 2.38-2.23 (m, 3H), 1.72 (d, J=13.2 Hz, 1H), 1.58 (d, J=9.9 Hz, 1H), 1.34 (d, J=12.5 Hz, 1H), 1.00 (d, J=11.4 Hz, 1H). LC/MS (518, [M+H]$^+$).

Example 2

1,4-Dimethyl-5-{5-[(S)-oxan-4-yl(phenyl)methyl]-7-(1,2-oxazol-3-yl)-5H-pyrido[3,2-b]indol-3-yl}-1H-1,2,3-triazole

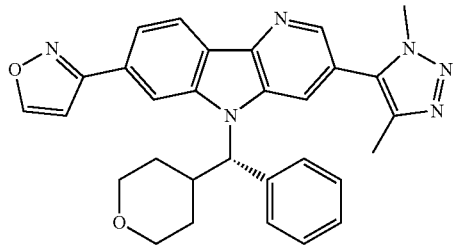 [SMILES: Cc1nnn(C)c1-c1cnc2c3ccc(-c4ccon4)cc3n([C@H](c3ccccc3)C3CCOCC3)c2c1]

Step 1: (E)-N-{[3-(Dimethyl-1H-1,2,3-triazol-5-yl)-5-[(S)-oxan-4-yl(phenyl)methyl]-5H-pyrido[3,2-b]indol-7-yl]methylidene}hydroxylamine To a mixture of 3-(dimethyl-1H-1,2,3-triazol-5-yl)-5-[(S)-oxan-4-yl(phenyl)methyl]-5H-pyrido[3,2-b]indole-7-carbaldehyde (57.0 mg, 0.122 mmol), hydroxylamine hydrochloride (9.4 mg, 0.135 mmol), and sodium carbonate (7.8 mg, 0.0730 mmol) was added MeOH (1.0 mL), and then water (1.0 mL). Upon addition of the water, a mass precipitation occurred, and the mixture would not stir. An additional 1.0 mL methanol was added, which with sonication provided a mostly homogenous solution. This mixture was stirred at room temperature overnight. A small amount (>0.5 mL) of water was added. The white precipitate was collected by filtration, rinsed with water, and dried in vacuo to give 34.0 mg of product as a white powder. The filtrate was extracted twice with ethyl acetate. These organic extracts were washed with brine, dried over $MgSO_4$, filtered, and concentrated under a stream of nitrogen to give additional product (18.0 mg) as a yellow film. The combined material was used without purification. $^1$H NMR (500 MHz, $CD_3OD$) δ 8.81 (s, 1H), 8.25-8.12 (m, 2H), 7.79 (d, J=7.7 Hz, 2H), 7.55 (d, J=8.1 Hz, 1H), 7.37-7.29 (m, 2H), 7.27-7.20 (m, 1H), 5.78 (d, J=8.4 Hz, 1H), 3.94-3.85 (m, 2H), 3.76 (d, J=8.8 Hz, 1H), 3.69 (br. s., 1H), 3.38 (d, J=9.2 Hz, 1H), 3.26 (t, J=11.6 Hz, 1H), 2.46 (s, 3H), 1.57 (s, 6H), 1.52-1.40 (m, 2H), 1.30 (d, J=11.7 Hz, 1H), 1.19 (d, J=11.7 Hz, 1H). LC/MS (481, [M+H]$^+$).

Step 2: 1,4-Dimethyl-5-{5-[(S)-oxan-4-yl(phenyl)methyl]-7-[5-(trimethylsilyl)-1,2-oxazol-3-yl]-5H-pyrido[3,2-b]indol-3-yl}-1H-1,2,3-triazole To a solution/suspension of (E)-N-{[3-(dimethyl-1H-1,2,3-triazol-5-yl)-5-[(S)-oxan-4-yl(phenyl)methyl]-5H-pyrido[3,2-b]indol-7-yl]methylidene}hydroxylamine (15.0 mg, 0.031 mmol) in a couple of drops of chloroform was added triethylamine (4 μL, 0.031 mmol) and trimethylsilylacetylene (9 μL, 0.062 mmol) (both dispensed via microliter pipet and rinsed into the reaction vial with chloroform to a total volume of ca. 0.5-1.0 mL). This mixture was cooled in an ice water bath and bleach (sodium hypochlorite, 0.128 mL, 0.125 mmol) was added dropwise over 2 min. The vial was removed from the cooling bath and stirred overnight. The resulting mixture was diluted with water and chloroform. The organic portion was separated, washed with brine, dried over $MgSO_4$, filtered, and concentrated to give the title compound (16.7 mg, 93%) as a light-yellow film. This material was used without purification. LC/MS (577, [M+H]$^+$).

Step 3: 1,4-Dimethyl-5-{5-[(S)-oxan-4-yl(phenyl)methyl]-7-(1,2-oxazol-3-yl)-5H-pyrido[3,2-b]indol-3-yl}-1H-1,2,3-triazole A mixture of 1,4-dimethyl-5-{5-[(S)-oxan-4-yl(phenyl)methyl]-7-[5-(trimethylsilyl)-1,2-oxazol-3-yl]-5H-pyrido[3,2-b]indol-3-yl}-1H-1,2,3-triazole (16.7 mg, 0.0290 mmol) and cesium fluoride (8.8 mg, 0.0580 mmol) was dissolved in acetonitrile (1.0 mL) and ethanol (0.1 mL) and heated to 80° C. After 20 min, the mixture was cooled to room temperature, concentrated under a stream of nitrogen, taken up in about 1 mL methanol, filtered through a 0.45 m PVDF syringe filter, and purified via preparative LC/MS with the following conditions: Column: XBridge C18, 19×mm, 5-μm particles; Mobile Phase A: 5:95 ACN: water with 10 mM $NH_4OAc$; Mobile Phase B: 95:5 ACN: water with 10 mM $NH_4OAc$; Gradient: 20-60% B over 20 min, then a 5-min hold at 100% B; Flow: 20 mL/min. Fractions containing the desired product were combined and dried via centrifugal evaporation. The material was further purified via preparative LC/MS with the following conditions: Column: XBridge C18, 19×mm, 5-μm particles; Mobile Phase A: 5:95 MeOH: water with 10 mM $NH_4OAc$; Mobile Phase B: 95:5 MeOH: water with 10 mM $NH_4OAc$; Gradient: 40-80% B over 40 min, then a 5-min hold at 100% B; Flow: 20 mL/min. Fractions containing the desired product were combined and dried via centrifugal evaporation to give the title compound (1.9 mg, 13%). $^1$H NMR (500 MHz, DMSO-$d_6$) δ 9.12 (s, 1H), 8.59 (s, 1H), 8.36 (d, J=8.1 Hz, 1H), 7.91 (d, J=8.1 Hz, 1H), 7.72 (d, J=7.3 Hz, 2H), 7.46 (br. s., 1H), 7.38-7.31 (m, 3H), 7.30-7.22 (m, 1H), 5.98 (d, J=11.4 Hz, 1H), 4.02 (s, 3H), 3.95-3.87 (m, 1H), 3.74 (d, J=9.5 Hz, 1H), 3.58-3.44 (m, 2H), 3.35 (d, J=4.8 Hz, 1H), 3.27 (t, J=11.6 Hz, 1H), 2.31 (s, 3H), 1.75 (d, J=14.7 Hz, 1H), 1.66-1.53 (m, 1H), 1.37 (d, J=12.8 Hz, 1H), 1.01 (d, J=11.4 Hz, 1H). LC/MS (505, [M+H]$^+$).

Example 3

(2R,6S)-4-[3-(Dimethyl-1H-1,2,3-triazol-5-yl)-5-[(R)-oxan-4-yl(phenyl)methyl]-5H-pyrido[3,2-b]indol-8-yl]-2,6-dimethylmorpholine

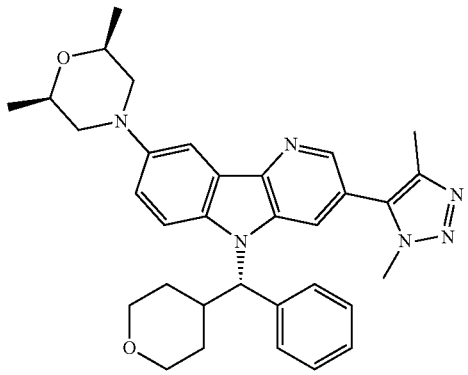 [SMILES: Cc1nnn(C)c1-c1cnc2c3cc(N4C[C@@H](C)O[C@@H](C)C4)ccc3n([C@H](c3ccccc3)C3CCOCC3)c2c1]

Step 1: 3-(1,4-Dimethyl-1H-1,2,3-triazol-5-yl)-5H-pyrido[3,2-b]indole

To a 100 mL round-bottomed flask containing 2-chloro-5-(1,4-dimethyl-1H-1,2,3-triazol-5-yl)pyridin-3-amine (1.00 g, 4.47 mmol), phenylboronic acid (1.09 g, 8.94 mmol), copper (II) acetate (1.22 g, 6.71 mmol), was added pyridine (0.723 mL, 8.94 mmol) and CHCl$_3$ (30 mL) to give a suspension. To this was added 2 g of powdered 4 Å molecular sieves. The atmosphere was exchanged with O$_2$ (g), and the reaction was stirred under an O$_2$ balloon for 16 h. The reaction mixture was diluted with chloroform (100 mL) and washed with ammonium hydroxide (9.29 mL, 71.5 mmol). The organic layer was dried with Na$_2$SO$_4$, filtered, and concentrated. The reaction mixture was purified using ISCO silica gel chromatography (40 g column, gradient from 0% to 100% EtOAc/DCM) to give 2-chloro-5-(1,4-dimethyl-1H-1,2,3-triazol-5-yl)-N-phenylpyridin-3-amine (0.695 g).

2-Chloro-5-(1,4-dimethyl-1H-1,2,3-triazol-5-yl)-N-phenylpyridin-3-amine was dissolved in DMA (5 mL) in a 25 mL round bottom flask. To this was added sodium acetate trihydrate (656 mg, 4.82 mmol) and bis(triphenylphosphine)palladium(II) chloride (111 mg, 0.157 mmol), then the suspension was heated to 180° C. for 30 min. The reaction was cooled, diluted with chloroform, filtered, and concentrated under reduced pressure. The reaction mixture was purified using ISCO silica gel chromatography (40 g column, gradient from 0% to 8% MeOH/DCM) to give the title compound (0.345 g, 67%). $^1$H NMR (400 MHz, DMSO-d$_6$) δ 11.65 (s, 1H), 8.52 (d, J=1.8 Hz, 1H), 8.25 (d, J=7.7 Hz, 1H), 8.02 (d, J=1.8 Hz, 1H), 7.65-7.61 (m, 1H), 7.60-7.56 (m, 1H), 7.31 (ddd, J=7.9, 6.9, 1.1 Hz, 1H), 4.01 (s, 3H), 2.30 (s, 3H). LCMS (M+H)=264; HPLC RT=0.88 min (Column: Waters Acquity BEH C18 2.0×50 mm; Mobile Phase A: 10:90 ACN:water with 0.1% TFA; Mobile Phase B: 90:10 ACN:water with 0.1% TFA; Temperature: 40° C.; Gradient: 0-100% B over 1.5 min; Flow: 1 mL/min).

Step 2: 8-Bromo-3-(1,4-dimethyl-1H-1,2,3-triazol-5-yl)-5H-pyrido[3,2-b]indole

To a 50 mL round-bottomed flask containing 3-(1,4-dimethyl-1H-1,2,3-triazol-5-yl)-5H-pyrido[3,2-b]indole (295 mg, 1.12 mmol) was added acetonitrile (5 mL) to give a solution. The reaction mixture was cooled to 0° C., and NBS (299 mg, 1.68 mmol) was added slowly over 5 min. After 90 min, NBS (299 mg, 1.68 mmol) was added. After 30 min, the reaction mixture was concentrated and dried under high vacuum. The reaction mixture was purified using ISCO silica gel chromatography (40 g column, gradient from 0% to 15% MeOH/DCM) to give the title compound (0.222 g, 58%). $^1$H NMR (400 MHz, DMSO-d$_6$) δ 11.85 (s, 1H), 8.57 (d, J=1.8 Hz, 1H), 8.36 (d, J=1.8 Hz, 1H), 8.08 (d, J=1.8 Hz, 1H), 7.73-7.67 (m, 1H), 7.64-7.57 (m, 1H), 2.57 (s, 3H), 2.30 (s, 3H). LCMS (M+H)=342; HPLC RT=1.12 min (Column: Waters Acquity BEH C18 2.0×50 mm; Mobile Phase A: 10:90 ACN:water with 0.1% TFA; Mobile Phase B: 90:10 ACN:water with 0.1% TFA; Temperature: 40° C.; Gradient: 0-100% B over 1.5 min; Flow: 1 mL/min).

Step 3: (S)-8-Bromo-3-(1,4-dimethyl-1H-1,2,3-triazol-5-yl)-5-(phenyl(tetrahydro-2H-pyran-4-yl)methyl)-5H-pyrido[3,2-b]indole Following a procedure analogous to that described for methyl 3-(3,5-dimethylisoxazol-4-yl)-5-(phenyl(tetrahydro-2H-pyran-4-yl)methyl)-5H-pyrido[3,2-b]indole-7-carboxylate, 8-bromo-3-(1,4-dimethyl-1H-1,2,3-triazol-5-yl)-5H-pyrido[3,2-b]indole (1.00 g, 3.28 mmol) and phenyl(tetrahydro-2H-pyran-4-yl)methanol (0.222 g, 0.649 mmol) were converted to the title compound (0.150 mg, 45%). $^1$H NMR (400 MHz, DMSO-d$_6$) δ 8.59 (d, J=1.8 Hz, 1H), 8.35 (d, J=2.0 Hz, 1H), 8.15 (dd, J=3.4, 1.9 Hz, 1H), 7.80-7.72 (m, 1H), 7.70-7.65 (m, 2H), 7.64-7.58 (m, 1H), 7.37-7.30 (m, 2H), 7.30-7.23 (m, 1H), 5.84 (d, J=11.2 Hz, 1H), 3.93-3.82 (m, 2H), 3.73 (dd, J=11.3, 2.5 Hz, 1H), 3.51-3.37 (m, 2H), 3.31 (s, 3H), 3.29-3.22 (m, 1H), 2.33-2.28 (m, 4H), 1.75-1.63 (m, 2H). LCMS (M+H)=516; HPLC RT=1.31 min (Column: Waters Acquity BEH C18 2.0×50 mm; Mobile Phase A: 10:90 ACN:water with 0.1% TFA; Mobile Phase B: 90:10 ACN:water with 0.1% TFA; Temperature: 40° C.; Gradient: 0-100% B over 1.5 min; Flow: 1 mL/min).

Step 4: (2R,6S)-4-[3-(Dimethyl-1H-1,2,3-triazol-5-yl)-5-[(S)-oxan-4-yl(phenyl)methyl]-5H-pyrido[3,2-b]indol-8-yl]-2,6-dimethylmorpholine Following a procedure analogous to that described for methyl 3-{[(2,4-dimethoxyphenyl)methyl]amino}-5-[(S)-oxan-4-yl(phenyl)methyl]-5H-pyrido[3,2-b]indole-7-carboxylate, using (S)-8-bromo-3-(1,4-dimethyl-1H-1,2,3-triazol-5-yl)-5-(phenyl(tetrahydro-2H-pyran-4-yl)methyl)-5H-pyrido[3,2-b]indole (25.0 mg, 0.0500 mmol) and (2R,6S)-2,6-dimethylmorpholine (19.5 mg, 0.170 mmol) were converted to the title compound (5.9 mg, 22%). The crude material was purified via preparative LC/MS with the following conditions: Column: XBridge C18, 19×200 mm, 5-μm particles; Mobile Phase A: 5:95 ACN: water with 10 mM NH$_4$OAc; Mobile Phase B: 95:5 ACN: water with 10 mM NH$_4$OAc; Gradient: 5-100% B over 20 min, then a 0-min hold at 100% B; Flow: 20 mL/min. Fractions containing the desired product were combined and dried via centrifugal evaporation. $^1$H NMR (500 MHz, DMSO-$d_6$) δ 8.47 (s, 1H), 8.43 (br. s., 1H), 8.02 (br. s., 1H), 7.96 (s, 1H), 7.71-7.61 (m, 3H), 7.40 (d, J=7.7 Hz, 1H), 7.35-7.29 (m, 2H), 7.28-7.19 (m, 1H), 5.74 (d, J=11.1 Hz, 1H), 4.02 (s, 3H), 3.94-3.85 (m, 1H), 3.82-3.71 (m, 2H), 3.61 (d, J=11.4 Hz, 1H), 2.90 (s, 3H), 2.74 (s, 3H), 2.36-2.30 (m, 3H), 1.66 (d, J=13.5 Hz, 1H), 1.59-1.46 (m, 1H), 1.30 (d, J=8.8 Hz, 1H), 1.20 (d, J=6.1 Hz, 6H), 1.04 (d, J=13.5 Hz, 1H). LCMS (M+H)=551; HPLC RT=1.09 min (Column: Waters Acquity BEH C18 2.0×50 mm; Mobile Phase A: 10:90 ACN:water with 0.1% TFA; Mobile Phase B: 90:10 ACN:water with 0.1% TFA; Temperature: 40° C.; Gradient: 0-100% B over 1.5 min; Flow: 1 mL/min).

Example 4

4-[3-(Dimethyl-1H-1,2,3-triazol-5-yl)-5-[(S)-oxan-4-yl(phenyl)methyl]-5H-pyrido[3,2-b]indol-8-yl]piperidine

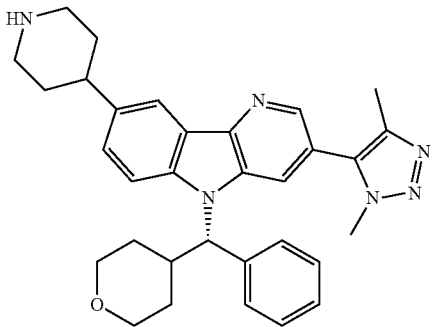 [SMILES: Cc1nnn(C)c1-c1cnc2c3cc(C4CCNCC4)ccc3n([C@H](c3ccccc3)C3CCOCC3)c2c1]

Step 1: tert-Butyl 4-[3-(dimethyl-1H-1,2,3-triazol-5-yl)-5-[(S)-oxan-4-yl(phenyl)methyl]-5H-pyrido[3,2-b]indol-8-yl]piperidine-1-carboxylate To a 100 mL round-bottomed flask containing tert-butyl 4-[3-(dimethyl-1H-1,2,3-triazol-5-yl)-5-[(S)-oxan-4-yl(phenyl)methyl]-5H-pyrido-[3,2-b]indol-8-yl]-1,2,3,6-tetrahydropyridine-1-carboxylate (95.0 mg, 0.154 mmol) and Pd/C (163 mg, 0.154 mmol) was added ethyl acetate (20 mL) to give a suspension. The mixture was purged 3 times with vacuum and nitrogen, purged 3 times with vacuum and hydrogen, and stirred 3 days under hydrogen. The reaction mixture was diluted with 100 mL ethyl acetate, filtered through Celite and concentrated under reduced pressure. The reaction mixture was purified using ISCO silica gel chromatography (24 g column, gradient from 0% to 100% EtOAc/DCM) to give the title compound (0.070 g, 73%). $^1$H NMR (500 MHz, DMSO-$d_6$) δ 8.53 (s, 1H), 8.06 (s, 2H), 7.96 (s, 1H), 7.67 (d, J=7.4 Hz, 2H), 7.53 (d, J=7.7 Hz, 1H), 7.36-7.29 (m, 2H), 7.27-7.18 (m, 1H), 5.79 (d, J=11.4 Hz, 1H), 4.12 (br. s., 2H), 4.02 (br. s., 4H), 3.95-3.84 (m, 2H), 3.73 (d, J=9.1 Hz, 2H), 3.47 (t, J=11.8 Hz, 1H), 3.27 (t, J=11.4 Hz, 1H), 2.90 (s, 3H), 2.88-2.82 (m, 2H), 2.74 (s, 3H), 2.31 (s, 3H), 1.86 (d, J=12.1 Hz, 1H), 1.72-1.51 (m, 2H), 1.44 (s, 5H), 1.35-1.22 (m, 1H), 1.01 (d, J=12.8 Hz, 1H). LCMS (M+H)=621; HPLC RT=1.31 min (Column: Waters Acquity BEH C18 2.0×50 mm; Mobile Phase A: 10:90 ACN:water with 0.1% TFA; Mobile Phase B: 90:10 ACN:water with 0.1% TFA; Temperature: 40° C.; Gradient: 0-100% B over 1.5 min; Flow: 1 mL/min).

Step 2: 4-[3-(Dimethyl-1H-1,2,3-triazol-5-yl)-5-[(S)-oxan-4-yl(phenyl)methyl]-5H-pyrido[3,2-b]indol-8-yl]piperidine In a 25 mL screw top vial containing tert-butyl 4-[3-(dimethyl-1H-1,2,3-triazol-5-yl)-5-[(S)-oxan-4-yl(phenyl)methyl]-5H-pyrido[3,2-b]indol-8-yl]piperidine-1-carboxylate (65.0 mg, 0.105 mmol) was added TFA (20% in DCM, 1 ml) in DCM (2 mL) to give a solution, and the reaction mixture was stirred at room temperature for 2 h. The reaction mixture was concentrated under reduced pressure and dried under high vacuum to give 55 mg (quant.). A small portion of the material was purified via preparative LC/MS with the following conditions: Column: Waters XBridge C18, 19×250 mm, 5-μm particles; Mobile Phase A: 5:95 ACN:water with 10 mM NH$_4$OAc; Mobile Phase B: 95:5 ACN:water with 10 mM NH$_4$OAc; Gradient: 10-50% B over 20 min, then a 5-min hold at 100% B; Flow: 20 mL/min. Fractions containing the desired product were combined and dried via centrifugal evaporation to give 0.9 mg of analytically pure material. $^1$H NMR (500 MHz, DMSO-$d_6$) δ 8.53 (s, 2H), 8.11-8.02 (m, 2H), 7.68 (d, J=7.4 Hz, 2H), 7.52 (br. s., 1H), 7.36-7.30 (m, 2H), 7.28-7.20 (m, 1H), 5.79 (d, J=11.1 Hz, 1H), 4.02 (br. s., 2H), 3.94-3.82 (m, 1H), 3.73 (d, J=9.4 Hz, 1H), 3.27 (t, J=11.4 Hz, 1H), 3.13 (d, J=11.8 Hz, 2H), 2.89-2.78 (m, 1H), 2.77-2.66 (m, 2H), 2.31 (s, 3H), 1.92-1.78 (m, 4H), 1.68 (d, J=12.1 Hz, 3H), 1.52 (d, J=12.1 Hz, 2H), 1.35-1.17 (m, 2H), 1.02 (d, J=13.1 Hz, 1H). LCMS (M+H)=521; HPLC RT=0.97 min (Column: Waters Acquity BEH C18 2.0×50 mm; Mobile Phase A: 10:90 ACN:water with 0.1% TFA; Mobile Phase B: 90:10 ACN:water with 0.1% TFA; Temperature: 40° C.; Gradient: 0-100% B over 1.5 min; Flow: 1 mL/min).

Example 5 tert-Butyl 4-[3-(dimethyl-1H-1,2,3-triazol-5-yl)-5-[(S)-oxan-4-yl(phenyl)methyl]-5H-pyrido[3,2-b]indol-8-yl]piperidine-1-carboxylate

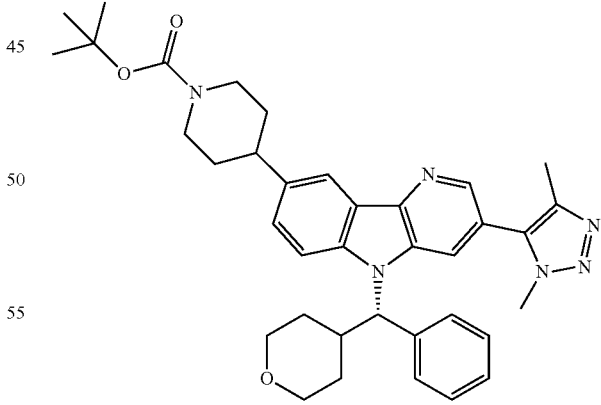

To a 25 mL screw top vial containing (S)-8-bromo-3-(1,4-dimethyl-1H-1,2,3-triazol-5-yl)-5-(phenyl(tetrahydro-2H-pyran-4-yl)methyl)-5H-pyrido[3,2-b]indole (125 mg, 0.242 mmol), 1,1'-bis(diphenylphosphino)ferrocenepalladium(II) dichloride, (10 mg, 0.0120 mmol), N-BOC-1,2,5,6-tetrahydropyridine-4-boronic acid pinacol ester (225 mg, 0.726 mmol), and phosphoric acid, potassium salt 3M (0.242 mL, 0.726 mmol) was added THF (1 mL) to give a suspension. The reaction mixture was purged 3 times with vacuum and nitrogen and heated to 80° C. with stirring for 16 h. The reaction mixture was diluted with ethyl acetate (50 mL), dried with Na$_2$SO$_4$, filtered, and concentrated under vacuum. The reaction mixture was purified using ISCO silica gel chromatography (4 g column, gradient from 0% to 100% EtOAc/hexanes) to give the title compound (0.980 g, 65%). $^1$H NMR (400 MHz, DMSO-d$_6$) δ 8.54 (d, J=1.8 Hz, 1H), 8.48 (br. s., 1H), 8.24 (s, 1H), 8.13 (br. s., 1H), 7.75 (d, J=9.0 Hz, 1H), 7.68 (d, J=7.0 Hz, 2H), 7.38-7.29 (m, 2H), 7.29-7.21 (m, 1H), 6.25 (br. s., 1H), 5.81 (d, J=11.4 Hz, 1H), 4.02 (s, 4H), 3.93-3.86 (m, 2H), 3.73 (d, J=8.6 Hz, 2H), 3.65-3.58 (m, 4H), 3.51-3.41 (m, 3H), 3.25 (s, 1H), 2.62 (br. s., 4H), 2.33 (dd, J=3.7, 2.0 Hz, 1H), 2.32-2.29 (m, 3H), 1.74-1.63 (m, 2H), 1.25 (d, J=2.4 Hz, 4H) LCMS (M+H)=619; HPLC RT=1.35 min (Column: Waters Acquity BEH C18 2.0×50 mm; Mobile Phase A: 10:90 ACN:water with 0.1% TFA; Mobile Phase B: 90:10 ACN:water with 0.1% TFA; Temperature: 40° C.; Gradient: 0-100% B over 1.5 min; Flow: 1 mL/min).

Example 6

1-{4-[3-(Dimethyl-1,2-oxazol-4-yl)-5-[(S)-oxan-4-yl (phenyl)methyl]-5H-pyrido[3,2-b]indol-8-yl]piperidin-1-yl}-2-hydroxyethan-1-one

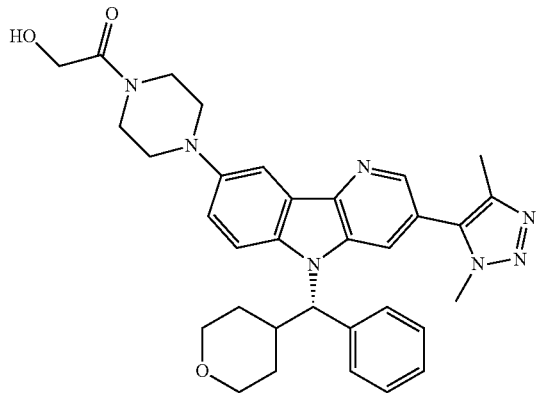 [SMILES: Cc1nnn(C)c1-c1cnc2c3cc(N4CCN(C(=O)CO)CC4)ccc3n([C@H](c3ccccc3)C3CCOCC3)c2c1]

In a 100 mL round-bottomed flask was charged with 2-{4-[3-(dimethyl-1H-1,2,3-triazol-5-yl)-5-[(S)-oxan-4-yl (phenyl)methyl]-5H-pyrido[3,2-b]indol-8-yl]piperidin-1-yl}-2-oxoethyl acetate (43.5 mg, 0.07 mmol) in THF (5 mL) to give a solution. Sodium hydroxide (2M, 0.280 ml, 1.40 mmol) was added and stirred at room temperature. After 2 h acetic acid was added (0.2 ml, 3.49 mmol) was added and the reaction mixture concentrate under reduced pressure and dried under high vacuum. The crude material was purified via preparative LC/MS with the following conditions: Column: Waters XBridge C18, 19×200 mm, 5-μm particles; Mobile Phase A: 5:95 ACN: water with 10 mM NH$_4$OAc; Mobile Phase B: 95:5 ACN:water with 10 mM NH$_4$OAc; Gradient: 18-60% B over 20 min, then a 5 min hold at 100% B; Flow: 20 mL/min. Fractions containing the desired product were combined and dried via centrifugal evaporation to give 1-{4-[3-(dimethyl-1,2-oxazol-4-yl)-5-[(S)-oxan-4-yl (phenyl)methyl]-5H-pyrido[3,2-b]indol-8-yl]piperidin-1-yl}-2-hydroxyethan-1-one (10.8 mg, 27%). $^1$H NMR (500 MHz, DMSO-d$_6$) δ 8.53 (s, 1H), 8.08 (s, 2H), 7.68 (d, J=7.7 Hz, 2H), 7.53 (d, J=6.1 Hz, 1H), 7.36-7.28 (m, 2H), 7.27-7.20 (m, 1H), 5.79 (d, J=11.4 Hz, 1H), 4.60-4.48 (m, 2H), 4.16 (qd, J=15.2, 4.9 Hz, 2H), 4.02 (br. s., 3H), 3.93-3.80 (m, 2H), 3.73 (d, J=9.1 Hz, 1H), 3.52-3.20 (m, 2H), 3.18-2.93 (m, 2H), 2.51 (br. s., 3H), 2.31 (s, 3H), 1.91 (d, J=9.1 Hz, 2H), 1.80-1.43 (m, 4H), 1.37-1.17 (m, 1H), 1.01 (d, J=12.5 Hz, 1H). LCMS: RT=1.46 min; (ES): m/z (M+H)$^+$=579.3. Waters BEH C18, 2.0×50 mm, 1.7-μm particles; Mobile Phase A: 5:95 ACN:water with 10 mM NH$_4$OAc; Mobile Phase B: 95:5 ACN:water with 10 mM NH$_4$OAc; Temperature: 50° C.; Gradient: 0% B, 0-100% B over 3 min, then a 0.5-min hold at 100% B; Flow: 1 mL/min; Detection: UV at 220 nm.

Example 7

1-{4-[3-(Dimethyl-1,2-oxazol-4-yl)-5-[(S)-oxan-4-yl (phenyl)methyl]-5H-pyrido[3,2-b]indol-8-yl]piperidin-1-yl}ethan-1-one

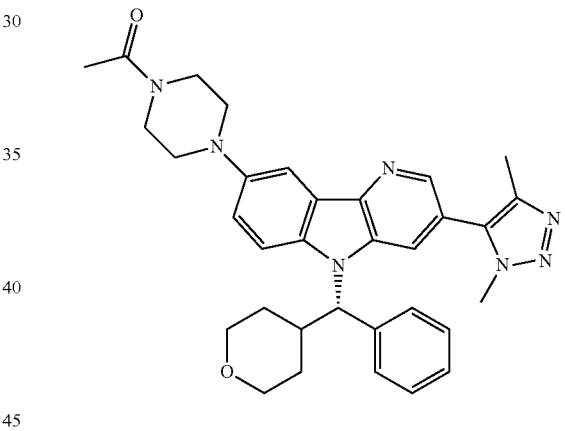

The titled compound was isolated from the reaction mixture in the preparation of 1-{4-[3-(dimethyl-1,2-oxazol-4-yl)-5-[(S)-oxan-4-yl(phenyl)methyl]-5H-pyrido[3,2-b]indol-8-yl]piperidin-1-yl}-2-hydroxyethan-1-one. The crude material was purified via preparative LC/MS with the following conditions: Column: Waters XBridge C18, 19×200 mm, 5-μm particles; Mobile Phase A: 5:95 ACN: water with 10 mM NH$_4$OAc; Mobile Phase B: 95:5 ACN: water with 10 mM NH$_4$OAc; Gradient: 18-60% B over 20 min, then a 5 min hold at 100% B; Flow: 20 mL/min. Fractions containing the desired product were combined and dried via centrifugal evaporation to give 1-{4-[3-(dimethyl-1,2-oxazol-4-yl)-5-[(S)-oxan-4-yl(phenyl)methyl]-5H-pyrido[3,2-b]indol-8-yl] piperidin-1-yl}ethan-1-one (13.3 mg, 34%). $^1$H NMR (500 MHz, DMSO-d$_6$) δ 8.60-8.39 (m, 2H), 8.08 (s, 2H), 7.68 (d, J=7.7 Hz, 2H), 7.54 (d, J=6.7 Hz, 1H), 7.37-7.28 (m, 2H), 7.28-7.17 (m, 1H), 5.79 (d, J=11.1 Hz, 1H), 4.58 (d, J=12.1 Hz, 1H), 4.02 (br. s., 3H), 4.01-3.84 (m, 3H), 3.73 (d, J=9.4 Hz, 1H), 3.47 (t, J=11.4 Hz, 1H), 3.32-3.12 (m, 2H), 2.97 (t, J=11.9 Hz, 1H), 2.64 (t, J=12.1 Hz, 1H), 2.31 (s, 3H), 2.06

(s, 3H), 1.97-1.83 (m, 2H), 1.79-1.63 (m, 2H), 1.60-1.46 (m, 2H), 1.36-1.23 (m, 1H), 1.02 (d, J=12.1 Hz, 1H) LCMS: RT=1.51 min; (ES): m/z (M+H)$^+$=563.3. Waters BEH C18, 2.0×50 mm, 1.7-μm particles; Mobile Phase A: 5:95 ACN: water with 10 mM NH$_4$OAc; Mobile Phase B: 95:5 ACN: water with 10 mM NH$_4$OAc; Temperature: 50° C.; Gradient: 0% B, 0-100% B over 3 min, then a 0.5-min hold at 100% B; Flow: 1 mL/min; Detection: UV at 220 nm.

Example 8

2-{4-[3-(Dimethyl-1H-1,2,3-triazol-5-yl)-5-[(S)-oxan-4-yl(phenyl)methyl]-5H-pyrido[3,2-b]indol-8-yl]piperidin-1-yl}-2-oxoethyl acetate

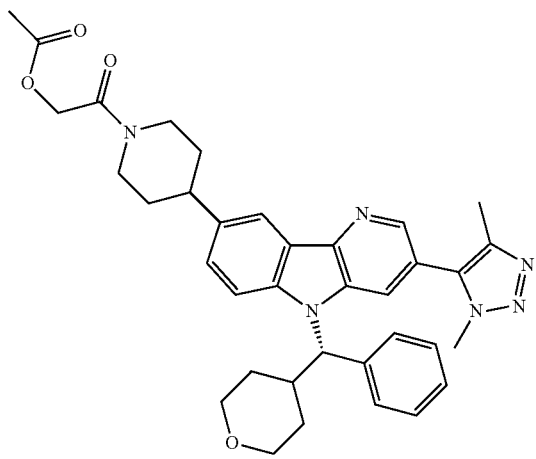 [SMILES: CC(=O)OCC(=O)N1CCC(c2ccc3c(c2)c2ncc(-c4c(C)nnn4C)cc2n3[C@H](c2ccccc2)C2CCOCC2)CC1]

To a 25 mL round-bottomed flask containing (S)-3-(1,4-dimethyl-1H-1,2,3-triazol-5-yl)-5-(phenyl(tetrahydro-2H-pyran-4-yl)methyl)-8-(piperidin-4-yl)-5H-pyrido[3,2-b]indole (0.0470 g, 0.090 mmol), o-benzotriazol-1-yl-N,N,N',N'-tetramethyluronium tetrafluoroborate (0.087 g, 0.270 mmol), acetoxyacetic acid (0.021 g, 0.180 mmol), and TEA (0.125 mL, 0.90 mmol) was added THF (5 mL) to give a solution. The reaction mixture was stirred at room temperature for 2 h. The reaction mixture was concentrated under reduced pressure and dried under high vacuum to give 56 mg (quant.). A small portion of the crude material was purified via preparative LC/MS with the following conditions: Column: Waters XBridge Phenyl, 19×250 mm, 5-μm particles; Mobile Phase A: 5:95 ACN: water with 10 mM NH$_4$OAc; Mobile Phase B: 95:5 ACN: water with 10 mM NH$_4$OAc; Gradient: 10-65% B over 25 min, then a 5-min hold at 100% B; Flow: 20 mL/min. Fractions containing the desired product were combined and dried via centrifugal evaporation to give 3.6 mg. $^1$H NMR (500 MHz, DMSO-d$_6$) δ 8.56-8.43 (m, 2H), 8.08 (s, 2H), 7.67 (d, J=7.4 Hz, 2H), 7.53 (br. s., 1H), 7.36-7.28 (m, 2H), 7.27-7.21 (m, 1H), 5.79 (d, J=11.4 Hz, 1H), 4.84 (s, 2H), 4.49 (d, J=12.5 Hz, 1H), 4.02 (br. s., 3H), 3.94-3.83 (m, 3H), 3.73 (d, J=8.8 Hz, 1H), 2.51 (br. s., 3H), 2.31 (s, 3H), 2.11 (s, 3H), 1.94-1.86 (m, 4H), 1.76 (d, J=9.8 Hz, 1H), 1.68 (d, J=13.1 Hz, 1H), 1.62-1.47 (m, 2H), 1.36-1.21 (m, 1H), 1.01 (d, J=12.8 Hz, 1H). LCMS (M+H)= 621; HPLC RT=1.09 min (Column: Waters Acquity BEH C18 2.0×50 mm; Mobile Phase A: 10:90 ACN:water with 0.1% TFA; Mobile Phase B: 90:10 ACN:water with 0.1% TFA; Temperature: 40° C.; Gradient: 0-100% B over 1.5 min; Flow: 1 mL/min).

Examples 9 and 10

5-[3-(Dimethyl-1H-1,2,3-triazol-5-yl)-5-[(S)-oxan-4-yl(phenyl)methyl]-5H-pyrido[3,2-b]indol-7-yl]-5-methyl-1,3-oxazolidin-2-one

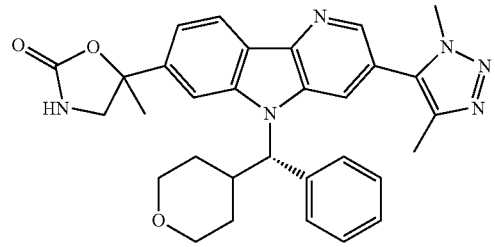

Diastereomer A, Example 9

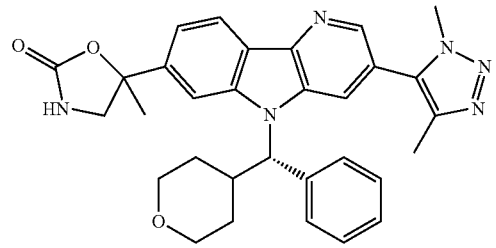

Diastereomer B, Example 10

Step 1: 2-(3-(1,4-Dimethyl-1H-1,2,3-triazol-5-yl)-5-((S)-phenyl(tetrahydro-2H-pyran-4-yl)methyl)-5H-pyrido[3,2-b]indol-7-yl)-2-hydroxypropyl methanesulfonate A 24/40-100 mL round bottom flask was charged 2-[3-(dimethyl-1H-1,2,3-triazol-5-yl)-5-[(S)-oxan-4-yl(phenyl)methyl]-5H-pyrido[3,2-b]indol-7-yl]propane-1,2-diol (67 mg, 0.131 mmol) and dissolved in DCM (1310 μL). The reaction mixture was placed in an ice bath and triethylamine (27 μL, 0.196 mmol) was added followed by methanesulfonyl chloride (11 μL, 0.144 mmol). After 1 h, the mixture was diluted with DCM and water and transferred into a separatory funnel were the layers were separated. The organic was washed with water and brine. The combined aqueous was extracted with DCM (2×), and the aqueous discarded. The combined organics were washed with brine and dried with sodium sulfate. The material (83 mg, quant.) was used without purification. $^1$H NMR (400 MHz, CDCl$_3$) δ 8.48-8.46 (m, 1H), 8.40 (d, J=8.3 Hz, 1H), 8.04-7.94 (m, 1H), 7.62-7.58 (m, 1H), 7.48-7.29 (m, 6H), 5.63-5.55 (m, 1H), 4.53-4.47 (m, 1H), 4.47-4.42 (m, 1H), 4.06 (d, J=8.8 Hz, 1H), 3.93-3.82 (m, 5H), 3.61-3.50 (m, 1H), 3.42-3.29 (m, 1H), 3.19-3.04 (m, 1H), 2.98 (d, J=10.5 Hz, 3H), 2.74-2.69 (m, 1H), 2.33-2.27 (m, 3H), 2.05 (d, J=12.8 Hz, 1H), 1.83-1.77 (m, 3H), 1.71-1.59 (m, 1H), 1.48-1.35 (m, 2H), 1.10 (d, J=11.3 Hz, 2H). Mass found 590 [M+H]$^+$.

Step 2: 1-Azido-2-(3-(1,4-dimethyl-1H-1,2,3-triazol-5-yl)-5-((S)-phenyl(tetrahydro-2H-pyran-4-yl)methyl)-5H-pyrido[3,2-b]indol-7-yl)propan-2-ol A 2-dram pressure vial was charged with 2-(3-(1,4-dimethyl-1H-1,2,3-triazol-5-yl)-5-((S)-phenyl(tetrahydro-2H-pyran-4-yl)methyl)-5H-pyrido[3,2-b]indol-7-yl)-2-hydroxypropyl methanesulfonate (82.6 mg, 0.140 mmol) and dissolved in DMF (280 μL). Sodium azide (36.4 mg, 0.560 mmol) was added, and the reaction vial was placed into a reaction block preheated to 80° C. After 19 h, the mixture was diluted with ethyl acetate and water, and the contents of the flask were transferred into a separatory funnel where the layers were separated. The organic was washed with water and brine (2×), dried with magnesium sulfate, concentrated under reduced pressure, and purified by silica gel column chromatography (4 g ISCO RediSep Rf, loaded in/with: DCM and dried, initial waste: 0 mL, fraction size: 6 mL 13×100 mm, and eluted with acetone in DCM 0% [30 mL], 0-100% [201 mL], 100% [102 mL]). The fractions were collected to give 56.9 mg (76%). $^1$H NMR (400 MHz, CDCl$_3$) δ 8.44 (d, J=1.8 Hz, 1H), 8.39 (d, J=8.3 Hz, 1H), 8.04-7.98 (m, 1H), 7.58 (d, J=1.8 Hz, 1H), 7.44 (d, J=7.0 Hz, 2H), 7.40-7.28 (m, 4H), 5.60 (d, J=10.3 Hz, 1H), 4.10-4.01 (m, 1H), 3.92-3.82 (m, 4H), 3.76-3.70 (m, 1H), 3.64-3.50 (m, 2H), 3.34 (td, J=11.9, 1.9 Hz, 1H), 3.16-3.02 (m, 1H), 2.83-2.77 (m, 1H), 2.32-2.26 (m, 3H), 2.04 (d, J=13.1 Hz, 1H), 1.78-1.74 (m, 3H), 1.68-1.56 (m, 1H), 1.42 (qd, J=12.4, 4.5 Hz, 1H), 1.10 (d, J=13.1 Hz, 1H). Mass found 536 [M+H]$^+$.

Step 3: 5-[3-(Dimethyl-1H-1,2,3-triazol-5-yl)-5-[(S)-oxan-4-yl(phenyl)methyl]-5H-pyrido[3,2-b]indol-7-yl]-5-methyl-1,3-oxazolidin-2-one A 2-dram pressure vial was charged with 1-azido-2-(3-(1,4-dimethyl-1H-1,2,3-triazol-5-yl)-5-((S)-phenyl(tetrahydro-2H-pyran-4-yl)methyl)-5H-pyrido[3,2-b]indol-7-yl) propan-2-ol (56.9 mg, 0.106 mmol) and dissolved in THF (1060 μL). 1 drop of water was added followed by trimethylphosphine (1.0M in THF, 265 μL, 0.265 mmol). After 1 h, CDI (86.0 mg, 0.530 mmol) was added, and the mixture was heated to 80° C. After 24 h, an additional 10 equiv. of CDI was added. After 1.5 h, the volatiles were removed under a stream of nitrogen. The crude material was diluted with 2 mL methanol, filtered through a 0.45 m syringe tip filter, and purified by preparative HPLC: Column: Waters XBridge C18 100×30 mm 5 u, Solvents: water/acetonitrile/NH$_4$OAc, % B gradient (time): 28% isocratic gradient, Flow Rate: 30 mL/min, 4 injections. The fractions were collected to give 18.5 mg (33%) as a diastereomeric mixture. The diastereomers were separated by chiral SFC. Chiralpak AS-H prep column, 30×250 mm, 5 mm Mobile phase: 25% MeOH in CO$_2$, 150 bar, Temp: 35° C., Flow rate: 70 mL/min. for 20 min. UV monitored at 220 nm Injection: 1.25 mL of ~3 mg/mL in MeOH to give Enantiomer A (2.0 mg, 19%) and Enantiomer B (2.2 mg, 21%). Enantiomer A: $^1$H NMR (400 MHz, CDCl$_3$) δ 8.47 (d, J=1.8 Hz, 1H), 8.42 (d, J=8.3 Hz, 1H), 7.95 (s, 1H), 7.61 (d, J=1.8 Hz, 1H), 7.44 (d, J=7.0 Hz, 2H), 7.39-7.29 (m, 3H), 7.22 (dd, J=8.2, 1.4 Hz, 1H), 5.60 (d, J=10.3 Hz, 1H), 5.07 (s, 1H), 4.11-4.03 (m, 1H), 3.93-3.83 (m, 6H), 3.60-3.51 (m, 1H), 3.41-3.30 (m, 1H), 3.09 (d, J=10.3 Hz, 1H), 2.31 (s, 3H), 2.02 (d, J=13.8 Hz, 1H), 1.95 (s, 3H), 1.47-1.34 (m, 3H). SFC retention time 6.66 min. Mass found 536 [M+H]$^+$. Enantiomer B: $^1$H NMR (400 MHz, CDCl$_3$) δ 8.48 (d, J=1.8 Hz, 1H), 8.42 (d, J=8.3 Hz, 1H), 7.92 (s, 1H), 7.65 (d, J=1.5 Hz, 1H), 7.49-7.42 (m, 2H), 7.40-7.29 (m, 3H), 7.23 (dd, J=8.2, 1.4 Hz, 1H), 5.58 (d, J=10.5 Hz, 1H), 5.05 (s, 1H), 4.06 (d, J=8.8 Hz, 1H), 3.95-3.81 (m, 6H), 3.61-3.51 (m, 1H), 3.41-3.31 (m, 1H), 3.12 (d, J=11.3 Hz, 1H), 2.33 (s, 3H), 2.02 (d, J=13.3 Hz, 1H), 1.95 (s, 3H), 1.46-1.35 (m, 3H). SFC retention time 15.48 min. Mass found 536 [M+H]$^+$.

Example 11

5-[3-(Dimethyl-1H-1,2,3-triazol-5-yl)-5-[(S)-oxan-4-yl(phenyl)methyl]-5H-pyrido[3,2-b]indol-7-yl]-1H-1,2,3,4-tetrazole

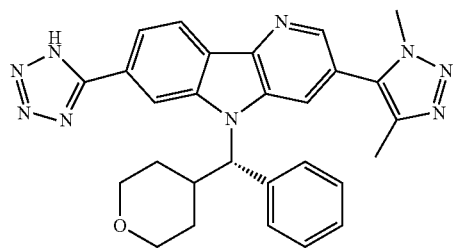 [SMILES: Cc1nnn(C)c1-c1cnc2c3ccc(-c4nnn[nH]4)cc3n([C@H](c3ccccc3)C3CCOCC3)c2c1]

Step 1: Methyl 4-(5-bromo-3-nitropyridin-2-yl)benzoate

A 24/40-500 mL round bottom flask was charged with 2,5-dibromo-3-nitropyridine (8.07 g, 28.6 mmol), 4-methoxycarbonylphenylboronic acid (4.97 g, 27.6 mmol), THF (143 ml), 1,1'-bis(diphenylphosphino)ferrocenedichloropalladium(II) (1.047 g, 1.43 mmol) and potassium phosphate tribasic (2M, 11.6 mL, 23.1 mmol). The flask was sealed with a rubber septum and the reaction mixture was degassed using ultra pure argon and sonicated for 5 min. The flask was transferred to an oil bath preheated to 65° C. and held there for 4 h. The mixture was quenched with water, diluted with ethyl acetate, and filtered through a pad of Celite. The contents of the flask were transferred into a separatory funnel and the layers were separated. The organic was washed with water (2×) and brine (2×). The combined aqueous was back extracted with ethyl acetate and the aqueous discarded. The combined organics were dried with magnesium sulfate, concentrated under reduced pressure, and purified by flash chromatography (80 g ISCO RediSep Rf, loaded in/with: DCM and dried, initial waste: 0 mL, fraction size: 9 mL 13×100 mm, and eluted with DCM in hexanes 0% [200 mL], 0-20% [300 mL], 20% [1000 mL], 20-50% [500 mL], 50% [300 mL]) to give 1.39 g (59%) of product. $^1$H NMR (400 MHz, CDCl$_3$) δ 8.95 (d, J=2.0 Hz, 1H), 8.36 (d, J=2.0 Hz, 1H), 8.18-8.11 (m, 2H), 7.66-7.58 (m, 2H), 3.96 (s, 3H). Mass found 337 (M+H)$^+$.

Step 2: Methyl 3-bromo-5H-pyrido[3,2-b]indole-7-carboxylate

A 14/20-100 mL round bottom flask was charged with methyl 4-(5-bromo-3-nitropyridin-2-yl)benzoate (6.68 g, 19.8 mmol) and 1,2-bis(diphenylphosphino)ethane (9.87 g, 24.8 mmol). The mixture was suspended in 1,2-dichlorobenzene (20 mL) and the flask was sealed and vented with a balloon full of nitrogen. The flask was placed into an oil bath preheated to 160° C. and held there for 1 h. Upon cooling, the solution was diluted with ether, causing a brown precipitate to form which was removed by filtration and discarded. The supernatant was concentrated under reduced pressure and purified by flash chromatography (80 g ISCO RediSep Rf, loaded in/with: DCM and dried, initial waste: 0 mL, fraction size: 9 mL 13×100 mm, and eluted with DCM in hexanes 0% [200 mL], 0-100% [300 mL], 100% [1500 mL]) to give 2.80 g (46%) of product. $^1$H NMR (400 MHz, CDCl$_3$) δ 8.95 (d, J=2.0 Hz, 1H), 8.36 (d, J=2.0 Hz, 1H), 8.18-8.11 (m, 2H), 7.66-7.58 (m, 2H), 3.96 (s, 3H). Mass found 305 (M+H)$^+$.

Step 3: Methyl 3-(1,4-dimethyl-1H-1,2,3-triazol-5-yl)-5H-pyrido[3,2-b]indole-7-carboxylate A 40 mL pressure vial was charged with 1,4-dimethyl-5-(tributylstannyl)-1H-1,2,3-triazole (3.90 g, 10.1 mmol) and diluted with DMF (23 ml). To that solution was added methyl 3-bromo-5H-pyrido[3,2-b]indole-7-carboxylate (2.8 g, 9.18 mmol), copper(I)iodide (0.262 g, 1.38 mmol), triethylamine (2.56 ml, 18.4 mmol) and Pd(Ph$_3$P)$_4$ (0.636 g, 0.551 mmol). The vial was sealed and the reaction mixture was degassed using ultra pure argon and sonication for 3 min. After which, the vial was placed into a reaction block preheated to 100° C. After 30 min, the mixture was diluted with ethyl acetate and water and the contents of the vial were filtered through a pad of Celite. The mixture was concentrated under reduced pressure and purified by flash chromatography (40 g ISCO RediSep Rf, loaded in/with: DCM and dried, initial waste: 0 mL, fraction size: 9 mL 13×100 mm, and eluted with acetone in DCM 0% [100 mL], 0-30% [150 mL], 30% [300 mL], 30-60% [500 mL], 60% [200 mL]) to give 1.748 g (59.3% yield) of product. $^1$H NMR (400 MHz, DMSO-d$_6$) δ 11.94 (s, 1H), 8.61 (d, J=2.0 Hz, 1H), 8.35 (dd, J=8.3, 0.5 Hz, 1H), 8.25 (dd, J=1.4, 0.6 Hz, 1H), 8.16 (d, J=1.8 Hz, 1H), 7.90 (dd, J=8.2, 1.4 Hz, 1H), 4.02 (s, 3H), 3.93 (s, 3H), 2.30 (s, 3H). Mass found 321 (M+H)$^+$.

Step 4: (S)-Methyl 3-(1,4-dimethyl-1H-1,2,3-triazol-5-yl)-5-(phenyl(tetrahydro-2H-pyran-4-yl)methyl)-5H-pyrido[3,2-b]indole-7-carboxylate A 24/40-50 mL round bottom flask was charged with methyl 3-(1,4-dimethyl-1H-1,2,3-triazol-5-yl)-5H-pyrido[3,2-b]indole-7-carboxylate (250 mg, 0.778 mmol), (R)-phenyl(tetrahydro-2H-pyran-4-yl)methanol (299 mg, 1.56 mmol) and triphenylphosphine (408 mg, 1.56 mmol). The mixture was suspended in THF (7780 μL) and cooled to 0° C. Di-tert-butyl azodicarboxylate (358 mg, 1.56 mmol) was added in one portion. After 30 min at 0° C., the reaction was warmed to room temperature and the reaction slowly turned to a deep red. After 30 min at room temperature, the reaction mixture was quenched with TFA (300 μL, 3.89 mmol) and stirred for 30 min. The mixture was concentrated under reduced pressure, diluted with ethyl acetate and neutralized using a 1.5M potassium phosphate. The contents of the flask were transferred into a separatory funnel and the layers were separated. The organic was washed with brine, dried over magnesium sulfate, concentrated under reduced pressure, and purified by flash chromatography (24 g ISCO RediSep Rf, loaded in/with: DCM and dried, fraction size: 21 mL 16×150 mm, and eluted with acetone in DCM 0% [50 mL], 0-20% [200 mL], 20% [150 mL], 20-30% [150 mL], 30% [350 mL]). Collected fractions to give 338 mg (88%) of product. $^1$H NMR (400 MHz, CDCl$_3$) δ 8.51 (d, J=1.8 Hz, 1H), 8.47 (d, J=8.3 Hz, 1H), 8.10 (dd, J=8.3, 1.3 Hz, 1H), 7.63 (d, J=1.8 Hz, 1H), 7.46 (d, J=7.3 Hz, 2H), 7.40-7.29 (m, 3H), 5.63 (d, J=10.5 Hz, 1H), 4.11-4.01 (m, 4H), 3.92-3.82 (m, 4H), 3.61-3.51 (m, 1H), 3.41-3.31 (m, 1H), 3.12 (q, J=11.3 Hz, 1H), 2.30 (s, 3H), 2.05 (d, J=13.8 Hz, 1H), 1.71-1.52 (m, 2H), 1.51-1.37 (m, 1H), 1.09 (d, J=12.3 Hz, 1H). Mass found 495 (M+H)$^+$.

Step 5: (S)-3-(1,4-Dimethyl-1H-1,2,3-triazol-5-yl)-5-(phenyl(tetrahydro-2H-pyran-4-yl)methyl)-5H-pyrido[3,2-b]indole-7-carboxylic acid A 20 mL pressure vial was charged with (S)-methyl 3-(1,4-dimethyl-1H-1,2,3-triazol-5-yl)-5-(phenyl(tetrahydro-2H-pyran-4-yl)methyl)-5H-pyrido[3,2-b]indole-7-carboxylate (200 mg, 0.404 mmol) and dissolved in THF (3.36 ml) and water (673 μL). To that solution was added potassium hydroxide (67.9 mg, 1.21 mmol). The vial was sealed and placed into a reaction block heated to 50° C. After 19 h, the THF was evaporated using a stream of nitrogen and the aqueous was transferred to a separatory funnel. The basic solution was extracted with ethyl acetate (×2) to remove any organic impurity and discarded. The combined aqueous was acidified to a pH of ~4, using 1 mL 1N HCl. The pH was adjusted to a pH of 5 using a 2M solution of potassium phosphate, tribasic. The contents of the Erlenmeyer flask were transferred back to the separatory funnel and the aqueous was extracted with ethyl acetate (×3). The combined organics were dried with magnesium sulfate and concentrated under reduced pressure to give 192 mg (99% yield) of product. $^1$H NMR (400 MHz, CDCl$_3$) δ 8.59 (s, 1H), 8.55 (d, J=1.5 Hz, 1H), 8.52 (d, J=8.3 Hz, 1H), 8.17 (dd, J=8.3, 1.0 Hz, 1H), 7.66 (d, J=1.5 Hz, 1H), 7.48 (d, J=7.3 Hz, 2H), 7.41-7.29 (m, 4H), 5.66 (d, J=10.5 Hz, 1H), 4.13-4.05 (m, 1H), 3.92-3.86 (m, 4H), 3.63-3.53 (m, 1H), 3.38 (td, J=12.0, 1.5 Hz, 1H), 3.14 (d, J=11.0 Hz, 1H), 2.32 (s, 3H), 2.10-2.02 (m, 1H), 1.74-1.61 (m, 1H), 1.55-1.43 (m, 1H), 1.11 (d, J=14.3 Hz, 1H). Mass found 482 (M+H)$^+$.

Step 6: (S)-3-(1,4-Dimethyl-1H-1,2,3-triazol-5-yl)-5-(phenyl(tetrahydro-2H-pyran-4-yl)methyl)-N-(2-phenylpropan-2-yl)-5H-pyrido[3,2-b]indole-7-carboxamide A 24/40-100 mL round bottom flask was charged with (S)-3-(1,4-dimethyl-1H-1,2,3-triazol-5-yl)-5-(phenyl(tetrahydro-2H-pyran-4-yl)methyl)-5H-pyrido[3,2-b]indole-7-carboxylic acid (192 mg, 0.399 mmol) and dissolved in DCM (3.99 mL). To that solution was added TEA (167 μL, 1.20 mmol), cumylamine (69 μL, 0.478 mmol) and HATU (227 mg, 0.598 mmol). After 1 h, the mixture was concentrated under reduced pressure and purified by flash chromatography: (12 g ISCO RediSep Rf, loaded in/with: DCM and dried, initial waste: 18 mL, fraction size: 9 mL 13×100 mm, and eluted with acetone in DCM 0% [51 mL], 20% [150 mL], 20-100% [150 mL], 100% [102 mL]). The fractions were collected fractions to give 197 mg (83% yield) of product. $^1$H NMR (400 MHz, CDCl$_3$) δ 8.50 (d, J=1.8 Hz, 1H), 8.45 (d, J=8.3 Hz, 1H), 8.40 (s, 1H), 7.69-7.62 (m, 2H), 7.58-7.53 (m, 2H), 7.47-7.39 (m, 5H), 7.36-7.28 (m, 5H), 6.67 (s, 1H), 5.60 (d, J=10.8 Hz, 1H), 4.07-4.00 (m, 1H), 3.89 (s, 3H), 3.84 (d, J=14.6 Hz, 1H), 3.57-3.48 (m, 1H), 3.33 (t, J=10.8 Hz, 1H), 3.09 (d, J=11.8 Hz, 1H), 2.31 (s, 3H), 1.99 (d, J=13.8 Hz, 1H), 1.93 (s, 6H), 1.06 (d, J=12.8 Hz, 1H). Mass found 599 (M+H)$^+$.

Step 7: (S)-3-(1,4-Dimethyl-1H-1,2,3-triazol-5-yl)-5-(phenyl(tetrahydro-2H-pyran-4-yl)methyl)-5H-pyrido[3,2-b]indole-7-carbonitrile A 24/40-50 mL round bottom flask was charged with (S)-3-(1,4-dimethyl-1H-1,2,3-triazol-5-yl)-5-(phenyl(tetrahydro-2H-pyran-4-yl)methyl)-N-(2-phenylpropan-2-yl)-5H-pyrido[3,2-b]indole-7-carboxamide (197 mg, 0.329 mmol) and partially dissolved in DCM (1645 µL). To that suspension was added pyridine (80 µL, 0.987 mmol) and the reaction mixture was cooled to −40° C. using an acetonitrile/dry ice bath. Triflic anhydride (72 µL, 0.428 mmol) was then added in one portion. The ice bath was allowed to expire and the reaction was let stir overnight. After 22 h, the reaction mixture was cooled to −40° C. and an additional 72 µL of triflic anhydride was added. After 1 h, the mixture was quenched with ethanol and a saturated solution of sodium bicarbonate. The mixture was let stir for 15 min and the contents of the flask were transferred into a separatory funnel where the layers were separated. The organic was washed with water and brine, dried with magnesium sulfate, concentrated under reduced pressure and purified by flash chromatography: (12 g ISCO RediSep Rf, loaded in/with: DCM and dried, initial waste: 18 mL, fraction size: 9 mL 13×100 mm, and eluted with acetone in DCM 0% [51 mL], 20% [150 mL], 20-100% [150 mL], 100% [102 mL]. Collected fractions to give 129 mg (85% yield) of product. $^1$H NMR (400 MHz, CDCl$_3$) δ 8.56 (d, J=1.8 Hz, 1H), 8.51 (d, J=8.0 Hz, 1H), 8.04 (s, 1H), 7.72 (d, J=1.5 Hz, 1H), 7.65 (dd, J=8.2, 1.1 Hz, 1H), 7.47-7.42 (m, 2H), 7.41-7.30 (m, 3H), 5.52 (d, J=10.5 Hz, 1H), 4.07 (dd, J=12.0, 3.0 Hz, 1H), 3.92 (s, 3H), 3.91-3.84 (m, 1H), 3.56 (td, J=11.9, 2.0 Hz, 1H), 3.37 (td, J=11.9, 2.0 Hz, 1H), 3.11 (qt, J=11.1, 3.5 Hz, 1H), 2.32 (s, 3H), 2.03 (d, J=13.3 Hz, 1H), 1.67-1.54 (m, 1H), 1.46-1.33 (m, 1H), 1.13-1.03 (m, 1H). Mass found 463 (M+H)$^+$.

Step 8: (S)-3-(1,4-Dimethyl-1H-1,2,3-triazol-5-yl)-5-(phenyl(tetrahydro-2H-pyran-4-yl)methyl)-7-(1H-tetrazol-5-yl)-5H-pyrido[3,2-b]indole A 0.5-2 mL microwave vial was charged with (S)-3-(1,4-dimethyl-1H-1,2,3-triazol-5-yl)-5-(phenyl(tetrahydro-2H-pyran-4-yl)methyl)-5H-pyrido[3,2-b]indole-7-carbonitrile (35 mg, 0.076 mmol) and sodium azide (14.8 mg, 0.227 mmol). The mixture was dissolved in NMP (500 µL) and aluminum chloride (1.5 mg, 0.011 mmol) was added. The vial was sealed and heated in the microwave at 200° C. for 10 min. After 10 min, the mixture was cooled and filtered through a 0.45µ syringe tip filter and submitted for final purification. The crude material was purified via preparative LC/MS with the following conditions: Column: XBridge C18, 19×200 mm, 5-µm particles; Mobile Phase A: 5:95 MeOH: water with 10 mM NH$_4$OAc; Mobile Phase B: 95:5 MeOH: water with 10 mM NH$_4$OAc; Gradient: 50-90% B over 15 min, then a 5 min hold at 100% B; Flow: 20 mL/min. Fractions containing the desired product were combined and dried via centrifugal evaporation. The yield of the product was 23.3 mg, and its estimated purity by LCMS analysis was 99%. Two analytical LC/MS injections were used to determine the final purity. Injection 1 conditions: Column: Waters BEH C18, 2.0×50 mm, 1.7-µm particles; Mobile Phase A: 5:95 ACN:water with 10 mM NH$_4$OAc; Mobile Phase B: 95:5 ACN:water with 10 mM NH$_4$OAc; Temperature: 50° C.; Gradient: 0% B, 0-100% B over 3 min, then a 0.5 min hold at 100% B; Flow: 1 mL/min; Detection: UV at 220 nm. Injection 2 conditions: Column: Waters BEH C18, 2.0×50 mm, 1.7-µm particles; Mobile Phase A: 5:95 MeOH:water with 10 mM NH$_4$OAc; Mobile Phase B: 95:5 MeOH:water with 10 mM NH$_4$OAc; temperature: 50° C.; Gradient: 0% B, 0-100% B over 3 min, then a 0.5 min hold at 100% B; Flow: 0.5 mL/min; Detection: UV at 220 nm. Proton NMR was acquired in deuterated DMSO. $^1$H NMR (500 MHz, DMSO-d$_6$) δ 8.52 (s, 1H), 8.24 (d, J=8.1 Hz, 1H), 8.01 (d, J=8.1 Hz, 1H), 7.95 (s, 1H), 7.69 (d, J=7.7 Hz, 2H), 7.34 (t, J=7.7 Hz, 2H), 7.28-7.21 (m, 1H), 5.84 (d, J=11.4 Hz, 1H), 4.02 (br. s., 3H), 3.92-3.85 (m, 1H), 3.73 (d, J=11.7 Hz, 1H), 3.49 (t, J=11.6 Hz, 1H), 3.45-3.32 (m, 2H), 3.31-3.23 (m, 1H), 2.31 (s, 3H), 1.72 (d, J=13.2 Hz, 1H), 1.60 (d, J=11.0 Hz, 1H), 1.34 (d, J=8.4 Hz, 1H), 1.07 (d, J=12.8 Hz, 1H). Mass found 506 (M+H)$^+$.

Example 12

3-[3-(Dimethyl-1H-1,2,3-triazol-5-yl)-5-[(S)-oxan-4-yl(phenyl)methyl]-5H-pyrido[3,2-b]indol-7-yl]-1,3-oxazinan-2-one

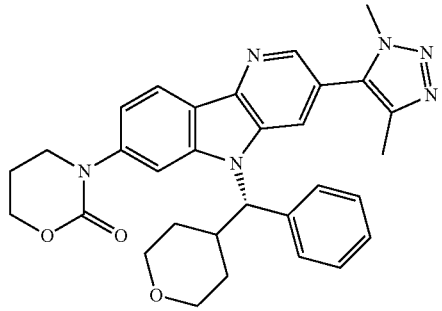 [SMILES: Cc1nnn(C)c1-c1cnc2c3ccc(N4CCCOC4=O)cc3n([C@H](c3ccccc3)C3CCOCC3)c2c1]

To 2 mL of a 0.05 M solution of 5-{7-isocyanato-5-[(S)-oxan-4-yl(phenyl)methyl]-5H-pyrido[3,2-b]indol-3-yl}-1,4-dimethyl-1H-1,2,3-triazole in dioxane was added 3-chloro-1-propanol (0.105 mL, 1.25 mmol), and the reaction mixture was heated to 80° C. for 70 h. The reaction mixture was diluted with acetone (10 mL), and potassium carbonate (276 mg, 2.00 mmol) was added, and the reaction mixture was heated to 80° C. for 48 h. The reaction was filtered, and the volatiles removed under reduced pressure. The crude material was purified via preparative LC/MS with the following conditions: Column: XBridge C18, 19×200 mm, 5-µm particles; Mobile Phase A: 5:95 ACN: water with 10 mM NH$_4$OAc; Mobile Phase B: 95:5 ACN: water with 10 mM NH$_4$OAc; Gradient: 15-100% B over 20 min, then a 3-min hold at 100% B; Flow: 20 mL/min. Fractions containing the desired product were combined and dried via centrifugal evaporation to give 10.4 mg (7.5%). $^1$H NMR (500 MHz, DMSO-d$_6$) δ 8.51 (s, 1H), 8.22 (d, J=8.4 Hz, 2H), 7.93 (s, 1H), 7.66 (d, J=7.7 Hz, 2H), 7.36-7.28 (m, 3H), 7.28-7.19 (m, 1H), 5.77 (d, J=11.4 Hz, 1H), 4.42 (t, J=5.2 Hz, 2H), 3.98 (br. s., 2H), 3.91-3.80 (m, 2H), 3.49-3.34 (m, 2H), 3.31-3.22 (m, 2H), 2.28 (s, 5H), 2.20 (t, J=5.4 Hz, 2H), 1.67 (d, J=11.4 Hz, 1H), 1.52 (d, J=14.8 Hz, 1H), 1.32 (d, J=8.8 Hz, 1H), 1.01 (d, J=12.5 Hz, 1H). LCMS (M+H)=537; HPLC RT=0.76 min (Column: Waters Acquity BEH C18 2.0×50 mm; Mobile Phase A: 10:90 ACN:water with 0.1% TFA; Mobile Phase B: 90:10 ACN:water with 0.1% TFA; Temperature: 40° C.; Gradient: 0-100% B over 1.5 min; Flow: 1 mL/min).

Example 13

1-[3-(Dimethyl-1H-1,2,3-triazol-5-yl)-5-[(S)-oxan-4-yl(phenyl)methyl]-5H-pyrido[3,2-b]indol-8-yl]piperazine

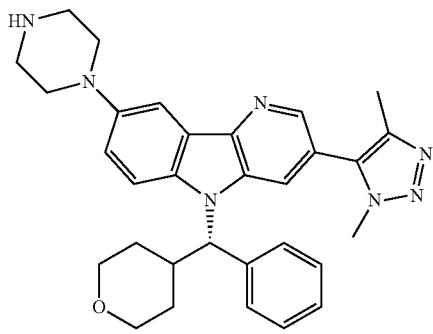 [SMILES: Cc1nnn(C)c1-c1cnc2c3cc(N4CCNCC4)ccc3n([C@H](c3ccccc3)C3CCOCC3)c2c1]

Step 1: tert-Butyl 4-[3-(dimethyl-1H-1,2,3-triazol-5-yl)-5-[(S)-oxan-4-yl(phenyl)methyl]-5H-pyrido[3,2-b]indol-8-yl]piperazine-1-carboxylate Following a procedure analogous to that described for (2R,6S)-4-[3-(dimethyl-1H-1,2,3-triazol-5-yl)-5-[(S)-oxan-4-yl(phenyl)methyl]-5H-pyrido[3,2-b]indol-8-yl]-2,6-dimethylmorpholine, tert-butyl piperazine-1-carboxylate (151 mg, 0.813 mmol) was converted to the title compound (169 mg, 78%). $^1$H NMR (500 MHz, DMSO-$d_6$) δ 8.52-8.36 (m, 2H), 8.03 (br. s., 1H), 7.71 (s, 1H), 7.66 (d, J=7.7 Hz, 2H), 7.40 (d, J=8.4 Hz, 1H), 7.39-7.26 (m, 2H), 7.28-7.19 (m, 1H), 5.74 (d, J=11.4 Hz, 1H), 3.88 (d, J=9.8 Hz, 1H), 3.73 (d, J=10.4 Hz, 1H), 3.53 (br. s., 2H), 3.43 (br. s., 2H), 3.27 (t, J=11.6 Hz, 2H), 3.14 (br. s., 4H), 2.31 (s, 3H), 1.66 (d, J=12.8 Hz, 2H), 1.51 (d, J=11.8 Hz, 2H), 1.44 (s, 9H), 1.35-1.20 (m, 2H), 1.02 (d, J=12.5 Hz, 2H). LCMS (M+H)=622; HPLC RT=1.18 min (Column: Waters Acquity BEH C18 2.0×50 mm; Mobile Phase A: 10:90 ACN:water with 0.1% TFA; Mobile Phase B: 90:10 ACN:water with 0.1% TFA; Temperature: 40° C.; Gradient: 0-100% B over 1.5 min; Flow: 1 mL/min).

Step 2: 1-[3-(Dimethyl-1H-1,2,3-triazol-5-yl)-5-[(S)-oxan-4-yl(phenyl)methyl]-5H-pyrido[3,2-b]indol-8-yl]piperazine Following a procedure analogous to that described for 4-[3-(dimethyl-1H-1,2,3-triazol-5-yl)-5-[(S)-oxan-4-yl(phenyl)methyl]-5H-pyrido[3,2-b]indol-8-yl]piperidine, tert-butyl 4-[3-(dimethyl-1H-1,2,3-triazol-5-yl)-5-[(S)-oxan-4-yl(phenyl)methyl]-5H-pyrido[3,2-b]indol-8-yl]piperazine-1-carboxylate (211 mg, 0.340 mmol) was converted to the title compound (133 mg, 75%). $^1$H NMR (500 MHz, DMSO-$d_6$) δ 8.47 (s, 2H), 8.01 (br. s., 1H), 7.66 (d, J=7.7 Hz, 3H), 7.44-7.19 (m, 4H), 5.74 (d, J=11.1 Hz, 1H), 4.02 (br. s., 3H), 3.89 (d, J=10.4 Hz, 1H), 3.74 (d, J=10.1 Hz, 1H), 3.48-3.37 (m, 1H), 3.27 (t, J=11.3 Hz, 1H), 3.18 (br. s., 4H), 3.02 (br. s., 3H), 2.65 (br. s., 1H), 2.31 (s, 3H), 1.91 (s, 2H), 1.66 (d, J=12.1 Hz, 1H), 1.51 (d, J=8.8 Hz, 1H), 1.29 (d, J=12.8 Hz, 1H), 1.02 (d, J=12.5 Hz, 1H). LCMS (M+H)=522; HPLC RT=0.96 min (Column: Waters Acquity BEH C18 2.0×50 mm; Mobile Phase A: 10:90 ACN:water with 0.1% TFA; Mobile Phase B: 90:10 ACN:water with 0.1% TFA; Temperature: 40° C.; Gradient: 0-100% B over 1.5 min; Flow: 1 mL/min).

Example 14

2-{4-[3-(Dimethyl-1H-1,2,3-triazol-5-yl)-5-[(S)-oxan-4-yl(phenyl)methyl]-5H-pyrido[3,2-b]indol-8-yl]piperazin-1-yl}-2-oxoethyl acetate

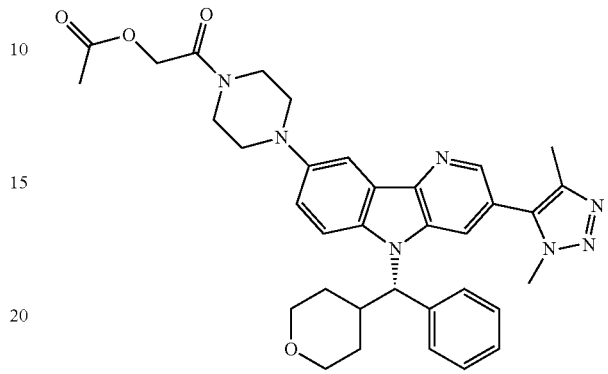

Following a procedure analogous to that described for 2-{4-[3-(dimethyl-1H-1,2,3-triazol-5-yl)-5-[(S)-oxan-4-yl(phenyl)methyl]-5H-pyrido[3,2-b]indol-8-yl]piperidin-1-yl}-2-oxoethyl acetate, 1-[3-(dimethyl-1H-1,2,3-triazol-5-yl)-5-[(S)-oxan-4-yl(phenyl)methyl]-5H-pyrido[3,2-b]indol-8-yl]piperazine (63.0 mg, 0.120 mmol) was converted to the title compound (12.6 mg, 17%). $^1$H NMR (500 MHz, DMSO-$d_6$) δ 8.50-8.40 (m, 2H), 8.03 (br. s., 1H), 7.70 (s, 1H), 7.66 (d, J=7.4 Hz, 2H), 7.42 (d, J=8.4 Hz, 1H), 7.36-7.28 (m, 2H), 7.28-7.20 (m, 1H), 5.74 (d, J=11.4 Hz, 1H), 4.86 (s, 2H), 4.02 (s, 3H), 3.93-3.84 (m, 1H), 3.73 (d, J=8.1 Hz, 1H), 3.68-3.55 (m, 4H), 3.47-3.41 (m, 2H), 3.27 (t, J=11.3 Hz, 2H), 3.24-3.12 (m, 3H), 2.30 (s, 3H), 2.10 (s, 3H), 1.66 (d, J=12.1 Hz, 1H), 1.51 (d, J=9.1 Hz, 1H), 1.30 (d, J=8.8 Hz, 1H), 1.02 (d, J=12.5 Hz, 1H). LCMS (M+H)=622; HPLC RT=0.1.04 min (Column: Waters Acquity BEH C18 2.0×50 mm; Mobile Phase A: 10:90 ACN:water with 0.1% TFA; Mobile Phase B: 90:10 ACN:water with 0.1% TFA; Temperature: 40° C.; Gradient: 0-100% B over 1.5 min; Flow: 1 mL/min).

Example 15

1-[3-(Dimethyl-1H-1,2,3-triazol-5-yl)-5-[(S)-oxan-4-yl(phenyl)methyl]-5H-pyrido[3,2-b]indol-8-yl]-4-(oxetan-3-yl)piperazine

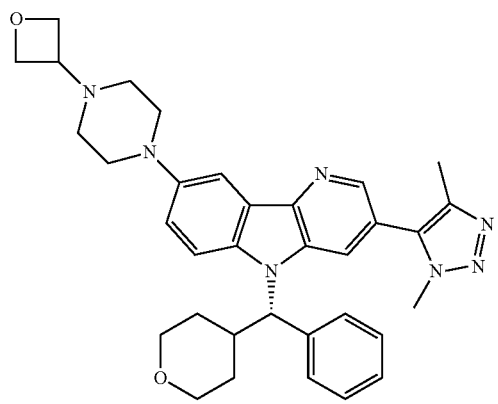 [SMILES: Cc1nnn(C)c1-c1cnc2c3cc(N4CCN(C5COC5)CC4)ccc3n([C@H](c3ccccc3)C3CCOCC3)c2c1]

To a 50 mL round-bottomed flask containing (S)-3-(1,4-dimethyl-1H-1,2,3-triazol-5-yl)-5-(phenyl(tetrahydro-2H-pyran-4-yl)methyl)-8-(piperazin-1-yl)-5H-pyrido[3,2-b]indole (62.6 mg, 12.0 mmol) and 3-oxetanone (0.077 mL, 1.20 mmol) was added THF (5 mL) to give a solution. The reaction mixture was diluted with MeOH (5 mL) and acetic acid (1 mL). Sodium cyanoborohydride (22.6 mg, 0.360 mmol) was then added over 5 min. After 16 h, the reaction mixture was diluted with acetic acid (1 mL), and sodium cyanoborohydride (22.6 mg, 0.360 mmol) was added, and the mixture heated to 60° C. After 16 h, sodium triacetoxyborohydride (254 mg, 1.20 mmol) was added. After 16 h, zinc chloride (16.4 mg, 0.120 mmol) was added. After 72 h, the reaction was partitioned between ethyl acetate and 1N aq. NaOH. The organic layer was dried with $Na_2SO_4$, filtered, and concentrated under reduced pressure. The crude material was purified via preparative LC/MS with the following conditions: Column: Waters XBridge C18, 19×200 mm, 5-μm particles; Mobile Phase A: 5:95 ACN: water with 10 mM $NH_4OAc$; Mobile Phase B: 95:5 ACN: water with 10 mM $NH_4OAc$; Gradient: 5-55% B over 25 min, then a 5-min hold at 100% B; Flow: 20 mL/min. Fractions containing the desired product were combined and dried via centrifugal evaporation. $^1H$ NMR (500 MHz, DMSO-$d_6$) δ 8.49-8.35 (m, 2H), 7.99 (br. s., 1H), 7.71-7.56 (m, 3H), 7.38 (d, J=8.4 Hz, 1H), 7.35-7.28 (m, 2H), 7.27-7.19 (m, 1H), 5.72 (d, J=11.1 Hz, 1H), 4.64-4.56 (m, 2H), 4.50 (t, J=5.9 Hz, 2H), 4.01 (s, 3H), 3.88 (d, J=9.4 Hz, 1H), 3.73 (d, J=8.8 Hz, 1H), 3.52-3.45 (m, 2H), 3.41-3.24 (m, 2H), 3.21 (br. s., 4H), 2.48 (br. s., 3H), 2.30 (s, 4H), 1.66 (d, J=12.1 Hz, 1H), 1.58-1.45 (m, 1H), 1.34-1.24 (m, 1H), 1.02 (d, J=11.8 Hz, 1H). LCMS (M+H)=578; HPLC RT=0.73 min (Column: Waters Acquity BEH C18 2.0×50 mm; Mobile Phase A: 10:90 ACN:water with 0.1% TFA; Mobile Phase B: 90:10 ACN:water with 0.1% TFA; Temperature: 40° C.; Gradient: 0-100% B over 1.5 min; Flow: 1 mL/min).

Example 16

1,4-Dimethyl-5-{5-[(S)-oxan-4-yl(phenyl)methyl]-7-[1-(propan-2-yl)-1H-pyrazol-4-yl]-5H-pyrido[3,2-b]indol-3-yl}-1H-1,2,3-triazole

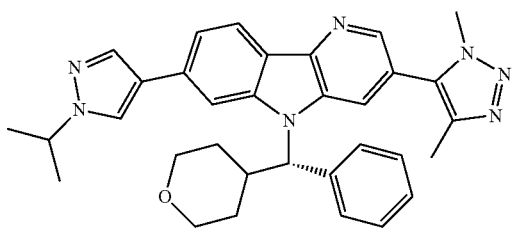 [SMILES: Cc1nnn(C)c1-c1cnc2c3ccc(-c4cnn(C(C)C)c4)cc3n([C@H](c3ccccc3)C3CCOCC3)c2c1]

Step 1: (S)-7-Chloro-3-(1,4-dimethyl-1H-1,2,3-triazol-5-yl)-5-(phenyl(tetrahydro-2H-pyran-4-yl)methyl)-5H-pyrido[3,2-b]indole A 25 mL round bottomed flask was charged with 7-chloro-3-(1,4-dimethyl-1H-1,2,3-triazol-5-yl)-5H-pyrido[3,2-b]indole (0.500 g, 1.68 mmol), (R)-phenyl(tetrahydro-2H-pyran-4-yl)methanol (0.549 g, 2.85 mmol) and triphenylphosphine (0.749 g, 2.85 mmol), a stir bar, and 6 mL DCM. The suspension was stirred while adding DIAD (0.555 mL, 2.85 mmol) dropwise, and the resulting solution stirred overnight. The reaction was purified on an 80 g ISCO column, eluting with 50% EtOAc/hexane for 400 mL, then 20% B/EtOAc to 70% B/EtOAc over 1200 mL. B=10% 2M ammonia in MeOH/90% EtOAc. Fractions containing the title compound were concentrated to afford 225 mg of a glassy white solid. LC/MS using LC/MS Method 6: HPLC RT=0.99 min. $^1H$ NMR (400 MHz, DMSO-$d_6$) δ 8.56 (d, J=1.5 Hz, 1H), 8.46 (br. s., 2H), 8.22 (d, J=8.5 Hz, 1H), 7.68 (d, J=7.3 Hz, 2H), 7.62 (s, 1H), 7.39-7.30 (m, 3H), 7.28-7.19 (m, 1H), 5.86 (d, J=11.3 Hz, 1H), 4.01-3.95 (m, 3H), 3.88 (d, J=11.0 Hz, 1H), 3.73 (d, J=11.0 Hz, 1H), 2.36-2.31 (m, 1H), 2.28 (s, 3H), 1.71-1.64 (m, 1H), 1.55 (d, J=13.6 Hz, 1H), 1.31 (d, J=12.0 Hz, 1H), 0.95 (d, J=13.6 Hz, 1H).

Step 2: 1,4-Dimethyl-5-{5-[(S)-oxan-4-yl(phenyl)methyl]-7-[1-(propan-2-yl)-1H-pyrazol-4-yl]-5H-pyrido[3,2-b]indol-3-yl}-1H-1,2,3-triazole (S)-7-Chloro-3-(1,4-dimethyl-1H-1,2,3-triazol-5-yl)-5-(phenyl(tetrahydro-2H-pyran-4-yl)methyl)-5H-pyrido[3,2-b]indole (47.2 mg, 0.100 mmol) and 1-isopropyl-4-(4,4,5,5-tetramethyl-1,3,2-dioxaborolan-2-yl)-1H-pyrazole (47.2 mg, 0.200 mmol) were dissolved in 1.7 mL dioxane. To this was added sodium carbonate (300 μL, 0.300 mmol) and $PdCl_2(dppf)$-$CH_2Cl_2$ adduct (8.2 mg, 10.0 μmol). Argon was bubbled through the mixture for 1 min while sonicating. The vial was sealed and heated in an oil bath at 100° C. for 4 h. Heat was discontinued, stirred 3 days at room temperature, and filtered. The crude material was purified via preparative LC/MS (Preparative HPLC Method 3), except with a gradient of 25-65% B over 20 min. Fractions containing the desired product were combined and dried via centrifugal evaporation. The yield of the product was 6.7 mg, and its estimated purity by LCMS analysis was 94%. Injection 1: LC/MS Method 3, HPLC RT=1.798. Injection 2: LC/MS Method 4, HPLC RT=3.125 min. $^1H$ NMR (500 MHz, DMSO-$d_6$) δ 8.45 (s, 1H), 8.48 (s, 1H), 8.18 (d, J=8.1 Hz, 1H), 8.14 (s, 1H), 7.72 (d, J=7.7 Hz, 2H), 7.33 (d, J=7.7 Hz, 2H), 7.25 (s, 1H), 4.64-4.54 (m, 1H), 3.99 (s, 3H), 4.01-3.96 (m, 3H), 3.94-3.87 (m, 1H), 3.79-3.69 (m, 1H), 3.33-3.23 (m, 1H), 2.28 (s, 3H), 1.79-1.68 (m, 2H), 1.65-1.55 (m, 1H), 1.52 (d, J=6.6 Hz, 6H), 1.42-1.30 (m, 1H), 1.29-1.20 (m, 2H), 1.06-0.97 (m, 2H).

Example 17

5-[7-(3,5-Dimethyl-1H-pyrazol-4-yl)-5-[(S)-oxan-4-yl(phenyl)methyl]-5H-pyrido[3,2-b]indol-3-yl]-1,4-dimethyl-1H-1,2,3-triazole

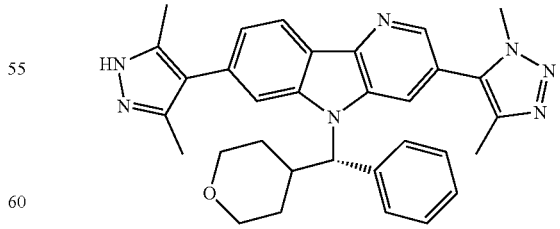

(S)-7-Chloro-3-(1,4-dimethyl-1H-1,2,3-triazol-5-yl)-5-(phenyl(tetrahydro-2H-pyran-4-yl)methyl)-5H-pyrido[3,2-b]indole (47.2 mg, 0.100 mmol) and 3,5-dimethyl-4-(4,4,5,5-tetramethyl-1,3,2-dioxaborolan-2-yl)-1H-pyrazole (44.4 mg, 0.200 mmol) were dissolved in 1.7 mL dioxane. To this was added sodium carbonate (300 μL, 0.300 mmol) and PdCl$_2$(dppf)-CH$_2$Cl$_2$ adduct (8.2 mg, 10.0 μmol). Argon was bubbled through the mixture for 1 min while sonicating. The vial was sealed and heated in an oil bath at 100° C. for 4 h. Heat was discontinued, the reaction stirred for 12 h and filtered. The crude material was purified via preparative LC/MS using Preparative HPLC Method 2, except using gradient 40-80% B over 20 min. Fractions containing the desired product were combined and dried via centrifugal evaporation. The material was further purified via preparative HPLC Method 3. Fractions containing the desired product were combined and dried via centrifugal evaporation. The yield of the product was 3.2 mg, and its estimated purity by LCMS analysis was 97%. Injection 1: LC/MS Method 3, HPLC RT=1.47. Injection 2: LC/MS Method 4, HPLC RT=2.895 min. $^1$H NMR (500 MHz, DMSO-d$_6$) δ 8.55 (s, 1H), 8.35 (br. s., 1H), 8.25 (d, J=8.1 Hz, 1H), 7.68 (d, J=7.3 Hz, 2H), 7.37-7.30 (m, 2H), 7.30-7.22 (m, 2H), 7.17 (s, 1H), 7.06 (s, 1H), 5.88 (d, J=11.0 Hz, 1H), 4.04 (br. s., 3H), 3.88 (d, J=10.3 Hz, 1H), 3.73 (d, J=9.9 Hz, 1H), 3.56 (br. s., 3H), 3.54-3.39 (m, 1H), 3.31-3.21 (m, 1H), 2.56 (t, J=5.3 Hz, 1H), 2.32 (d, J=9.2 Hz, 7H), 1.70 (br. s., 1H), 1.56 (d, J=12.5 Hz, 1H), 1.31 (d, J=12.1 Hz, 1H), 1.02 (d, J=11.7 Hz, 1H).

Example 18

5-[3-(Dimethyl-1H-1,2,3-triazol-5-yl)-5-[(S)-oxan-4-yl(phenyl)methyl]-5H-pyrido[3,2-b]indol-7-yl]-4-($^2$H$_3$)methyl-1-methyl-1H-1,2,3-triazole

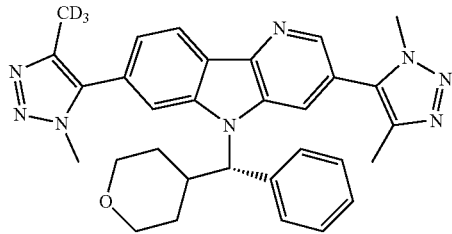 [SMILES: [2H]C([2H])([2H])c1nnn(C)c1-c1ccc2c3ncc(-c4c(C)nnn4C)cc3n([C@H](c3ccccc3)C3CCOCC3)c2c1]

(S)-7-Chloro-3-(1,4-dimethyl-1H-1,2,3-triazol-5-yl)-5-(phenyl(tetrahydro-2H-pyran-4-yl)methyl)-5H-pyrido[3,2-b]indole (47.2 mg, 0.1 mmol) was dissolved in 2 mL DMF. To this was added 4-($^2$H$_3$)methyl-1-methyl-1H-1,2,3-triazole (40.1 mg, 0.400 mmol), PdCl$_2$(dppf)-CH$_2$Cl$_2$Adduct (8.2 mg, 10.0 μmol) and tetramethylammonium acetate (33.3 mg, 0.250 mmol). Bubbled in argon for 1 min while sonicating. The vial was sealed and heated in the microwave at 100° C. for 1 h. The crude material was purified via preparative LC/MS with the following conditions: Column: XBridge C18, 19×200 mm, 5-μm particles; Mobile Phase A: 5:95 ACN: water with 0.1% trifluoroacetic acid; Mobile Phase B: 95:5 ACN: water with 0.1% trifluoroacetic acid; Gradient: 15-55% B over 15 min, then a 5 min hold at 100% B; Flow: 20 mL/min. Fractions containing the desired product were combined and dried via centrifugal evaporation. The yield of the product was 2.4 mg, and its estimated purity by LCMS analysis was 97%. Two analytical LC/MS injections were used to determine the final purity. Injection 1 conditions: Column: Waters BEH C18, 2.0×50 mm, 1.7-μm particles; Mobile Phase A: 5:95 ACN:water with 10 mM NH$_4$OAc, Rt=1.44 min, M+H=536; Mobile Phase B: 95:5 ACN:water with 10 mM NH$_4$OAc; Temperature: 50° C.; Gradient: 0% B, 0-100% B over 3 min, then a 0.5 min hold at 100% B; Flow: 1 mL/min; Detection: UV at 220 nm. Injection 2 conditions: Column: Waters BEH C18, 2.0×50 mm, 1.7-μm particles; Mobile Phase A: 5:95 MeOH:water with 10 mM NH$_4$OAc Mobile Phase B: 95:5 MeOH:water with 10 mM NH$_4$OAc; Temperature: 50° C.; Gradient: 0% B, 0-100% B over 3 min, then a 0.5 min hold at 100% B; Flow: 0.5 mL/min, Rt=2.42 min, M+H=536; Detection: UV at 220 nm. $^1$H NMR (500 MHz, DMSO-d$_6$) δ 8.60 (s, 2H), 8.39 (d, J=8.1 Hz, 1H), 7.70 (d, J=7.7 Hz, 2H), 7.43 (d, J=7.7 Hz, 1H), 7.37-7.30 (m, 2H), 7.29-7.20 (m, 1H), 5.92 (d, J=11.4 Hz, 1H), 4.10-3.97 (m, 5H), 3.88 (d, J=10.3 Hz, 1H), 3.73 (d, J=8.8 Hz, 1H), 3.58-3.46 (m, 7H), 3.26 (t, J=11.4 Hz, 1H), 2.36-2.23 (m, 3H), 1.70 (d, J=13.2 Hz, 1H), 1.54 (d, J=8.8 Hz, 1H), 1.33 (d, J=9.5 Hz, 1H), 1.03 (d, J=11.7 Hz, 1H).

Example 19

2-[3-(Dimethyl-1H-1,2,3-triazol-5-yl)-6-methanesulfonyl-5-[(S)-oxan-4-yl(phenyl)methyl]-5H-pyrido[3,2-b]indol-9-yl]-1λ$^6$,2-thiazolidine-1,1-dione

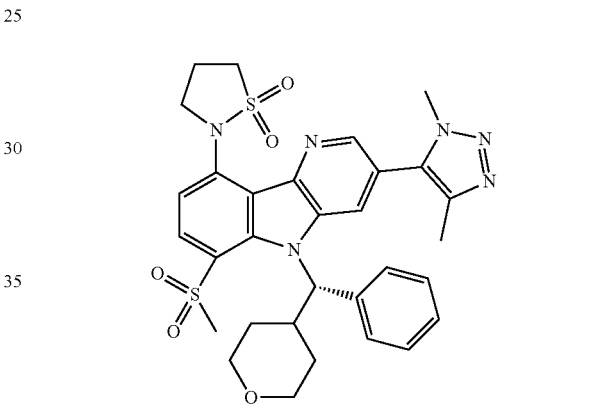

To a stirred solution of 5-{9-fluoro-6-methanesulfonyl-5-[(S)-oxan-4-yl(phenyl)methyl]-5H-pyrido[3,2-b]indol-3-yl}-1,4-dimethyl-1H-1,2,3-triazole (25.0 mg, 0.0500 mmol) and isothiazolidine-1,1-dione (5.7 mg, 0.0500 mmol) in DMF (0.25 mL) was added t-BuOK (21.0 mg, 0.190 mmol). This mixture was heated at 65° C. for 1.5 h and cooled to room temperature. The mixture was then diluted with MeOH and purified via preparative LC/MS with the following conditions: Column: Waters XBridge Phenyl, 19×200 mm, 5-μm particles; Mobile Phase A: 5:95 ACN: water with 10 mM NH$_4$OAc; Mobile Phase B: 95:5 ACN: water with 10 mM NH$_4$OAc; Gradient: 15-70% B over 20 min, then a 5-min hold at 100% B; Flow: 20 mL/min. Fractions containing the desired product were combined and dried via centrifugal evaporation to give 2-[3-(dimethyl-1H-1,2,3-triazol-5-yl)-6-methanesulfonyl-5-[(S)-oxan-4-yl(phenyl)methyl]-5H-pyrido[3,2-b]indol-9-yl]-1λ$^6$,2-thiazolidine-1,1-dione (12.3 mg, 41%). $^1$H NMR (500 MHz, DMSO-d$_6$) δ 8.72 (s, 1H), 8.38 (d, J=8.4 Hz, 1H), 7.88 (s, 1H), 7.62 (br d, J=8.4 Hz, 3H), 7.36-7.30 (m, 2H), 7.27 (br d, J=7.1 Hz, 1H), 6.81 (br d, J=10.1 Hz, 1H), 4.11 (br d, J=2.0 Hz, 2H), 3.86 (br d, J=9.8 Hz, 1H), 3.76 (s, 3H), 3.74 (s, 2H), 3.64 (br d, J=8.8 Hz, 1H), 3.57 (br t, J=7.4 Hz, 1H), 3.19 (br t, J=12.1 Hz, 1H), 2.65-2.57 (m, 2H), 2.54 (s, 3H), 2.07 (s, 3H), 1.95

(br d, J=12.5 Hz, 1H), 1.75-1.56 (m, 2H), 0.42 (br d, J=12.1 Hz, 1H). LCMS: RT=1.414 min; (ES): m/z (M+H)+=634.95; LCMS: Column: Waters Acquity UPLC BEH C18, 2.1×50 mm, 1.7-μm particles; Mobile Phase A: 5:95 ACN:water with 10 mM NH$_4$OAc; Mobile Phase B: 95:5 ACN:water with 10 mM NH$_4$OAc; Temperature: 50° C.; Gradient: 0-100% B over 3 min, then a 0.75-min hold at 100% B; Flow: 1.11 mL/min. HPLC Purity at 220 nm: 100%.

Example 20

2-[3-(Dimethyl-1H-1,2,3-triazol-5-yl)-6-methanesulfonyl-5-[(S)-oxan-4-yl(phenyl)methyl]-5H-pyrido[3,2-b]indol-9-yl]-1λ$^6$,2-thiazinane-1,1-dione

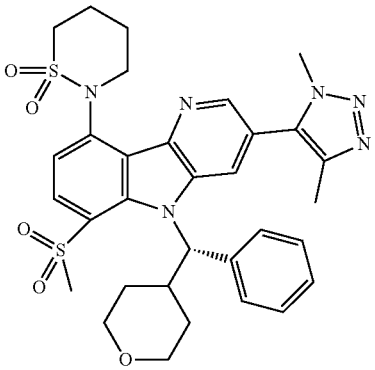 [SMILES: Cc1nnn(C)c1-c1cnc2c3c(N4CCCCS4(=O)=O)ccc(S(C)(=O)=O)c3n([C@H](c3ccccc3)C3CCOCC3)c2c1]

To a stirred mixture of 5-{9-fluoro-6-methanesulfonyl-5-[(S)-oxan-4-yl(phenyl)methyl]-5H-pyrido[3,2-b]indol-3-yl}-1,4-dimethyl-1H-1,2,3-triazole (25.0 mg, 0.047 mmol) and 1,2-thiazinane 1,1-dioxide (19.0 mg, 0.141 mmol) in NMP (0.25 mL) was added t-BuOK (21.0 mg, 0.187 mmol). The mixture was heated at 65° C. for 3 h and cooled to room temperature. The mixture was directly purified via preparative LC/MS with the following conditions: Column: Waters XBridge Phenyl, 19×200 mm, 5-μm particles; Mobile Phase A: 5:95 ACN: water with 10 mM NH$_4$OAc; Mobile Phase B: 95:5 ACN: water with 10 mM NH$_4$OAc; Gradient: 15-70% B over 20 min, then a 5 min hold at 100% B; Flow: 20 mL/min. Fractions containing the desired product were combined and dried via centrifugal evaporation to give 2-[3-(dimethyl-1H-1,2,3-triazol-5-yl)-6-methanesulfonyl-5-[(S)-oxan-4-yl(phenyl)methyl]-5H-pyrido[3,2-b]indol-9-yl]-1λ$^6$,2-thiazinane-1,1-dione (2.6 mg, 8.38%). $^1$H NMR (500 MHz, DMSO-d$_6$) δ 8.71 (s, 1H), 8.33 (d, J=8.4 Hz, 1H), 7.85 (br s, 1H), 7.62 (br s, 2H), 7.55 (br d, J=8.4 Hz, 1H), 7.33 (br t, J=7.1 Hz, 2H), 7.27 (br d, J=7.1 Hz, 1H), 6.79 (br d, J=10.1 Hz, 1H), 3.86 (br d, J=11.4 Hz, 1H), 3.77 (s, 3H), 3.74 (s, 2H), 3.64 (br d, J=8.8 Hz, 1H), 3.54-3.32 (m, 2H), 3.18 (br s, 1H), 2.54 (s, 3H), 2.30 (br d, J=14.5 Hz, 3H), 2.21-2.14 (m, 1H), 2.07 (br s, 3H), 1.95 (br d, J=12.8 Hz, 1H), 1.79-1.56 (m, 3H), 0.54-0.29 (m, 1H); LCMS: RT=1.631 min; (ES): m/z (M+H)+=649.05; LCMS: Column: Waters Acquity UPLC BEH C18, 2.1×50 mm, 1.7-μm particles; Mobile Phase A: 5:95 ACN:water with 10 mM NH$_4$OAc; Mobile Phase B: 95:5 ACN:water with 10 mM NH$_4$OAc; Temperature: 50° C.; Gradient: 0-100% B over 3 min, then a 0.75 min hold at 100% B; Flow: 1.11 mL/min. HPLC Purity @ 220 nm: 98%.

Example 21

1-[3-(Dimethyl-1H-1,2,3-triazol-5-yl)-6-methanesulfonyl-5-[(S)-oxan-4-yl(phenyl)methyl]-5H-pyrido[3,2-b]indol-9-yl]piperazine

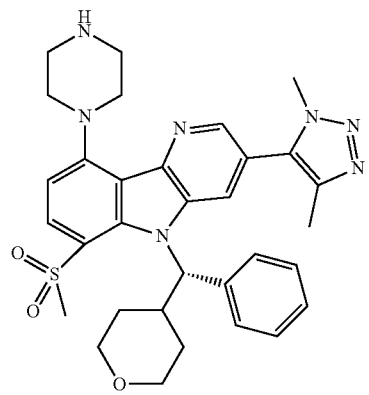 [SMILES: Cc1nnn(C)c1-c1cnc2c3c(N4CCNCC4)ccc(S(C)(=O)=O)c3n([C@H](c3ccccc3)C3CCOCC3)c2c1]

Step 1: tert-Butyl 4-[3-(dimethyl-1H-1,2,3-triazol-5-yl)-6-methanesulfonyl-5-[(S)-oxan-4-yl(phenyl) methyl]-5H-pyrido[3,2-b]indol-9-yl]piperazine-1-carboxylate 5-{9-Fluoro-6-methanesulfonyl-5-[(S)-oxan-4-yl(phenyl)methyl]-5H-pyrido[3,2-b]indol-3-yl}-1,4-dimethyl-1H-1,2,3-triazole (95.0 mg, 0.180 mmol) and tert-butyl piperazine-1-carboxylate (232 mg, 1.25 mmol) were combined in NMP (1.50 mL) and heated at 80° C. for 4 h, at which time the temperature was increased to 95° C. for another 3 h. The mixture was cooled to room temperature and diluted with EtOAc. The resulting mixture was washed with 10% aq. LiCl solution. The EtOAc layer was separated, dried (MgSO$_4$), filtered, and concentrated to give the crude mixture. The crude material was purified by silica gel column chromatography (Teledyne ISCO CombiFlash 0% to 100% solvent A/B=hexane/EtOAc, RediSep SiO$_2$ 24 g, detecting at 254 nM, and monitoring at 220 nM). Concentration of appropriate fractions provided tert-butyl 4-[3-(dimethyl-1H-1,2,3-triazol-5-yl)-6-methanesulfonyl-5-[(S)-oxan-4-yl (phenyl)methyl]-5H-pyrido[3,2-b]indol-9-yl]piperazine-1-carboxylate (114 mg. 91%). $^1$H NMR (500 MHz, DMSO-d$_6$) δ 8.64 (s, 1H), 8.22 (d, J=8.8 Hz, 1H), 7.75 (s, 1H), 7.57 (br d, J=7.7 Hz, 2H), 7.36-7.28 (m, 2H), 7.27-7.21 (m, 1H), 6.99 (d, J=8.8 Hz, 1H), 6.76 (br d, J=10.1 Hz, 1H), 3.85 (br d, J=9.1 Hz, 1H), 3.74 (s, 3H), 3.70-3.62 (m, 2H), 3.54-3.46 (m, 1H), 3.23-3.13 (m, 1H), 2.54 (s, 3H), 2.50 (br s, 4H), 2.06 (s, 4H), 1.95 (br d, J=12.5 Hz, 1H), 1.70 (br d, J=9.4 Hz, 1H), 1.58 (br d, J=8.8 Hz, 1H), 1.43 (s, 12H), 0.41 (br d, J=11.4 Hz, 1H). HPLC: RT=3.155 min (Chromolith ODS 4.6×50 mm (4 min grad) eluting with 10-90% aqueous MeOH over 4 min containing 0.1% TFA, 4 mL/min, monitoring at 220 nm); LCMS (ES): m/z=700.3 [M+H]+.

Step 2: 1-[3-(Dimethyl-1H-1,2,3-triazol-5-yl)-6-methanesulfonyl-5-[(S)-oxan-4-yl(phenyl)methyl]-5H-pyrido[3,2-b]indol-9-yl]piperazine tert-Butyl 4-[3-(dimethyl-1H-1,2,3-triazol-5-yl)-6-methanesulfonyl-5-[(S)-oxan-4-yl(phenyl)methyl]-5H-pyrido[3,2-b]indol-9-yl]piperazine-1-carboxylate (96.0 mg, 0.140 mmol) was dissolved in DCM (2 mL) and treated with TFA (1 mL, 13.0 mmol). The mixture was stirred at room temperature for 15 min and concentrated to give the crude product, 1-[3-(dimethyl-1H-1,2,3-triazol-5-yl)-6-methanesulfonyl-5-[(S)-oxan-4-yl(phenyl)methyl]-5H-pyrido[3,2-b]indol-9-yl]piperazine (52.4 mg). 10.0 mg of this crude product was further purified via preparative LC/MS with the following conditions: Column: Waters XBridge Phenyl, 19×200 mm, 5-μm particles; Mobile Phase A: 5:95 ACN: water with 10 mM NH$_4$OAc; Mobile Phase B: 95:5 ACN: water with 10 mM NH$_4$OAc; Gradient: 15-70% B over 20 min, then a 5-min hold at 100% B; Flow: 20 mL/min. Fractions containing the desired product were combined and dried via centrifugal evaporation to give 1-[3-(dimethyl-1H-1,2,3-triazol-5-yl)-6-methanesulfonyl-5-[(S)-oxan-4-yl(phenyl)methyl]-5H-pyrido[3,2-b]indol-9-yl]piperazine (8.7 mg, 10.6%). $^1$H NMR (500 MHz, DMSO-d$_6$) δ 8.56 (s, 1H), 8.17 (d, J=8.8 Hz, 1H), 7.68 (s, 1H), 7.51 (br d, J=7.7 Hz, 2H), 7.33-7.24 (m, 2H), 7.23-7.17 (m, 1H), 6.95 (br d, J=8.8 Hz, 1H), 6.70 (br d, J=10.1 Hz, 1H), 3.80 (br d, J=11.8 Hz, 1H), 3.53 (s, 1H), 3.47-3.39 (m, 1H), 3.34 (br s, 2H), 3.27 (br d, J=10.1 Hz, 1H), 3.18-3.12 (m, 1H), 3.08 (br s, 3H), 2.46 (br s, 7H), 2.00 (s, 3H), 1.91 (br d, J=12.5 Hz, 1H), 1.82 (s, 3H), 1.65 (br d, J=12.5 Hz, 1H), 1.53 (br d, J=12.5 Hz, 1H), 0.36 (br d, J=12.8 Hz, 1H); LCMS: RT=1.230 min; (ES): m/z (M+H)+=600.10; LCMS: Column: Waters Acquity UPLC BEH C18, 2.1×50 mm, 1.7-μm particles; Mobile Phase A: 5:95 ACN:water with 10 mM NH$_4$OAc; Mobile Phase B: 95:5 ACN:water with 10 mM NH$_4$OAc; temperature: 50° C.; Gradient: 0-100% B over 3 min, then a 0.75-min hold at 100% B; Flow: 1.11 mL/min. HPLC Purity at 220 nm: 100%.

Example 22

2-{4-[3-(Dimethyl-1H-1,2,3-triazol-5-yl)-6-methanesulfonyl-5-[(S)-oxan-4-yl(phenyl)methyl]-5H-pyrido[3,2-b]indol-9-yl]piperazin-1-yl}acetamide

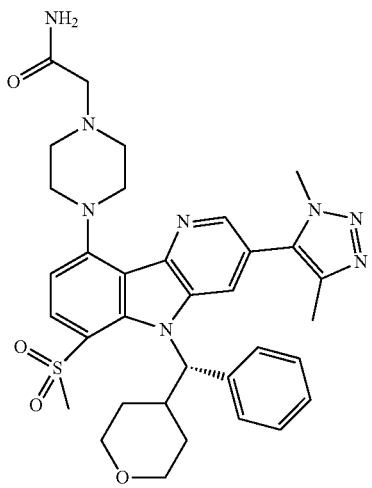 [SMILES: Cc1nnn(C)c1-c1cnc2c3c(N4CCN(CC(N)=O)CC4)ccc(S(C)(=O)=O)c3n([C@H](c3ccccc3)C3CCOCC3)c2c1]

To a stirred mixture of tert-butyl 4-[3-(dimethyl-1H-1,2,3-triazol-5-yl)-6-methanesulfonyl-5-[(S)-oxan-4-yl(phenyl)methyl]-5H-pyrido[3,2-b]indol-9-yl]piperazine-1-carboxylate (20.0 mg, 0.033 mmol) and 2-bromoacetamide (9.2 mg, 0.067 mmol) in DMF (1.0 mL) was added Cs$_2$CO$_3$ (16.3 mg, 0.050 mmol). The mixture was stirred at room temperature for 30 min and then directly purified via preparative LC/MS with the following conditions: Column: Waters XBridge Phenyl, 19×200 mm, 5-μm particles; Mobile Phase A: 5:95 ACN: water with 10 mM NH$_4$OAc; Mobile Phase B: 95:5 ACN: water with 10 mM NH$_4$OAc; Gradient: 15-70% B over 20 min, then a 5 min hold at 100% B; Flow: 20 mL/min. Fractions containing the desired product were combined and dried via centrifugal evaporation to give 2-{4-[3-(dimethyl-1H-1,2,3-triazol-5-yl)-6-methanesulfonyl-5-[(S)-oxan-4-yl(phenyl)methyl]-5H-pyrido[3,2-b]indol-9-yl]piperazin-1-yl}acetamide (14.8 mg, 64.2%). $^1$H NMR (500 MHz, DMSO-d$_6$) δ 8.62 (s, 1H), 8.26 (d, J=8.8 Hz, 1H), 8.01 (br s, 1H), 7.75 (br d, J=15.5 Hz, 2H), 7.56 (br d, J=7.7 Hz, 2H), 7.37-7.21 (m, 4H), 7.18 (s, 1H), 7.08 (s, 1H), 7.04 (s, 1H), 6.75 (br d, J=10.1 Hz, 1H), 4.06 (s, 3H), 3.85 (br d, J=6.7 Hz, 1H), 3.69-3.57 (m, 8H), 3.48 (br t, J=11.9 Hz, 1H), 3.37-3.26 (m, 1H), 3.21-3.12 (m, 1H), 2.50 (br s, 3H), 2.05 (s, 3H), 1.95 (br d, J=12.1 Hz, 1H), 1.75-1.64 (m, 1H), 1.57 (br d, J=8.1 Hz, 1H), 0.37 (br d, J=11.4 Hz, 1H); LCMS: RT=1.312 min; (ES): m/z (M+H)+=657.10; LCMS: Column: Waters Acquity UPLC BEH C18, 2.1×50 mm, 1.7-μm particles; Mobile Phase A: 5:95 ACN:water with 10 mM NH$_4$OAc; Mobile Phase B: 95:5 ACN:water with 10 mM NH$_4$OAc; Temperature: 50° C.; Gradient: 0-100% B over 3 min, then a 0.75 min hold at 100% B; Flow: 1.11 mL/min. HPLC Purity @ 220 nm: 95%.

Example 23

1-[3-(Dimethyl-1H-1,2,3-triazol-5-yl)-6-methanesulfonyl-5-[(S)-oxan-4-yl(phenyl)methyl]-5H-pyrido[3,2-b]indol-9-yl]-4-(oxetan-3-yl)piperazine

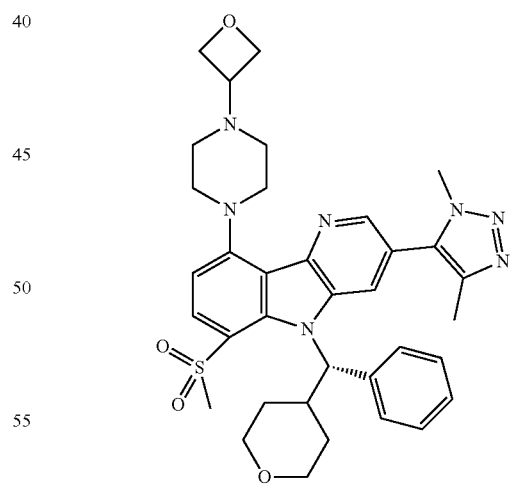

Step 1: 1-[3-(Dimethyl-1H-1,2,3-triazol-5-yl)-6-methanesulfonyl-5-[(S)-oxan-4-yl(phenyl)methyl]-5H-pyrido[3,2-b]indol-9-yl]piperazine tert-Butyl 4-[3-(dimethyl-1H-1,2,3-triazol-5-yl)-6-methanesulfonyl-5-[(S)-oxan-4-yl(phenyl)methyl]-5H-pyrido[3,2-b]indol-9-yl]piperazine-1-carboxylate (96.0 mg, 0.14 mmol) was dissolved in DCM (2 mL) and treated with TFA (1 mL, 13.0 mmol). The mixture was stirred at room temperature for 15 min and concentrated to give the crude product 1-[3-(dimethyl-H-1,2,3-triazol-5-yl)-6-methanesulfonyl-5-[(S)-oxan-4-yl(phenyl)methyl]-5H-pyrido[3,2-b]indol-9-yl]piperazine (52.4 mg). 10 mg of this crude product was further purified via preparative LC/MS with the following conditions: Column: Waters XBridge Phenyl, 19×200 mm, 5-μm particles; Mobile Phase A: 5:95 ACN: water with 10 mM NH$_4$OAc; Mobile Phase B: 95:5 ACN: water with 10 mM NH$_4$OAc; Gradient: 15-70% B over 20 min, then a 5 min hold at 100% B; Flow: 20 mL/min. Fractions containing the desired product were combined and dried via centrifugal evaporation to give 1-[3-(dimethyl-1H-1,2,3-triazol-5-yl)-6-methanesulfonyl-5-[(S)-oxan-4-yl(phenyl)methyl]-5H-pyrido[3,2-b]indol-9-yl]piperazine (8.7 mg, 10.6%). $^1$H NMR (500 MHz, DMSO-d$_6$) δ 8.56 (s, 1H), 8.17 (d, J=8.8 Hz, 1H), 7.68 (s, 1H), 7.51 (br d, J=7.7 Hz, 2H), 7.33-7.24 (m, 2H), 7.23-7.17 (m, 1H), 6.95 (br d, J=8.8 Hz, 1H), 6.70 (br d, J=10.1 Hz, 1H), 3.80 (br d, J=11.8 Hz, 1H), 3.53 (s, 1H), 3.47-3.39 (m, 1H), 3.34 (br s, 2H), 3.27 (br d, J=10.1 Hz, 1H), 3.18-3.12 (m, 1H), 3.08 (br s, 3H), 2.46 (br s, 7H), 2.00 (s, 3H), 1.91 (br d, J=12.5 Hz, 1H), 1.82 (s, 3H), 1.65 (br d, J=12.5 Hz, 1H), 1.53 (br d, J=12.5 Hz, 1H), 0.36 (br d, J=12.8 Hz, 1H); LCMS: RT=1.230 min; (ES): m/z (M+H)$^+$=600.10; LCMS: Column: Waters Acquity UPLC BEH C18, 2.1×50 mm, 1.7-μm particles; Mobile Phase A: 5:95 ACN:water with 10 mM NH$_4$OAc; Mobile Phase B: 95:5 ACN:water with 10 mM NH$_4$OAc; Temperature: 50° C.; Gradient: 0-100% B over 3 min, then a 0.75 min hold at 100% B; Flow: 1.11 mL/min. HPLC Purity @ 220 nm: 100%.

Step 2: 1-[3-(Dimethyl-1H-1,2,3-triazol-5-yl)-6-methanesulfonyl-5-[(S)-oxan-4-yl(phenyl)methyl]-5H-pyrido[3,2-b]indol-9-yl]-4-(oxetan-3-yl)piperazine To a stirred mixture of 1-[3-(dimethyl-1H-1,2,3-triazol-5-yl)-6-methanesulfonyl-5-[(S)-oxan-4-yl(phenyl)methyl]-5H-pyrido[3,2-b]indol-9-yl]piperazine (20.0 mg, 0.033 mmol) and 3-oxetanone (0.021 mL, 0.033 mmol) in MeOH (0.3 mL) was added THF (0.30 mL) and HOAc (0.30 mL). The mixture at room temperature was added sodium cyanoborohydride (6.3 mg, 0.10 mmol). The mixture was stirred at room temperature for 15 min, and then diluted with saturated NaHCO$_3$ solution (8 mL). The mixture was concentrated and diluted with water (10 ml). The aqueous mixture was extracted with EtOAc. The combined EtOAc extracts were dried over MgSO$_4$, filtered and concentrated to give a crude oil. The crude product was purified via preparative LC/MS with the following conditions: Column: Waters XBridge Phenyl, 19×200 mm, 5-μm particles; Mobile Phase A: 5:95 ACN: water with 10 mM NH$_4$OAc; Mobile Phase B: 95:5 ACN: water with 10 mM NH$_4$OAc; Gradient: 15-70% B over 20 min, then a 5 min hold at 100% B; Flow: 20 mL/min. Fractions containing the desired product were combined and dried via centrifugal evaporation to give 1-[3-(dimethyl-1H-1,2,3-triazol-5-yl)-6-methanesulfonyl-5-[(S)-oxan-4-yl(phenyl)methyl]-5H-pyrido[3,2-b]indol-9-yl]-4-(oxetan-3-yl)piperazine (16.9 mg, 73.4%). $^1$H NMR (500 MHz, DMSO-d$_6$) δ 8.56 (s, 1H), 8.23 (d, J=8.8 Hz, 1H), 7.74 (s, 1H), 7.52 (br d, J=7.7 Hz, 2H), 7.31-7.18 (m, 3H), 7.04-6.99 (m, 1H), 6.71 (br d, J=10.1 Hz, 1H), 4.76 (br s, 3H), 4.57-4.47 (m, 1H), 3.81 (br d, J=9.1 Hz, 1H), 3.70-3.51 (m, 4H), 3.44 (br t, J=11.3 Hz, 1H), 3.35-3.22 (m, 2H), 3.18-3.08 (m, 1H), 2.50 (s, 3H), 2.46 (br s, 8H), 2.02 (s, 3H), 1.91 (br d, J=12.1 Hz, 1H), 1.65 (br d, J=10.8 Hz, 1H), 1.54 (br d, J=8.4 Hz, 1H), 0.34 (br d, J=11.4 Hz, 1H); LCMS: RT=1.365 min; (ES): m/z (M+H)$^+$=656.10; LCMS: Column: Waters Acquity UPLC BEH C18, 2.1×50 mm, 1.7-μm particles; Mobile Phase A: 5:95 ACN:water with 10 mM NH$_4$OAc; Mobile Phase B: 95:5 ACN:water with 10 mM NH$_4$OAc; Temperature: 50° C.; Gradient: 0-100% B over 3 min, then a 0.75 min hold at 100% B; Flow: 1.11 mL/min. HPLC Purity @ 220 nm: 95%.

Example 24

4-{6-Methanesulfonyl-3-[4-($^2$H$_3$)methyl-1-methyl-1H-1,2,3-triazol-5-yl]-5-[(S)-oxan-4-yl(phenyl)methyl]-5H-pyrido[3,2-b]indol-9-yl}-1λ$^6$-thiomorpholine-1,1-dione

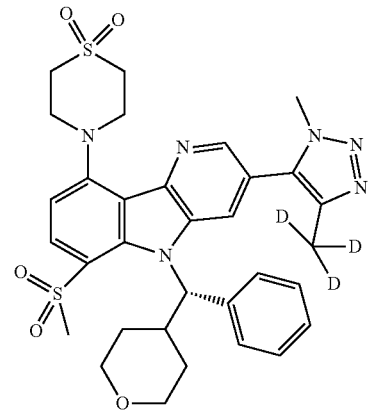 [SMILES: [2H]C([2H])([2H])c1nnn(C)c1-c1cnc2c3c(N4CCS(=O)(=O)CC4)ccc(S(C)(=O)=O)c3n([C@H](c3ccccc3)C3CCOCC3)c2c1]

To a stirred mixture of 5-{9-fluoro-6-methanesulfonyl-5-[(S)-oxan-4-yl(phenyl)methyl]-5H-pyrido[3,2-b]indol-3-yl}-4-($^2$H$_3$)methyl-1-methyl-1H-1,2,3-triazole (35.0 mg, 0.065 mmol) in NMP (0.50 mL) was added thiomorpholine 1,1-dioxide (35.3 mg, 0.261 mmol). The mixture was heated at 80° C. for 2 h, at 95° C. for 19 h and then at 125° C. for 2 h. The cooled reaction mixture was directly purified via preparative LC/MS with the following conditions: Column: Waters XBridge Phenyl, 19×200 mm, 5-μm particles; Mobile Phase A: 5:95 ACN: water with 10 mM NH$_4$OAc; Mobile Phase B: 95:5 ACN: water with 10 mM NH$_4$OAc; Gradient: 15-70% B over 20 min, then a 5 min hold at 100% B; Flow: 20 mL/min. Fractions containing the desired product were combined and dried via centrifugal evaporation to give 4-{6-methanesulfonyl-3-[4-($^2$H$_3$)methyl-1-methyl-1H-1,2,3-triazol-5-yl]-5-[(S)-oxan-4-yl(phenyl)methyl]-5H-pyrido[3,2-b]indol-9-yl}-1λ$^6$-thiomorpholine-1,1-dione (19.2 mg, 41.6%). $^1$H NMR (500 MHz, DMSO-d$_6$) δ 8.70 (s, 1H), 8.24 (d, J=8.8 Hz, 1H), 7.76 (s, 1H), 7.56 (br d, J=7.4 Hz, 2H), 7.32 (br t, J=7.6 Hz, 2H), 7.27-7.21 (m, 1H), 7.11 (d, J=8.8 Hz, 1H), 6.76 (br d, J=10.1 Hz, 1H), 3.88-3.82 (m, 1H), 3.79 (br s, 1H), 3.74 (s, 3H), 3.62 (br s, 2H), 3.61-3.42 (m, 5H), 3.33 (br d, J=10.4 Hz, 1H), 3.17 (br t, J=11.3 Hz, 1H), 2.54 (s, 5H), 1.95 (br d, J=12.5 Hz, 1H), 1.75-1.63 (m, 1H), 1.61-1.51 (m, 1H), 0.39 (br d, J=12.1 Hz, 1H); LCMS: RT=1.382 min; (ES): m/z (M+H)+=652.00; LCMS: Column: Waters Acquity UPLC BEH C18, 2.1×50 mm, 1.7-µm particles; Mobile Phase A: 5:95 ACN:water with 10 mM NH₄OAc; Mobile Phase B: 95:5 ACN:water with 10 mM NH₄OAc; Temperature: 50° C.; Gradient: 0-100% B over 3 min, then a 0.75 min hold at 100% B; Flow: 1.11 mL/min. HPLC Purity @ 220 nm: 92%.

Example 25 tert-Butyl 4-[3-(dimethyl-1H-1,2,3-triazol-5-yl)-6-methanesulfonyl-5-[(S)-oxan-4-yl(phenyl)methyl]-5H-pyrido[3,2-b]indol-9-yl]piperazine-1-carboxylate

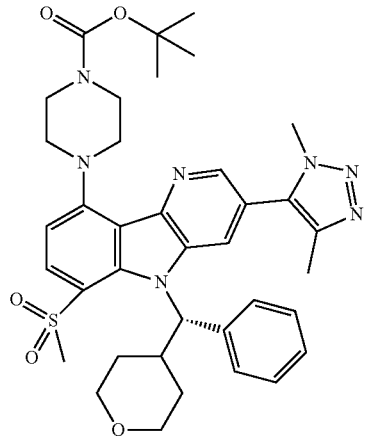 [SMILES: Cc1nnn(C)c1-c1cnc2c3c(N4CCN(C(=O)OC(C)(C)C)CC4)ccc(S(C)(=O)=O)c3n([C@H](c3ccccc3)C3CCOCC3)c2c1]

5-{9-Fluoro-6-methanesulfonyl-5-[(S)-oxan-4-yl(phenyl)methyl]-5H-pyrido[3,2-b]indol-3-yl}-1,4-dimethyl-1H-1,2,3-triazole (95.0 mg, 0.18 mmol) and tert-butyl piperazine-1-carboxylate (232 mg, 1.25 mmol) were combined in NMP (1.50 mL). The reaction mixture was heated at 80° C. for 4 h and then at 95° C. for another 3 h. The mixture was cooled to room temperature and diluted with EtOAc. The resulting mixture was washed with 10% LiCl solution. The organic layer was separated, dried (MgSO₄), filtered and concentrated to give the crude product. The crude product was purified by flash chromatography (Teledyne ISCO Combi-Flash 0% to 100% solvent A/B=Hexane/EtOAc, RediSep SiO₂ 24 g, detecting at 254 nM, and monitoring at 220 nM). Concentration of appropriate fractions provided tert-butyl 4-[3-(dimethyl-1H-1,2,3-triazol-5-yl)-6-methanesulfonyl-5-[(S)-oxan-4-yl(phenyl)methyl]-5H-pyrido[3,2-b]indol-9-yl]piperazine-1-carboxylate (114 mg. 91%). ¹H NMR (500 MHz, DMSO-d₆) δ 8.64 (s, 1H), 8.22 (d, J=8.8 Hz, 1H), 7.75 (s, 1H), 7.57 (br d, J=7.7 Hz, 2H), 7.36-7.28 (m, 2H), 7.27-7.21 (m, 1H), 6.99 (d, J=8.8 Hz, 1H), 6.76 (br d, J=10.1 Hz, 1H), 3.85 (br d, J=9.1 Hz, 1H), 3.74 (s, 3H), 3.70-3.62 (m, 2H), 3.54-3.46 (m, 1H), 3.23-3.13 (m, 1H), 2.54 (s, 3H), 2.50 (br s, 4H), 2.06 (s, 4H), 1.95 (br d, J=12.5 Hz, 1H), 1.70 (br d, J=9.4 Hz, 1H), 1.58 (br d, J=8.8 Hz, 1H), 1.43 (s, 12H), 0.41 (br d, J=11.4 Hz, 1H). HPLC: RT=3.155 min (Chromolith ODS 4.6×50 mm (4 min grad) eluting with 10-90% aqueous MeOH over 4 min containing 0.% TFA, 4 mL/min, monitoring at 220 nm); LCMS (ES): m/z=700.3 [M+H]⁺.

Example 26

2-{6-Methanesulfonyl-3-[4-(²H₃)methyl-1-methyl-1H-1,2,3-triazol-5-yl]-5-[(S)-oxan-4-yl(phenyl)methyl]-5H-pyrido[3,2-b]indol-9-yl}-1λ⁶,2-thiazolidine-1,1-dione

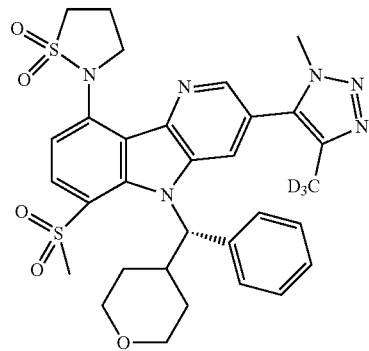 [SMILES: [2H]C([2H])([2H])c1nnn(C)c1-c1cnc2c3c(N4CCCS4(=O)=O)ccc(S(C)(=O)=O)c3n([C@H](c3ccccc3)C3CCOCC3)c2c1]

To a stirred solution of 5-{9-fluoro-6-methanesulfonyl-5-[(S)-oxan-4-yl(phenyl)methyl]-5H-pyrido[3,2-b]indol-3-yl}-4-(²H₃)methyl-1-methyl-1H-1,2,3-triazole (40.0 mg, 0.075 mmol) and isothiazolidine 1,1-dioxide (36.1 mg, 0.298 mmol) in NMP (0.40 mL) was added t-BuOK (29.2 mg, 0.261 mmol). This mixture was heated at 65° C. for 2 h and cooled to room temperature. The mixture was purified via preparative LC/MS with the following conditions: Column: Waters XBridge Phenyl, 19×200 mm, 5-m particles; Mobile Phase A: 5:95 ACN: water with 10 mM NH₄OAc; Mobile Phase B: 95:5 ACN: water with 10 mM NH₄OAc; Gradient: 15-70% B over 20 min, then a 5-min hold at 100% B; Flow: 20 mL/min. Fractions containing the desired product were combined and dried via centrifugal evaporation to give 9.6 mg. (20%). ¹H NMR (500 MHz, DMSO-d₆) δ 8.72 (s, 1H), 8.38 (d, J=8.4 Hz, 1H), 7.89 (s, 1H), 7.62 (br d, J=8.1 Hz, 3H), 7.37-7.30 (m, 2H), 7.26 (s, 1H), 6.82 (br d, J=10.4 Hz, 1H), 4.11 (br s, 2H), 3.86 (br d, J=8.4 Hz, 1H), 3.77 (s, 3H), 3.75 (s, 3H), 3.65 (br d, J=8.8 Hz, 1H), 3.57 (br t, J=7.4 Hz, 1H), 3.53-3.45 (m, 1H), 3.40 (br d, J=12.1 Hz, 1H), 3.19 (br t, J=11.6 Hz, 1H), 2.62 (quin, J=7.1 Hz, 2H), 2.52-2.52 (m, 1H), 1.95 (br d, J=12.5 Hz, 1H), 1.77-1.58 (m, 2H), 0.43 (br d, J=12.5 Hz, 1H); LCMS: RT=1.573 min; (ES): m/z (M+H)+=638.05; LCMS: Column: Waters Acquity UPLC BEH C18, 2.1×50 mm, 1.7-µm particles; Mobile Phase A: 5:95 ACN:water with 10 mM NH₄OAc; Mobile Phase B: 95:5 ACN:water with 10 mM NH₄OAc; Temperature: 50° C.; Gradient: 0-100% B over 3 min, then a 0.75 min hold at 100% B; Flow: 1.11 mL/min. HPLC Purity @ 220 nm: 99%.

Examples 27 & 28

2-({3,7-Bis[4-($^2$H$_3$)methyl-1-methyl-1H-1,2,3-triazol-5-yl]-5H-pyrido[3,2-b]indol-5-yl}(oxan-4-yl)methyl)-3-fluoropyridine Example 27

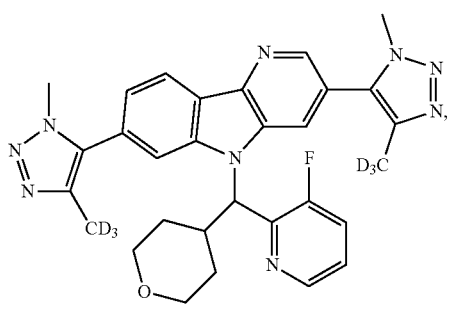

Enantiomer A

Example 28

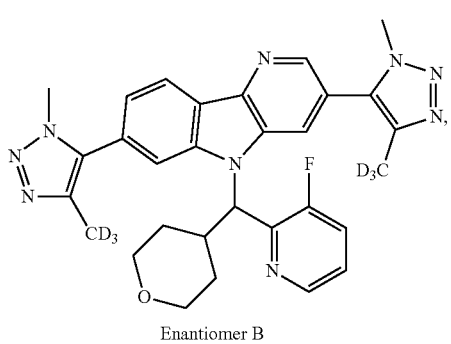

Enantiomer B

Step 1: 5-Bromo-2-(4-bromophenyl)-3-nitropyridine

In a 100 mL pressure flask was added 2,5-dibromo-3-nitropyridine (0.702 g, 2.49 mmol), (4-bromophenyl)boronic acid (0.5 g, 2.49 mmol) in 20 mL THF. To this was added potassium phosphate tribasic (2.490 ml, 4.98 mmol) and PdCl$_2$(dppf)-CH$_2$Cl$_2$ adduct (0.041 g, 0.050 mmol). Bubbled in argon through the mixture while sonicating for 5 min. The flask was sealed and heated in an oil bath at 65° C. overnight. The reaction was concentrated and the resulting residue dissolved in DCM and purified on a 40 g Isco column, eluting with 5% EtOAc/hexanes to 30% EtOAc/hexanes over 600 mL. Concentrated fractions containing the title compound to afford 820 mg (92%) of a light yellow solid. LC/MS Method 6; Rt=1.925 min, M+H=358. $^1$H NMR (400 MHz, DMSO-d$_6$) δ 9.11 (d, J=2.0 Hz, 1H), 8.84 (d, J=2.0 Hz, 1H), 7.75-7.69 (m, 2H), 7.52-7.44 (m, 2H)

Step 2: 3,7-Dibromo-5H-pyrido[3,2-b]indole

A thick-walled 20 mL scintillation vial was charged with 5-bromo-2-(4-bromophenyl)-3-nitropyridine (0.82 g, 2.29 mmol) and 1,2-DPPE (1.369 g, 3.44 mmol) and 8 mL 1,2-dichlorobenzene. Sealed vial and placed in an oil bath at 160° C. for 15 min. Treated with 200 mL ether. Collected solid and washed with ether. Discarded solid. Concentrated filtrate on rotovap, then under a stream of nitrogen overnight to afford 1.8 g of a dark yellow oil. The residue was dissolved in DCM and purified on a 40 g Isco column, eluting with 5% THF/hexane to 100% THF over 600 mL. Concentrated fractions containing the title compound. Separately concentrated fractions containing impure title compound, dissolved the residue in DCM and purified on a 40 g Isco column, eluting with 5% THF/hexane to 50% THF/hexane over 600 mL. Combined all fractions containing the title compound to afford 0.36 g (49% yield). LC/MS Method 6; Rt=1.723 min, M+H=325. $^1$H NMR (400 MHz, DMSO-d$_6$) δ 11.71 (br. s., 1H), 8.54 (d, J=2.0 Hz, 1H), 8.20 (d, J=2.0 Hz, 1H), 8.10 (d, J=8.3 Hz, 1H), 7.81 (d, J=1.3 Hz, 1H), 7.42 (dd, 5 J=8.3, 1.8 Hz, 1H)

Step 3: 4-($^2$H$_3$)Methyl-1-methyl-5-{7-[4-($^2$H$_3$)methyl-1-methyl-1H-1,2,3-triazol-5-yl]-5H-pyrido-[3,2-b]indol-3-yl}-1H-1,2,3-triazole 3,7-Dibromo-5H-pyrido[3,2-b]indole (165 mg, 0.506 mmol) and 4-($^2$H$_3$)methyl-1-methyl-5-(tributylstannyl)-1H-1,2,3-triazole (394 mg, 1.012 mmol) were dissolved in 4 mL DMF. To this was added copper (I) iodide (19.3 mg, 0.101 mmol), triethyl amine (282 μL, 2.03 mmol) and Pd(PPh$_3$)$_4$ (58.5 mg, 0.051 mmol). Bubbled in argon for 0.5 min while sonicating. The vial was sealed and placed in an oil bath at 100° C. and heated for 14 h. Partitioned reaction between EtOAc and water. Filtered through celite. Washed celite with EtOAc. Separated layers, washed organic layer with brine, dried over MgSO$_4$, filtered and concentrated. The residue was dissolved in DCM and purified on a 24 g Isco column, eluting with 10% MeOH/EtOAc to 15% MeOH/EtOAc over 300 mL, then 15% MeOH for 300 mL. Combined fractions containing the title compound and concentrated to dryness to afford 46 mg (25%). LC/MS conditions 1; Rt=0.63 min, M+H=365. $^1$H NMR (400 MHz, Acetone) δ 11.04 (br. s., 1H), 8.60 (d, J=1.5 Hz, 1H), 8.47 (d, J=8.0 Hz, 1H), 8.09 (d, J=1.8 Hz, 1H), 7.79-7.73 (m, 1H), 7.42 (dd, J=8.0, 1.5 Hz, 1H), 4.07-4.05 (m, 3H), 4.05-4.03 (m, 3H).

Step 4: 2-({3,7-Bis[4-($^2$H$_3$)methyl-1-methyl-1H-1,2,3-triazol-5-yl]-5H-pyrido-[3,2-b]indol-5-yl}(oxan-4-yl)methyl)-3-fluoropyridine A 5 mL pressure vial was charged with (3-fluoropyridin-2-yl)(tetrahydro-2H-pyran-4-yl)methyl methanesulfonate (119 mg, 0.412 mmol). To this was added 4-($^2$H$_3$)methyl-1-methyl-5-{7-[4-($^2$H$_3$)methyl-1-methyl-1H-1,2,3-triazol-5-yl]-5H-pyrido-[3,2-b]indol-3-yl}-1H-1,2,3-triazole (30 mg, 0.082 mmol) and 2 mL DMF, then cesium carbonate (134 mg, 0.412 mmol). Bubbled in nitrogen for 0.5 min, sealed vial and heated at 100° C. for 20 h. The crude material was purified via preparative LC/MS with the following conditions: Column: XBridge C18, 19×200 mm, 5-μm particles; Mobile Phase A: 5:95 MeOH: water with 10 mM NH$_4$OAc; Mobile Phase B: 95:5 MeOH: water with 10 mM NH$_4$OAc; Gradient: 40-80% B over 20 min, then a 5 min hold at 100% B; Flow: 20 mL/min. Fractions containing the desired product were combined and dried via centrifugal evaporation. The material was further purified via preparative LC/MS with the following conditions: Column:

XBridge C18, 19×200 mm, 5-μm particles; Mobile Phase A: 5:95 ACN: water with 10 mM NH₄OAc; Mobile Phase B: 95:5 ACN: water with 10 mM NH₄OAc; Gradient: 10-50% B over 15 min, then a 5 min hold at 100% B; Flow: 20 mL/min. Fractions containing the desired racemic product were combined and dried via centrifugal evaporation. The racemate was separated on a chiracel OD 21×250 mm column, 10 μm particle size, eluting with 12% ethanol/88% 0.1% diethylamine in heptane over 110 min; detection: UV at 254 nM. Fractions eluting from 68 to 76 min were concentrated to give Enantiomer A which was was further purified via preparative LC/MS with the following conditions: Column: XBridge Shield RP18, 19×200 mm, 5-m particles; Mobile Phase A: 5:95 MeOH: water with 10 mM NH₄OAc; Mobile Phase B: 95:5 MeOH: water with 10 mM NH₄OAc; Gradient: 15-55% B over 30 min, then a 5 min hold at 100% B; Flow: 20 mL/min. Fractions containing the desired product were combined and dried via centrifugal evaporation. The yield of Enantiomer A was 2.7 mg, and its estimated purity by LCMS analysis was 97%. Two analytical LC/MS injections were used to determine the final purity. Injection 1 conditions: Column: Waters BEH C18, 2.0×50 mm, 1.7-μm particles; Mobile Phase A: 5:95 ACN:water with 10 mM NH₄OAc; Mobile Phase B: 95:5 ACN:water with 10 mM NH₄OAc; Temperature: 50° C.; Gradient: 0% B, 0-100% B over 3 min, then a 0.5 min hold at 100% B; Flow: 1 mL/min; Detection: UV at 220 nm, Rt=1.39 min, M+H=558. Injection 2 conditions: Column: Waters BEH C18, 2.0×50 mm, 1.7-μm particles; Mobile Phase A: 5:95 MeOH:water with 10 mM NH₄OAc; Mobile Phase B: 95:5 MeOH:water with 10 mM NH₄OAc; Temperature: 50° C.; Gradient: 0% B, 0-100% B over 3 min, then a 0.5 min hold at 100% B; Flow: 0.5 mL/min; Detection: UV at 220 nm, Rt=2.34 min, M+H=558. $^1$H NMR (500 MHz, DMSO-d₆) δ 8.68-8.60 (m, 2H), 8.39 (d, J=8.1 Hz, 1H), 7.72 (t, J=9.2 Hz, 1H), 7.50 (dt, J=8.5, 4.4 Hz, 1H), 7.45 (d, J=7.7 Hz, 1H), 6.30 (d, J=10.3 Hz, 1H), 4.05 (br. s., 6H), 3.84 (d, J=11.0 Hz, 1H), 3.68 (d, J=9.2 Hz, 1H), 3.52 (br. s., 1H), 3.21 (t, J=11.7 Hz, 1H), 1.72-1.52 (m, 2H), 1.35 (br. s., 1H), 0.75 (d, J=12.1 Hz, 1H).

Fractions eluting from 81 to 90 min were concentrated to give Enantiomer B which was further purified via preparative LC/MS with the following conditions: Column: XBridge Shield RP18, 19×200 mm, 5-μm particles; Mobile Phase A: 5:95 MeOH: water with 10 mM NH₄OAc; Mobile Phase B: 95:5 MeOH: water with 10 mM 5 NH₄OAc; Gradient: 15-55% B over 30 min, then a 5 min hold at 100% B; Flow: 20 mL/min. Fractions containing the desired product were combined and dried via centrifugal evaporation. The yield of Enantiomer B was 2.7 mg, and its estimated purity by LCMS analysis was 97%. Two analytical LC/MS injections were used to determine the final purity. Injection 1 conditions: Column: Waters BEH C18, 2.0×50 mm, 1.7-μm particles; Mobile Phase A: 5:95 ACN:water with 10 mM NH₄OAc; Mobile Phase B: 95:5 ACN:water with 10 mM NH₄OAc; Temperature: 50° C.; Gradient: 0% B, 0-100% B over 3 min, then a 0.5 min hold at 100% B; Flow: 1 mL/min; Detection: UV at 220 nm, Rt=1.39 min, M+H=558. Injection 2 conditions: Column: Waters BEH C18, 2.0×50 mm, 1.7-μm particles; Mobile Phase A: 5:95 MeOH:water with 10 mM NH₄OAc; Mobile Phase B: 95:5 MeOH:water with 10 mM NH₄OAc; Temperature: 50° C.; Gradient: 0% B, 0-100% B over 3 min, then a 0.5 min hold at 100% B; Flow: 0.5 mL/min; Detection: UV at 220 nm, Rt=2.34 min, M+H=558. $^1$H NMR (500 MHz, DMSO-d₆) δ 8.68-8.60 (m, 2H), 8.39 (d, J=8.1 Hz, 1H), 7.72 (t, J=9.2 Hz, 1H), 7.50 (dt, J=8.5, 4.4 Hz, 1H), 7.45 (d, J=7.7 Hz, 1H), 6.30 (d, J=10.3 Hz, 1H), 4.05 (br. s., 6H), 3.84 (d, J=11.0 Hz, 1H), 3.68 (d, J=9.2 Hz, 1H), 3.52 (br. s., 1H), 3.21 (t, J=11.7 Hz, 1H), 1.72-1.52 (m, 2H), 1.35 (br. s., 1H), 0.75 (d, J=12.1 Hz, 1H).

Example 29

4-($^2$H₃)Methoxy-5-{7-[4-($^2$H)methoxy-1-methyl-1H-1,2,3-triazol-5-yl]-5-[(S)-oxan-4-yl-(phenyl)methyl]-5H-pyrido[3,2-b]indol-3-yl}-1-methyl-1H-1,2,3-triazole

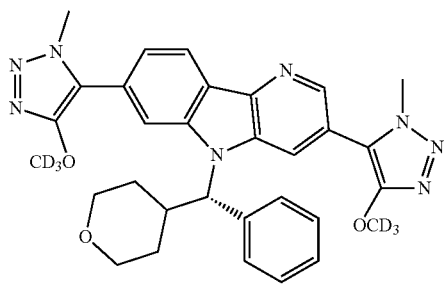

To a 5 mL, thick walled vial was added 4-($^2$H₃)methoxy-1-[(trimethylsilyl)methyl]-1H-1,2,3-triazole (37.7 mg, 0.200 mmol). (S)-3,7-Dibromo-5-(phenyl(tetrahydro-2H-pyran-4-yl)methyl)-5H-pyrido[3,2-b]indole (0.050 g, 0.1 mmol) was dissolved in 1.5 mL DMF and added to the vial. To this was added tetramethylammonium acetate (0.053 g, 0.400 mmol) and bis(triphenylphosphine)palladium (II) chloride (7.0 mg, 10.0 μmol). Bubbled argon through the mixture for 1 min while sonicating. The vial was sealed and heated for 15 h. The crude material was purified via preparative LC/MS with the following conditions: Column: XBridge C18, 19×200 mm, 5-μm particles; Mobile Phase A: 5:95 ACN: water with 10 mM NH₄OAc; Mobile Phase B: 95:5 ACN: water with 10 mM NH₄OAc; Gradient: 20-60% B over 20 min, then a 5 min hold at 100% B; Flow: 20 mL/min. Fractions containing the desired product were combined and dried via centrifugal evaporation. The yield of the product was 17.9 mg, and its estimated purity by LCMS analysis was 99%. Two analytical LC/MS injections were used to determine the final purity. Injection 1 conditions: Column: Waters BEH C18, 2.0×50 mm, 1.7-μm particles; Mobile Phase A: 5:95 ACN:water with 10 mM NH₄OAc; Mobile Phase B: 95:5 ACN:water with 10 mM NH₄OAc; Temperature: 50° C.; Gradient: 0% B, 0-100% B over 3 min, then a 0.5 min hold at 100% B; Flow: 1 mL/min; Detection: UV at 220 nm, Rt=1.59 min. Injection 2 conditions: Column: Waters BEH C18, 2.0×50 mm, 1.7-μm particles; Mobile Phase A: 5:95 MeOH:water with 10 mM NH₄OAc; Mobile Phase B: 95:5 MeOH:water with 10 mM NH₄OAc; Temperature: 50° C.; Gradient: 0% B, 0-100% B over 3 min, then a 0.5 min hold at 100% B; Flow: 0.5 mL/min; Detection: UV at 220 nm, Rt=2.59 min, M+H=571. $^1$H NMR (500 MHz, DMSO-d₆) δ 8.62 (s, 1H), 8.34 (d, J=8.1 Hz, 1H), 8.24 (br. s., 1H), 7.70 (d, J=7.3 Hz, 2H), 7.47 (d, J=8.1 Hz, 1H), 7.36 (t, J=7.5 Hz, 2H), 7.27 (t, J=7.5 Hz, 1H), 5.89 (d, J=11.4 Hz, 1H), 4.12 (br. s., 6H), 3.90 (d, J=11.4 Hz, 1H), 3.73 (d, J=9.5 Hz, 1H), 3.54-3.40 (m, 2H), 3.27 (t, J=11.4 Hz, 1H), 1.72 (d, J=12.5 Hz, 1H), 1.65-1.48 (m, 1H), 1.32 (d, J=9.2 Hz, 1H), 0.99 (d, J=12.8 Hz, 1H).

Example 30

4-Methoxy-5-{7-[4-methoxy-1-($^2$H$_3$)methyl-1H-1,2,3-triazol-5-yl]-5-[(S)-oxan-4-yl(phenyl)-methyl]-5H-pyrido[3,2-b]indol-3-yl}-1-($^2$H$_3$)methyl-1H-1,2,3-triazole

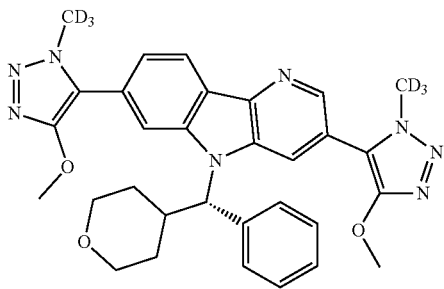 [SMILES: [2H]C([2H])([2H])n1nnc(OC)c1-c1ccc2c3ncc(-c4c(OC)nnn4C([2H])([2H])[2H])cc3n([C@H](c3ccccc3)C3CCOCC3)c2c1]

To a 5 mL, thick walled vial was added 4-methoxy-1-($^2$H$_3$)methyl-1H-1,2,3-triazole (23.2 mg, 0.200 mmol). (S)-3,7-Dibromo-5-(phenyl(tetrahydro-2H-pyran-4-yl)methyl)-5H-pyrido[3,2-b]indole (0.050 g, 0.1 mmol) was dissolved in 1.5 mL DMF and added to the vial. To this was added tetramethylammonium acetate (0.053 g, 0.400 mmol) and bis(triphenylphosphine)palladium (II) chloride (7.0 mg, 10.0 µmol). Bubbled argon through the mixture for 1 min while sonicating. The vial was sealed and heated for 15 h. The crude material was purified via preparative LC/MS with the following conditions: Column: XBridge C18, 19×200 mm, 5-µm particles; Mobile Phase A: 5:95 ACN: water with 10 mM NH$_4$OAc; Mobile Phase B: 95:5 ACN: water with 10 mM NH$_4$OAc; Gradient: 20-60% B over 20 min, then a 5 min hold at 100% B; Flow: 20 mL/min. Fractions containing the desired product were combined and dried via centrifugal evaporation. The yield of the product was 28.0 mg, and its estimated purity by LCMS analysis was 100%. Two analytical LC/MS injections were used to determine the final purity. Injection 1 conditions: Column: Waters BEH C18, 2.0×50 mm, 1.7-µm particles; Mobile Phase A: 5:95 ACN: water with 10 mM NH$_4$OAc; Mobile Phase B: 95:5 ACN: water with 10 mM NH$_4$OAc; Temperature: 50° C.; Gradient: 0% B, 0-100% B over 3 min, then a 0.5 min hold at 100% B; Flow: 1 mL/min; Detection: UV at 220 nm, Rt=1.58 min. Injection 2 conditions: Column: Waters BEH C18, 2.0×50 mm, 1.7-µm particles; Mobile Phase A: 5:95 MeOH:water with 10 mM NH$_4$OAc; Mobile Phase B: 95:5 MeOH:water with 10 mM NH$_4$OAc; Temperature: 50° C.; Gradient: 0% B, 0-100% B over 3 min, then a 0.5 min hold at 100% B; Flow: 0.5 mL/min; Detection: UV at 220 nm, Rt=2.61 min, M+H=571. $^1$H NMR (500 MHz, DMSO-d$_6$) δ 8.62 (s, 1H), 8.34 (d, J=8.1 Hz, 1H), 8.22 (br. s., 1H), 7.70 (d, J=7.7 Hz, 2H), 7.47 (d, J=8.1 Hz, 1H), 7.36 (t, J=7.5 Hz, 2H), 7.27 (t, J=7.7 Hz, 1H), 5.89 (d, J=11.7 Hz, 1H), 4.04 (s, 6H), 3.94-3.85 (m, 1H), 3.73 (d, J=10.6 Hz, 1H), 3.58-3.43 (m, 2H), 3.27 (t, J=11.4 Hz, 1H), 1.72 (d, J=11.7 Hz, 1H), 1.56 (d, J=10.3 Hz, 1H), 1.32 (d, J=11.4 Hz, 1H), 0.99 (d, J=12.1 Hz, 1H).

Example 31

4-($^2$H$_3$)Methyl-1-methyl-5-{7-[4-($^2$H$_3$)methyl-1-methyl-1H-1,2,3-triazol-5-yl]-5-[(S)-oxan-4-yl(phenyl)methyl]-5H-pyrido[3,2-b]indol-3-yl}-1H-1,2,3-triazole

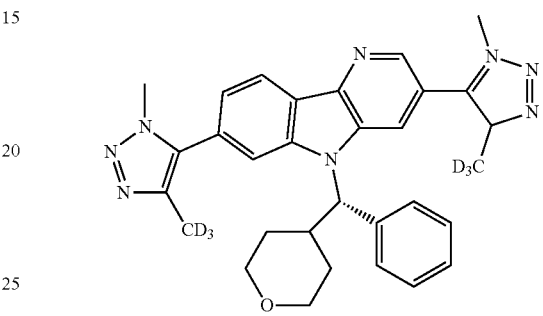

(S)-3,7-Dibromo-5-(phenyl(tetrahydro-2H-pyran-4-yl) methyl)-5H-pyrido[3,2-b]indole (50.0 mg, 0.1 mmol) and 4-($^2$H$_3$)methyl-1-methyl-5-(tributylstannyl)-1H-1,2,3-triazole (156 mg, 0.400 mmol) were dissolved in 1.5 mL DMF. To this was added copper (I) iodide (3.8 mg, 0.020 mmol), triethyl amine (112 µL, 0.800 mmol) and Pd(PPh$_3$)$_4$ (11.6 mg, 10.0 µmol). Bubbled in argon for 0.5 min while sonicating. The vial was sealed and placed in an oil bath at 100° C. for 14 h. The crude material was purified via preparative LC/MS with the following conditions: Column: XBridge C18, 19×200 mm, 5-µm particles; Mobile Phase A: 5:95 ACN: water with 10 mM NH$_4$OAc; Mobile Phase B: 95:5 ACN: water with 10 mM NH$_4$OAc; Gradient: 20-60% B over 20 min, then a 5 min hold at 100% B; Flow: 20 mL/min. Fractions containing the desired product were combined and dried via centrifugal evaporation. The yield of the product was 19.8 mg, and its estimated purity by LCMS analysis was 99%. Two analytical LC/MS injections were used to determine the final purity. Injection 1 conditions: Column: Waters BEH C18, 2.0×50 mm, 1.7-µm particles; Mobile Phase A: 5:95 ACN:water with 10 mM NH$_4$OAc; Mobile Phase B: 95:5 ACN:water with 10 mM NH$_4$OAc; Temperature: 50° C.; Gradient: 0% B, 0-100% B over 3 min, then a 0.5 min hold at 100% B; Flow: 1 mL/min; Detection: UV at 220 nm, Rt=1.45 min, M+H=539. Injection 2 conditions: Column: Waters BEH C18, 2.0×50 mm, 1.7-µm particles; Mobile Phase A: 5:95 MeOH:water with 10 mM NH$_4$OAc; Mobile Phase B: 95:5 MeOH:water with 10 mM NH$_4$OAc; Temperature: 50° C.; Gradient: 0% B, 0-100% B over 3 min, then a 0.5 min hold at 100% B; Flow: 0.5 mL/min; Detection: UV at 220 nm, Rt=2.45 min, M−H=537. $^1$H NMR (500 MHz, DMSO-d$_6$) δ 8.61 (br. s., 1H), 8.54 (d, J=7.3 Hz, 1H), 8.39 (d, J=8.1 Hz, 1H), 8.22 (br. s., 1H), 7.71 (d, J=7.3 Hz, 2H), 7.43 (d, J=7.7 Hz, 1H), 7.38-7.30 (m, 2H), 7.29-7.22 (m, 1H), 5.92 (d, J=11.0 Hz, 1H), 4.04 (br. s., 6H), 3.89 (d, J=9.2 Hz, 1H), 3.73 (d, J=9.2 Hz, 1H), 3.53-3.45 (m, 2H), 3.26 (t, J=11.4 Hz, 1H), 1.70 (d, J=13.6 Hz, 1H), 1.55 (d, J=12.1 Hz, 1H), 1.33 (d, J=9.5 Hz, 1H), 1.03 (d, J=11.0 Hz, 1H).

Example 32

4-Methoxy-5-[7-(4-methoxy-1-methyl-1H-1,2,3-triazol-5-yl)-5-[(S)-oxan-4-yl(phenyl)methyl]-5H-pyrido[3,2-b]indol-3-yl]-1-methyl-1H-1,2,3-triazole

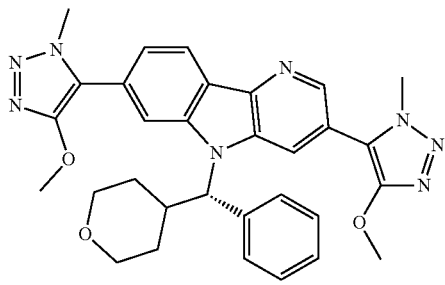 [SMILES: COc1nnn(C)c1-c1ccc2c3ncc(-c4c(OC)nnn4C)cc3n([C@H](c3ccccc3)C3CCOCC3)c2c1]

Step 1: 5-Bromo-2-(4-bromophenyl)-3-nitropyridine

A 250 mL pressure flask was charged with (4-bromophenyl)boronic acid (2.00 g, 9.96 mmol), 2,5-dibromo-3-nitropyridine (2.81 g, 9.96 mmol), and 100 mL THF. To this was added tripotassium phosphate (4.23 g, 19.9 mmol) and PdCl$_2$(dppf)-CH$_2$Cl$_2$ adduct (0.163 g, 0.199 mmol). Argon was bubbled through the mixture while sonicating for 1 min. The flask was sealed and heated in an oil bath at 65° C. overnight. Heating was discontinued and the reaction stirred for 2 days. Volatiles were removed. The residue was dissolved in DCM, treated with silica gel, and concentrated to dryness. The material was purified on an 80 g ISCO column, eluting with 5% EtOAc/hexanes to 30% EtOAc/hexanes over 1200 mL. Fractions containing the title compound were concentrated to afford 1.32 g (37%) of a yellow solid. LC/MS using LC/MS Method 6, HPLC RT=1.11 min. $^1$H NMR (400 MHz, DMSO-d$_6$) δ 9.11 (d, J=2.0 Hz, 1H), 8.84 (d, J=2.0 Hz, 1H), 7.74-7.70 (m, 2H), 7.51-7.47 (m, 2H).

Step 2: 3,7-Dibromo-5H-pyrido[3,2-b]indole

In a 20 mL scintillation vial, 5-bromo-2-(4-bromophenyl)-3-nitropyridine (1.46 g, 4.08 mmol) and DPPE (2.44 g, 6.12 mmol) were suspended in 12 mL 1,2-dichlorobenzene. The vial was placed in an oil bath at 160° C. and heated for 15 min after complete dissolution of reactants. After cooling to room temperature, the contents were poured into 200 mL ether. Insoluble materials were removed by filtration and discarded. The eluent was concentrated on a rotovap, first with house vacuum, then with high vacuum. The residue was dissolved in DCM and purified on an 80 g ISCO column, eluting with 5% THF/hexanes to 50% THF hexanes over 1200 mL. Fractions containing the title compound were concentrated to afford 330 mg (25%) of a white solid. LC/MS using LC/MS Method 6, HPLC RT=0.97 min.

Step 3: (S)-3,7-Dibromo-5-(phenyl(tetrahydro-2H-pyran-4-yl)methyl)-5H-pyrido[3,2-b]indole 3,7-Dibromo-5H-pyrido[3,2-b]indole (0.330 g, 1.01 mmol) was suspended in 10 mL DCM. To this was added (R)-phenyl(tetrahydro-2H-pyran-4-yl)methanol (0.389 g, 2.03 mmol) and triphenylphosphine (0.531 g, 2.03 mmol). To this was added DIAD (0.394 mL, 2.03 mmol) dropwise at 0° C. The reaction was sealed, stirred overnight, concentrated to about 1 mL, and purified on a 24 g ISCO column, eluting with 5% EtOAc/hexane to 25% EtOAc/hexane over 800 mL. Fraction containing the title compound was concentrated to afford 302 mg (60%) of a clear, glassy oil. LC/MS using LC/MS Method 6, HPLC RT=1.19 min. $^1$H NMR (500 MHz, CDCl$_3$) δ 8.58 (d, J=1.8 Hz, 1H), 8.21-8.17 (m, 1H), 7.98-7.95 (m, 1H), 7.81-7.77 (m, 1H), 7.48-7.44 (m, 3H), 7.41-7.35 (m, 2H), 7.34-7.30 (m, 1H), 5.33 (d, J=11.0 Hz, 1H), 4.06 (dd, J=11.7, 2.7 Hz, 1H), 3.88 (dd, J=11.7, 3.1 Hz, 1H), 3.56 (td, J=11.9, 2.1 Hz, 1H), 3.39 (td, J=11.9, 2.0 Hz, 1H), 1.97 (d, J=13.4 Hz, 1H), 1.64-1.50 (m, 2H), 1.43-1.33 (m, 2H), 1.06 (d, J=12.1 Hz, 1H).

Step 4: 4-Methoxy-5-[7-(4-methoxy-1-methyl-1H-1,2,3-triazol-5-yl)-5-[(S)-oxan-4-yl(phenyl)methyl]-5H-pyrido[3,2-b]indol-3-yl]-1-methyl-1H-1,2,3-triazole To a 5 mL, thick walled vial was added 4-methoxy-1-((trimethylsilyl)methyl)-1H-1,2,3-triazole (37.1 mg, 0.200 mmol). A solution of (S)-3,7-dibromo-5-(phenyl(tetrahydro-2H-pyran-4-yl)methyl)-5H-pyrido[3,2-b]indole (50.0 mg, 0.100 mmol) in 1.5 mL DMF was added to the vial. To this was added tetramethylammonium acetate (53.3 mg, 0.400 mmol) and bis(triphenylphosphine)palladium (II) chloride (7.0 mg, 10.0 μmol). Argon was bubbled through the mixture for 1 min while sonicating. The vial was sealed and heated for 15 h. The reaction was filtered, treated with 0.5 mL of 1M tetrabutyl ammonium fluoride in THF, and stirred for 15 min. The crude material was purified via preparative LC/MS using Preparative HPLC Method 1, except with a gradient of 20-60% B over 20 min. Fractions containing the desired product were combined and dried via centrifugal evaporation. The yield of the product was 26.1 mg, and its estimated purity by LCMS analysis was 99%. Injection 1: LC/MS Method 3, HPLC RT=1.59 min. Injection 2: LC/MS Method 4, HPLC RT=2.61 min. $^1$H NMR (500 MHz, DMSO-d$_6$) δ 8.61 (s, 1H), 8.54 (br. s., 1H), 8.35 (d, J=8.1 Hz, 1H), 8.22 (br. s., 1H), 7.69 (d, J=7.7 Hz, 2H), 7.46 (d, J=8.1 Hz, 1H), 7.36 (t, J=7.5 Hz, 2H), 7.27 (t, J=7.2 Hz, 1H), 5.88 (d, J=11.4 Hz, 1H), 4.11 (br. s., 6H), 4.04 (s, 6H), 3.95-3.85 (m, 1H), 3.73 (d, J=9.5 Hz, 1H), 3.56-3.44 (m, 1H), 3.26 (t, J=11.7 Hz, 1H), 1.72 (d, J=13.6 Hz, 1H), 1.56 (d, J=8.4 Hz, 2H), 1.31 (d, J=7.0 Hz, 2H), 1.02-0.94 (m, 1H).

Example 33

2-{5-[(S)-(4-Fluorophenyl)(oxan-4-yl)methyl]-6-methanesulfonyl-3-[4-($^2$H$_3$)methyl-1-methyl-1H-1,2,3-triazol-5-yl]-5H-pyrido[3,2-b]indol-9-yl}-1λ$^6$,2-thiazolidine-1,1-dione

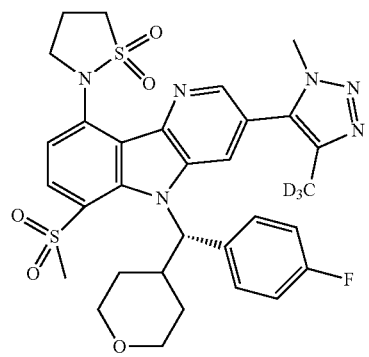 [SMILES: [2H]C([2H])([2H])c1nnn(C)c1-c1cnc2c3c(N4CCCS4(=O)=O)ccc(S(C)(=O)=O)c3n([C@H](c3ccc(F)cc3)C3CCOCC3)c2c1]

To a stirred solution of 5-{9-fluoro-5-[(S)-(4-fluorophenyl)(oxan-4-yl)methyl]-6-methanesulfonyl-5H-pyrido[3,2-b]indol-3-yl}-4-($^2$H$_3$)methyl-1-methyl-1H-1,2,3-triazole (24.0 mg, 0.0400 mmol) and isothiazolidine-1,1-dione (26.2 mg, 0.220 mmol) in NMP (0.25 mL) was added t-BuOK (19.4 mg, 0.170 mmol). This mixture was heated at 65° C. for 2 h and cooled to room temperature. The mixture was then diluted with MeOH and purified via preparative LC/MS with the following conditions: Column: Waters XBridge Phenyl, 19×200 mm, 5-µm particles; Mobile Phase A: 5:95 ACN: water with 10 mM NH$_4$OAc; Mobile Phase B: 95:5 ACN: water with 10 mM NH$_4$OAc; Gradient: 15-70% B over 20 min, then a 5-min hold at 100% B; Flow: 20 mL/min. Fractions containing the desired product were combined and dried via centrifugal evaporation to give 2-{5-[(S)-(4-fluorophenyl)(oxan-4-yl)methyl]-6-methanesulfonyl-3-[4-($^2$H$_3$)methyl-1-methyl-1H-1,2,3-triazol-5-yl]-5H-pyrido[3,2-b]indol-9-yl}-1λ$^6$,2-thiazolidine-1,1-dione (11.6 mg, 40%). $^1$H NMR (500 MHz, DMSO-d$_6$) δ 8.73 (s, 1H), 8.37 (d, J=8.5 Hz, 1H), 7.90 (s, 1H), 7.71-7.65 (m, 2H), 7.61 (d, J=8.4 Hz, 1H), 7.16 (br t, J=8.7 Hz, 2H), 6.78 (br d, J=10.2 Hz, 1H), 4.10 (br t, J=6.8 Hz, 2H), 3.88 (br d, J=10.7 Hz, 1H), 3.83 (s, 3H), 3.64 (br d, J=8.7 Hz, 1H), 3.57 (br t, J=7.5 Hz, 1H), 3.47 (br s, 2H), 3.39 (br s, 1H), 3.17 (br t, J=11.4 Hz, 1H), 2.66-2.57 (m, 2H), 2.54 (s, 3H), 1.90 (br d, J=12.6 Hz, 1H), 1.64 (br t, J=12.1 Hz, 2H), 0.42 (br d, J=11.8 Hz, 1H). LCMS: RT=1.670 min; (ES): m/z (M+H)$^+$=656.15. LCMS: Column: Waters Acquity UPLC BEH C18, 2.1×50 mm, 1.7-µm particles; Mobile Phase A: 5:95 ACN: water with 10 mM NH$_4$OAc; Mobile Phase B: 95:5 ACN: water with 10 mM NH$_4$OAc; Temperature: 50° C.; Gradient: 0-100% B over 3 min, then a 0.75-min hold at 100% B; Flow: 1.11 mL/min. HPLC Purity at 220 nm: 98%.

Example 34

2-{5-[(S)-(2-Fluorophenyl)(oxan-4-yl)methyl]-6-methanesulfonyl-3-[4-($^2$H$_3$)methyl-1-methyl-1H-1,2,3-triazol-5-yl]-5H-pyrido[3,2-b]indol-9-yl}-1λ$^6$,2-thiazolidine-1,1-dione

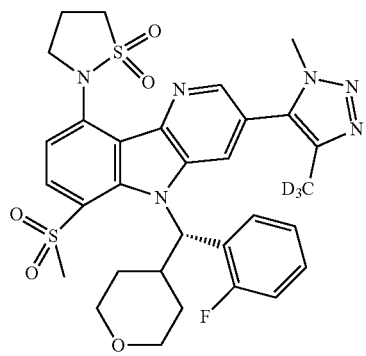 [SMILES: [2H]C([2H])([2H])c1nnn(C)c1-c1cnc2c3c(N4CCCS4(=O)=O)ccc(S(C)(=O)=O)c3n([C@H](c3ccccc3F)C3CCOCC3)c2c1]

To a stirred solution of 5-{9-fluoro-5-[(S)-(2-fluorophenyl)(oxan-4-yl)methyl]-6-methanesulfonyl-5H-pyrido[3,2-b]indol-3-yl}-4-($^2$H$_3$)methyl-1-methyl-1H-1,2,3-triazole (7.8 mg, 0.0140 mmol) and isothiazolidine-1,1-dione (8.5 mg, 0.0560 mmol) in NMP (0.15 mL) was added t-BuOK (6.3 mg, 0.0560 mmol). This mixture was heated at 65° C. for 100 min and cooled to room temperature. The mixture was then diluted with MeOH and purified via preparative LC/MS with the following conditions: Column: Waters XBridge Phenyl, 19×200 mm, 5-µm particles; Mobile Phase A: 5:95 ACN: water with 10 mM NH$_4$OAc; Mobile Phase B: 95:5 ACN: water with 10 mM NH$_4$OAc; Gradient: 15-70% B over 20 min, then a 5-min hold at 100% B; Flow: 20 mL/min. Fractions containing the desired product were combined and dried via centrifugal evaporation to give 2-{5-[(S)-(2-fluorophenyl)(oxan-4-yl)methyl]-6-methanesulfonyl-3-[4-($^2$H$_3$)methyl-1-methyl-1H-1,2,3-triazol-5-yl]-5H-pyrido[3,2-b]indol-9-yl}-1λ$^6$,2-thiazolidine-1,1-dione (6.1 mg, 64%). $^1$HNMR (500 MHz, DMSO-d$_6$) δ 8.69 (s, 1H), 8.42 (d, J=8.5 Hz, 1H), 8.15-8.06 (m, 1H), 7.99 (s, 1H), 7.63 (d, J=8.5 Hz, 1H), 7.31 (br d, J=4.2 Hz, 2H), 7.06-6.95 (m, 2H), 4.18-4.09 (m, 1H), 4.06-3.99 (m, 1H), 3.93-3.84 (m, 1H), 3.76 (s, 3H), 3.72 (br d, J=8.3 Hz, 1H), 3.60 (s, 1H), 3.53 (br s, 3H), 3.27 (br t, J=11.3 Hz, 1H), 2.66-2.58 (m, 3H), 2.54 (s, 2H), 1.96-1.84 (m, 1H), 1.79 (br s, 2H), 0.71 (br d, J=12.3 Hz, 1H). LCMS: RT=1.610 min; (ES): m/z (M+H)$^+$=656.10, LCMS: Column: Waters Acquity UPLC BEH C18, 2.1×50 mm, 1.7-µm particles; Mobile Phase A: 5:95 ACN:water with 10 mM NH$_4$OAc; Mobile Phase B: 95:5 ACN:water with 10 mM NH$_4$OAc; Temperature: 50° C.; Gradient: 0-100% B over 3 min, then a 0.75-min hold at 100% B; Flow: 1.11 mL/min. HPLC Purity at 220 nm: 97%.

Examples 35 & 36

2-{5-[(3-Fluoropyridin-2-yl)(oxan-4-yl)methyl]-6-methanesulfonyl-3-[4-($^2$H$_3$)methyl-1-methyl-1H-1,2,3-triazol-5-yl]-5H-pyrido[3,2-b]indol-9-yl}-1λ$^6$,2-thiazolidine-1,1-dione

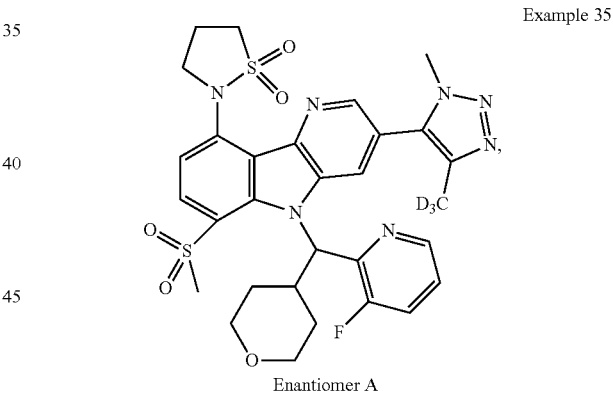

Enantiomer A

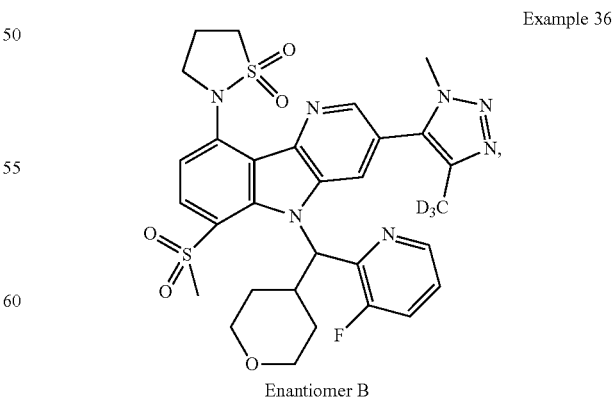

Enantiomer B

To a stirred solution of racemic 3-fluoro-2-({9-fluoro-6-methanesulfonyl-3-[4-($^2$H$_3$)methyl-1-methyl-1H-1,2,3-triazol-5-yl]-5H-pyrido[3,2-b]indol-5-yl}(oxan-4-yl)methyl) pyridine (80.0 mg, 0.140 mmol) and isothiazolidine-1,1-dione (69.8 mg, 0.580 mmol) in NMP (0.70 mL) was added t-BuOK (56.5 mg, 0.500 mmol). The mixture was heated at 65° C. for 70 min and cooled to room temperature. The mixture was diluted with water and extracted with EtOAc. Combined EtOAc extracts were dried (MgSO$_4$), filtered, and concentrated. The crude product was purified by silica gel column chromatography (Teledyne ISCO CombiFlash 0% to 100% solvent A/B=DCM/10% MeOH/DCM, RediSep SiO$_2$ 12 g, detecting at 254 nM, and monitoring at 220 nM). Concentration of appropriate fractions provided racemic 2-{5-[(3-fluoropyridin-2-yl)(oxan-4-yl)methyl]-6-methanesulfonyl-3-[4-($^2$H$_3$)methyl-1-methyl-1H-1,2,3-triazol-5-yl]-5H-pyrido[3,2-b]indol-9-yl}-1λ$^6$,2-thiazolidine-1,1-dione (110 mg). This racemic mixture was separated by chiral prep SFC (Berger SFC MGII, Column:Chiral IB 25×2.1 cm ID, 5 m Flow rate: 50.0 mL/min. Mobile Phase: 80/20 CO$_2$/MeOH Detector Wavelength: 220 nm) to give Enantiomers A (13.3 mg, 13%) and B (10.5 mg, 11%). Enantiomer A: $^1$H NMR (400 MHz, CDCl$_3$) δ 8.57 (d, J=1.8 Hz, 1H), 8.46 (dt, J=4.4, 1.5 Hz, 1H), 8.40 (d, J=8.6 Hz, 1H), 8.15 (d, J=2.0 Hz, 1H), 7.77 (d, J=8.6 Hz, 1H), 7.41-7.28 (m, 3H), 4.34-4.24 (m, 1H), 4.21-4.11 (m, 1H), 4.01 (br dd, J=12.0, 2.7 Hz, 1H), 3.95 (s, 3H), 3.82 (br dd, J=11.6, 3.1 Hz, 1H), 3.61-3.53 (m, 2H), 3.46 (br d, J=2.3 Hz, 1H), 3.43 (s, 3H), 3.34 (br d, J=11.7 Hz, 1H), 3.20 (td, J=11.9, 1.9 Hz, 1H), 2.84-2.71 (m, 2H), 1.89-1.74 (m, 3H), 0.54 (br d, J=13.0 Hz, 1H); SFC RT=10.07 min (Column: Chiralcel IB 250×4.6 mm, 5 m; Mobile Phase: 80/20 CO$_2$/MeOH; Flow: 2 mL/min); Enantiomer B: $^1$H NMR (400 MHz, CDCl$_3$) δ 8.56 (d, J=1.8 Hz, 1H), 8.45 (dt, J=4.3, 1.4 Hz, 1H), 8.40 (d, J=8.6 Hz, 1H), 8.15 (d, J=1.8 Hz, 1H), 7.76 (d, J=8.6 Hz, 1H), 7.42-7.28 (m, 3H), 4.34-4.24 (m, 1H), 4.22-4.12 (m, 1H), 4.01 (br dd, J=11.7, 2.8 Hz, 1H), 3.95 (s, 3H), 3.82 (br dd, J=11.3, 3.2 Hz, 1H), 3.56 (dt, J=7.7, 3.9 Hz, 2H), 3.46 (br d, J=2.4 Hz, 1H), 3.43 (s, 3H), 3.37-3.28 (m, 1H), 3.23-3.15 (m, 1H), 2.84-2.69 (m, 2H), 1.79 (br dd, J=12.8, 4.2 Hz, 3H), 0.54 (br d, J=12.8 Hz, 1H) LCMS (M+H)=556.2; SFC RT=12.21 min (Column: Chiralcel IB 250×4.6 mm, 5 m; Mobile Phase: 80/20 CO$_2$/MeOH; Flow: 2 mL/min).

Example 37

2-{5-[(S)-(2-Fluorophenyl)(oxan-4-yl)($^2$H)methyl]-6-methanesulfonyl-3-[4-($^2$H$_3$)methyl-1-methyl-1H-1,2,3-triazol-5-yl]-5H-pyrido[3,2-b]indol-9-yl}-1λ$^6$,2-thiazolidine-1,1-dione

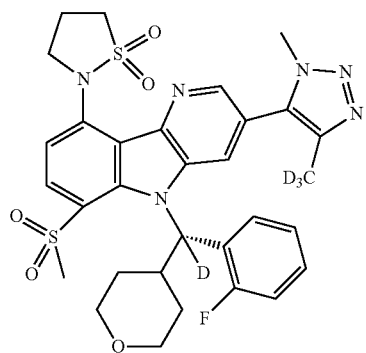 [SMILES: [2H]C([2H])([2H])c1nnn(C)c1-c1cnc2c3c(N4CCCS4(=O)=O)ccc(S(C)(=O)=O)c3n([C@]([2H])(c3ccccc3F)C3CCOCC3)c2c1]

To a stirred solution of 2-{6-methanesulfonyl-3-[4-($^2$H$_3$)methyl-1-methyl-1H-1,2,3-triazol-5-yl]-5H-pyrido[3,2-b]indol-9-yl}-1λ$^6$,2-thiazolidine-1,1-dione (50.0 mg, 0.108 mmol) and (S)-(2-fluorophenyl)(oxan-4-yl)($^2$H)methanol (45.6 mg, 0.216 mmol) in toluene (0.50 mL) was added triphenylphosphine (56.6 mg, 0.216 mmol) and DIAD (0.0420 mL, 0.216 mmol). The mixture was stirred at room temperature for 70 min. The reaction mixture was then directly purified by silica gel column chromatography (Teledyne ISCO CombiFlash 0% to 100% solvent A/B=DCM/10% MeOH in DCM, RediSep SiO$_2$ 24 g, detecting at 254 nM, and monitoring at 220 nM). Concentration of appropriate fractions provided an impure product (142 mg). It was diluted with DMF and purified via preparative LC/MS with the following conditions: Column: Waters XBridge Phenyl, 19×200 mm, 5-μm particles; Mobile Phase A: 5:95 ACN:water with 10 mM NH$_4$OAc; Mobile Phase B: 95:5 ACN:water with 10 mM NH$_4$OAc; Gradient: 15-70% B over 20 min, then a 5-min hold at 100% B; Flow: 20 mL/min. Fractions containing the desired product were combined and dried via centrifugal evaporation to give 2-{5-[(S)-(2-fluorophenyl)(oxan-4-yl)($^2$H)methyl]-6-methanesulfonyl-3-[4-($^2$H$_3$)methyl-1-methyl-1H-1,2,3-triazol-5-yl]-5H-pyrido[3,2-b]indol-9-yl}-1λ$^6$,2-thiazolidine-1,1-dione (27.0 mg, 36%). $^1$H NMR (500 MHz, DMSO-d$_6$) δ 8.70 (d, J=1.2 Hz, 1H), 8.43 (d, J=8.5 Hz, 1H), 8.16-8.08 (m, 1H), 8.01 (s, 1H), 7.63 (d, J=8.5 Hz, 1H), 7.37-7.26 (m, 2H), 7.04-6.96 (m, 1H), 4.19-4.10 (m, 1H), 4.08-4.00 (m, 1H), 3.88 (br d, J=8.4 Hz, 1H), 3.77 (s, 3H), 3.73 (br d, J=7.9 Hz, 1H), 3.60 (s, 2H), 3.56 (br t, J=6.9 Hz, 1H), 3.43 (br s, 1H), 3.27 (br t, J=11.5 Hz, 1H), 2.67-2.56 (m, 2H), 2.54 (s, 3H), 1.97-1.85 (m, 1H), 1.79 (br s, 2H), 0.72 (br d, J=11.9 Hz, 1H) LCMS: RT=1.52 min; (ES): m/z (M+H)$^+$=657.2. LCMS: Column: Waters Acquity UPLC BEH C18, 2.1×50 mm, 1.7-μm particles; Mobile Phase A: 5:95 ACN:water with 10 mM NH$_4$OAc; Mobile Phase B: 95:5 ACN:water with 10 mM NH$_4$OAc; Temperature: 50° C.; Gradient: 0-100% B over 3 min, then a 0.75-min hold at 100% B; Flow: 1.11 mL/min. HPLC Purity at 220 nm: 95%.

Example 38

2-{6-Methanesulfonyl-3-[4-($^2$H$_3$)methyl-1-methyl-1H-1,2,3-triazol-5-yl]-5-[(S)-oxan-4-yl(phenyl)($^2$H)methyl]-5H-pyrido[3,2-b]indol-9-yl}-1λ$^6$,2-thiazolidine-1,1-dione

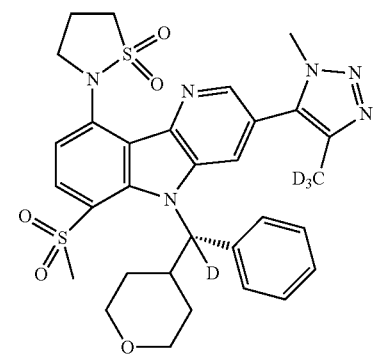 [SMILES: [2H]C([2H])([2H])c1nnn(C)c1-c1cnc2c3c(N4CCCS4(=O)=O)ccc(S(C)(=O)=O)c3n([C@]([2H])(c3ccccc3)C3CCOCC3)c2c1]

Step 1: 2-(3-Bromo-6-(methylsulfonyl)-5H-pyrido[3,2-b]indol-9-yl)isothiazolidine-1,1-dione To a stirred solution of 3-bromo-9-fluoro-6-methanesulfonyl-5H-pyrido[3,2-b]indole (200 mg, 0.583 mmol) and isothiazolidine-1,1-dione (278 mg, 2.30 mmol) in NMP (2.40 mL) was added t-BuOK (203 mg, 1.81 mmol). This mixture was heated at 115° C. for 11 h and cooled to room temperature. The mixture was diluted with EtOAc (20 mL) and 10% aq. LiCl solution (20 mL). Some insoluble solid was filtered to give the desired product, 2-(3-bromo-6-(methylsulfonyl)-5H-pyrido[3,2-b]indol-9-yl)isothiazolidine-1,1-dione (115 mg, 44%). $^1$H NMR (400 MHz, DMSO-$d_6$) δ 11.94 (br s, 1H), 8.72 (br s, 1H), 8.32 (br s, 1H), 8.04 (br d, J=7.6 Hz, 1H), 7.55 (br s, 1H), 4.22 (br s, 2H), 3.59 (br s, 2H), 3.39 (br s, 3H), 2.61 (br s, 2H). HPLC: RT=2.055 min (Chromolith ODS 4.6×50 mm (4 min grad) eluting with 10-90% aqueous MeOH over 4 min containing 0.1% TFA, 4 mL/min, monitoring at 220 nm); MS (ES): m/z=444.1; 445.9 (Br pattern) [M+H]$^+$.

Step 2: 2-{6-Methanesulfonyl-3-[4-($^2$H$_3$)methyl-1-methyl-1H-1,2,3-triazol-5-yl]-5H-pyrido[3,2-b]indol-9-yl}-1λ$^6$,2-thiazolidine-1,1-dione To a stirred solution of 2-(3-bromo-6-(methylsulfonyl)-5H-pyrido[3,2-b]indol-9-yl)isothiazolidine-1,1-dione (112 mg, 0.252 mmol) and 4-($^2$H$_3$)methyl-1-methyl-5-(tributylstannyl)-1-H-1,2,3-triazole (177 mg, 0.454 mmol) in DMF (1.0 mL) was added Et$_3$N (0.0770 mL, 0.555 mmol), and the mixture was then purged with nitrogen. While purging, copper (I) iodide (7.2 mg, 0.0380 mmol) and tetrakis(triphenylphosphine) palladium (0) (35.0 mg, 0.0300 mmol) were added. The reaction mixture was purged with nitrogen for another 5 min and then heated at 95° C. for 4.5 h. The cooled mixture was diluted with 10% aq. LiCl solution and extracted with EtOAc. Combined EtOAc extracts were washed with brine, dried (MgSO$_4$), filtered, and concentrated to give the crude mixture. The crude product was purified by silica gel column chromatography (Teledyne ISCO CombiFlash 0% to 100% solvent A/B=DCM/10% MeOH in DCM, RediSep SiO$_2$ 24 g, detecting at 254 nM, and monitoring at 220 nM). Concentration of appropriate fractions provided 2-{6-methanesulfonyl-3-[4-($^2$H$_3$)methyl-1-methyl-1H-1,2,3-triazol-5-yl]-5H-pyrido[3,2-b]indol-9-yl}-1λ$^6$,2-thiazolidine-1,1-dione (82.5 mg, 71%). $^1$H NMR (400 MHz, DMSO-$d_6$) δ 12.00 (s, 1H), 8.76 (s, 1H), 8.23 (s, 1H), 8.08 (d, J=8.3 Hz, 1H), 7.60 (br d, J=8.2 Hz, 1H), 4.33 (br t, J=6.6 Hz, 2H), 4.03 (s, 3H), 3.62 (br t, J=7.3 Hz, 2H), 3.41 (s, 3H), 2.67-2.60 (m, 2H). HPLC: RT=1.763 min (Chromolith ODS 4.6×50 mm (4 min grad) eluting with 10-90% aqueous MeOH over 4 min containing 0.1% TFA, 4 mL/min, monitoring at 220 nm); MS (ES): m/z=464.1 [M+H]$^+$.

Step 3: 2-{6-Methanesulfonyl-3-[4-($^2$H$_3$)methyl-1-methyl-1H-1,2,3-triazol-5-yl]-5-[(S)-oxan-4-yl(phenyl)($^2$H)methyl]-5H-pyrido[3,2-b]indol-9-yl}-1λ$^6$,2-thiazolidine-1,1-dione To a stirred solution of 2-{6-methanesulfonyl-3-[4-($^2$H$_3$) methyl-1-methyl-1H-1,2,3-triazol-5-yl]-5H-pyrido[3,2-b] indol-9-yl}-1λ$^6$,2-thiazolidine-1,1-dione (32.5 mg, 0.0700 mmol) and (S)-oxan-4-yl(phenyl)($^2$H)methanol (27.1 mg, 0.140 mmol) in toluene (0.50 mL) was added triphenylphosphine (36.8 mg, 0.140 mmol) and DIAD (0.0270 mL, 0.140 mmol). The mixture was stirred at room temperature for 1 h. The reaction mixture was then directly purified by silica gel column chromatography (Teledyne ISCO CombiFlash 0% to 100% solvent A/B=DCM/10% MeOH in DCM, RediSep SiO$_2$ 12 g, detecting at 254 nM, and monitoring at 220 nM). Concentration of appropriate fractions provided an impure product (102 mg). It was diluted with DMF and purified via preparative LC/MS with the following conditions: Column: Waters XBridge Phenyl, 19×200 mm, 5-μm particles; Mobile Phase A: 5:95 ACN: water with 10 mM NH$_4$OAc; Mobile Phase B: 95:5 ACN: water with 10 mM NH$_4$OAc; Gradient: 15-70% B over 20 min, then a 5-min hold at 100% B; Flow: 20 mL/min. Fractions containing the desired product were combined and dried via centrifugal evaporation to give 2-{6-methanesulfonyl-3-[4-($^2$H$_3$)methyl-1-methyl-1H-1,2,3-triazol-5-yl]-5-[(S)-oxan-4-yl(phenyl)($^2$H)methyl]-5H-pyrido[3,2-b]indol-9-yl}-1λ$^6$,2-thiazolidine-1,1-dione (22.5 mg, 48%). $^1$H NMR (500 MHz, DMSO-$d_6$) δ 8.72 (s, 1H), 8.39 (d, J=8.5 Hz, 1H), 7.62 (br d, J=7.0 Hz, 3H), 7.38-7.30 (m, 2H), 7.13 (s, 1H), 7.03 (s, 1H), 4.12 (br s, 2H), 3.87 (br d, J=8.8 Hz, 1H), 3.77 (s, 3H), 3.75 (s, 2H), 3.65 (br d, J=7.8 Hz, 1H), 3.57 (t, J=7.5 Hz, 1H), 3.53-3.45 (m, 1H), 3.19 (br t, J=11.6 Hz, 1H), 2.62 (quin, J=7.1 Hz, 2H), 2.54 (s, 3H), 1.94 (br d, J=13.2 Hz, 1H), 1.74-1.58 (m, 2H), 0.43 (br d, J=11.9 Hz, 1H). LCMS: RT=1.51 min; (ES): m/z (M+H)$^+$=639.3. LCMS: Column: Waters Acquity UPLC BEH C18, 2.1×50 mm, 1.7-μm particles; Mobile Phase A: 5:95 ACN:water with 10 mM NH$_4$OAc; Mobile Phase B: 95:5 ACN:water with 10 mM NH$_4$OAc; Temperature: 50° C.; Gradient: 0-100% B over 3 min, then a 0.75-min hold at 100% B; Flow: 1.11 mL/min. HPLC Purity at 220 nm: 95%.

Example 39

4-{5-[(S)-(4-Fluorophenyl)(oxan-4-yl)methyl]-3-[4-($^2$H$_3$)methyl-1-methyl-1H-1,2,3-triazol-5-yl]-5H-pyrido[3,2-b]indol-8-yl}-1λ$^6$-thiomorpholine-1,1-dione

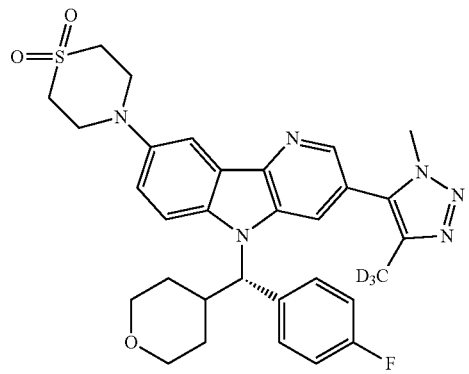 [SMILES: [2H]C([2H])([2H])c1nnn(C)c1-c1cnc2c3cc(N4CCS(=O)(=O)CC4)ccc3n([C@H](c3ccc(F)cc3)C3CCOCC3)c2c1]

Step 1: 5-Bromo-3-nitro-2-phenylpyridine

In a 500 ml flask was added phenylboronic acid (4 g, 32.8 mmol),2,5-dibromo-3-nitropyridine (9.25 g, 32.8 mmol) and 250 mL THF. To this was added tripotassium phosphate (49.2 ml, 98 mmol) and PdCl$_2$(dppf)-CH$_2$Cl$_2$ adduct (1.875 g, 2.30 mmol). Bubbled in nitrogen through the mixture while adding reagents. The flask was fitted with a condenser and heated at reflux overnight under nitrogen. The reaction was concentrated, partitioned residue between EtOAc and water. Obtained emulsion. Filtered through celite. Washed organic layer with brine. Dried organic layer over MgSO$_4$, filtered and concentrated to afford 12.5 g of a black oil. The crude material was purified on a 120 g Isco column, eluting with 0-25% EtOAc/hexanes over 17 column volumes. Fractions containing the title compound were pooled and concentrated to afford 6.24 g. ¹H NMR (400 MHz, CDCl₃) δ 8.94 (d, J=2.0 Hz, 1H), 8.33-8.27 (m, 1H), 7.62-7.54 (m, 2H), 7.54-7.44 (m, 3H).

Step 2: 3-Bromo-5H-pyrido[3,2-b]indole

5-Bromo-3-nitro-2-phenylpyridine (6.24 g, 22.4 mmol) was dissolved in 20 mL dichlorobenzene. To this was added DPPE (11.58 g, 29.1 mmol) and heated at 160° C. for 2 h. Concentrated the reaction and purified in three lots on a 120 g Isco column. Concentrated fractions containing the title compound to afford 3.28 g. ¹H NMR (400 MHz, DMSO-d₆) δ 11.60 (s, 1H), 8.51 (d, J=2.0 Hz, 1H), 8.21-8.06 (m, 2H), 7.63-7.39 (m, 2H), 7.27 (ddd, J=7.9, 6.8, 1.1 Hz, 1H).

Step 3: (S)-3-Bromo-5-((4-fluorophenyl)(tetrahydro-2H-pyran-4-yl)methyl)-5H-pyrido[3,2-b]indole 3-Bromo-5H-pyrido[3,2-b]indole (1.4 g, 5.67 mmol) was dissolved in 40 mL DCM. To this was added (R)-(4-fluorophenyl)(tetrahydro-2H-pyran-4-yl)methanol (1.6 g, 7.61 mmol) and triphenylphosphine (2.081 g, 7.93 mmol). Cooled in an ice bath, then added DIAD (2.20 ml, 11.3 mmol) dropwise and stirred for 15 min. Removed bath and stirred overnight. Concentrated reaction and purified on a 80 g Isco column, eluting with 0-30% EtOAc/hexanes over 15 column volumes. Pooled and concentrated fractions to afford 0.71 g of the title compound. ¹H NMR (400 MHz, CDCl₃) δ 8.59 (d, J=1.7 Hz, 1H), 8.36 (d, J=7.8 Hz, 1H), 7.93 (d, J=1.7 Hz, 1H), 7.65-7.55 (m, 2H), 7.46 (dd, J=8.8, 5.1 Hz, 2H), 7.42-7.31 (m, 1H), 7.12-6.99 (m, 2H), 5.37 (d, J=11.0 Hz, 1H), 4.11-4.02 (m, 1H), 3.87 (dd, J=11.6, 3.8 Hz, 1H), 3.56 (td, J=11.9, 1.8 Hz, 1H), 3.38 (td, J=11.9, 2.1 Hz, 1H), 3.15-2.91 (m, 1H), 1.95 (d, J=13.7 Hz, 1H), 1.41-1.35 (m, 1H), 1.10 (d, J=11.7 Hz, 1H).

Step 4: (S)-5-{5-[(4-Fluorophenyl)(oxan-4-yl)methyl]-5H-pyrido[3,2-b]indol-3-yl}-4-(²H₃)methyl-1-methyl-1H-1,2,3-triazole (S)-3-Bromo-5-((4-fluorophenyl)(tetrahydro-2H-pyran-4-yl)methyl)-5H-pyrido[3,2-b]indole (0.73 g, 1.66 mmol) was dissolved in DMF (20 ml). Bubbled in argon while sonicating for 1 min, then continued to bubble in argon and sonicate while adding 4-(²H₃)methyl-1-methyl-5-(tributylstannyl)-1H-1,2,3-triazole (0.711 g, 1.83 mmol), Copper (I) iodide (0.063 g, 0.332 mmol), triethylamine (0.278 ml, 1.99 mmol) and Pd(PPh₃)₄ (0.192 g, 0.166 mmol). Sealed flask and heated at 100° C. for 2 h. Partitioned reaction between EtOAc and water. Filtered mixture through celite. Extracted water twice with EtOAc. Washed the combined organic layer with brine, dried over MgSO₄ filtered and concentrated. Purified residue on an 80 g Isco column, eluting with DCM to 20% MeOH/DCM over 20 column volumes. Pooled fractions containing the title compound and concentrated to afford 0.58 g. ¹H NMR (400 MHz, DMSO-d₆) δ 8.55 (d, J=1.5 Hz, 1H), 8.24 (d, J=7.3 Hz, 1H), 7.73 (dd, J=8.8, 5.5 Hz, 2H), 7.67-7.37 (m, 2H), 7.33 (t, J=7.4 Hz, 1H), 7.15 (t, J=8.8 Hz, 2H), 5.84 (d, J=11.3 Hz, 1H), 4.02 (s, 3H), 3.89 (d, J=11.3 Hz, 1H), 3.80-3.67 (m, 1H), 3.53-3.36 (m, 1H), 3.25 (t, J=10.9 Hz, 1H), 1.71-1.59 (m, 1H), 1.52 (dd, J=12.0, 3.3 Hz, 1H), 1.36-1.23 (m, 1H), 0.99 (d, J=13.6 Hz, 1H). LC/MS Method 6, Rt=1.64 min, M+H=459.

Step 5: (S)-5-{8-Bromo-5-[(4-fluorophenyl)(oxan-4-yl)methyl]-5H-pyrido[3,2-b]indol-3-yl}-4-(²H₃)methyl-1-methyl-1H-1,2,3-triazole (S)-5-{5-[(4-Fluorophenyl)(oxan-4-yl)methyl]-5H-pyrido[3,2-b]indol-3-yl}-4-(²H₃)methyl-1-methyl-1H-1,2,3-triazole (0.58 g, 1.27 mmol) was dissolved in acetonitrile (18.1 ml). Cooled in an ice bath and added NBS (0.248 g, 1.39 mmol). Removed bath and stirred overnight. The reaction was concentrated and the resulting residue dissolved in DCM and purified on a 40 g Isco column, eluting with DCM to 15% MeOH/DCM over 600 mL. Combined fractions containing major peak to afford 605 mg of the title compound as a yellow solid. ¹H NMR (400 MHz, DMSO-d₆) δ 8.59 (d, J=1.5 Hz, 1H), 8.51 (br. s., 1H), 8.35 (d, J=2.3 Hz, 1H), 8.14 (br. s., 1H), 7.78-7.67 (m, 3H), 7.65-7.50 (m, 1H), 7.15 (t, J=8.8 Hz, 2H), 5.84 (d, J=11.3 Hz, 1H), 4.02 (s, 3H), 3.88 (d, J=10.3 Hz, 1H), 3.72 (d, J=8.3 Hz, 1H), 3.48-3.41 (m, 1H), 3.25 (t, J=10.8 Hz, 1H), 1.71-1.59 (m, 1H), 1.59-1.44 (m, 1H), 1.35-1.17 (m, 2H). LC/MS using Method 5, Rt=1.02 min, M+H=537.

Step 6: 4-{5-[(S)-(4-Fluorophenyl)(oxan-4-yl)methyl]-3-[4-(²H₃)methyl-1-methyl-1H-1,2,3-triazol-5-yl]-5H-pyrido[3,2-b]indol-8-yl}-1λ⁶-thiomorpholine-1,1-dione In a 20 mL, thick walled scintillation vial equipped with a stir bar, (S)-5-{8-bromo-5-[(4-fluorophenyl)(oxan-4-yl)methyl]-5H-pyrido[3,2-b]indol-3-yl}-4-(²H₃)methyl-1-methyl-1H-1,2,3-triazole (0.018 g, 0.033 mmol) was dissolved in 2 mL dioxane. Bubbled in nitrogen while adding thiomorpholine 1,1-dioxide (9.1 mg, 0.067 mmol), cesium carbonate (0.044 g, 0.134 mmol), then 2nd generation X-Phosprecatalyst (CAS #1310584-14-5, 5.3 mg, 6.70 μmol). The via was sealed and heated in a oil bath at 100° C. for 14 h. The crude material was purified via preparative LC/MS with the following conditions: Column: XBridge C18, 19×200 mm, 5-μm particles; Mobile Phase A: 5:95 MeOH: water with 10 mM NH₄OAc; Mobile Phase B: 95:5 MeOH: water with 10 mM NH₄OAc; Gradient: 50-90% B over 20 min, then a 5 min hold at 100% B; Flow: 20 mL/min. Fractions containing the desired product were combined and dried via centrifugal evaporation. The yield of the product was 1.7 mg, and its estimated purity by LCMS analysis was 98%. Two analytical LC/MS injections were used to determine the final purity. Injection 1 conditions: Column: Waters BEH C18, 2.0×50 mm, 1.7-μm particles; Mobile Phase A: 5:95 ACN:water with 10 mM NH₄OAc; Mobile Phase B: 95:5 ACN:water with 10 mM NH₄OAc; Temperature: 50° C.; Gradient: 0% B, 0-100% B over 3 min, then a 0.5 min hold at 100% B; Flow: 1 mL/min; Detection: UV at 220 nm, Rt=1.53 min. Injection 2 conditions: Column: Waters BEH C18, 2.0×50 mm, 1.7-μm particles; Mobile Phase A: 5:95 MeOH:water with 10 mM NH₄OAc; Mobile Phase B: 95:5 MeOH:water with 10 mM NH₄OAc; Temperature: 50° C.; Gradient: 0% B, 0-100% B over 3 min, then a 0.5 min hold at 100% B; Flow: 0.5 mL/min; Detection: UV at 220 nm, Rt=2.32, M+H=592. ¹H NMR (500 MHz, DMSO-d₆) δ 8.48 (s, 1H), 8.43 (br. s., 1H), 8.01 (br. s., 1H), 7.76-7.66 (m, 2H), 7.43 (br. s., 1H), 7.15 (t, J=8.8 Hz, 2H), 5.75 (d, J=11.4 Hz, 1H), 4.02 (br. s., 3H), 3.94-3.83 (m, 3H), 3.83-3.66 (m, 6H), 3.35 (d, J=9.2 Hz, 1H), 3.23 (br. s., 4H), 1.63 (d, J=12.8 Hz, 1H), 1.50 (d, J=13.6 Hz, 1H), 1.28 (d, J=8.8 Hz, 1H), 1.02 (d, J=11.0 Hz, 1H)

Example 40

1-{5-[(S)-(4-Fluorophenyl)(oxan-4-yl)methyl]-3-[4-($^2$H$_3$)methyl-1-methyl-1H-1,2,3-triazol-5-yl]-5H-pyrido[3,2-b]indol-8-yl}-4-methanesulfonylpiperazine

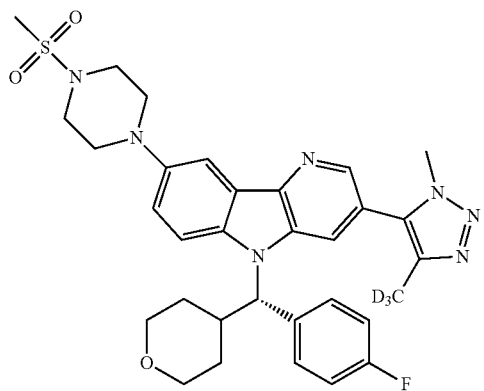 [SMILES: [2H]C([2H])([2H])c1nnn(C)c1-c1cnc2c3cc(N4CCN(S(C)(=O)=O)CC4)ccc3n([C@H](c3ccc(F)cc3)C3CCOCC3)c2c1]

In a v-shaped microwave vial equipped with a stir bar, added (S)-5-{8-bromo-5-[(4-fluorophenyl)(oxan-4-yl)methyl]-5H-pyrido[3,2-b]indol-3-yl}-4-($^2$H$_3$)methyl-1-methyl-1H-1,2,3-triazole (0.018 g, 0.033 mmol), 1-(methylsulfonyl)piperazine (0.011 g, 0.067 mmol), 2-dicyclohexylphosphino-2',6'-di-isopropoxy-1,1'-biphenyl (4.7 mg, 10.0 mol), and (2-dicyclohexylphosphino-2',6'-diisopropyl-1,1'-biphenyl)[2-(2-aminoethyl)phenyl]-palladium(II) (7.3 mg, 10.0 μmol) and sodium tert-butoxide (0.013 g, 0.134 mmol). 2 mL THF was added and the vial flushed with argon while sonicating for 1 min. Heated in the microwave at 120° C. for 1 h. The crude material was purified via preparative LC/MS with the following conditions: Column: XBridge C18, 19×200 mm, 5-μm particles; Mobile Phase A: 5:95 ACN: water with 10 mM NH$_4$OAc; Mobile Phase B: 95:5 ACN: water with 10 mM NH$_4$OAc; Gradient: 25-65% B over 15 min, then a 5 min hold at 100% B; Flow: 20 mL/min. Fractions containing the desired product were combined and dried via centrifugal evaporation. The yield of the product was 7.5 mg, and its estimated purity by LCMS analysis was 98%. Two analytical LC/MS injections were used to determine the final purity. Injection 1 conditions: Column: Waters BEH C18, 2.0×50 mm, 1.7-μm particles; Mobile Phase A: 5:95 ACN:water with 10 mM NH$_4$OAc; Mobile Phase B: 95:5 ACN:water with 10 mM NH$_4$OAc; Temperature: 50° C.; Gradient: 0-100% B over 3 min, then a 0.5 min hold at 100% B; Flow: 1.0 mL/min; Detection: UV at 220 nm, Rt=1.66 min, M=H=621. Injection 2 conditions: Column: Waters BEH C18, 2.0×50 mm, 1.7-μm particles; Mobile Phase A: 5:95 MeOH:water with 10 mM NH$_4$OAc; Mobile Phase B: 95:5 MeOH:water with 10 mM NH$_4$OAc; Temperature: 50° C.; Gradient: 0-100% B over 3 min, then a 0.5 min hold at 100% B; Flow: 0.5 mL/min; Detection: UV at 220 nm Rt=2.66 min, M=H=621. $^1$H NMR (500 MHz, DMSO-d$_6$) δ 8.48 (s, 1H), 8.42 (br. s., 1H), 8.03 (br. s., 1H), 7.81-7.65 (m, 3H), 7.41 (d, J=8.4 Hz, 1H), 7.15 (t, J=8.6 Hz, 2H), 5.75 (d, J=11.4 Hz, 1H), 4.02 (s, 3H), 3.89 (d, J=13.9 Hz, 1H), 3.73 (d, J=11.0 Hz, 1H), 3.49-3.40 (m, 9H), 3.37 (br. s., 1H), 3.30-3.26 (m, 5H), 1.63 (d, J=11.7 Hz, 1H), 1.58-1.44 (m, 1H), 1.28 (d, J=8.4 Hz, 1H), 1.02 (d, J=12.5 Hz, 1H).

Example 41

4-{5-[(S)-(2-Fluorophenyl)(oxan-4-yl)methyl]-3-[4-($^2$H$_3$)methyl-1-methyl-1H-1,2,3-triazol-5-yl]-5H-pyrido[3,2-b]indol-8-yl}-1λ$^6$-thiomorpholine-1,1-dione

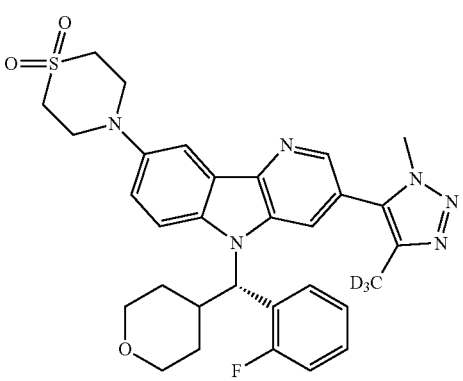 [SMILES: [2H]C([2H])([2H])c1nnn(C)c1-c1cnc2c3cc(N4CCS(=O)(=O)CC4)ccc3n([C@H](c3ccccc3F)C3CCOCC3)c2c1]

In a manner similar to the preparation of 4-{5-[(S)-(4-fluorophenyl)(oxan-4-yl)methyl]-3-[4-($^2$H$_3$)methyl-1-methyl-1H-1,2,3-triazol-5-yl]-5H-pyrido[3,2-b]indol-8-yl}-1λ$^6$-thiomorpholine-1,1-dione, the title compound was prepared starting with 3-bromo-5H-pyrido[3,2-b]indole and (R)-(2-fluorophenyl)(tetrahydro-2H-pyran-4-yl)methanol.

The crude material was purified via preparative LC/MS with the following conditions: Column: XBridge C18, 19×200 mm, 5-μm particles; Mobile Phase A: 5:95 MeOH: water with 10 mM NH$_4$OAc; Mobile Phase B: 95:5 MeOH: water with 10 mM NH$_4$OAc; Gradient: 45-85% B over 15 min, then a 5 min hold at 100% B; Flow: 20 mL/min. Fractions containing the desired product were combined and dried via centrifugal evaporation. The yield of the product was 20.5 mg, and its estimated purity by LCMS analysis was 96%. Two analytical LC/MS injections were used to determine the final purity. Injection 1 conditions: Column: Waters BEH C18, 2.0×50 mm, 1.7-μm particles; Mobile Phase A: 5:95 ACN:water with 10 mM NH$_4$OAc; Mobile Phase B: 95:5 ACN:water with 10 mM NH$_4$OAc; Temperature: 50° C.; Gradient: 0% B, 0-100% B over 3 min, then a 0.5 min hold at 100% B; Flow: 1 mL/min; Detection: UV at 220 nm, Rt=1.46 min. Injection 2 conditions: Column: Waters BEH C18, 2.0×50 mm, 1.7-μm particles; Mobile Phase A: 5:95 MeOH:water with 10 mM NH$_4$OAc; Mobile Phase B: 95:5 MeOH:water with 10 mM NH$_4$OAc; Temperature: 50° C.; Gradient: 0% B, 0-100% B over 3 min, then a 0.5 min hold at 100% B; Flow: 0.5 mL/min; Detection: UV at 220 nm, Rt=2.32 min. $^1$H NMR (500 MHz, DMSO-d$_6$) δ 8.50 (s, 1H), 8.20 (t, J=7.2 Hz, 1H), 7.89 (br. s., 1H), 7.80 (s, 1H), 7.34-7.29 (m, 4H), 7.23 (s, 3H), 7.15-7.10 (m, 4H), 5.97 (d, J=11.4 Hz, 1H), 4.01 (br. s., 3H), 3.88 (d, J=9.5 Hz, 1H), 3.77 (br. s., 4H), 3.71 (d, J=9.9 Hz, 1H), 3.62-3.53 (m, 2H), 3.53-3.30 (m, 2H), 1.71 (d, J=11.7 Hz, 1H), 1.64-1.49 (m, 1H), 1.33 (d, J=9.2 Hz, 1H), 0.82 (d, J=11.4 Hz, 1H).

Example 42

1-{5-[(S)-(2-Fluorophenyl)(oxan-4-yl)methyl]-3-[4-(²H₃)methyl-1-methyl-1H-1,2,3-triazol-5-yl]-5H-pyrido[3,2-b]indol-8-yl}-4-methanesulfonylpiperazine

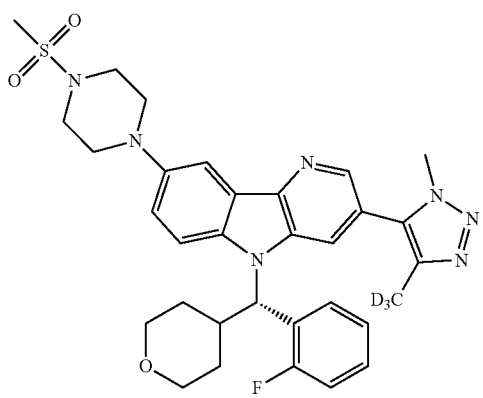 [SMILES: [2H]C([2H])([2H])c1nnn(C)c1-c1cnc2c3cc(N4CCN(S(C)(=O)=O)CC4)ccc3n([C@H](c3ccccc3F)C3CCOCC3)c2c1]

In a manner similar to the preparation 1-{5-[(S)-(4-fluorophenyl)(oxan-4-yl)methyl]-3-[4-(²H₃)methyl-1-methyl-1H-1,2,3-triazol-5-yl]-5H-pyrido[3,2-b]indol-8-yl}-4-methanesulfonylpiperazine, the title compound was prepared starting with 3-bromo-5H-pyrido[3,2-b]indole and (R)-(2-fluorophenyl)(tetrahydro-2H-pyran-4-yl)methanol. The crude material was purified via preparative LC/MS with the following conditions: Column: XBridge C18, 19×200 mm, 5-μm particles; Mobile Phase A: 5:95 MeOH: water with 10 mM NH₄OAc; Mobile Phase B: 95:5 MeOH: water with 10 mM NH₄OAc; Gradient: 35-75% B over 20 min, then a 5 min hold at 100% B; Flow: 20 mL/min. Fractions containing the desired product were combined and dried via centrifugal evaporation. The yield of the product was 6.5 mg, and its estimated purity by LCMS analysis was 98%. Two analytical LC/MS injections were used to determine the final purity. Injection 1 conditions: Column: Waters BEH C18, 2.0×50 mm, 1.7-μm particles; Mobile Phase A: 5:95 ACN:water with 10 mM NH₄OAc; Mobile Phase B: 95:5 ACN:water with 10 mM NH₄OAc; Temperature: 50° C.; Gradient: 0% B, 0-100% B over 3 min, then a 0.5 min hold at 100% B; Flow: 1 mL/min; Detection: UV at 220 nm, Rt=1.56 min. Injection 2 conditions: Column: Waters BEH C18, 2.0×50 mm, 1.7-μm particles; Mobile Phase A: 5:95 MeOH:water with 10 mM NH₄OAc; Mobile Phase B: 95:5 MeOH:water with 10 mM NH₄OAc; Temperature: 50° C.; Gradient: 0% B, 0-100% B over 3 min, then a 0.5 min hold at 100% B; Flow: 0.5 mL/min; Detection: UV at 220 nm, Rt=2.41 min. $^1$H NMR (500 MHz, DMSO-d₆) δ 8.50 (s, 2H), 8.20 (t, J=7.3 Hz, 1H), 7.88 (br. s., 1H), 7.43-7.23 (m, 5H), 7.18 (s, 1H), 7.15-7.03 (m, 3H), 5.97 (d, J=11.4 Hz, 1H), 4.01 (br. s., 3H), 3.89 (d, J=8.8 Hz, 1H), 3.71 (d, J=11.0 Hz, 1H), 3.50-3.38 (m, 7H), 3.06 (br. s., 1H), 2.56 (t, J=5.1 Hz, 1H), 1.71 (d, J=12.5 Hz, 1H), 1.57 (d, J=9.9 Hz, 1H), 1.33 (d, J=11.4 Hz, 1H), 0.82 (d, J=12.8 Hz, 1H)

Example 43

2-{5-[(S)-(4-Fluorophenyl)(oxan-4-yl)methyl]-3-[4-(²H₃)methyl-1-methyl-1H-1,2,3-triazol-5-yl]-5H-pyrido[3,2-b]indol-8-yl}-1,2,3,4-tetrahydroisoquinoline

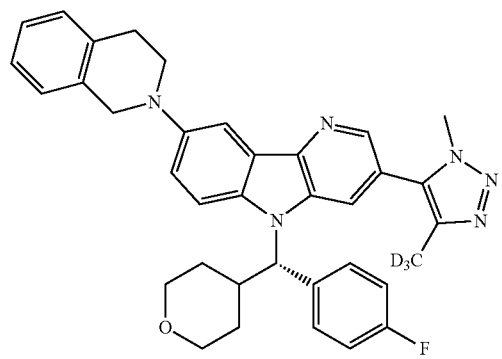 [SMILES: [2H]C([2H])([2H])c1nnn(C)c1-c1cnc2c3cc(N4CCc5ccccc5C4)ccc3n([C@H](c3ccc(F)cc3)C3CCOCC3)c2c1]

To 5.0 mL microwave vial containing a stir bar was added (S)-5-{8-bromo-5-[(4-fluorophenyl)(oxan-4-yl)methyl]-5H-pyrido[3,2-b]indol-3-yl}-4-(²H₃)methyl-1-methyl-1H-1,2,3-triazole (0.018 g 0.033 mmol), 1,2,3,4-tetrahydroisoquinoline (8.9 mg, 0.067 mmol), sodium tert-butoxide (0.013 g, 0.134 mmol), 2nd generation RuPhos precatalyst (CAS #1375325-68-0, 7.8 mg, 10.1 μmol) and RuPhos (3.1 mg, 6.70 μmol). To the vial was added 2.0 mL anhydrous THF. The vial was purged with nitrogen and then sealed. The sample was purged with nitrogen again and then irradiated in the Biotage microwave at 120° C. for 1 h. The sample was filtered through 0.45 μM Whatman filter and washed with methanol. The sample was dried down and then dissolved in DMF and methanol to give a final volume of 1.7 mL and sonicated till everything dissolved. The crude material was purified via preparative LC/MS with the following conditions: Column: XBridge C18, 19×200 mm, 5-μm particles; Mobile Phase A: 5:95 MeOH: water with 0.1% trifluoroacetic acid; Mobile Phase B: 95:5 MeOH: water with 0.1% trifluoroacetic acid; Gradient: 30-100% B over 20 min, then a 5 min hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 ACN: water with 10 mM NH₄OAc; Mobile Phase B: 95:5 ACN: water with 10 mM NH₄OAc; Gradient: 45-85% B over 15 min, then a 5 min hold at 100% B; Flow: 20 mL/min. Fractions containing the desired product were combined and dried via centrifugal evaporation. The yield of the product was 3.5 mg, and its estimated purity by LCMS analysis was 92%. Two analytical LC/MS injections were used to determine the final purity. Injection 1 conditions: Column: Waters BEH C18, 2.0×50 mm, 1.7-μm particles; Mobile Phase A: 5:95 ACN:water with 10 mM NH₄OAc; Mobile Phase B: 95:5 ACN:water with 10 mM NH₄OAc; Temperature: 50° C.; Gradient: 0% B, 0-100% B over 3 min, then a 0.5 min hold at 100% B; Flow: 1 mL/min; Detection: UV at 220 nm. Injection 2 conditions: Column: Waters BEH C18, 2.0×50 mm, 1.7-μm particles; Mobile Phase A: 5:95 MeOH:water with 10 mM NH₄OAc; Mobile Phase B: 95:5 MeOH:water with 10 mM NH₄OAc; Temperature: 50° C.; Gradient: 0% B, 0-100% B over 3 min, then a 0.5 min hold at 100% B; Flow: 0.5 mL/min; Detection: UV at 220 nm. Rt=3.11 mins., M+H=590. $^1$H NMR (500 MHz, DMSO-$d_6$) δ 8.47 (d, J=1.5 Hz, 1H), 8.45 (br. s., 1H), 8.03 (b, s, 1H), 7.75 (m, 2H), 7.48 (m, 3H), 7.27 (d, J=7.3, 1H), 7.15 (m, 5H), 5.75 (d, J=11 Hz, 1H), 4.44 (s, 2H), 4.03 (s, 3H), 3.88 (d, J=10.3 Hz, 1H), 3.72 (d, J=8.3 Hz, 1H), 3.60 (t, J=5.7 Hz, 2H), 3.46 (m, 1H), 3.36 (d, J=18.0 Hz, 1H), 3.27 (t, J=11.2 Hz, 1H), 3.18 (s, 1H), 1.63 (m, 1H), 1.51 (m, 1H), 1.27 (m, 2H)

Example 44

4-[3-(Dimethyl-1H-1,2,3-triazol-5-yl)-5-[(S)-oxan-4-yl(phenyl)methyl]-5H-pyrido[3,2-b]-indol-7-yl]-1λ$^6$-thiomorpholine-1,1-dione

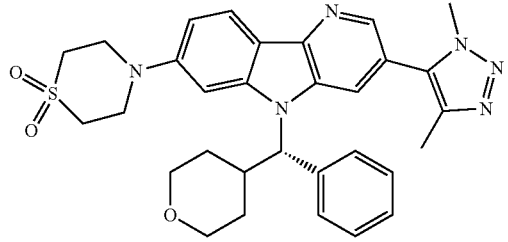 [SMILES: Cc1nnn(C)c1-c1cnc2c3ccc(N4CCS(=O)(=O)CC4)cc3n([C@H](c3ccccc3)C3CCOCC3)c2c1]

To a 20 mL thick walled scintillation vial equipped with a stir bar was added (S)-7-chloro-3-(1,4-dimethyl-1H-1,2,3-triazol-5-yl)-5-(phenyl(tetrahydro-2H-pyran-4-yl)methyl)-5H-pyrido[3,2-b]indole (0.025 g, 0.053 mmol), thiomorpholine 1,1-dioxide (0.014 g, 0.106 mmol), (2-dicyclohexylphosphino-2',6'-diisopropyl-1,1'-biphenyl)[2-(2-aminoethyl)phenyl]palladium(II) (0.012 g, 0.016 mmol), 2-dicyclohexylphosphino-2',6'-di-i-propoxy-1,1'-biphenyl (7.4 mg, 0.016 mmol), and sodium tert-butoxide (0.020 g, 0.212 mmol). To this was added 2 mL THF and bubbled in argon for 1 min while sonicating. The vial was sealed and heated in a oil bath at 120° C. for 1 h. The crude material was purified via preparative LC/MS with the following conditions: Column: XBridge C18, 19×200 mm, 5-μm particles; Mobile Phase A: 5:95 ACN: water with 10 mM NH$_4$OAc; Mobile Phase B: 95:5 ACN: water with 10 mM NH$_4$OAc; Gradient: 20-60% B over 15 min, then a 5 min hold at 100% B; Flow: 20 mL/min. Fractions containing the desired product were combined and dried via centrifugal evaporation. The yield of the product was 4.0 mg, and its estimated purity by LCMS analysis was 96%. Two analytical LC/MS injections were used to determine the final purity. Injection 1 conditions: Column: Waters BEH C18, 2.0×50 mm, 1.7-μm particles; Mobile Phase A: 5:95 ACN:water with 10 mM NH$_4$OAc; Mobile Phase B: 95:5 ACN:water with 10 mM NH$_4$OAc; Temperature: 50° C.; Gradient: 0% B, 0-100% B over 3 min, then a 0.5 min hold at 100% B; Flow: 1 mL/min; Detection: UV at 220 nm, Rt=1.45 min, M+H=571. Injection 2 conditions: Column: Waters BEH C18, 2.0×50 mm, 1.7-μm particles; Mobile Phase A: 5:95 ethanol:water with 10 mM NH$_4$OAc; Mobile Phase B: 95:5 MeOH:water with 10 mM NH$_4$OAc; Temperature: 50° C.; Gradient: 0% B, 0-100% B over 3 min, then a 0.5 min hold at 100% B; Flow: 0.5 mL/min; Detection: UV at 220 nm, Rt=2.27 min, M+H=571. $^1$H NMR (500 MHz, DMSO-$d_6$) δ 8.39 (s, 1H), 8.21 (d, J=8.1 Hz, 1H), 8.06 (d, J=8.4 Hz, 1H), 7.67 (d, J=7.7 Hz, 2H), 7.59 (br. s., 1H), 7.33 (t, J=7.5 Hz, 2H), 7.25 (t, J=7.3 Hz, 1H), 7.08 (d, J=8.8 Hz, 1H), 5.81 (d, J=11.0 Hz, 1H), 4.02 (br. s., 4H), 3.97 (br. s., 3H), 3.92-3.85 (m, 2H), 3.74 (d, J=8.4 Hz, 1H), 3.39 (d, J=11.0 Hz, 1H), 3.32-3.24 (m, 1H), 3.24-3.13 (m, 4H), 2.31-2.24 (m, 3H), 1.72 (d, J=13.6 Hz, 1H), 1.62-1.52 (m, 1H), 1.34 (d, J=9.9 Hz, 1H), 0.98 (d, J=12.8 Hz, 1H).

Example 45

4-{3-[4-($^2$H$_3$)Methyl-1-methyl-1H-1,2,3-triazol-5-yl]-5-[(S)-oxan-4-yl(phenyl)methyl]-5H-pyrido[3,2-b]indol-7-yl}-1λ$^6$-thiomorpholine-1,1-dione

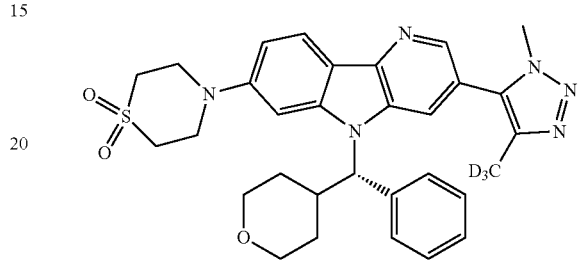

Step 1: 5-{7-Chloro-5H-pyrido[3,2-b]indol-3-yl}-4-($^2$H$_3$)methyl-1-methyl-1H-1,2,3-triazole 3-Bromo-7-chloro-5H-pyrido[3,2-b]indole (0.5 g, 1.78 mmol) was dissolved in DMF (4.44 ml). Bubbled in argon while sonicating for 1 min, then continued to bubble in argon and sonicate while adding 4-($^2$H$_3$)methyl-1-methyl-5-(tributylstannyl)-1H-1,2,3-triazole (1.382 g, 3.55 mmol), copper (I) iodide (0.051 g, 0.266 mmol), triethylamine (0.272 ml, 1.95 mmol) and Pd(PPh$_3$)$_4$ (0.123 g, 0.107 mmol). Sealed flask and heated in the microwave at 100° C. for 45 min. Diluted with EtOAc and water. Filtered through celite. Washed organic layer with water and brine, dried over MgSO$_4$, filtered and concentrated to dryness. The residue was dissolved in DCM and purified on a 40 g Isco column, eluting with 2% MeOH/CH$_2$Cl$_2$ to 10% MeOH/CH$_2$Cl$_2$ over 600 mL. Concentrated fractions 9-13, diluted with methanol, adsorbed onto silica gel and concentrated. Purified residue on a 40 g Isco column, eluting with 80% THF/hexane over 600 mL. Combined like fractions and concentrated to afford 0.54 g of the title compound. LC/MS using method 5; Rt=0.76 min, M+H=301. $^1$H NMR (400 MHz, DMSO-$d_6$) δ 11.77 (s, 1H), 8.55 (d, J=1.8 Hz, 1H), 8.23 (d, J=8.3 Hz, 1H), 8.06 (d, J=1.8 Hz, 1H), 7.68 (d, J=1.5 Hz, 1H), 7.32 (dd, J=8.4, 1.9 Hz, 1H), 4.00 (s, 3H).

Step 2: 5-{7-Chloro-5-[(S)-oxan-4-yl(phenyl)methyl]-5H-pyrido[3,2-b]indol-3-yl}-4-($^2$H$_3$)methyl-1-methyl-1H-1,2,3-triazole 5-{7-Chloro-5H-pyrido[3,2-b]indol-3-yl}-4-($^2$H$_3$)methyl-1-methyl-1H-1,2,3-triazole (0.11 g, 0.366 mmol) was dissolved in 4 mL DCM. To this was added (R)-phenyl(tetrahydro-2H-pyran-4-yl)methanol (0.141 g, 0.731 mmol) and triphenylphosphine (0.192 g, 0.731 mmol) and triethylamine (0.102 ml, 0.731 mmol). Cooled in an ice bath, then added DIAD (0.142 ml, 0.731 mmol) dropwise. Sealed flask and stirred for 15 min. Removed bath and stirred overnight. Purified on a 24 g Isco column, eluting with 5% EtOAc/hexane to 25% EtOAc/hexane over 800 mL. Switched collection racks, then eluted with 20% THF/hexane to 80% THF/hexane over 400 mL. Combined like fractions to afford 180 mg of a clear, glassy oil. LC/MS and $^1$H NMR were consistent with the title compound and triphenylphosphine oxide in a 1:1 ratio. Used material directly in subsequent reactions. LC/MS using Method 5; Rt=0.87 min, M+H=279, Rt=0.99 min, M+H=475. $^1$H NMR (400 MHz, DMSO-$d_6$) δ 8.56 (d, J=1.8 Hz, 1H), 8.23 (d, J=8.3 Hz, 1H), 7.67 (d, J=7.3 Hz, 2H), 7.66-7.52 (m, 18H), 7.38-7.29 (m, 3H), 7.29-7.18 (m, 1H), 5.86 (d, J=11.5 Hz, 1H), 4.03-3.97 (m, 3H), 3.93-3.87 (m, 1H), 3.79-3.71 (m, 1H), 3.51-3.37 (m, 2H), 3.27-3.20 (m, 1H), 1.72-1.64 (m, 1H), 1.57 (d, J=3.3 Hz, 1H), 1.34-1.27 (m, 1H), 1.02-0.89 (m, 1H).

Step 3: 4-{3-[4-($^2$H$_3$)Methyl-1-methyl-1H-1,2,3-triazol-5-yl]-5-[(S)-oxan-4-yl(phenyl)methyl]-5H-pyrido[3,2-b]indol-7-yl}-1λ$^6$-thiomorpholine-1,1-dione To a 20 mL, thick walled scintillation vial equipped with a stir bar was added 5-{7-chloro-5-[(S)-oxan-4-yl(phenyl)methyl]-5H-pyrido[3,2-b]indol-3-yl}-4-($^2$H$_3$)methyl-1-methyl-1H-1,2,3-triazole (0.050 g, 0.053 mmol), thiomorpholine 1,1-dioxide (0.014 g, 0.105 mmol), (2-dicyclohexylphosphino-2',6'-diisopropyl-1,1'-biphenyl)[2-(2-aminoethyl)phenyl]palladium(II) (0.012 g, 0.016 mmol), 2-dicyclohexylphosphino-2',6'-di-i-propoxy-1,1'-biphenyl (7.4 mg, 0.016 mmol), then sodium tert-butoxide (0.020 g, 0.211 mmol). 2 mL THF was added to the vial and bubbled in argon for 1 min while sonicating. The vial was sealed and heated in a oil bath at 120° C. for 1 h. The crude material was purified via preparative LC/MS with the following conditions: Column: XBridge C18, 19×200 mm, 5-µm particles; Mobile Phase A: 5:95 MeOH: water with 10 mM NH$_4$OAc; Mobile Phase B: 95:5 MeOH: water with 10 mM NH$_4$OAc; Gradient: 45-85% B over 15 min, then a 5 min hold at 100% B; Flow: 20 mL/min. Fractions containing the desired product were combined and dried via centrifugal evaporation. The yield of the product was 20.8 mg, and its estimated purity by LCMS analysis was 98%. Two analytical LC/MS injections were used to determine the final purity. Injection 1 conditions: Column: Waters BEH C18, 2.0×50 mm, 1.7-µm particles; Mobile Phase A: 5:95 ACN:water with 10 mM NH$_4$OAc; Mobile Phase B: 95:5 ACN:water with 10 mM NH$_4$OAc; Temperature: 50° C.; Gradient: 0-100% B over 3 min, then a 0.5 min hold at 100% B; Flow: 1.0 mL/min; Detection: UV at 220 nm, Rt=1.50 min, M+H=574. Injection 2 conditions: Column: Waters BEH C18, 2.0×50 mm, 1.7-µm particles; Mobile Phase A: 5:95 MeOH:water with 10 mM NH$_4$OAc; Mobile Phase B: 95:5 MeOH:water with 10 mM NH$_4$OAc; Temperature: 50° C.; Gradient: 0-100% B over 3 min, then a 0.5 min hold at 100% B; Flow: 0.5 mL/min; Detection: UV at 220 nm, Rt=2.70 min, M+H=574. $^1$H NMR (500 MHz, DMSO-$d_6$) δ 8.40 (s, 1H), 8.26 (br. s., 1H), 8.05 (d, J=8.4 Hz, 1H), 7.68 (d, J=7.7 Hz, 2H), 7.58 (d, J=10.6 Hz, 1H), 7.34 (t, J=7.7 Hz, 2H), 7.25 (t, J=7.3 Hz, 1H), 7.14 (br. s., 1H), 7.09 (d, J=8.8 Hz, 2H), 5.82 (d, J=11.0 Hz, 1H), 4.02 (br. s., 4H), 3.98 (br. s., 3H), 3.93-3.86 (m, 2H), 3.74 (d, J=8.1 Hz, 1H), 3.49 (t, J=11.7 Hz, 1H), 3.28-3.20 (m, 4H), 3.18 (d, J=5.1 Hz, 2H), 2.51 (br. s., 8H), 1.72 (d, J=12.8 Hz, 1H), 1.57 (d, J=11.0 Hz, 1H), 1.34 (d, J=8.1 Hz, 1H), 0.99 (d, J=11.7 Hz, 1H).

Example 46

1-Methanesulfonyl-4-{3-[4-($^2$H$_3$)methyl-1-methyl-1H-1,2,3-triazol-5-yl]-5-[(S)-oxan-4-yl(phenyl)methyl]-5H-pyrido[3,2-b]indol-7-yl}piperazine

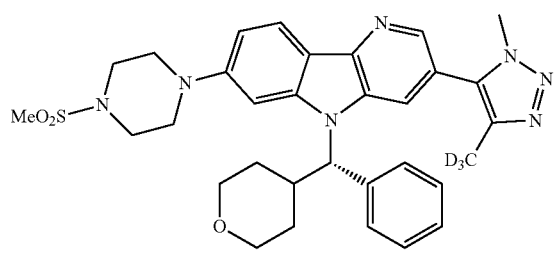 [SMILES: [2H]C([2H])([2H])c1nnn(C)c1-c1cnc2c3ccc(N4CCN(S(C)(=O)=O)CC4)cc3n([C@H](c3ccccc3)C3CCOCC3)c2c1]

To a 20 mL, thick walled scintillation vial equipped with a stir bar was added 5-{7-chloro-5-[(S)-oxan-4-yl(phenyl)methyl]-5H-pyrido[3,2-b]indol-3-yl}-4-($^2$H$_3$)methyl-1-methyl-1H-1,2,3-triazole (0.050 g, 0.053 mmol), 1-(methylsulfonyl)piperazine (0.019 g, 0.116 mmol), (2-dicyclohexylphosphino-2',6'-diisopropyl-1,1'-biphenyl)[2-(2-aminoethyl)phenyl]palladium(II) (0.013 g, 0.017 mmol), 2-dicyclohexylphosphino-2',6'-di-i-propoxy-1,1'-biphenyl (8.1 mg, 0.017 mmol), then sodium tert-butoxide (0.022 g, 0.232 mmol). 2 mL THF was added and bubbled in argon for 1 min while sonicating. The vial was sealed and heated in a oil bath at 120° C. for 2 h. The crude material was purified via preparative LC/MS with the following conditions: Column: XBridge C18, 19×200 mm, 5-µm particles; Mobile Phase A: 5:95 ACN: water with 0.1% trifluoroacetic acid; Mobile Phase B: 95:5 ACN: water with 0.1% trifluoroacetic acid; Gradient: 20-60% B over 15 min, then a 5 min hold at 100% B; Flow: 20 mL/min. Fractions containing the desired product were combined and dried via centrifugal evaporation. The yield of the product was 1.2 mg, and its estimated purity by LCMS analysis was 100%. $^1$H NMR indicated a mixture of free base and TFA salts. Two analytical LC/MS injections were used to determine the final purity. Injection 1 conditions: Column: Waters Acquity UPLC BEH C18, 2.1×50 mm, 1.7-µm particles; Mobile Phase A: 5:95 ACN:water with 10 mM NH$_4$OAc; Mobile Phase B: 95:5 ACN:water with 10 mM NH$_4$OAc; Temperature: 50° C.; Gradient: 0-100% B over 3 min, then a 0.75 min hold at 100% B; Flow: 1.0 mL/min; Detection: UV at 220 nm, Rt=1.64 min, M+H=603. Injection 2 conditions: Column: Waters Acquity UPLC BEH C18, 2.1×50 mm, 1.7-µm particles; Mobile Phase A: 5:95 ACN:water with 0.1% trifluoroacetic acid; Mobile Phase B: 95:5 ACN:water with 0.1% trifluoroacetic acid; Temperature: 50° C.; Gradient: 0-100% B over 3 min, then a 0.75 min hold at 100% B; Flow: 1.0 mL/min; Detection: UV at 220 nm, Rt=1.47 min, M+H=603. $^1$H NMR (500 MHz, DMSO-$d_6$) δ 8.54 (br. s., 1H), 8.45 (br. s., 2H), 8.32 (br. s., 2H), 8.20 (d, J=8.8 Hz, 1H), 8.07 (d, J=8.4 Hz, 2H), 7.68 (d, J=7.0 Hz, 5H), 7.59 (d, J=8.1 Hz, 3H), 7.49 (br. s., 1H), 7.44 (d, J=9.5 Hz, 3H), 7.34 (d, J=7.3 Hz, 5H), 7.29-7.21 (m, 4H), 7.13 (s, 2H), 7.09 (d, J=8.1 Hz, 2H), 7.03 (s, 2H), 6.43 (br. s., 1H), 5.83 (d, J=11.0 Hz, 2H), 3.99 (br. s., 6H), 3.91 (s, 8H), 3.75 (d, J=9.5 Hz, 3H), 3.50 (d, J=8.1 Hz, 12H), 3.26 (br. s., 4H), 2.31 (br. s., 1H), 2.26 (br. s., 1H), 1.72 (d, J=11.4 Hz, 3H), 1.58 (d, J=11.0 Hz, 3H), 1.34 (d, J=7.3 Hz, 4H), 1.22 (d, J=14.3 Hz, 2H), 1.16 (d, J=12.1 Hz, 2H), 1.10-0.94 (m, 3H), 0.83 (br. s., 1H), 0.73 (d, J=13.2 Hz, 2H).

Example 47

1-[3-(Dimethyl-1H-1,2,3-triazol-5-yl)-5-[(S)-oxan-4-yl(phenyl)methyl]-5H-pyrido[3,2-b]indol-7-yl]-4-methylpiperazine

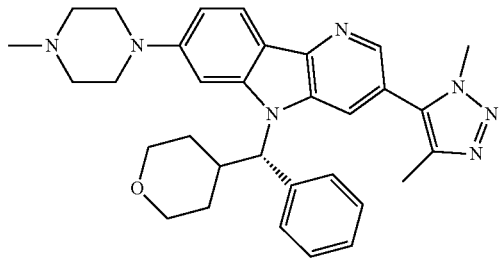 [SMILES: Cc1nnn(C)c1-c1cnc2c3ccc(N4CCN(C)CC4)cc3n([C@H](c3ccccc3)C3CCOCC3)c2c1]

In a small pressure vial equipped with a magnetic stirring bar was added (S)-7-chloro-3-(1,4-dimethyl-1H-1,2,3-triazol-5-yl)-5-(phenyl(tetrahydro-2H-pyran-4-yl)methyl)-5H-pyrido[3,2-b]indole (20 mg, 0.042 mmol), 1-methylpiperazine (6.4 mg, 0.064 mmol) and THF (2 mL). RuPhos precatalyst (CAS #1375325-68-0, 1.9 mg, 2.54 µmol), RuPhos (CAS #787618-22-8, 1.2 mg, 2.54 µmol) and sodium t-butoxide (12.2 mg, 0.127 mmol) were added. Argon was bubbled into the mixture with sonication for 5 min. The vial was sealed, placed into a preheated oil bath at 100° C. and the reaction mixture was stirred for 16 h. Solids were removed by filtration, and the filtrate was purified by preparative HPLC: Column: Waters XBridge C18, 19×200 mm, 5-µm particles; Mobile Phase A: 5:95 MeOH: water with 10 mM NH$_4$OAc; Mobile Phase B: 95:5 MeOH: water with 10 mM NH$_4$OAc; Gradient: 55-95% B over 15 min, then a 5 min hold at 100% B; Flow: 20 mL/min. Fractions containing the desired product were combined and dried via centrifugal evaporation to give 0.8 mg (3%) of the title compound with an average purity by LC/MS analysis of 92%. Two analytical LC/MS injections were used to determine the final purity. Injection 1 conditions: Column: Waters Acquity UPLC BEH C18, 2.1×50 mm, 1.7-µm particles; Mobile Phase A: 5:95 ACN:water with 10 mM NH$_4$OAc; Mobile Phase B: 95:5 ACN:water with 10 mM NH$_4$OAc; Temperature: 50° C.; Gradient: 0-100% B over 3 min, then a 0.75 min hold at 100% B; Flow: 1.0 mL/min; Detection: UV at 220 nm. Rt=1.45 min.; LC/MS (M+H)=536.1. Injection 2 conditions: Column: Waters Acquity UPLC BEH C18, 2.1×50 mm, 1.7-µm particles; Mobile Phase A: 5:95 ACN: water with 0.1% trifluoroacetic acid; Mobile Phase B: 95:5 ACN:water with 0.1% trifluoroacetic acid; Temperature: 50° C.; Gradient: 0-100% B over 3 min, then a 0.75 min hold at 100% B; Flow: 1.0 mL/min; Detection: UV at 220 nm. R$_t$=1.16 min.; LC/MS (M+H)=536.0. $^1$H NMR (500 MHz, DMSO-d$_6$) δ 8.37 (s, 1H), 8.23 (br. s., 1H), 8.00 (s, 1H), 7.66 (d, J=7.7 Hz, 2H), 7.33 (t, J=7.3 Hz, 2H), 7.29-7.20 (m, 1H), 7.02 (d, J=8.1 Hz, 1H), 5.80 (d, J=10.6 Hz, 1H), 3.97 (br. s., 3H), 3.94-3.85 (m, 2H), 3.74 (d, J=10.6 Hz, 1H), 3.55-3.45 (m, 1H), 3.37 (s, 4H), 3.26 (t, J=11.0 Hz, 1H), 2.54 (br. s., 4H), 2.28 (s, 7H), 1.76-1.65 (m, 1H), 1.59 (d, J=9.9 Hz, 1H), 1.33 (d, J=10.3 Hz, 1H), 1.08-0.87 (m, 1H). LC/MS (M+H)=536.2; HPLC conditions: Rt=0.67 min.: Column: Waters Aquity BEH C18 2.1×50 mm 1.7 u; Mobile Phase A: water with 0.05% TFA; Mobile Phase B: acetonitrile with 0.05% TFA; Temperature: 40° C.; Gradient: 2-98% B over 1.5 min; Flow: 0.8 mL/min).

Example 48

1-[3-(Dimethyl-1H-1,2,3-triazol-5-yl)-5-[(S)-oxan-4-yl(phenyl)methyl]-5H-pyrido[3,2-b]indol-7-yl]-4-(1-methylpiperidin-4-yl)piperazine

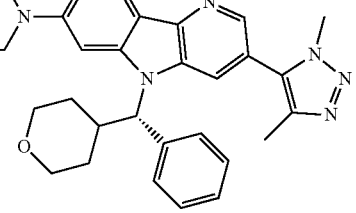

In a small pressure vial equipped with a magnetic stirring bar was added (S)-7-chloro-3-(1,4-dimethyl-1H-1,2,3-triazol-5-yl)-5-(phenyl(tetrahydro-2H-pyran-4-yl)methyl)-5H-pyrido[3,2-b]indole (20 mg, 0.042 mmol), 1-(1-methylpiperidin-4-yl)piperazine (11.7 mg, 0.064 mmol) and dioxane (2 mL). RuPhos precatalyst (CAS #1375325-68-0, 1.85 mg, 2.54 µmol), Pd(OAc)$_2$ (0.6 mg, 2.54 µmol), RuPhos (CAS #787618-22-8, 1.2 mg, 2.54 µmol) and sodium t-butoxide (12.2 mg, 0.127 mmol) were added. Argon was bubbled into the mixture with sonication for 5 min. The vial was sealed, placed into a preheated oil bath at 100° C. and the reaction mixture was stirred for 16 h. Solids were removed by filtration, and the filtrate was purified by preparative HPLC: Column: Waters XBridge C18, 19×200 mm, 5-µm particles; Mobile Phase A: 5:95 MeOH: water with 10 mM NH$_4$OAc; Mobile Phase B: 95:5 MeOH: water with 10 mM NH$_4$OAc; Gradient: 20-100% B over 15 min, then a 5 min hold at 100% B; Flow: 20 mL/min. Fractions containing the desired product were combined and dried via centrifugal evaporation to give 18.2 mg (69%) of the title compound with an average purity by LC/MS analysis of >99%. Two analytical LC/MS injections were used to determine the final purity. Injection 1 conditions: Column: Waters Acquity UPLC BEH C18, 2.1×50 mm, 1.7-µm particles; Mobile Phase A: 5:95 ACN:water with 10 mM NH$_4$OAc; Mobile Phase B: 95:5 ACN:water with 10 mM NH$_4$OAc; Temperature: 50° C.; Gradient: 0-100% B over 3 min, then a 0.75 min hold at 100% B; Flow: 1.0 mL/min; Detection: UV at 220 nm. Rt=1.40 min.; LC/MS (M+H)=619.2. Injection 2 conditions: Column: Waters Acquity UPLC BEH C18, 2.1×50 mm, 1.7-µm particles; Mobile Phase A: 5:95 ACN: water with 0.1% trifluoroacetic acid; Mobile Phase B: 95:5 ACN:water with 0.1% trifluoroacetic acid; Temperature: 50° C.; Gradient: 0-100% B over 3 min, then a 0.75 min hold at 100% B; Flow: 1.0 mL/min; Detection: UV at 220 nm. R$_t$=1.04 min.; LC/MS (M+H)=619.2. $^1$H NMR (500 MHz, DMSO-d$_6$) δ 8.38 (br. s., 1H), 8.05-7.95 (m, 1H), 7.66 (d, J=7.3 Hz, 2H), 7.57 (br. s., 1H), 7.35-7.29 (m, 2H), 7.25 (d, J=7.0 Hz, 1H), 7.01 (d, J=8.4 Hz, 1H), 5.79 (d, J=11.4 Hz, 1H), 3.98 (br. s., 3H), 3.90 (br. s., 2H), 3.73 (br. s., 1H), 3.26 (br. s., 2H), 3.18 (br. s., 2H), 2.90 (s, 1H), 2.84 (d, J=9.9 Hz, 2H), 2.77-2.64 (m, 4H), 2.28 (br. s., 3H), 2.22 (br. s., 1H), 2.22-2.10 (m, 5H), 1.80 (d, J=12.5 Hz, 3H), 1.70 (d, J=14.7 Hz, 2H), 1.57 (br. s., 1H), 1.48 (d, J=10.3 Hz, 2H), 1.31 (br.

s., 2H), 1.00 (d, J=12.1 Hz, 1H). LC/MS (M+H)=619.3; HPLC conditions: Rt=2.59 min.: Column: Phenomenex LUNA C18 2×50 mm (4 min grad) eluting with 10-90% aqueous MeOH containing 0.1% TFA, 0.8 mL/min, monitoring at 254 nm); Temperature: 40° C.

Example 49

4-[3-(Dimethyl-1H-1,2,3-triazol-5-yl)-5-[(S)-oxan-4-yl(phenyl)methyl]-5H-pyrido[3,2-b]indol-7-yl]-N,N-dimethylpiperazine-1-carboxamide

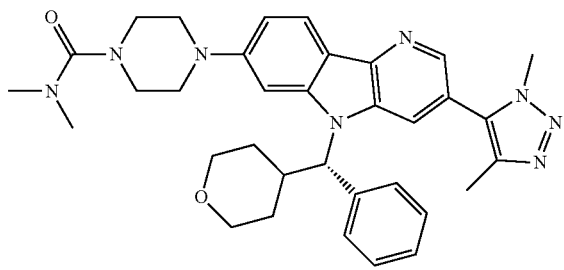 [SMILES: Cc1nnn(C)c1-c1cnc2c3ccc(N4CCN(C(=O)N(C)C)CC4)cc3n([C@H](c3ccccc3)C3CCOCC3)c2c1]

In a small pressure vial equipped with a magnetic stirring bar was added was added (S)-7-chloro-3-(1,4-dimethyl-1H-1,2,3-triazol-5-yl)-5-(phenyl(tetrahydro-2H-pyran-4-yl) methyl)-5H-pyrido[3,2-b]indole (30 mg, 0.064 mmol), N,N-dimethylpiperazine-1-carboxamide (15.0 mg, 0.095 mmol) and dioxane (2 mL). RuPhos precatalyst (CAS #1375325-68-0, 2.8 mg, 3.81 μmol) or Pd(OAc)$_2$ (0.9 mg, 3.81 μmol), RuPhos (CAS #787618-22-8, 1.8 mg, 3.81 μmol) and sodium t-butoxide (18.3 mg, 0.191 mmol) were added. Argon was bubbled into the mixture with sonication for 5 min. The vial was sealed, placed into a preheated oil bath at 100° C. and the reaction mixture was stirred for 16 h. Solids were removed by filtration, and the filtrate was purified by preparative HPLC: Column: Waters XBridge C18, 19×200 mm, 5-μm particles; Mobile Phase A: 5:95 MeOH: water with 10 mM NH$_4$OAc; Mobile Phase B: 95:5 MeOH: water with 10 mM NH$_4$OAc; Gradient: 30-70% B over 15 min, then a 5 min hold at 100% B; Flow: 20 mL/min. Fractions containing the desired product were combined and dried via centrifugal evaporation to give 17.8 mg (47%) of the title compound with an average purity by LC/MS analysis of >99%. Two analytical LC/MS injections were used to determine the final purity. Injection 1 conditions: Column: Waters Acquity UPLC BEH C18, 2.1×50 mm, 1.7-μm particles; Mobile Phase A: 5:95 ACN:water with 10 mM NH$_4$OAc; Mobile Phase B: 95:5 ACN:water with 10 mM NH$_4$OAc; Temperature: 50° C.; Gradient: 0-100% B over 3 min, then a 0.75 min hold at 100% B; Flow: 1.0 mL/min; Detection: UV at 220 nm. Rt=2.16 min.; LC/MS (M+H)=593.2. Injection 2 conditions: Column: Waters Acquity UPLC BEH C18, 2.1×50 mm, 1.7-μm particles; Mobile Phase A: 5:95 ACN: water with 0.1% trifluoroacetic acid; Mobile Phase B: 95:5 ACN:water with 0.1% trifluoroacetic acid; Temperature: 50° C.; Gradient: 0-100% B over 3 min, then a 0.75 min hold at 100% B; Flow: 1.0 mL/min; Detection: UV at 220 nm. Rt=1.46 min.; LC/MS (M+H)=593.2. $^1$H NMR (500 MHz, DMSO-d$_6$) δ 8.39 (s, 1H), 8.23 (br. s., 1H), 8.02 (d, J=8.8 Hz, 1H), 7.67 (d, J=7.3 Hz, 2H), 7.49 (br. s., 1H), 7.33 (t, J=7.5 Hz, 2H), 7.25 (d, J=7.3 Hz, 1H), 7.04 (d, J=9.2 Hz, 1H), 5.80 (d, J=11.0 Hz, 1H), 3.97 (br. s., 3H), 3.89 (d, J=9.5 Hz, 1H), 3.74 (d, J=9.2 Hz, 1H), 3.55-3.45 (m, 1H), 3.35 (br. s., 8H), 3.25 (d, J=11.0 Hz, 1H), 2.83 (s, 6H), 2.27 (br. s., 3H), 1.71 (d, J=12.1 Hz, 1H), 1.58 (d, J=8.1 Hz, 1H), 1.33 (br. s., 1H), 1.00 (d, J=10.6 Hz, 1H). LC/MS (M+H)=593.2; HPLC conditions: Rt=3.39 min.: Column: Phenomenex LUNA C18 2×50 mm (4 min grad) eluting with 10-90% aqueous MeOH containing 0.1% TFA, 0.8 mL/min, monitoring at 254 nm); Temperature: 40° C.

Example 50

4-[3-(Dimethyl-1H-1,2,3-triazol-5-yl)-5-[(S)-oxan-4-yl(phenyl)methyl]-5H-pyrido[3,2-b]indol-7-yl]-N,N-dimethylpiperazine-1-sulfonamide

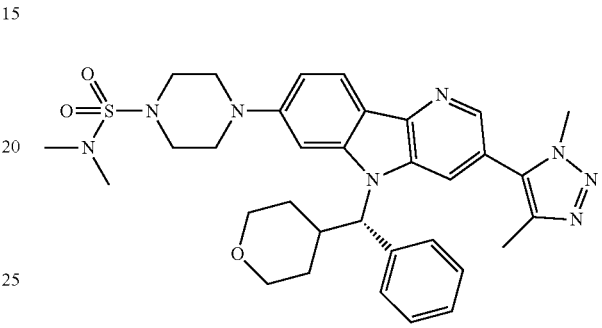

In a small pressure vial equipped with a magnetic stirring bar was added (S)-7-chloro-3-(1,4-dimethyl-1H-1,2,3-triazol-5-yl)-5-(phenyl(tetrahydro-2H-pyran-4-yl)methyl)-5H-pyrido[3,2-b]indole (30 mg, 0.064 mmol), N,N-dimethylpiperazine-1-sulfonamide (18.4 mg, 0.095 mmol) and dioxane (2 mL). RuPhos precatalyst (CAS #1375325-68-0, 2.8 mg, 3.81 μmol), Pd(OAc)$_2$ (0.9 mg, 3.81 μmol), RuPhos (CAS #787618-22-8, 1.8 mg, 3.81 μmol) and sodium t-butoxide (18.3 mg, 0.191 mmol) were added. Argon was bubbled into the mixture with sonication for 5 min. The vial was sealed, placed into a preheated oil bath at 100° C. and the reaction mixture was stirred for 16 h. Solids were removed by filtration, and the filtrate was purified by preparative HPLC: Column: Waters XBridge C18, 19×200 mm, 5-μm particles; Mobile Phase A: 5:95 MeOH: water with 10 mM NH$_4$OAc; Mobile Phase B: 95:5 MeOH: water with 10 mM NH$_4$OAc; Gradient: 30-70% B over 20 min, then a 5 min hold at 100% B; Flow: 20 mL/min. Fractions containing the desired product were combined and dried via centrifugal evaporation to give 9.1 mg (22%) of the title compound with an average purity by LC/MS analysis of 96%. Two analytical LC/MS injections were used to determine the final purity. Injection 1 conditions: Column: Waters Acquity UPLC BEH C18, 2.1×50 mm, 1.7-μm particles; Mobile Phase A: 5:95 ACN:water with 10 mM NH$_4$OAc; Mobile Phase B: 95:5 ACN:water with 10 mM NH$_4$OAc; Temperature: 50° C.; Gradient: 0-100% B over 3 min, then a 0.75 min hold at 100% B; Flow: 1.0 mL/min; Detection: UV at 220 nm. Rt=1.79 min.; LC/MS (M+H)=629.1. Injection 2 conditions: Column: Waters Acquity UPLC BEH C18, 2.1×50 mm, 1.7-μm particles; Mobile Phase A: 5:95 ACN:water with 0.1% trifluoroacetic acid; Mobile Phase B: 95:5 ACN:water with 0.1% trifluoroacetic acid; Temperature: 50° C.; Gradient: 0-100% B over 3 min, then a 0.75 min hold at 100% B; Flow: 1.0 mL/min; Detection: UV at 220 nm. Rt=1.60 min.; LC/MS (M+H)=629.0. $^1$H NMR (500 MHz, DMSO-d$_6$) δ 8.40 (s, 1H), 8.24 (br. s., 1H), 8.04 (d, J=8.4 Hz, 1H), 7.67 (d, J=7.7 Hz, 2H), 7.49 (br. s., 1H), 7.33 (t, J=7.5 Hz, 2H), 7.25 (t, J=7.2 Hz, 1H), 7.04 (d, J=8.8 Hz, 1H), 5.80 (d, J=11.0 Hz, 1H), 3.98 (br. s., 3H), 3.90 (d, J=8.4 Hz, 1H), 3.74 (d, J=8.4 Hz, 1H), 3.47 (d, J=9.2 Hz, 4H), 3.26 (t, J=11.6 Hz, 2H), 2.85 (s, 7H), 2.28 (s, 3H), 1.71 (d, J=12.8 Hz, 1H), 1.57 (d, J=12.8 Hz, 1H), 1.34 (d, J=8.8 Hz, 1H), 0.99 (d, J=11.0 Hz, 1H). LC/MS (M+H)=629.2; HPLC conditions: Rt=3.39 min.: Column: Phenomenex LUNA C18 2×50 mm (4 min grad) eluting with 10-90% aqueous MeOH containing 0.1% TFA, 0.8 mL/min, monitoring at 254 nm); Temperature: 40° C.

Example 51

(2R)-4-{5-[(S)-(2-Fluorophenyl)(oxan-4-yl)methyl]-3-[4-($^2$Ha)methyl-1-methyl-1H-1,2,3-triazol-5-yl]-5H-pyrido[3,2-b]indol-8-yl}-2-methyl-1$\lambda^6$,4-thiomorpholine-1,1-dione

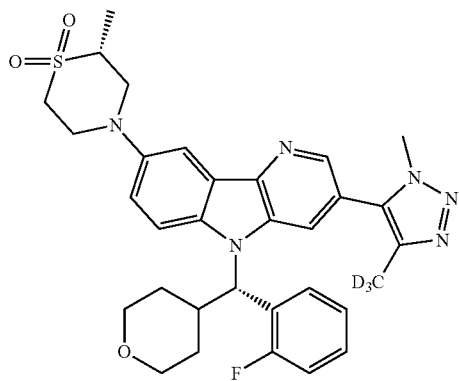 [SMILES: [2H]C([2H])([2H])c1nnn(C)c1-c1cnc2c3cc(N4CCS(=O)(=O)[C@H](C)C4)ccc3n([C@H](c3ccccc3F)C3CCOCC3)c2c1]

In a manner similar to the preparation of 4-{5-[(S)-(4-fluorophenyl)(oxan-4-yl)methyl]-3-[4-($^2$H$_3$)methyl-1-methyl-1H-1,2,3-triazol-5-yl]-5H-pyrido[3,2-b]indol-8-yl}-1$\lambda^6$-thiomorpholine-1,1-dione, the title compound was prepared starting with 3-bromo-5H-pyrido[3,2-b]indole and (R)-(2-fluorophenyl)(tetrahydro-2H-pyran-4-yl)methanol. For the final step, the following conditions were employed: To a v-shaped microwave vial equipped with a stir bar was added 5-{8-bromo-5-[(S)-(2-fluorophenyl)(oxan-4-yl)methyl]-5H-pyrido-[3,2-b]indol-3-yl}-4-($^2$H$_3$)methyl-1-methyl-1H-1,2,3-triazole (24 mg, 0.045 mmol), (R)-2-methylthiomorpholine 1,1-dioxide, HCl (18 mg, 0.097 mmol), (2-dicyclohexylphosphino-2',6'-diisopropyl-1,1'-biphenyl)[2-(2-aminoethyl)phenyl]palladium(II) (9.8 mg, 0.013 mmol), 2-dicyclohexylphosphino-2',6'-di-i-propoxy-1,1'-biphenyl (6.2 mg, 0.013 mmol) and sodium tert-butoxide (25.7 mg, 0.268 mmol). 2 mL THF was added to the vial and bubbled in argon for 1 min while sonicating. The vial was sealed and heated in a oil bath at 120° C. for 1 h. The crude material was purified via preparative LC/MS with the following conditions: Column: XBridge C18, 19×200 mm, 5-μm particles; Mobile Phase A: 5:95 ACN: water with 10 mM NH$_4$OAc; Mobile Phase B: 95:5 ACN: water with 10 mM NH$_4$OAc; Gradient: 25-65% B over 15 min, then a 5 min hold at 100% B; Flow: 20 mL/min. Fractions containing the desired product were combined and dried via centrifugal evaporation. The yield of the product was 7.0 mg, and its estimated purity by LCMS analysis was 97%. Two analytical LC/MS injections were used to determine the final purity. Injection 1 conditions: Column: Waters Acquity UPLC BEH C18, 2.1×50 mm, 1.7-μm particles; Mobile Phase A: 5:95 ACN:water with 10 mM NH$_4$OAc; Mobile Phase B: 95:5 ACN:water with 10 mM NH$_4$OAc; Temperature: 50° C.; Gradient: 0-100% B over 3 min, then a 0.75 min hold at 100% B; Flow: 1.0 mL/min; Detection: UV at 220 nm, Rt=2.02 min, M+H=606. Injection 2 conditions: Column: Waters Acquity UPLC BEH C18, 2.1×50 mm, 1.7-μm particles; Mobile Phase A: 5:95 ACN:water with 0.1% trifluoroacetic acid; Mobile Phase B: 95:5 ACN:water with 0.1% trifluoroacetic acid; Temperature: 50° C.; Gradient: 0-100% B over 3 min, then a 0.75 min hold at 100% B; Flow: 1.0 mL/min; Detection: UV at 220 nm, Rt=1.61 min, M+H=606. $^1$H NMR (500 MHz, DMSO-d$_6$) δ 8.50 (s, 2H), 8.20 (t, J=7.3 Hz, 1H), 7.95 (s, 1H), 7.89 (br. s., 1H), 7.39 (br. s., 1H), 7.36-7.27 (m, 3H), 7.25 (s, 2H), 7.19-7.07 (m, 3H), 7.05 (s, 2H), 5.97 (d, J=11.7 Hz, 1H), 4.01 (br. s., 4H), 3.95 (d, J=14.3 Hz, 2H), 3.89 (d, J=12.8 Hz, 2H), 3.71 (d, J=10.6 Hz, 1H), 3.28 (br. s., 3H), 3.24-3.15 (m, 3H), 1.71 (d, J=11.7 Hz, 1H), 1.57 (d, J=11.0 Hz, 1H), 1.33 (d, J=9.5 Hz, 1H), 1.27 (d, J=6.6 Hz, 4H), 0.81 (d, J=14.3 Hz, 1H).

Example 52

(2S)-4-{5-[(S)-(2-Fluorophenyl)(oxan-4-yl)methyl]-3-[4-($^2$H$_3$)methyl-1-methyl-1H-1,2,3-triazol-5-yl]-5H-pyrido[3,2-b]indol-8-yl}-2-methyl-11λ$^6$,4-thiomorpholine-1,1-dione

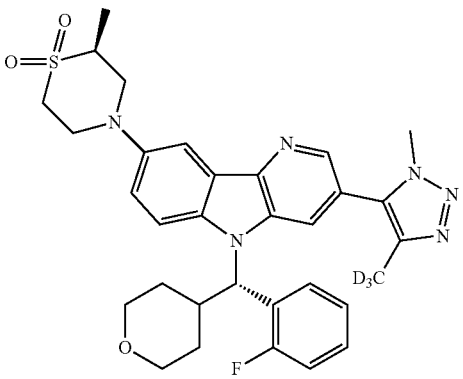 [SMILES: [2H]C([2H])([2H])c1nnn(C)c1-c1cnc2c3cc(N4CCS(=O)(=O)[C@@H](C)C4)ccc3n([C@H](c3ccccc3F)C3CCOCC3)c2c1]

In a manner similar to the preparation of 4-{5-[(S)-(4-fluorophenyl)(oxan-4-yl)methyl]-3-[4-($^2$H$_3$)methyl-1-methyl-1H-1,2,3-triazol-5-yl]-5H-pyrido[3,2-b]indol-8-yl}-1$\lambda^6$-thiomorpholine-1,1-dione, the title compound was prepared starting with 3-bromo-5H-pyrido[3,2-b]indole and (R)-(2-fluorophenyl)(tetrahydro-2H-pyran-4-yl)methanol. For the final step, the following conditions were employed: To a v-shaped microwave vial equipped with a stir bar was added 5-{8-bromo-5-[(S)-(2-fluorophenyl)(oxan-4-yl)methyl]-5H-pyrido-[3,2-b]indol-3-yl}-4-($^2$H$_3$)methyl-1-methyl-1H-1,2,3-triazole (24 mg, 0.045 mmol), (S)-2-methylthiomorpholine 1,1-dioxide, HCl (18 mg, 0.097 mmol), (2-dicyclohexylphosphino-2',6'-diisopropyl-1,1'-biphenyl)[2-(2-aminoethyl)phenyl]palladium(II) (9.8 mg, 0.013 mmol), 2-dicyclohexylphosphino-2',6'-di-i-propoxy-1,1'-biphenyl (6.3 mg, 0.013 mmol), sodium tert-butoxide (25.7 mg, 0.268 mmol). 2 mL THF was added to the vial and bubbled in argon for 1 min while sonicating. The vial was sealed and heated in a oil bath at 120° C. for 1 h. The crude material was purified via preparative LC/MS with the following conditions: Column: XBridge C18, 19×200 mm, 5-μm particles; Mobile Phase A: 5:95 MeOH: water with 10 mM NH$_4$OAc; Mobile Phase B: 95:5 MeOH: water with 10 mM NH₄OAc; Gradient: 50-90% B over 15 min, then a 5 min hold at 100% B; Flow: 20 mL/min. Fractions containing the desired product were combined and dried via centrifugal evaporation. The yield of the product was 9.6 mg, and its estimated purity by LCMS analysis was 98%. Two analytical LC/MS injections were used to determine the final purity. Injection 1 conditions: Column: Waters Acquity UPLC BEH C18, 2.1×50 mm, 1.7-μm particles; Mobile Phase A: 5:95 ACN:water with 10 mM NH₄OAc; Mobile Phase B: 95:5 ACN:water with 10 mM NH₄OAc; Temperature: 50° C.; Gradient: 0-100% B over 3 min, then a 0.75 min hold at 100% B; Flow: 1.0 mL/min; Detection: UV at 220 nm, Rt=1.66, M+H=606. Injection 2 conditions: Column: Waters Acquity UPLC BEH C18, 2.1×50 mm, 1.7-μm particles; Mobile Phase A: 5:95 ACN:water with 0.1% trifluoroacetic acid; Mobile Phase B: 95:5 ACN:water with 0.1% trifluoroacetic acid; Temperature: 50° C.; Gradient: 0-100% B over 3 min, then a 0.75 min hold at 100% B; Flow: 1.0 mL/min; Detection: UV at 220 nm, Rt=1.58, M+H=606. ¹H NMR (500 MHz, DMSO-d₆) δ 8.50 (s, 1H), 8.21 (t, J=7.3 Hz, 1H), 7.96 (s, 1H), 7.40 (br. s., 1H), 7.38-7.27 (m, 2H), 7.23 (s, 1H), 7.20-7.06 (m, 2H), 7.03 (s, 1H), 5.98 (d, J=11.7 Hz, 1H), 4.15-3.93 (m, 5H), 3.89 (d, J=13.2 Hz, 1H), 3.72 (d, J=11.0 Hz, 1H), 3.60-3.40 (m, 3H), 3.38 (br. s., 2H), 3.35-3.26 (m, 3H), 3.26-3.12 (m, 3H), 1.71 (d, J=13.9 Hz, 1H), 1.57 (d, J=12.1 Hz, 1H), 1.34 (d, J=9.2 Hz, 1H), 1.27 (d, J=6.6 Hz, 3H), 0.83 (br. s., 1H).

Example 53

4-{6-Fluoro-3-[4-(²H₃)methyl-1-methyl-1H-1,2,3-triazol-5-yl]-5-[(S)-oxan-4-yl(phenyl)methyl]-5H-pyrido[3,2-b]indol-7-yl}piperidin-4-ol

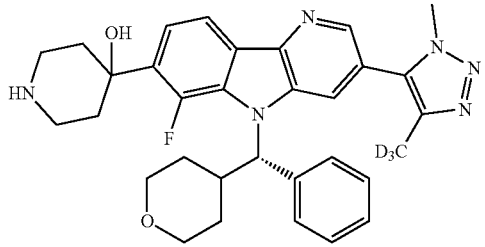 [SMILES: [2H]C([2H])([2H])c1nnn(C)c1-c1cnc2c3ccc(C4(O)CCNCC4)c(F)c3n([C@H](c3ccccc3)C3CCOCC3)c2c1]

Step 1: tert-Butyl 4-{6-fluoro-3-[4-(²H)methyl-1-methyl-1H-1,2,3-triazol-5-yl]-5-[(S)-oxan-4-yl(phenyl)methyl]-5H-pyrido[3,2-b]indol-7-yl}-1,2,3,6-tetrahydropyridine-1-carboxylate A microwave vial was charged with 5-{7-chloro-6-fluoro-5-[(S)-oxan-4-yl(phenyl)methyl]-5H-pyrido[3,2-b]indol-3-yl}-4-(²H₃)methyl-1-methyl-1H-1,2,3-triazole (130 mg, 0.264 mmol) and dioxane (1.8 mL). The mixture was degassed bubbling with a stream of nitrogen. To this was added cesium carbonate (172 mg, 0.527 mmol), Pd₂(dba)₃ (24.2 mg, 0.026 mmol), tert-butyl 4-(tributylstannyl)-5,6-dihydropyridine-1(2H)-carboxylate (249 mg, 0.527 mmol), and tricyclohexylphosphine (20% wt in toluene, 82 μL, 0.053 mmol). The vial was degassed using nitrogen and sealed. The vial was placed in an oil bath preheated to 120° C. The reaction mixture was stirred overnight at this temperature. The reaction was concentrated, diluted with ethyl acetate, washed with water, then brine, dried over MgSO₄, filtered, and concentrated. The residue was purified by column chromatography (10%-40% DCM/acetone) to give 100 mg (59%) which was tainted with significant amounts of starting material and de-chlorinated material. Material was used without further purification. LC/MS (M+H)=640.4; LC/MS T_R=2.13 min (Column: Phenomenex Luna C18 30×2.0 mm 3 u; Mobile Phase A: 10:90 acetonitrile:water with 0.1% TFA; Mobile Phase B: 90:10 acetonitrile:water with 0.1% TFA; Temperature: 40° C.; Gradient: 0-100% B over 2 min; Flow: 1 mL/min).

Step 2: tert-Butyl 4-{6-fluoro-3-[4-(²H₃)methyl-1-methyl-1H-1,2,3-triazol-5-yl]-5-[(S)-oxan-4-yl(phenyl)methyl]-5H-pyrido[3,2-b]indol-7-yl}-4-hydroxypiperidine-1-carboxylate A RBF was charged with tert-butyl 4-{6-fluoro-3-[4-(²H₃)methyl-1-methyl-1H-1,2,3-triazol-5-yl]-5-[(S)-oxan-4-yl(phenyl)methyl]-5H-pyrido[3,2-b]indol-7-yl}-1,2,3,6-tetrahydropyridine-1-carboxylate (impure) (100 mg, 0.156 mmol). To this was added DCM (0.3 mL) and 2-propanol (2 mL). The resulting solution was vigorously stirred under a stream of oxygen. The reaction was placed in a 0° C. bath and stirring continued under the stream of oxygen for 5 min. To this was added tris(2,2,6,6-tetramethyl-3,5-heptanedionato)manganese (III) (9.5 mg, 0.016 mmol) followed by phenylsilane (0.039 mL, 0.313 mmol). After 30 min at 0° C., the reaction was quenched by addition of 2 mL of saturated sodium thiosulfate. The reaction was blown down under a stream of nitrogen. The residue was suspended in EtOAc/water and the layers separated. The organics were washed with brine, dried over MgSO₄, filtered, and concentrated to give 100 mg (97%) which was used without purification. LC/MS (M+H)=658.4; LC/MS T_R=3.10 min (Column: Phenomenex Luna C18 50×2.0 mm 3 u; Mobile Phase A: 10:90 acetonitrile:water with 0.1% TFA; Mobile Phase B: 90:10 acetonitrile:water with 0.1% TFA; Temperature: 40° C.; Gradient: 0-100% B over 4 min; Flow: 0.8 mL/min).

Step 3: 4-{6-Fluoro-3-[4-(²H₃)methyl-1-methyl-1H-1,2,3-triazol-5-yl]-5-[(S)-oxan-4-yl(phenyl)methyl]-5H-pyrido[3,2-b]indol-7-yl}piperidin-4-ol tert-Butyl 4-{6-fluoro-3-[4-(²H₃)methyl-1-methyl-1H-1,2,3-triazol-5-yl]-5-[(S)-oxan-4-yl(phenyl)methyl]-5H-pyrido[3,2-b]indol-7-yl}-4-hydroxypiperidine-1-carboxylate (impure, 100 mg, 0.152 mmol) was dissolved in a solution of TFA (0.55 mL) in dichloroethane (5 mL). The reaction was stirred for 45 min and concentrated. The resulting residue was dissolved in DCE and concentrated again. The resulting residue was purified by preparative HPLC (Column: Phenomenex Luna Axia, 30×100 mm, S10; Mobile Phase A: 10:90 methanol: water with 0.1% TFA; Mobile Phase B: 90:10 methanol: water with 0.1% TFA; Gradient: 10-100% B over 15 min, then a 3-min hold at 100% B; Flow: 40 mL/min). Fractions containing product were concentrated to give 46 mg (36%) of the title compound as the bis-TFA salt. LC/MS (M+H)=558.4. ¹H NMR (500 MHz, METHANOL-d₄) δ 8.52 (s, 1H), 8.22 (d, J=8.4 Hz, 1H), 8.18-8.04 (m, 1H), 7.72 (dd, J=8.1, 6.9 Hz, 1H), 7.62 (d, J=6.5 Hz, 2H), 7.39 (t, J=7.6 Hz, 2H), 7.35-7.27 (m, 1H), 6.15 (br. s., 1H), 5.10 (s, 3H), 4.97 (s, 1H), 4.05-3.81 (m, 6H), 3.69-3.56 (m, 4H), 3.48-3.40 (m, 4H), 2.75 (d, J=14.3 Hz, 2H), 2.26-2.01 (m, 3H), 1.51 (dd, J=12.4, 3.9 Hz, 2H), 1.11 (d, J=12.3 Hz, 1H)

Example 54

4-{6-Fluoro-3-[4-($^2$H$_3$)methyl-1-methyl-1H-1,2,3-triazol-5-yl]-5-[(S)-oxan-4-yl(phenyl)methyl]-5H-pyrido[3,2-b]indol-7-yl}-1-methylpiperidin-4-ol

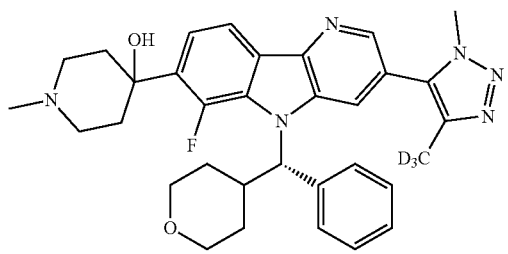 [SMILES: [2H]C([2H])([2H])c1nnn(C)c1-c1cnc2c3ccc(C4(O)CCN(C)CC4)c(F)c3n([C@H](c3ccccc3)C3CCOCC3)c2c1]

4-{6-Fluoro-3-[4-($^2$H$_3$)methyl-1-methyl-1H-1,2,3-triazol-5-yl]-5-[(S)-oxan-4-yl(phenyl)methyl]-5H-pyrido[3,2-b]indol-7-yl}piperidin-4-ol (bis-TFA salt, 15 mg, 0.019 mmol) and N-ethyl-N-isopropylpropan-2-amine (7 μL, 0.04 mmol) were suspended in 1,2-dichloroethane (295 μL, 3.82 mmol). To this was added formaldehyde (10 μL, 0.13 mmol). After 1 min, sodium triacetoxyborohydride (8.1 mg, 0.038 mmol) was also added. The resulting solution was stirred at room temperature for 1 h. The reaction was quenched by addition of saturated NaHCO$_3$ and stirred for 5 min. The reaction was diluted with EtOAc and the layers separated. The organics were washed with brine, dried over MgSO$_4$, filtered, and concentrated. The resulting residue was purified by preparative HPLC (Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 30-70% B over 20 min, then a 5-min hold at 100% B; Flow: 20 mL/min). Fractions containing product were concentrated to give 9.7 mg (87%). LC/MS (M+H)=572.1. $^1$H NMR (500 MHz, DMSO-d$_6$) δ 8.54 (br. s., 1H), 8.23 (br. s., 1H), 8.03 (d, J=7.7 Hz, 1H), 7.96 (s, 1H), 7.64 (br. s., 2H), 7.42-7.20 (m, 3H), 6.00 (br. s., 1H), 4.01-3.83 (m, 3H), 3.77 (d, J=11.0 Hz, 1H), 3.53-3.45 (m, 2H), 3.32-3.25 (m, 2H), 3.18 (br. s., 1H), 2.90 (s, 1H), 2.74 (s, 1H), 2.66 (br. s., 1H), 2.45 (br. s., 2H), 2.26 (br. s., 2H), 1.91 (s, 3H), 1.77 (d, J=7.0 Hz, 2H), 1.36 (br. s., 1H), 1.08 (d, J=13.2 Hz, 1H)

Examples 55 & 56

4-{6-Fluoro-3-[4-($^2$H$_3$)methyl-1-methyl-1H-1,2,3-triazol-5-yl]-5-[(S)-oxan-4-yl(phenyl)methyl]-5H-pyrido[3,2-b]indol-7-yl}-4-methyl-1,3-oxazolidin-2-one Example 55

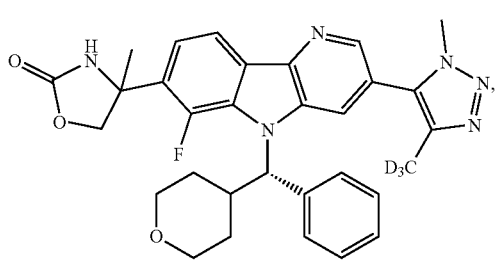

Diasteromer A

Example 56

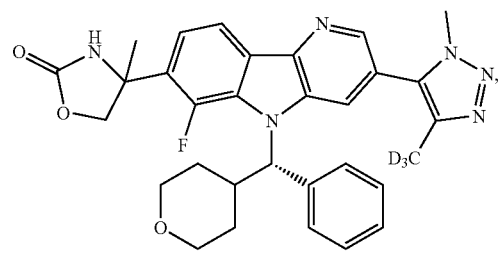

Diasteromer B

Step 1: 5-{6-Fluoro-5-[(S)-oxan-4-yl(phenyl)methyl]-7-(prop-1-en-2-yl)-5H-pyrido[3,2-b]indol-3-yl}-4-($^2$H$_3$)methyl-1-methyl-1H-1,2,3-triazole A microwave vial was charged with 5-{7-chloro-6-fluoro-5-[(S)-oxan-4-yl(phenyl)methyl]-5H-pyrido[3,2-b]indol-3-yl}-4-($^2$H$_3$)methyl-1-methyl-1H-1,2,3-triazole (0.200 g, 0.406 mmol) and dioxane (2.70 mL). The mixture was degassed by bubbling nitrogen through it. To this was added cesium carbonate (0.330 g, 1.01 mmol), Pd$_2$(dba)$_3$ (0.037 g, 0.041 mmol), isopropenylboronic acid pinacol ester (0.191 mL, 1.01 mmol), and tricyclohexylphosphine (20% wt in toluene, 0.126 mL, 0.081 mmol). The vial was degassed with nitrogen and sealed. The vial was placed in an oil bath preheated to 120° C. The reaction mixture was let to stir overnight at that temperature. The reaction was concentrated, diluted with ethyl acetate, washed with water, then brine, dried over MgSO$_4$, filtered, and concentrated. The residue was purified by column chromatography (10%-40% DCM/acetone) to give 182 mg (90%) as a foam solid. LC/MS (M+H)=499.3. $^1$H NMR (500 MHz, CDCl$_3$) δ 8.45 (d, J=1.7 Hz, 1H), 8.13 (d, J=8.0 Hz, 1H), 7.57-7.48 (m, 3H), 7.42-7.36 (m, 2H), 7.35-7.30 (m, 2H), 6.17 (br. s., 1H), 5.47-5.38 (m, 2H), 4.07 (dd, J=11.7, 2.5 Hz, 1H), 3.91 (dd, J=11.7, 2.4 Hz, 1H), 3.83 (s, 3H), 3.57 (td, J=11.9, 2.0 Hz, 1H), 3.36 (td, J=11.9, 1.8 Hz, 1H), 3.05 (d, J=7.9 Hz, 1H), 2.34 (s, 3H), 2.08 (d, J=13.6 Hz, 1H), 1.95 (s, 1H), 1.69-1.62 (m, 1H), 1.56 (dd, J=12.5, 3.6 Hz, 1H), 1.03 (d, J=12.6 Hz, 1H).

Step 2: 4-{6-Fluoro-3-[4-($^2$H$_3$)methyl-1-methyl-1H-1,2,3-triazol-5-yl]-5-[(S)-oxan-4-yl(phenyl)methyl]-5H-pyrido[3,2-b]indol-7-yl}-4-methyl-1,3-oxazolidin-2-one To a suspension of 5-{6-fluoro-5-[(S)-oxan-4-yl(phenyl)methyl]-7-(prop-1-en-2-yl)-5H-pyrido[3,2-b]indol-3-yl}-4-($^2$H$_3$)methyl-1-methyl-1H-1,2,3-triazole (180 mg, 0.361 mmol) and silver cyanate (65 mg, 0.43 mmol) in acetonitrile (0.5 mL) at 0° C. was added a solution of iodine (101 mg, 0.397 mmol) in ethyl acetate (1.0 mL) dropwise, while excluding light to the extent possible. After addition was complete, the reaction was allowed to gradually warm to room temperature in the dewar overnight. The solid was removed by filtration, rinsing with ethyl acetate. The eluent was washed with aqueous sodium sulfite (1%), then brine, dried over sodium sulfate, filtered, and concentrated. The crude intermediate was dissolved in DMF (2 mL) and treated with tert-butanol (0.069 mL, 0.722 mmol) and silver (I) tetrafluoroborate (77 mg, 0.40 mmol). The reaction was warmed to 80° C. and held at that temperature overnight. The reaction was diluted with EtOAc and treated with celite. The solids were removed by filtration, rinsing with EtOAc. The organics were washed with water, then brine, dried over MgSO$_4$, filtered, and concentrated. The residue was purified by preparative HPLC to give the title compound as a mixture of diastereomers. The material was repurified by chiral SFC (Column: ChiralPak AS-H, 30×250 mm, 5-μm particles; Mobile Phase 25% MeOH in CO$_2$ @150 Bar, Temp-35° C.; Flow: 70 mL/min) to give Diastereomer A (TR=5.6 min, 9.0 mg, 4%) and Diastereomer B(TR=16.9 min, 8.0 mg, 3%). Diastereomer A: LC/MS (M+H)=558.3. $^1$H NMR (500 MHz, CD$_3$OD) δ 8.53 (d, J=1.4 Hz, 1H), 8.23 (d, J=8.2 Hz, 1H), 8.16 (br. s., 1H), 7.63 (d, J=6.6 Hz, 2H), 7.45 (dd, J=8.2, 6.5 Hz, 1H), 7.39 (t, J=7.6 Hz, 2H), 7.35-7.27 (m, 1H), 6.10 (br. s., 1H), 4.84-4.80 (m, 1H), 4.79-4.71 (m, 1H), 4.01 (dd, J=11.5, 2.7 Hz, 1H), 3.93 (br. s., 2H), 3.86 (dd, J=11.6, 2.6 Hz, 1H), 3.63 (td, J=11.8, 1.9 Hz, 1H), 3.49-3.36 (m, 2H), 3.30-3.27 (m, 1H), 3.19 (t, J=1.6 Hz, 1H), 2.05 (d, J=13.1 Hz, 1H), 1.86 (br. s., 2H), 1.67-1.43 (m, 2H), 1.12 (d, J=11.7 Hz, 1H), 0.99-0.85 (m, 1H). Diastereomer B: LC/MS (M+H)=558.3. $^1$H NMR (500 MHz, CD$_3$OD) δ 8.53 (d, J=1.3 Hz, 1H), 8.23 (d, J=8.2 Hz, 1H), 8.20-8.11 (m, 1H), 7.61 (d, J=6.9 Hz, 4H), 7.45 (dd, J=8.1, 6.4 Hz, 2H), 7.39 (t, J=7.6 Hz, 4H), 7.34-7.27 (m, 2H), 6.09 (br. s., 2H), 4.84-4.78 (m, 1H), 4.68 (d, J=8.2 Hz, 1H), 4.01 (dd, J=11.8, 2.7 Hz, 3H), 3.94 (br. s., 6H), 3.87 (dd, J=11.7, 2.8 Hz, 3H), 3.63 (td, J=11.8, 1.9 Hz, 3H), 3.48-3.40 (m, 5H), 3.31-3.27 (m, 2H), 3.19 (dt, J=3.3, 1.7 Hz, 1H), 2.03 (d, J=12.9 Hz, 4H), 1.95-1.82 (m, 11H), 1.67-1.47 (m, 9H), 1.14 (d, J=13.2 Hz, 7H), 0.98-0.71 (m, 11H).

Example 57

1-{6-Fluoro-3-[4-($^2$H$_3$)methyl-1-methyl-1H-1,2,3-triazol-5-yl]-5-[(S)-oxan-4-yl(phenyl)methyl]-5H-pyrido[3,2-b]indol-7-yl}pyrrolidin-2-one

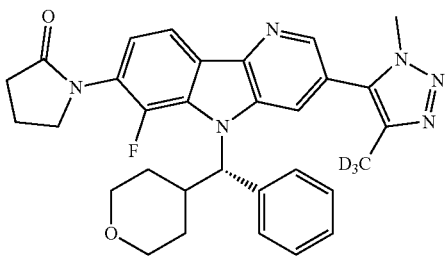 [SMILES: [2H]C([2H])([2H])c1nnn(C)c1-c1cnc2c3ccc(N4CCCC4=O)c(F)c3n([C@H](c3ccccc3)C3CCOCC3)c2c1]

A microwave vial was charged with (5-{7-chloro-6-fluoro-5-[(S)-oxan-4-yl(phenyl)methyl]-5H-pyrido[3,2-b]indol-3-yl}-4-($^2$H$_3$)methyl-1-methyl-1H-1,2,3-triazole (30 mg, 0.061 mmol), pyrrolidin-2-one (7.8 mg, 0.091 mmol), tripotassium phosphate (18.1 mg, 0.085 mmol), Pd$_2$(dba)$_3$ (2.8 mg, 3.0 μmol), 2-di-tert-butylphosphino-3,4,5,6-tetramethyl-2',4',6'-triisopropyl-1,1'-biphenyl (2.9 mg, 6.1 μmol), and dry tert-butanol (0.5 mL). The reaction was heated at 84° C. overnight. It was diluted with water and extracted with ethyl acetate. The organic layer was concentrated and purified by preparative HPLC (Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 15-55% B over 15 min, then a 5-min hold at 100% B; Flow: 20 mL/min) to give 12.2 mg (36%). $^1$H NMR (500 MHz, DMSO) δ 8.59 (s, 1H), 8.10 (m, 1H), 7.96 (s, 1H), 7.65 (m, 2H), 7.35 (m, 3H), 7.28 (m, 1H), 5.91 (m, 1H), 3.92 (m, 6H), 3.76 (m, 1H), 3.48 (m, 2H), 3.29 (m, 1H), 2.55 (m, 2H), 2.22 (m, 2H), 1.78 (m, 1H), 1.36 (m, 2H), 1.10 (m, 1H); LCMS (M+H)=542.3.

Example 58

2-{6-Fluoro-3-[4-($^2$H$_3$)methyl-1-methyl-1H-1,2,3-triazol-5-yl]-5-[(S)-oxan-4-yl(phenyl)methyl]-5H-pyrido[3,2-b]indol-7-yl}-1λ$^6$,2-thiazolidine-1,1-dione

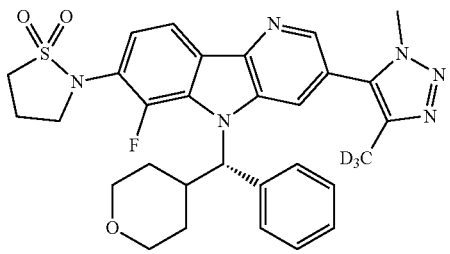 [SMILES: [2H]C([2H])([2H])c1nnn(C)c1-c1cnc2c3ccc(N4CCCS4(=O)=O)c(F)c3n([C@H](c3ccccc3)C3CCOCC3)c2c1]

A microwave vial was charged with (5-{7-chloro-6-fluoro-5-[(S)-oxan-4-yl(phenyl)methyl]-5H-pyrido[3,2-b]indol-3-yl}-4-($^2$H$_3$)methyl-1-methyl-1H-1,2,3-triazole (30 mg, 0.061 mmol), isothiazolidine 1,1-dioxide (11.1 mg, 0.091 mmol), tripotassium phosphate (18.1 mg, 0.085 mmol), Pd$_2$(dba)$_3$ (2.8 mg, 3.0 μmol), 2-di-tert-butylphosphino-3,4,5,6-tetramethyl-2',4',6'-triisopropyl-1,1'-biphenyl (2.9 mg, 6.1 μmol), and dry tert-butanol (0.5 mL). The reaction was heated at 84° C. overnight. It was diluted with water and extracted with ethyl acetate. The organic layer was concentrated and purified by preparative HPLC (Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 15-55% B over 15 min, then a 5-min hold at 100% B; Flow: 20 mL/min) to give 2.1 mg (6%). $^1$H NMR (500 MHz, DMSO) δ 8.61 (s, 1H), 8.11 (m, 1H), 7.96 (s, 1H), 7.64 (m, 2H), 7.45 (m, 1H), 7.35 (m, 2H), 7.28 (m, 1H), 5.91 (m, 1H), 3.9 (m, 5H), 3.77 (m, 1H), 3.52 (m, 3H), 3.29 (m, 1H), 2.55 9m, 2H), 1.78 (m, 1H), 1.35 (m, 2H), 1.1 (m, 1H); LCMS (M+H)=578.35.

Example 59

1-{6-Fluoro-3-[4-($^2$H$_3$)methyl-1-methyl-1H-1,2,3-triazol-5-yl]-5-[(S)-oxan-4-yl(phenyl)methyl]-5H-pyrido[3,2-b]indol-7-yl}imidazolidin-2-one

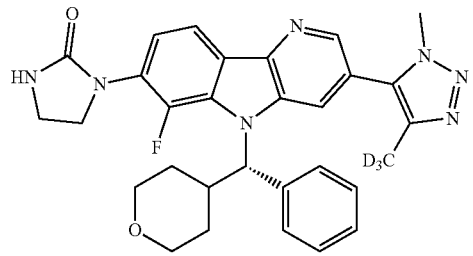 [SMILES: [2H]C([2H])([2H])c1nnn(C)c1-c1cnc2c3ccc(N4CCNC4=O)c(F)c3n([C@H](c3ccccc3)C3CCOCC3)c2c1]

A microwave vial was charged with (5-{7-chloro-6-fluoro-5-[(S)-oxan-4-yl(phenyl)methyl]-5H-pyrido[3,2-b]indol-3-yl}-4-($^2$H$_3$)methyl-1-methyl-1H-1,2,3-triazole (30 mg, 0.061 mmol), imidazolidin-2-one (7.9 mg, 0.091 mmol), tripotassium phosphate (18.1 mg, 0.085 mmol), Pd$_2$(dba)$_3$ (2.8 mg, 3.0 μmol), 2-di-tert-butylphosphino-3,4,5,6-tetramethyl-2',4',6'-triisopropyl-1,1'-biphenyl (2.9 mg, 6.1 μmol), and dry tert-butanol (0.5 mL). The reaction was heated at 84° C. overnight. It was diluted with water and extracted with ethyl acetate. The organic layer was concentrated and purified by preparative HPLC (Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 25-65% B over 15 min, then a 5-min hold at 100% B; Flow: 20 mL/min) to give 7.2 mg (21%). LCMS (M+H)=543.47, T$_R$=1.36 min (Column: Phenomenex LUNA C18, 30×2, 3 u; Mobile Phase A: 90:10 water: acetonitrile with 0.1% TFA; Mobile Phase B: 10:90 water: acetonitrile with 0.1% TFA; Temperature: 40° C.; Gradient: 0-100% B over 2 min, hold 1 min; Flow rate: 1 mL/min).

Example 60

3-{6-Fluoro-3-[4-($^2$H$_3$)methyl-1-methyl-1H-1,2,3-triazol-5-yl]-5-[(S)-oxan-4-yl(phenyl)methyl]-5H-pyrido[3,2-b]indol-7-yl}-1,3-oxazolidin-2-one

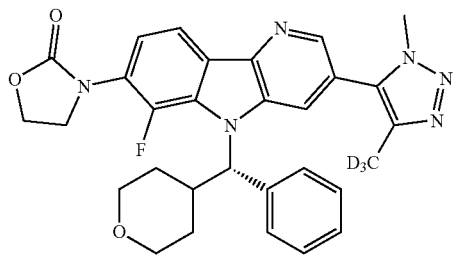 [SMILES: [2H]C([2H])([2H])c1nnn(C)c1-c1cnc2c3ccc(N4CCOC4=O)c(F)c3n([C@H](c3ccccc3)C3CCOCC3)c2c1]

A microwave vial was charged with (5-{7-chloro-6-fluoro-5-[(S)-oxan-4-yl(phenyl)methyl]-5H-pyrido[3,2-b]indol-3-yl}-4-($^2$H$_3$)methyl-1-methyl-1H-1,2,3-triazole (30 mg, 0.061 mmol), oxazolidin-2-one (8.0 mg, 0.091 mmol), tripotassium phosphate (18.1 mg, 0.085 mmol), Pd$_2$(dba)$_3$ (2.8 mg, 3.0 μmol), 2-di-tert-butylphosphino-3,4,5,6-tetramethyl-2',4',6'-triisopropyl-1,1'-biphenyl (2.9 mg, 6.01 mol), and dry tert-butanol (0.5 mL). The reaction was heated at 84° C. overnight. It was diluted with water and extracted with ethyl acetate. The organic layer was concentrated and purified by preparative HPLC (Column: XBridge C18, 19×mm, 5-μm particles; Mobile Phase A: 5:95 acetonitrile: water with 10-mM ammonium acetate; Mobile Phase B: 95:5 acetonitrile: water with 10-mM ammonium acetate; Gradient: 20-60% B over 15 min, then a 5-min hold at 100% B; Flow: 20 mL/min) to give 13 mg (39%). $^1$H NMR (500 MHz, DMSO) δ 8.6 (s, 1H), 8.12 (m, 1H), 7.96 (s, 1H), 7.65 (m, 2H), 7.49 (m, 1H), 7.34 (m, 2H), 7.28 (m, 1H), 5.92 (m, 1H), 4.58 (m, 2H), 4.20 (m, 2H), 3.95 (s, 3H), 3.9 (m, 1H), 3.77 (m, 1H), 3.48 (m, 1H), 3.29 (m, 1H), 2.55 (m, 1H), 1.78 (m, 1H), 1.36 (m, 2H), 1.09 (m, 1H); LCMS (M+H)=544.3

Example 61

2-{6-Fluoro-5-[(S)-(3-fluoropyridin-2-yl)(oxan-4-yl)methyl]-3-[4-($^2$H$_3$)methyl-1-methyl-1H-1,2,3-triazol-5-yl]-5H-pyrido[3,2-b]indol-7-yl}-1λ$^6$,2-thiazolidine-1,1-dione

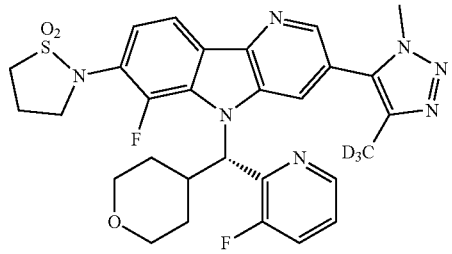 [SMILES: [2H]C([2H])([2H])c1nnn(C)c1-c1cnc2c3ccc(N4CCCS4(=O)=O)c(F)c3n([C@H](c3ncccc3F)C3CCOCC3)c2c1]

A microwave vial was charged with 2-[(S)-{7-chloro-6-fluoro-3-[4-($^2$H$_3$)methyl-1-methyl-1H-1,2,3-triazol-5-yl]-5H-pyrido[3,2-b]indol-5-yl}(oxan-4-yl)methyl]-3-fluoropyridine (46 mg, 0.090 mmol), isothiazolidine 1,1-dioxide (16.3 mg, 0.135 mmol), tripotassium phosphate (26.7 mg, 0.126 mmol), Pd$_2$(dba)$_3$ (4.1 mg, 4.5 μmol), 2-di-tert-butylphosphino-3,4,5,6-tetramethyl-2',4',6'-triisopropyl-1,1'-biphenyl (4.3 mg, 9.0 μmol), and dry tert-butanol (0.85 mL). The reaction was heated at 84° C. overnight. It was diluted with water and extracted with ethyl acetate. The organic layer was concentrated and purified by preparative HPLC (Column: XBridge C18, 19×200 mm, 5-μm particles; Mobile Phase A: 5:95 acetonitrile: water with 0.1% trifluoroacetic acid; Mobile Phase B: 95:5 acetonitrile: water with 0.1% trifluoroacetic acid; Gradient: 22-62% B over 20 min, then a 5-min hold at 100% B; Flow: 20 mL/min) to give 12.3 mg (22%). LCMS (M+H)=597.3, T$_R$=1.30 min (Column: Phenomenex LUNA C18, 30×2, 3 u; Mobile Phase A: 90:10 water:acetonitrile with 0.1% TFA; Mobile Phase B: 10:90 water:acetonitrile with 0.1% TFA; Temperature: 40° C.; Gradient: 0-100% B over 2 min, hold 1 min; Flow rate: 1 mL/min).

Example 62

4-{6-Fluoro-3-[4-($^2$H$_3$)methyl-1-methyl-1H-1,2,3-triazol-5-yl]-5-[(S)-oxan-4-yl(phenyl)methyl]-5H-pyrido[3,2-b]indol-7-yl}oxan-4-ol

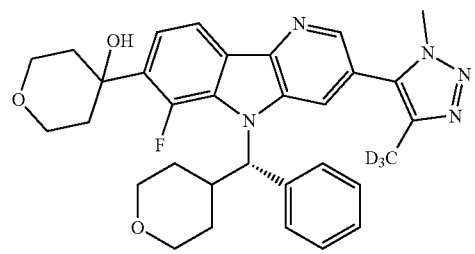 [SMILES: [2H]C([2H])([2H])c1nnn(C)c1-c1cnc2c3ccc(C4(O)CCOCC4)c(F)c3n([C@H](c3ccccc3)C3CCOCC3)c2c1]

Step 1: 5-[7-(3,6-Dihydro-2H-pyran-4-yl)-6-fluoro-5-[(S)-oxan-4-yl(phenyl)methyl]-5H-pyrido[3,2-b]indol-3-yl]-4-($^2$H$_3$)methyl-1-methyl-1H-1,2,3-triazole A microwave vial was charged with (5-{7-chloro-6-fluoro-5-[(S)-oxan-4-yl(phenyl)methyl]-5H-pyrido[3,2-b]

indol-3-yl}-4-(²H₃)methyl-1-methyl-1H-1,2,3-triazole (30.0 mg, 0.061 mmol) and dioxane (609 µL) and degassed with a stream of nitrogen. To this was added cesium carbonate (39.7 mg, 0.122 mmol), Pd₂(dba)₃ (5.6 mg, 6.1 µmol), 2-(3,6-dihydro-2H-pyran-4-yl)-4,4,5,5-tetramethyl-1,3,2-dioxaborolane (32.0 mg, 0.152 mmol), and tricyclohexylphosphine (20% wt in toluene, 19 µL, 0.012 mmol). The vial was sealed and degassed with nitrogen. The vial was placed in an oil bath preheated to 130° C. and held at that temperature for 5 h. The reaction was concentrated, diluted with ethyl acetate, washed with water and brine, dried over MgSO₄, filtered, and concentrated. Flash chromatography (100% ethyl acetate) gave 21 mg (64%). LCMS (M+H)=541.4, $T_R$=1.65 min (Column: Phenomenex LUNA C18, 30×2, 3 u; Mobile Phase A: 90:10 water:acetonitrile with 0.1% TFA; Mobile Phase B: 10:90 water:acetonitrile with 0.1% TFA; Temperature: 40° C.; Gradient: 0-100% B over 2 min, hold 1 min; Flow rate: 1 mL/min).

Step 2: 4-{6-Fluoro-3-[4-(²H₃)methyl-1-methyl-1H-1,2,3-triazol-5-yl]-5-[(S)-oxan-4-yl(phenyl)methyl]-5H-pyrido[3,2-b]indol-7-yl}oxan-4-ol A flask was charged with 5-[7-(3,6-dihydro-2H-pyran-4-yl)-6-fluoro-5-[(S)-oxan-4-yl(phenyl)methyl]-5H-pyrido[3,2-b]indol-3-yl]-4-(²H₃)methyl-1-methyl-1H-1,2,3-triazole (21 mg, 0.039 mmol), DCM (0.15 mL), and 2-propanol (1 mL). The resulting solution was vigorously stirred under a stream of oxygen. The reaction was placed in a 0° C. bath and stirring continued under the stream of oxygen for 5 min. To this was added tris(2,2,6,6-tetramethyl-3,5-heptanedionato)manganese (III) (2.3 mg, 3.9 µmol) followed by phenylsilane (10 µL, 0.078 mmol). After 30 min at 0° C., the reaction was quenched by addition of 1 mL of saturated sodium thiosulfate and concentrated under a stream of nitrogen. The reaction was suspended in EtOAc and water. The organics were washed with brine, dried over MgSO₄, filtered, and concentrated. Preparative HPLC (Column: XBridge C18, 19×mm, 5-µm particles; Mobile Phase A: 5:95 acetonitrile: water with 10-mM ammonium acetate; Mobile Phase B: 95:5 acetonitrile: water with 10-mM ammonium acetate; Gradient: 20-60% B over 15 min, then a 5-min hold at 100% B; Flow: 20 mL/min) gave 9.5 mg (43%). ¹H NMR (500 MHz, DMSO) δ 8.55 (m, 1H), 8.05 (m, 1H), 7.64 (m, 3H), 7.35 (m, 2H), 7.27 (m, 1H), 6.00 (m, 1H), 5.52 (m, 1H), 3.90 (m, 6H), 3.80 (m, 2H), 3.76 (m, 1H), 3.50 (m, 1H), 3.26 (m, 1H), 2.46 (m, 2H), 1.80 (m, 2H), 1.73 (m, 1H), 1.37 (m, 2H), 1.08 (m, 1H); LCMS (M+H)=559.54

Examples 63 & 64

3-{6-Fluoro-3-[4-(²H₃)methyl-1-methyl-1H-1,2,3-triazol-5-yl]-5-[(S)-oxan-4-yl(phenyl)methyl]-5H-pyrido[3,2-b]indol-7-yl}oxolan-3-ol Example 63

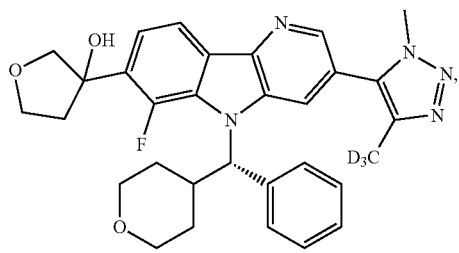

Diasteromer 1

Example 64

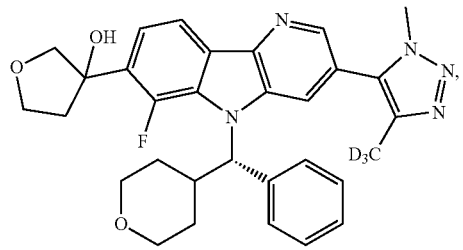

Diasteromer 2

The title compound was prepared by the method used to prepare 4-{6-fluoro-3-[4-(²H₃)methyl-1-methyl-1H-1,2,3-triazol-5-yl]-5-[(S)-oxan-4-yl(phenyl)methyl]-5H-pyrido[3,2-b]indol-7-yl}oxan-4-ol, using 2-(2,5-dihydrofuran-3-yl)-4,4,5,5-tetramethyl-1,3,2-dioxaborolane (29.8 mg, 0.152 mmol). Diastereomers were separated by chiral preparative HPLC (Chiralpak AD 21×250 mm 5 u, Isocratic 18% B for 40 min, Solvent A: 100% Heptane, Solvent B: 100% Ethanol, Flow Rate: 15 mL/min, UV254) to give 4.1 mg first eluting diastereomer (15% yield) and 2 mg of the second eluting diastereomer (7% yield). LCMS (M+H)=545.4, $T_R$=1.33 min (Column: Phenomenex LUNA C18, 30×2, 3 u; Mobile Phase A: 90:10 water:acetonitrile with 0.1% TFA; Mobile Phase B: 10:90 water:acetonitrile with 0.1% TFA; Temperature: 40° C.; Gradient: 0-100% B over 2 min, hold 1 min; Flow rate: 1 mL/min).

Examples 65 & 66

2-{[7-(4,4-Difluoropiperidin-1-yl)-3-[4-(²H₃)methyl-1-methyl-1H-1,2,3-triazol-5-yl]-5H-pyrido[3,2-b]indol-5-yl](oxan-4-yl)methyl}-3-fluoropyridine Example 65

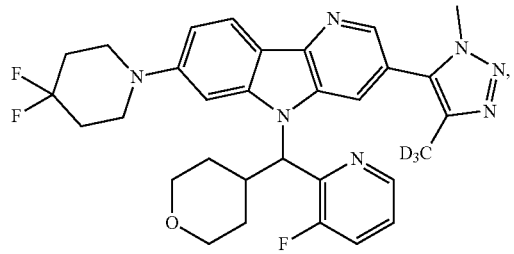

Enantiomer A

Example 66

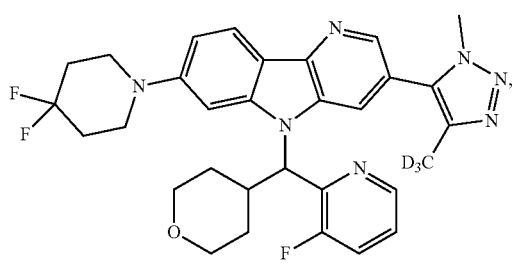

Enantiomer B

Step 1: 2-({7-Chloro-3-[4-($^2$H$_3$)methyl-1-methyl-1H-1,2,3-triazol-5-yl]-5H-pyrido[3,2-b]indol-5-yl}(oxan-4-yl)methyl)-3-fluoropyridine To a stirred solution of 5-{7-chloro-5H-pyrido[3,2-b]indol-3-yl}-4-($^2$H$_3$)methyl-1-methyl-1H-1,2,3-triazole (100 mg, 0.332 mmol) in 2 mL of THF was added (3-fluoropyridin-2-yl)(tetrahydro-2H-pyran-4-yl)methanol (140 mg, 0.665 mmol), triphenylphosphine (174 mg, 0.665 mmol), and triethylamine (93 µL, 0.67 mmol). The reaction was cooled to 0° C. and treated with di-tert-butyl azodicarboxylate (153 mg, 0.665 mmol). After stirring at 0° C. for 15 min, the ice bath was removed and stirring continued for 3 d. The reaction was concentrated and purified by flash chromatography (24 g biotage column, eluting with 0% EtOAc/hexanes to 100% EtOAc over 400 mL, then eluted with 0-20% methanol/EtOAc over 400 mL to afford 125 mg. LCMS (M+H)=494. 1H NMR (400 MHz, CD$_3$OD) δ 8.64-8.56 (m, 2H), 8.52 (d, J=1.5 Hz, 1H), 8.25 (d, J=8.5 Hz, 1H), 8.19-8.09 (m, 1H), 7.62-7.50 (m, 1H), 7.43 (dt, J=8.5, 4.3 Hz, 1H), 7.30 (d, J=8.5 Hz, 1H), 6.10 (d, J=10.3 Hz, 1H), 3.96-3.87 (m, 1H), 3.75 (dd, J=11.5, 3.0 Hz, 1H), 3.68-3.41 (m, 2H), 1.77 (d, J=11.3 Hz, 1H), 1.57 (qd, J=12.1, 4.4 Hz, 2H), 1.51-1.30 (m, 2H), 0.89-0.77 (m, 2H).

Step 2: 2-{[7-(4,4-Difluoropiperidin-1-yl)-3-[4-($^2$H$_3$)methyl-1-methyl-1H-1,2,3-triazol-5-yl]-5H-pyrido[3,2-b]indol-5-yl](oxan-4-yl)methyl}-3-fluoropyridine A microwave vial was charged with 2-({7-chloro-3-[4-($^2$H$_3$)methyl-1-methyl-1H-1,2,3-triazol-5-yl]-5H-pyrido[3,2-b]indol-5-yl}(oxan-4-yl)methyl)-3-fluoropyridine (37 mg, 0.075 mmol), 4,4-difluoropiperidine hydrochloride (23.6 mg, 0.150 mmol), (2-dicyclohexylphosphino-2',6'-diisopropyl-1,1'-biphenyl)[2-(2-aminoethyl)phenyl]palladium(II) (16.4 mg, 0.022 mmol), 2-dicyclohexylphosphino-2',6'-di-i-propoxy-1,1'-biphenyl (10.5 mg, 0.022 mmol), sodium tert-butoxide (43.2 mg, 0.449 mmol), and THF (2 mL). The resulting mixture was bubbled with argon for 1 min with sonication. The vial was sealed and heated in an oil bath at 120° C. for 1 h. The reaction mixture was concentrated and purified via preparative LC/MS (Column: XBridge C18, 19×200 mm, 5-µm particles; Mobile Phase A: 5:95 acetonitrile: water with 10-mM ammonium acetate; Mobile Phase B: 95:5 acetonitrile: water with 10-mM ammonium acetate; Gradient: 35-75% B over 15 min, then a 5-min hold at 100% B; Flow: 20 mL/min). Fractions containing the desired product were combined and dried via centrifugal evaporation. The enantiomers were separated on a chiracel OD column, 21×250 mm, 10 u, eluting with 11% ethanol/89% heptane; flow rate=15 mL/min.; Detection: UV at 254 nM. Enantiomer A eluted between 54.03 and 56.72 min to give 6.4 mg. Enantiomer B eluted between 62.39 min to 67.73 min to give 6.5 mg. Enantiomer A: HPLC T$_R$=1.659 min (Column: Waters Acquity UPLC BEH C18, 2.1×50 mm, 1.7-µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 min, then a 0.75-min hold at 100% B; Flow: 1.0 mL/min). 1H NMR (500 MHz, DMSO-d$_6$) δ 8.59 (br. s., 1H), 8.40 (br. s., 1H), 8.04 (d, J=8.8 Hz, 1H), 7.66 (t, J=8.6 Hz, 1H), 7.47 (br. s., 1H), 7.05 (br. s., 1H), 6.12 (d, J=10.6 Hz, 1H), 4.00 (br. s., 2H), 3.85 (d, J=9.9 Hz, 1H), 3.52 (br. s., 1H), 3.45 (br. s., 1H), 3.39 (d, J=12.1 Hz, 1H), 3.19 (t, J=11.4 Hz, 1H), 2.09 (br. s., 3H), 1.67 (br. s., 1H), 1.59 (br. s., 1H), 1.34 (br. s., 1H), 0.72 (d, J=13.2 Hz, 1H).
Enantiomer B: HPLC T$_R$=1.659 min (Column: Waters Acquity UPLC BEH C18, 2.1×50 mm, 1.7-µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 min, then a 0.75-min hold at 100% B; Flow: 1.0 mL/min). 1H NMR (500 MHz, DMSO-d$_6$) δ 8.59 (br. s., 1H), 8.40 (br. s., 1H), 8.04 (d, J=8.8 Hz, 1H), 7.66 (t, J=8.6 Hz, 1H), 7.47 (br. s., 1H), 7.05 (br. s., 1H), 6.12 (d, J=10.6 Hz, 1H), 4.00 (br. s., 2H), 3.85 (d, J=9.9 Hz, 1H), 3.52 (br. s., 1H), 3.45 (br. s., 1H), 3.39 (d, J=12.1 Hz, 1H), 3.19 (t, J=11.4 Hz, 1H), 2.09 (br. s., 3H), 1.67 (br. s., 1H), 1.59 (br. s., 1H), 1.34 (br. s., 1H), 0.72 (d, J=13.2 Hz, 1H).

Examples 67 & 68

4-{5-[(3-Fluoropyridin-2-yl)(oxan-4-yl)methyl]-3-[4-($^2$H$_3$)methyl-1-methyl-1H-1,2,3-triazol-5-yl]-5H-pyrido[3,2-b]indol-7-yl}-1λ$^6$,4-thiomorpholine-1,1-dione

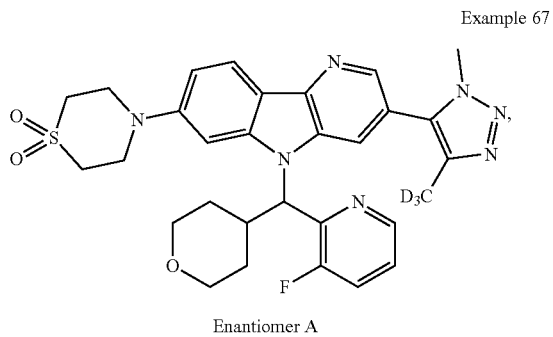

Enantiomer A

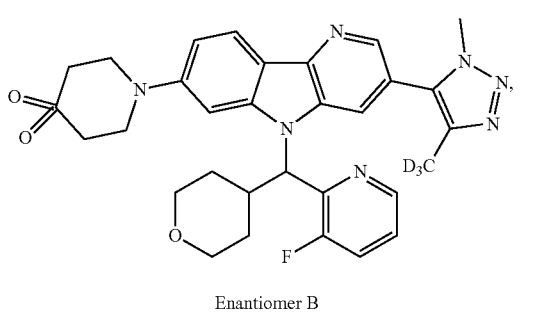

Enantiomer B

A microwave vial was charged with 2-({7-chloro-3-[4-($^2$H$_3$)methyl-1-methyl-1H-1,2,3-triazol-5-yl]-5H-pyrido[3,2-b]indol-5-yl}(oxan-4-yl)methyl)-3-fluoropyridine (37 mg, 0.075 mmol), thiomorpholine 1,1-dioxide (20 mg, 0.150 mmol), (2-dicyclohexylphosphino-2',6'-diisopropyl-1,1'-biphenyl)[2-(2-aminoethyl)phenyl]palladium(II) (16.4 mg, 0.022 mmol), 2-dicyclohexylphosphino-2',6'-di-i-propoxy-1,1'-biphenyl (10.5 mg, 0.022 mmol), sodium tert-butoxide (43.2 mg, 0.449 mmol), and THF (2 mL). The mixture was bubbled with argon for 1 min with sonication. The vial was sealed and heated in a oil bath at 120° C. for 1 h. The reaction was concentrated and purified by preparative LC/MS (Column: XBridge C18, 19×200 mm, 5-µm particles; Mobile Phase A: 5:95 acetonitrile: water with 10-mM ammonium acetate; Mobile Phase B: 95:5 acetonitrile: water with 10-mM ammonium acetate; Gradient: 35-75% B over 15 min, then a 5-min hold at 100% B; Flow: 20 mL/min). The enantiomers were separated on a chiracel OD column, 21×250 mm, 10 u, eluting with 18% ethanol/82% 0.1% diethylamine/heptane; flow rate=15 mL/min.; Detection: UV at 254 nM. Enantiomer A eluted between 77.99 and 87.50 min to give 6.3 mg. Enantiomer B eluted between 88.87 and 104.50 min to give 5.1 mg. Enantiomer A: HPLC $T_R$=1.33 min (Column: Waters Acquity UPLC BEH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 min, then a 0.75-min hold at 100% B; Flow: 1.0 mL/min). 1H NMR (500 MHz, DMSO-$d_6$) δ 8.64 (br. s., 1H), 8.45 (br. s., 1H), 8.05 (d, J=8.8 Hz, 1H), 7.72 (t, J=9.2 Hz, 1H), 7.50 (br. s., 1H), 7.09 (br. s., 1H), 6.17 (d, J=9.9 Hz, 1H), 4.03 (br. s., 5H), 3.86 (d, J=10.3 Hz, 2H), 3.70 (d, J=9.2 Hz, 1H), 3.49 (br. s., 1H), 3.40 (br. s., 1H), 3.37-3.27 (m, 6H), 3.22 (br. s., 3H), 2.93-2.86 (m, 3H), 2.74 (s, 1H), 1.62 (br. s., 2H), 1.37 (br. s., 1H), 0.74 (d, J=12.5 Hz, 1H).

Enantiomer B: HPLC $T_R$=1.659 min (Column: Waters Acquity UPLC BEH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 min, then a 0.75-min hold at 100% B; Flow: 1.0 mL/min). 1H NMR (500 MHz, DMSO-$d_6$) δ 8.64 (br. s., 1H), 8.45 (br. s., 1H), 8.05 (d, J=8.8 Hz, 1H), 7.72 (t, J=9.2 Hz, 1H), 7.50 (br. s., 1H), 7.09 (br. s., 1H), 6.17 (d, J=9.9 Hz, 1H), 4.03 (br. s., 5H), 3.86 (d, J=10.3 Hz, 2H), 3.70 (d, J=9.2 Hz, 1H), 3.49 (br. s., 1H), 3.40 (br. s., 1H), 3.37-3.27 (m, 6H), 3.22 (br. s., 3H), 2.93-2.86 (m, 3H), 2.74 (s, 1H), 1.62 (br. s., 2H), 1.37 (br. s., 1H), 0.74 (d, J=12.5 Hz, 1H).

Examples 69 & 70

3-Fluoro-2-{[7-(4-methanesulfonylpiperidin-1-yl)-3-[4-($^2$H$_3$)methyl-1-methyl-1H-1,2,3-triazol-5-yl]-5H-pyrido[3,2-b]indol-5-yl](oxan-4-yl)methyl}pyridine Example 69

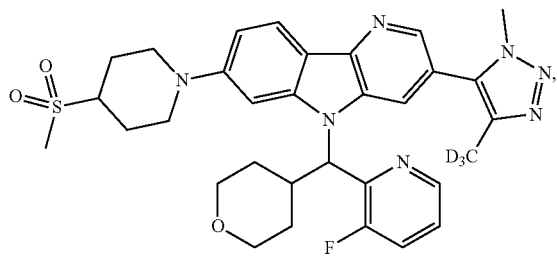

Enantiomer A

Example 70

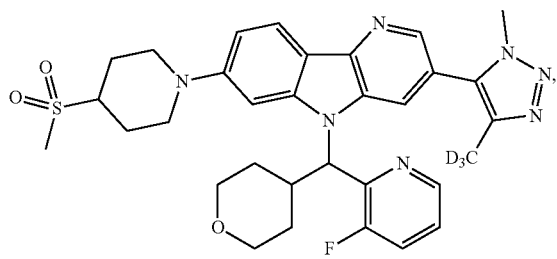

Enantiomer B

A microwave vial was charged with 2-({7-chloro-3-[4-($^2$H$_3$)methyl-1-methyl-1H-1,2,3-triazol-5-yl]-5H-pyrido[3,2-b]indol-5-yl}(oxan-4-yl)methyl)-3-fluoropyridine (37 mg, 0.075 mmol), 4-methylsulfonyl piperdine hydrochloride (30 mg, 0.15 mmol), (2-dicyclohexylphosphino-2',6'-diisopropyl-1,1'-biphenyl)[2-(2-aminoethyl)phenyl]palladium(II) (16.4 mg, 0.022 mmol), 2-dicyclohexylphosphino-2',6'-di-i-propoxy-1,1'-biphenyl (10.5 mg, 0.022 mmol), sodium tert-butoxide (43.2 mg, 0.449 mmol), and THF (2 mL). The mixture was bubbled with argon for 1 min with sonication. The vial was sealed and heated in a oil bath at 120° C. for 1 h. The reaction was concentrated and purified via preparative LC/MS (Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 35-75% B over 15 min, then a 5-min hold at 100% B; Flow: 20 mL/min). The enantiomers were separated on a chiracel OJ-H column, 30×250 mm, 5 um, eluting with 30% MeOH in CO$_2$, 150 bar; flow rate=70 mL/min.; Temperature=35° C. Detection: UV at 254 nM. Enantiomer A eluted at 8.13 min to give 3.4 mg. Enantiomer B eluted at 16.52 min to give 3.5 mg. Enantiomer A: HPLC $T_R$=1.296 min (Column: Waters Acquity UPLC BEH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 min, then a 0.75-min hold at 100% B; Flow: 1.0 mL/min). 1H NMR (500 MHz, DMSO-$d_6$) δ 8.63 (br. s., 1H), 8.43 (br. s., 1H), 8.01 (d, J=8.8 Hz, 1H), 7.70 (t, J=9.2 Hz, 1H), 7.55-7.44 (m, 2H), 7.04 (d, J=6.6 Hz, 1H), 6.15 (d, J=10.3 Hz, 1H), 4.03 (br. s., 5H), 3.86 (d, J=9.5 Hz, 1H), 3.70 (d, J=8.8 Hz, 1H), 3.47 (br. s., 1H), 3.21 (t, J=12.1 Hz, 1H), 3.09-2.92 (m, 6H), 2.90 (s, 2H), 2.74 (s, 1H), 2.16 (d, J=11.7 Hz, 2H), 1.89 (br. s., 1H), 1.76 (br. s., 1H), 1.70 (br. s., 2H), 1.62 (br. s., 2H), 1.35 (br. s., 1H), 0.74 (d, J=11.7 Hz, 1H).

Enantiomer B: HPLC $T_R$=1.296 min (Column: Waters Acquity UPLC BEH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 min, then a 0.75-min hold at 100% B; Flow: 1.0 mL/min). 1H NMR (500 MHz, DMSO-$d_6$) δ 8.63 (br. s., 1H), 8.43 (br. s., 1H), 8.01 (d, J=8.8 Hz, 1H), 7.70 (t, J=9.2 Hz, 1H), 7.55-7.44 (m, 2H), 7.04 (d, J=6.6 Hz, 1H), 6.15 (d, J=10.3 Hz, 1H), 4.03 (br. s., 5H), 3.86 (d, J=9.5 Hz, 1H), 3.70 (d, J=8.8 Hz, 1H), 3.47 (br. s., 1H), 3.21 (t, J=12.1 Hz, 1H), 3.09-2.92 (m, 6H), 2.90 (s, 2H), 2.74 (s, 1H), 2.16 (d, J=11.7 Hz, 2H), 1.89 (br. s., 1H), 1.76 (br. s., 1H), 1.70 (br. s., 2H), 1.62 (br. s., 2H), 1.35 (br. s., 1H), 0.74 (d, J=11.7 Hz, 1H).

Example 71

1-[3-(Dimethyl-1H-1,2,3-triazol-5-yl)-5-[(S)-oxan-4-yl(phenyl)methyl]-5H-pyrido[3,2-b]indol-7-yl]-4,4-difluoropiperidine

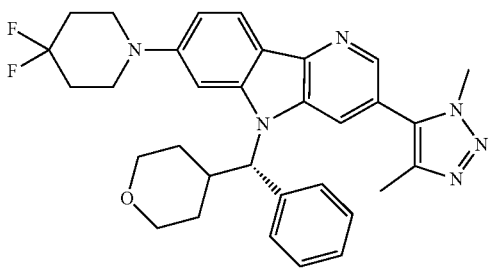 [SMILES: Cc1nnn(C)c1-c1cnc2c3ccc(N4CCC(F)(F)CC4)cc3n([C@H](c3ccccc3)C3CCOCC3)c2c1]

A pressure vial was charged with (S)-7-chloro-3-(1,4-dimethyl-1H-1,2,3-triazol-5-yl)-5-(phenyl(tetrahydro-2H-pyran-4-yl)methyl)-5H-pyrido[3,2-b]indole (30 mg, 0.064 mmol), 4,4-difluoropiperidine (11.6 mg, 0.095 mmol), and dioxane (2 mL). (2-Dicyclohexylphosphino-2',6'-diisopropyl-1,1'-biphenyl)[2-(2-aminoethyl)phenyl]palladium(II) (2.8 mg, 3.81 µmol), RuPhos (1.8 mg, 3.81 µmol) and sodium t-butoxide (18.3 mg, 0.191 mmol) was added. Argon was bubbled into the mixture with sonication for 5 min. The vial was capped, placed in a preheated oil bath at 100° C. and the reaction mixture stirred for 2 h. Solids were removed by filtration, and the filtrate purified by preparative HPLC: Column: Water XBridge C18, 19×200 mm, 5-µm particles; Mobile Phase A: 5:95 methanol: water with 10 mM ammonium acetate; Mobile Phase B: 95:5 methanol: water with 10 mM ammonium acetate; Gradient: 40-80% B over 20 min, then a 5-min hold at 100% B; Flow: 20 mL/min. Fractions containing the desired product were combined and dried via centrifugal evaporation to give 19.5 mg (55%). 1H NMR (500 MHz, DMSO-d$_6$) δ 8.39 (s, 1H), 8.25 (br. s., 1H), 8.02 (d, J=8.8 Hz, 1H), 7.67 (d, J=7.3 Hz, 2H), 7.51 (br. s., 1H), 7.33 (t, J=7.5 Hz, 2H), 7.25 (t, J=7.2 Hz, 1H), 7.07 (d, J=8.4 Hz, 1H), 5.82 (d, J=11.4 Hz, 1H), 3.98 (br. s., 3H), 3.90 (d, J=10.6 Hz, 1H), 3.74 (d, J=7.7 Hz, 1H), 3.49 (t, J=11.4 Hz, 1H), 3.39 (d, J=11.7 Hz, 1H), 3.37-3.29 (m, 4H), 3.26 (t, J=11.7 Hz, 1H), 2.28 (s, 3H), 2.14 (br. s., 4H), 1.71 (d, J=11.7 Hz, 1H), 1.65-1.51 (m, 1H), 1.34 (d, J=11.4 Hz, 1H), 1.00 (d, J=11.0 Hz, 1H). LC/MS (M+H)=557.32.

Example 72

1-[3-(Dimethyl-1H-1,2,3-triazol-5-yl)-5-[(S)-oxan-4-yl(phenyl)methyl]-5H-pyrido[3,2-b]indol-7-yl]-4-(trifluoromethyl)piperidine

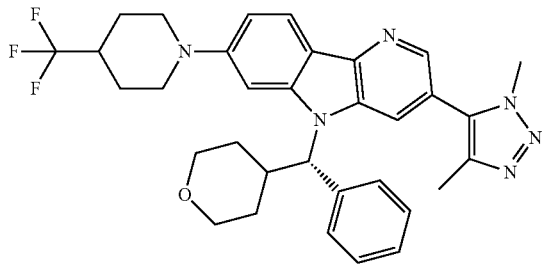 [SMILES: Cc1nnn(C)c1-c1cnc2c3ccc(N4CCC(C(F)(F)F)CC4)cc3n([C@H](c3ccccc3)C3CCOCC3)c2c1]

A pressure vial was charged with (S)-7-chloro-3-(1,4-dimethyl-1H-1,2,3-triazol-5-yl)-5-(phenyl(tetrahydro-2H-pyran-4-yl)methyl)-5H-pyrido[3,2-b]indole (25 mg, 0.053 mmol), 4-(trifluoromethyl)piperidine (12.2 mg, 0.079 mmol), and dioxane (2 mL). (2-Dicyclohexylphosphino-2',6'-diisopropyl-1,1'-biphenyl)[2-(2-aminoethyl)phenyl]palladium(II) (2.3 mg, 3.18 µmol), RuPhos (1.5 mg, 3.18 µmol) and sodium t-butoxide (15.3 mg, 0.159 mmol) was added. Argon was bubbled into the mixture with sonication for 5 min. The vial was capped, placed in a preheated oil bath at 100° C., and the reaction mixture stirred for 2 h. Solids were removed by filtration, and the filtrate purified by preparative HPLC: Column: Water XBridge C18, 19×200 mm, 5-µm particles; Mobile Phase A: 5:95 methanol: water with 10 mM ammonium acetate; Mobile Phase B: 95:5 methanol: water with 10 mM ammonium acetate; Gradient: 40-80% B over 20 min, then a 5-min hold at 100% B; Flow: 20 mL/min. Fractions containing the desired product were combined and dried via centrifugal evaporation to give 20.7 mg (64%) 1H NMR (500 MHz, DMSO-d$_6$) δ 8.38 (s, 1H), 8.22 (br. s., 1H), 8.00 (d, J=8.8 Hz, 1H), 7.66 (d, J=7.3 Hz, 2H), 7.48 (br. s., 1H), 7.38-7.29 (m, 2H), 7.25 (d, J=7.3 Hz, 1H), 7.03 (d, J=8.1 Hz, 1H), 5.81 (d, J=11.0 Hz, 1H), 4.10 (br. s., 2H), 3.98 (br. s., 3H), 3.90 (d, J=13.6 Hz, 1H), 3.74 (d, J=10.6 Hz, 1H), 3.48 (t, J=11.2 Hz, 1H), 3.26 (t, J=11.9 Hz, 1H), 3.18 (d, J=5.1 Hz, 1H), 3.02-2.85 (m, 2H), 2.60 (br. s., 1H), 2.28 (br. s., 3H), 2.02-1.91 (m, 2H), 1.71 (d, J=13.6 Hz, 1H), 1.62 (d, J=11.7 Hz, 3H), 1.33 (d, J=8.4 Hz, 1H), 1.00 (d, J=13.6 Hz, 1H). LC/MS (M+H)=589.32.

Examples 73 & 74

1-{5-[(4,4-Difluorocyclohexyl)(phenyl)methyl]-6-methanesulfonyl-3-[4-($^2$H$_3$)methyl-1-methyl-1H-1,2,3-triazol-5-yl]-5H-pyrido[3,2-b]indol-9-yl}-4,4-difluoropiperidine

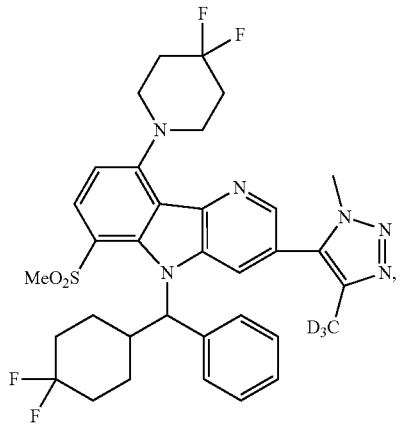

Enantiomer A

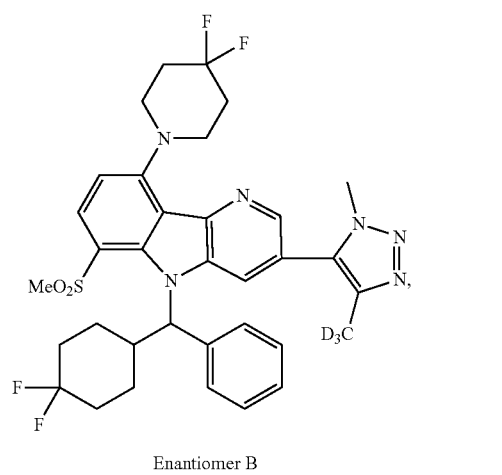

Enantiomer B

A pressure vial was charged with 5-{5-[(4,4-difluorocyclohexyl)(phenyl)methyl]-9-fluoro-6-methanesulfonyl-5H-pyrido[3,2-b]indol-3-yl]-4-($^2$H$_3$)methyl-1-methyl-1H-1,2,3-triazole (40 mg, 0.070 mmol) and NMP (2 mL). 4,4-Difluoropiperidine hydrochloride (22.1 mg, 0.140 mmol) and triethylamine (0.020 mL, 0.140 mmol) were added and the vial capped. The vial was placed in a heating block preheated to 100° C. for 16 h. Solids were removed by filtration. The crude product was purified according to the following method: Chiralcel OD preparative column, 21×250 mm, 10 m; Mobile Phase: 20% ethanol/heptane over 60 min, Flow rate: 15.0 mL/min; UV monitored at 254 nm; Enantiomer A: $T_R$=33.8 min; Enantiomer B: $T_R$=43.2 min. Fractions containing the desired products were combined and dried via evaporation to give 7.9 mg (17%) of enantiomer A and 6.7 mg (14%) of enantiomer B. Enantiomer A: LC/MS (M+H)=672.1.

Enantiomer B: LC/MS (M+H)=672.1. 1H NMR (500 MHz, DMSO-$d_6$) δ 8.69 (s, 1H), 8.24 (d, J=8.8 Hz, 1H), 7.78 (s, 1H), 7.56 (d, J=7.7 Hz, 2H), 7.40-7.29 (m, 2H), 7.29-7.22 (m, 1H), 7.05 (d, J=8.4 Hz, 1H), 6.77 (d, J=10.3 Hz, 1H), 3.77 (s, 3H), 3.62 (s, 3H), 3.39-3.26 (m, 2H), 2.36 (br. s., 4H), 2.18-1.98 (m, 3H), 1.84 (br. s., 1H), 1.78-1.57 (m, 3H), 0.75 (br. s., 1H).

Examples 75 & 76

1-{5-[(4,4-Difluorocyclohexyl)(phenyl)methyl]-3-(dimethyl-1H-1,2,3-triazol-5-yl)-5H-pyrido[3,2-b]indol-7-yl}-4,4-difluoropiperidine Example 75

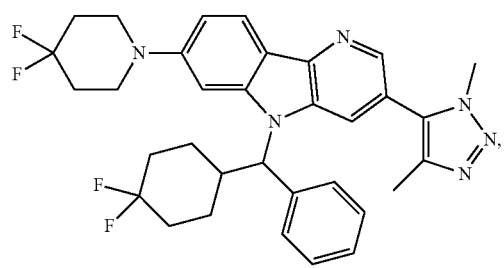

Enantiomer A

Example 76

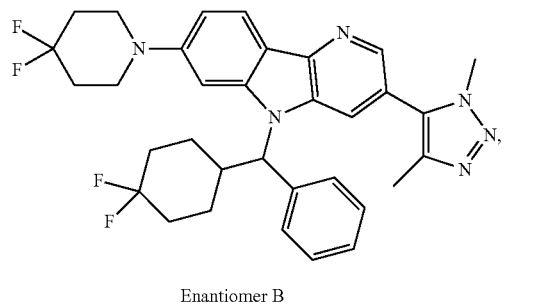

Enantiomer B

A pressure vessel was charged with 7-chloro-5-((4,4-difluorocyclohexyl)(phenyl) methyl)-3-(1,4-dimethyl-1H-1,2,3-triazol-5-yl)-5H-pyrido[3,2-b]indole (40 mg, 0.079 mmol), 4,4-difluoropiperidine hydrochloride (18.7 mg, 0.119 mmol) and dioxane (2 mL). (2-Dicyclohexylphosphino-2',6'-diisopropyl-1,1'-biphenyl) [2-(2-aminoethyl)phenyl]palladium(II) (3.5 mg, 4.74 μmol), Pd(OAc)$_2$ (1.1 mg, 4.74 μmol), RuPhos (2.2 mg, 4.74 μmol), and sodium t-butoxide (22.8 mg, 0.237 mmol) was then added. Argon was bubbled into the mixture with sonication for 5 min. The vial was capped and placed in a preheated oil bath at 100° C. and the reaction mixture stirred for 2 h. Solids were removed by filtration and the resulting residue purified using the following conditions: Chiralcel OD preparative column, 21×250 mm, 10 μm; Mobile Phase: 60% ethanol/0.1% diethylamine heptane over 15 min, Flow rate: 15.0 mL/min; UV monitored at 254 nm; $T_R$=Enantiomer A: 5.53 min; Enantiomer B: 10.59 min. Fractions containing the desired products were combined and dried via evaporation to give 12.1 mg (26%) of enantiomer A and 12.5 mg (27%) of enantiomer B. Enantiomer A: LC/MS (M+H)=591.1.

Enantiomer B: LC/MS (M+H)=591.1. 1H NMR (500 MHz, DMSO-$d_6$) δ 8.40 (s, 1H), 8.27 (br. s., 1H), 8.02 (d, J=8.8 Hz, 1H), 7.66 (d, J=7.7 Hz, 2H), 7.50 (br. s., 1H), 7.33 (t, J=7.5 Hz, 2H), 7.25 (t, J=7.3 Hz, 1H), 7.08 (d, J=8.8 Hz, 1H), 5.85 (d, J=11.0 Hz, 1H), 3.99 (s, 3H), 3.41-3.24 (m, 3H), 2.28 (s, 3H), 2.11 (s, 3H), 2.14 (s, 2H), 2.00-1.83 (m, 3H), 1.83-1.63 (m, 1H), 1.58 (d, J=10.6 Hz, 1H), 1.39-1.19 (m, 3H).

Examples 77 & 78

1-{5-[(4,4-Difluorocyclohexyl)(phenyl)methyl]-3-(dimethyl-1H-1,2,3-triazol-5-yl)-5H-pyrido[3,2-b]indol-7-yl}-4-(trifluoromethyl)piperidine Example 77

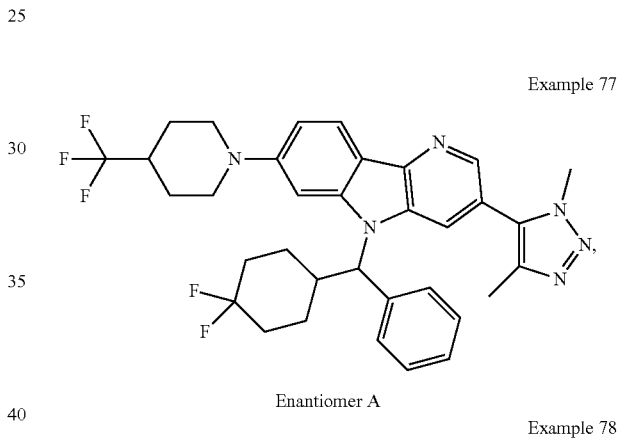

Enantiomer A

Example 78

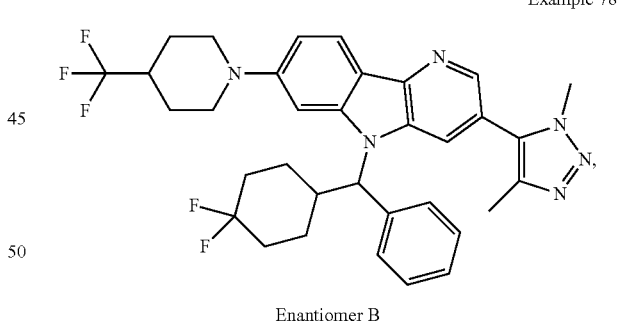

Enantiomer B

A pressure vessel was charged with 7-chloro-5-((4,4-difluorocyclohexyl)(phenyl) methyl)-3-(1,4-dimethyl-1H-1,2,3-triazol-5-yl)-5H-pyrido[3,2-b]indole (40 mg, 0.079 mmol), 4-(trifluoromethyl)piperidine (18.2 mg, 0.119 mmol) and dioxane (2 mL). (2-Dicyclohexylphosphino-2',6'-diisopropyl-1,1'-biphenyl)[2-(2-aminoethyl)phenyl]palladium(II) (3.5 mg, 4.74 μmol), Pd(OAc)$_2$ (1.1 mg, 4.74 μmol), RuPhos (2.2 mg, 4.74 μmol) and sodium t-butoxide (22.8 mg, 0.237 mmol) was then added. Argon was bubbled into the mixture with sonication for 5 min. The vial was capped and placed in a preheated oil bath set at 100° C. and the reaction mixture was stirred for 2 h. Solids were removed by filtration and the resulting residue purified using the following conditions: Chiralcel AD preparative column, 21×250 mm, 10 μm; Mobile Phase: 25% ethanol/0.1% diethylamine heptane over 120 min, Flow rate: 15.0 mL/min; UV monitored at 254 nm; $T_R$=Enantiomer A: 11.64 min; Enantiomer B: 20.54 min. Fractions containing the desired products were combined and dried via evaporation to give 5.5 mg (11%) of enantiomer A and 5.5 mg (11%) of enantiomer B. Enantiomer A: LC/MS (M+H)=623.1. Enantiomer B: LC/MS (M+H)=623.1. 1H NMR (500 MHz, DMSO-$d_6$) δ 8.40 (s, 1H), 8.25 (br. s., 1H), 8.00 (d, J=8.4 Hz, 1H), 7.65 (d, J=7.7 Hz, 2H), 7.48 (br. s., 1H), 7.33 (t, J=7.5 Hz, 2H), 7.24 (t, J=7.3 Hz, 1H), 7.03 (d, J=8.8 Hz, 1H), 5.85 (d, J=11.7 Hz, 1H), 4.09 (br. s., 2H), 3.99 (br. s., 3H), 3.00-2.85 (m, 2H), 2.60 (br. s., 1H), 2.28 (s, 3H), 2.09 (br. s., 2H), 1.96 (d, J=11.0 Hz, 2H), 1.87 (d, J=15.4 Hz, 1H), 1.78 (br. s., 1H), 1.71 (br. s., 1H), 1.68-1.51 (m, 3H), 1.41-1.26 (m, 2H), 1.24 (br. s., 1H).

Evaluation of Biological Activity

Exemplary compounds were tested for inhibition of BRD2, BRD3, BRD4 and BRDT activity. Experimental procedures and results are provided below. Cloning, Expression, and Purification of Human Bromodomains for Thermal Shift Assays (TSA)

Recombinant DNA clones encoding bromodomains of human proteins were optimized for *E. coli* expression, chemically synthesized (GenScript, Piscataway N.J.), and inserted into a modified pET28 expression vector to construct tobacco vein mottling virus (TVMV) protease cleavable N-terminal hexahistidine fusions. The non-native amino acids (MGSSHHHHHHSSGETVRFQSM) (SEQ ID NO: 1) were immediately followed by bromodomain proteins with the amino acid residue sequences (followed by accessions referenced from and numbered according to the Uniprot Knowledgebase; Uniprot Consortium; www.uniprot.org) as follows:
CECR2(420-543), Q9BXF3-1; FALZ(2917-3037), Q12830-1; GCN5(731-837), Q92830-1; PCAF(715-831), Q92831-1; BRD2(24-472), P25440-1; BRD3(1-434), Q15059-1; BRD4 (44-168), BRD4(333-460), BRD4(44-460), O60885-1; BRDT(1-383), Q58F21-1; BAZ1B(1340-1457), Q9UIG0-1; CREBBP(1081-1197), Q92793-1; EP300(1040-1161), Q09472-1; WDR9(1310-1430), Q9NSI6-1; ATAD2(981-1108), Q6PL18-1; BRD1(556-688), O95696-1; BRD7(129-236), Q9NPI1-1; BRD9(134-239), Q9H8M2-1; BRPF1 (626-740), P55201-2; ATAD2B(952-1086), Q9ULI0-1; BAZ2B(2054-2168), Q9UIF8-1; SP140L(400-580), Q9H930-4; SP140(687-862), Q13342-1; TIF1(896-1014), O15164-1; TRIM28(619-805), Q13263-1; BRWD3(1295-1443), Q6RI45-1; TAF1(1377-1503), TAF1(1501-1635), P21675-1; TAF1L(1402-1522), TAF1L(1523-1654), Q8IZX4-1; ASH1L(2433-2564), Q9NR48-1; PB1(43-156), PB1(178-291), PB1(388-494), PB1(645-766), PB1(773-917), Q86U86-1; SMARCA2(1367-1511), P51531-1; SMARCA2-2(1367-1493), P51531-2.

The recombinant vectors were transformed into *E. coli* BL21(DE3). The transformed cells were cultured in 1 L terrific broth in 2.5 L Thomson Ultra Yield shaker flasks at 37° C., 230 rpm and, at a cell density of OD600 nm=1.0, were induced with 0.5 mM IPTG and incubated in the shaker at 20° C. for 16-18 h. The cell pellets were harvested by sedimentation and lysed by sonication in buffer containing 0.1 mg/ml lysozyme. Each sample was clarified by sedimentation, and the supernatant was loaded onto a HisTrap affinity column (GE Healthcare Life Sciences). The column was washed and then eluted with an imidazole gradient. The peak protein fractions containing the bromodomain protein were pooled, concentrated, and the protein was purified further by size exclusion chromatography on a Superdex 200 column (GE Healthcare Life Sciences) equilibrated with the final storage buffer (20 mM Tris-HCl pH 8.0, 200 mM NaCl, 5% glycerol, 2 mM DTT). The SEC peak fractions containing purified protein at 2-5 mg/ml were pooled, and the pool was divided into aliquots, flash frozen in liquid nitrogen, and store at −80° C.

Cloning, Expression, and Purification of Biotinylated Human Bromodomains for TR-FRET Assays Recombinant DNA clones encoding bromodomains of human BRD2, BRD3, BRD4 and BRDT were optimized for *E. coli* expression, chemically synthesized (GenScript, Piscataway N.J.), and inserted into a modified pET28 expression vector to construct tobacco vein mottling virus (TVMV) protease cleavable N-terminal hexahistidine fusions followed by a site specific biotinylation motif recognized by *E. coli* biotin ligase (BirA). The non-native amino acids (MGSSHHHHHHSSGETVRFQGLN-DIFEAQKIEWHEDTGHM) (SEQ ID NO: 2) were immediately followed by bromodomain constructs of BRD4 with the amino acid residue sequences (followed by the BRD4 accession referenced from and numbered according to the Uniprot Knowledgebase; Uniprot Consortium; www.uniprot.org) as follows: BRD4(44-168), BRD4(333-460), BRD4 (44-460), BRD4(1-477), O60885-1.

Each of the recombinant vectors were co-transformed into *E. coli* BL21 STAR (DE3) together with a plasmid encoding BirA under chloramphenicol selection. The transformed cells were cultured at 37° C. in 2.5 L Thomson Ultra Yield shaker flasks containing 1 L M9-CAS medium (Teknova) supplemented with 40 μg/ml kanamycin, 35 μg/ml chloramphenicol, and 100 μM biotin. At a cell density corresponding to an OD600 nm=0.6, the cultures were induced with 0.5 mM IPTG and incubated in the shaker for an additional 20 h at 20° C. The cell pellets were harvested by sedimentation and lysed by sonication in buffer containing 0.1 mg/ml lysozyme. Each sample was clarified by sedimentation, and the supernatant was loaded onto a HisTrap affinity column. The column was washed and then eluted with an imidazole gradient. The peak protein fractions containing the bromodomain protein were pooled and incubated for 18 h at 4° C. with purified His-TVMV protease (1:15 mass ratio of TVMV:BRD4 protein). The sample was exchanged into low imidazole buffer and passed through a HisTrap column to capture the cleaved His-tag and His-TVMV enzyme. The protein in the HisTrap column flow through was further purified and exchanged into the final storage buffer (PBS pH 7.0, 5% Glycerol, 1 mM DTT) by size exclusion chromatography on a Superdex 200 column. To improve purity, the BRD4(1-477) and BRD4(44-460) proteins were subjected to an additional cation exchange chromatography purification step prior to size exclusion chromatography. Essentially quantitative mono-biotinylation (+226 Da) of each protein was confirmed by electrospray ionization mass spectrometry analysis on the final sample. The purified samples were divided into aliquots, flash frozen in liquid nitrogen, and stored at −80° C.

Time Resolved Fluorescence Resonance Energy Transfer (TR-FRET) Assay

The binding of compounds to bromodomain BRD4 (44-168), BRD4 (333-460), and BRD4 (1-477 or 44-460) was assessed using a time resolved fluorescent resonance energy transfer binding assay (1), that measures the binding of a fluorescently labeled probe molecule to the bromodomain protein. The bromodomain protein, fluorescent probe molecule (either a biotinylated histone peptide or a fluorescently labeled small molecule), and dose-responsed test compound are incubated together to reach thermodynamic equilibrium. In the absence of a test compound, the bromodomain and small molecule are bound, resulting in a high fluorescent signal. In the presence of a sufficient concentration of inhibitor, this interaction is disrupted resulting in a lost of fluorescent resonance energy transfer.

All assay components were dissolved in buffer composition 20 mM Hepes pH 7.5, 150 mM NaCl, 5 mM DTT, 0.005% Tween 20, and 100 ug/ml BSA for BRD4 (1-477 and 44-460). The final concentrations of the bromodomain proteins are 1.6 nM BRD4(44-168), 1 nM BRD4(333-460), and 1 nM BRD4(1-477 or 44-460), and the fluorescent probe molecule is 100 nM, 50 nM, and 7.5 nM respectively. All proteins were biotinylated. A streptavidin labeled with terbium cryptate (Cisbio SA-Tb) was used as detection, and pre-mixed with the bromodomain protein at a final concentration of 0.2 nM. In some instances for BRD4 (44-460), anti-His terbium cryptate was used as a detection. 7.5 nl of dose-responsed test compound or dmso vehicle (0.0375%) was pre-spotted in a black Corning 384 well plate and 10 ul each of bromodomain/detection reagent and fluorescent small molecule solution were added to the plate, and the reaction incubated for 60 min at room temperature. Plates were then read on EnVision plate reader, ($\lambda$ex=340 nm, acceptor $\lambda$Em=520 nm, and donor $\lambda$Em=615 nm, LANCE D400 mirror). Time resolved fluorescence intensity measurements were made at both emissions, and the ratio of acceptor/donor was calculated and used for data analysis. All data was normalized to 16 high vehicle wells and 8 low reference control wells, and then a four parameter curve fit was applied:

$$Y=a+((b-a)/(1+(10x/10c)d)$$

Where 'a' is the minimum, 'b' is the Hill slope, 'c' is the IC50, and 'd' is the maximum.

Histone peptide: Purchased from GenScript

H4K5K8K12K16
(SEQ ID NO: 3)
Biotin-AHA-SGRGK(Ac)GGK(Ac)GLGK(Ac)GGAK(Ac)RHRKV

The fluorescently labeled small molecule used was a BRD4 inhibitor known in the art
1. F. Degorce, A. Card, S. Soh, E. Trinquet, G. P. Knapik and B. Xie, HTRF: A technology tailored for drug discovery—a review of theoretical aspects and recent applications. Current Chemical Genomics (2009) 3, 22-32

Thermal Shift Assay

The effect of compound binding on the thermal stability of the bromodomains was measured using a BioRad CFX real time PCR instrument by monitoring the fluorescence enhancement of an external probe (SYPRO orange) as it binds preferentially to the unfolded protein. The unfolding reactions were carried out in a 384-well plate in a 4 uL volume with 2-8 uM of bromodomain protein, 1-2% (v/v) DMSO in buffer containing 10 mM Hepes, pH 7.4, 500 mM NaCl. SYPRO orange dye was added at a dilution of 1:500. Compound concentrations ranged from 1.6-100 uM. Unfolding reactions were monitored by first equilibrating the instrument at 25° C. for 2.4 sec, followed by ramping the temperature in 0.5° C. increments from 25 to 95° C. with 60 s equilibration prior to a read at each temperature. Excitation and emission filters for the SYPRO orange dye were set to FRET with the excitation range from 450-490 nm and the emission range from 560-580 nm. The midpoint temperature was determined by calculating the inflection point using the second derivative. The observed temperature shifts were recorded as the difference between the midpoint between a reference well containing protein with DMSO but no ligand and a well containing protein with compound.

The thermal shift assay is a biophysical technique that compares the change in unfolding transition temperature of a protein obtained in the presence and absence of a ligand (1). Typically, a fluorescent dye is used to monitor the protein unfolding as the protein is heated. During the unfolding process, hydrophobic regions of the protein are exposed, resulting in an increase in the dye binding and an increase in fluorescence intensity. The midpoint of the protein unfolding transition is defined as the Tm. A ligand that binds to the protein causes an increase in the protein thermal stability, thus increasing the Tm, proportionally to both the ligand concentration and its binding affinity.
1. M. W. Pantoliano, E. C. Petrella, J. D. Kwasnoski, V. S. Lobanov, J. Myslik, E. Graf, T. Carver, E. Asel, B. A. Springer, P. Lane, F. R. Salemme, High-density miniaturized thermal shift assays as a general strategy for drug discovery. J. Biomol. Screen 6(2001) 429-440.
2. M. D. Cummings, M. A. Farnum, M. I. Nelen, Universal screening methods and application of Thermo-Fluor. J. Biomol. Screen 11 (2006) 854-863

MYC HCS Assay

Tumor cells in complete RPMI growth media (Gibco, 11875-085) supplemented with 10% FBS were harvested and plated into 384 black clear-bottom PDL cell culture plates in 30 ul media with 10,000 cells per well. After compound treatment at 37 C for 4 h, cells were fixed in 4% Formaldehyde at room temperature for 30 min and subsequently permeabilized. After washing and blocking, the plates were then incubated with anti-myc primary antibody 1:1000 (Cell Signaling Technology, 5605) at RT overnight. The following day, cells were washed and blocked before adding secondary antibody Alexa 488 Goat-anti Rabbit 1:2000 (Invitrogen, A11034) at RT in the dark for 1 hr. Cells were subsequently washed and scanned on the Cellomics ArrayScan with 10× objective lens.

MTS Cell Proliferation Assay

Tumor cells were plated at certain seeding densities in 384-well black clear bottom Matrix plates at 40 ul per well and incubated overnight at 37° C. in 5% $CO_2$ before assaying. On the next day, one set of cell plates (T0 plates) were used to determine time zero cell density, and 3-(4,5-dimethylthiazol-2-yl)-5-(3-carboxymethoxyphenyl)-2-(4-sulfophenyl)-2H-tetrazolium from the CellTiter 96 AQueous Non-Radioactive Cell proliferation Kit (Promega, G5440) was added at 4 µl/well into T0 plates followed by incubation at 37° C. in 5% $CO_2$ for 3 h. Absorbance at 490 nm was measured on an Envision reader (Perkin Elmer, Boston, Mass.). On the same day, the remaining cell plates (T72 plates) were treated with compounds at 37° C. in 5% $CO_2$. After 72 h, 4 ul MTS reagents were then added onto those cell plates. The plates were further incubated at 37 C in 5% $CO_2$ for 3 h and the absorbance values at A490 were measured on an Envision reader.

Human Tumor Xenograft Models in Mice

All rodents were obtained from Jackson Laboratory. (Bar Harbor, Me.), and maintained in an ammonia-free environment in a defined and pathogen-free colony. All mice were quarantined approximately 1 week prior to their use for tumor propagation and drug efficacy testing. Mice were fed food and water ad libitum. The animal care program of Bristol-Myers Squibb Pharmaceutical Research Institute is fully accredited by the American Association for Accreditation of Laboratory Animal Care (AAALAC). All experiments were performed in accordance with Bristol-Myers Squibb (BMS) animal test methods and guidelines.

Tumor xenografts were grown and maintained subcutaneously (SC) in NSG (NOD scid IL2 receptor gamma chain knockout) mice (Jackson Lab). Tumors were propagated as subcutaneous transplants using tumor fragments obtained from donor mice.

Preclinical Chemotherapy Trials

The required numbers of animals needed to detect a meaningful response were pooled at the start of the experiment and each was given bilateral subcutaneous implants of two tumor fragments (~20 mg) with a 13-gauge trocar. Tumors were allowed to grow to the pre-determined size window (tumors outside the range were excluded) and animals were evenly distributed to various treatment and control groups. There were typically 6-8 mice per treatment and control groups, consisting of 10-12 tumors. Treatment of each animal was based on individual body weight. Treated animals were checked daily for treatment related toxicity/mortality. Each group of animals was weighed before the initiation of treatment ($Wt_1$) and then again following the last treatment dose ($Wt_2$). The difference in body weight ($Wt_2-Wt_1$) provides a measure of treatment-related toxicity.

Tumor response was determined by measurement of tumors with a caliper twice a week, until the tumors reached a predetermined "target" size of 0.5 gm or 1 gm depending on the tumor type. Tumor weights (mg) were estimated from the formula:

Tumor weight=(length×width$^2$)÷2

Tumor response criteria are expressed in terms of tumor growth inhibition (% TGI). Tumor growth delay is defined as the difference in time (days) required for the treated tumors (T) to reach a predetermined target size compared to those of the control group (C). For this purpose, the tumor weight of a group is expressed as medium tumor weight (MTW).

Tumor growth inhibition is calculated as follows:

$$\% \text{ Tumor Growth Inhibition} = \frac{\left(1 - \frac{T_t}{T_0} * \frac{C_0}{C_t}\right)}{\left(1 - \frac{C_0}{C_t}\right)}$$

where,
$C_t$=Median control tumor size at end of treatment
$C_0$=Median control tumor size at treatment initiation
$T_t$=Median tumor size of treated group at end of treatment
$T_0$=Median tumor size of treated group at treatment initiation Activity is defined as the achievement of durable tumor growth inhibition of 50% or greater (i.e. TGI≥50%) for a period equivalent to at least 1 tumor volume doubling time and drug treatment must be for a period equivalent to at least 2 tumor volume doubling time.

Tumor response was also expressed in terms of tumor growth delay and expressed as log cell kill (LCK value), defined as the difference in time (days) required for the treated tumors (T) to reach a predetermined target size compared to those of the control group (C).

Whenever possible, antitumor activity was determined at a range of dose levels up to the maximum tolerated dose (MTD) which is defined as the dose level immediately below which excessive toxicity (i.e. more than one death) occurred. When death occurred, the day of death was recorded. Treated mice dying prior to having their tumors reach target size were considered to have died from drug toxicity. No control mice died bearing tumors less than target size. Treatment groups with more than one death caused by drug toxicity were considered to have had excessively toxic treatments and their data were not included in the evaluation of a compound's antitumor efficacy.

Potential drug toxicity interaction affecting treatment tolerability is an important consideration in combination chemotherapy trials. Interpretation of combination therapeutic results must be based on comparison of antitumor activity of the best possible response for the single agents versus the combination at comparably tolerated doses. Therefore, therapeutic synergism was defined as a therapeutic effect achieved with a tolerated regimen of the combined agents that exceeded the optimal effect achieved at any tolerated dose of monotherapy. Statistical evaluations of data were performed using Gehan's generalized Wilcoxon test. Statistical significance was declared at $P<0.05$.

Drug Administration

For administration of BET inhibitors to rodents, compounds were dissolved in 90% PEG300/10% TPGS/10% Ethanol. BET inhibitors were typically administered orally on a schedule of QDx7 or QDx10 (5 day-on-2 day-off), although other schedules had also been evaluated and shown to be efficacious The activity data shown below is based on the use of one of the FRET assays described. Compounds with an $IC_{50}$ less than 1500 nM are shown with (+), compounds with an $IC_{50}$ less than 5 nM are shown with (++) and those with an $IC_{50}$ less than 1 nM are shown with (+++).

| Example # | FRET BRD4 $IC_{50}$ (nM) |
|---|---|
| Example 1 | ++ |
| Example 2 | ++ |
| Example 3 | ++ |
| Example 4 | +++ |
| Example 5 | ++ |
| Example 6 | ++ |
| Example 7 | +++ |
| Example 8 | ++ |
| Example 9 | ++ |
| Example 10 | ++ |
| Example 11 | +++ |
| Example 12 | ++ |
| Example 13 | ++ |
| Example 14 | ++ |
| Example 15 | ++ |
| Example 16 | ++ |
| Example 17 | +++ |
| Example 18 | +++ |
| Example 19 | +++ |
| Example 20 | +++ |
| Example 21 | ++ |
| Example 22 | ++ |
| Example 23 | ++ |
| Example 24 | ++ |
| Example 25 | ++ |
| Example 26 | + |
| Example 27 | ++ |
| Example 28 | ++ |
| Example 29 | ++ |
| Example 30 | ++ |
| Example 31 | +++ |
| Example 32 | +++ |
| Example 33 | +++ |
| Example 34 | +++ |
| Example 35 | +++ |
| Example 36 | + |
| Example 37 | ++ |
| Example 38 | ++ |

| Example # | FRET BRD4 IC$_{50}$ (nM) |
|---|---|
| Example 39 | ++ |
| Example 40 | +++ |
| Example 41 | + |
| Example 42 | ++ |
| Example 43 | ++ |
| Example 44 | +++ |
| Example 45 | ++ |
| Example 46 | +++ |
| Example 47 | NA |
| Example 48 | +++ |
| Example 49 | ++ |
| Example 50 | ++ |
| Example 51 | +++ |
| Example 52 | +++ |
| Example 53 | +++ |
| Example 54 | +++ |
| Example 55 | +++ |
| Example 56 | +++ |
| Example 57 | +++ |
| Example 58 | +++ |
| Example 59 | ++ |
| Example 60 | +++ |
| Example 61 | ++ |
| Example 62 | +++ |
| Example 63 | +++ |
| Example 64 | +++ |
| Example 65 | +++ |
| Example 66 | ++ |
| Example 67 | ++ |
| Example 68 | ++ |
| Example 69 | +++ |
| Example 70 | +++ |
| Example 71 | +++ |
| Example 72 | +++ |
| Example 73 | + |
| Example 74 | + |
| Example 75 | ++ |
| Example 76 | ++ |
| Example 77 | +++ |
| Example 78 | ++ |

NA = Not available

What is claimed is:

1. A compound of the formula

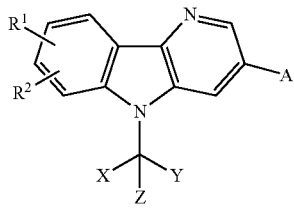

(I)

wherein:
- A is optionally substituted heterocyclo or optionally substituted heteroaryl, wherein the substituents are one or more R;
- R is independently one or more hydrogen, $CD_3$, halogen, haloalkyl, hydroxyalkyl, CN, $CF_3$, $CH_2F$, $CHF_2$, $(C_1$-$C_6)$alkyl, $(C_1$-$C_6)$alkoxy, or $(C_3$-$C_6)$cycloalkyl;
- X and Y are independently selected from hydrogen, $(C_1$-$C_6)$alkyl, optionally substituted $(C_3$-$C_5)$cycloalkyl, optionally substituted aryl, optionally substituted heteroaryl or optionally substituted heterocyclo; wherein the substituents are one or more hydrogen, halogen, $CD_3$, $OCD_3$ or $(C_1$-$C_6)$alkyl;
- Z is hydrogen, halogen, —OH, $(C_1$-$C_6)$alkyl or $(C_1$-$C_6)$ alkoxy;
- $R^1$ is optionally substituted heteroaryl or optionally substituted 5-8 membered heterocyclyl; wherein the substituents are one or more hydrogen, halogen, OH, $CF_3$, $CD_3$, $OCD_3$, $(C_1$-$C_4)$alkyl, $(C_1$-$C_3)$alkoxy, CO $(C_1$-$C_4)$ alkyl, $CON(C_1$-$C_4)$alkyl, COO $(C_1$-$C_4)$alkyl, $SO_2$ $(C_1$-$C_4)$alkyl, $SO_2N$ $(C_1$-$C_4)$alkyl, $COCH_2OH$, $COCH_2OCOCH_3$ or $CH_2CONH_2$;
- $R^2$ is hydrogen, halogen, $(C_1$-$C_6)$alkyl, —$SO_2$ $(C_1$-$C_6)$ alkyl, $(C_1$-$C_6)$ alkoxy, aryl, $SO_2$ 5-8 membered heteroaryl or 5-8 membered heterocyclo;
- or a pharmaceutically acceptable salt, tautomer or stereoisomer thereof.

2. A compound according to claim 1

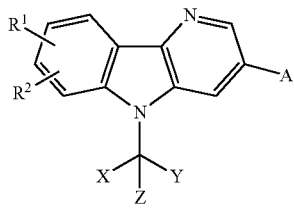

(I)

wherein:
A is

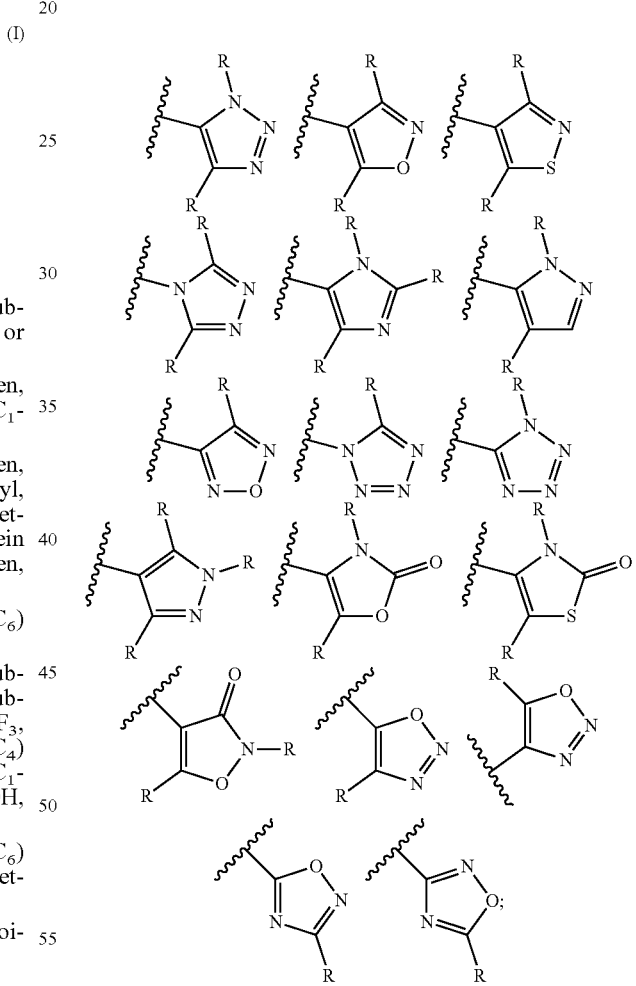

R is independently one or more hydrogen, $CD_3$, halogen, haloalkyl, hydroxyalkyl, CN, $CF_3$, $CH_2F$, $CHF_2$, $(C_1$-$C_6)$alkyl, $(C_1$-$C_6)$alkoxy, or $(C_3$-$C_6)$cycloalkyl;

X and Y are independently selected from hydrogen, $(C_1$-$C_6)$alkyl, optionally substituted $(C_3$-$C_5)$cycloalkyl, optionally substituted aryl, optionally substituted heteroaryl or optionally substituted heterocyclo; wherein the substituents are one or more hydrogen, halogen, $CD_3$, $OCD_3$ or $(C_1$-$C_6)$alkyl;

Z is hydrogen, halogen, —OH, $(C_1-C_6)$alkyl or $(C_1-C_6)$alkoxy;

$R^1$ is optionally substituted heteroaryl or optionally substituted 5-8 membered heterocyclyl; wherein the substituents are one or more hydrogen, halogen, OH, $CF_3$, $CD_3$, $OCD_3$, $(C_1-C_4)$alkyl, $(C_1-C_3)$alkoxy, CO $(C_1-C_4)$alkyl, CON$(C_1-C_4)$alkyl, COO $(C_1-C_4)$alkyl, $SO_2$ $(C_1-C_4)$alkyl, $SO_2N$ $(C_1-C_4)$alkyl, $COCH_2OH$, $COCH_2OCOCH_3$ or $CH_2CONH_2$;

$R^2$ is hydrogen, halogen, $(C_1-C_6)$alkyl, —$SO_2$ $(C_1-C_6)$alkyl, $(C_1-C_6)$ alkoxy, aryl, $SO_2$ 5-8 membered heteroaryl or 5-8 membered heterocyclo;

or a pharmaceutically acceptable salt, tautomer or stereoisomer thereof.

3. A compound according to claim 2

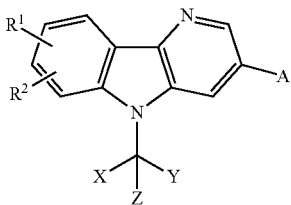

(II)

wherein:
A is

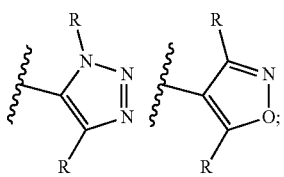

R is independently one or more hydrogen, $CD_3$, halogen, haloalkyl, hydroxyalkyl, CN, $CF_3$, $CH_2F$, $CHF_2$, $(C_1-C_6)$alkyl, $(C_1-C_6)$alkoxy, or $(C_3-C_6)$cycloalkyl;

X and Y are independently selected from hydrogen, $(C_1-C_6)$alkyl, optionally substituted $(C_3-C_8)$cycloalkyl, optionally substituted aryl, optionally substituted heteroaryl or optionally substituted heterocyclo; wherein the substituents are one or more hydrogen, halogen, $CD_3$, $OCD_3$ or $(C_1-C_6)$alkyl;

Z is hydrogen, halogen, —OH, $(C_1-C_6)$alkyl or $(C_1-C_6)$alkoxy;

$R^1$ is optionally substituted heteroaryl or optionally substituted 5-8 membered heterocyclyl; wherein the substituents are one or more hydrogen, halogen, OH, $CF_3$, $CD_3$, $OCD_3$, $(C_1-C_4)$alkyl, $(C_1-C_3)$alkoxy, CO $(C_1-C_4)$alkyl, CON$(C_1-C_4)$alkyl, COO $(C_1-C_4)$alkyl, $SO_2$ $(C_1-C_4)$alkyl, $SO_2N$ $(C_1-C_4)$alkyl, $COCH_2OH$, $COCH_2OCOCH_3$ or $CH_2CONH_2$;

$R^2$ is hydrogen, halogen, $(C_1-C_6)$alkyl, —$SO_2$ $(C_1-C_6)$alkyl, $(C_1-C_6)$ alkoxy, aryl, $SO_2$ 5-8 membered heteroaryl or 5-8 membered heterocyclo;

or a pharmaceutically acceptable salt, tautomer or stereoisomer thereof.

4. A compound according to claim 1 of the formula

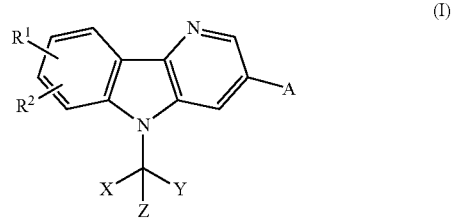

(I)

wherein
A is

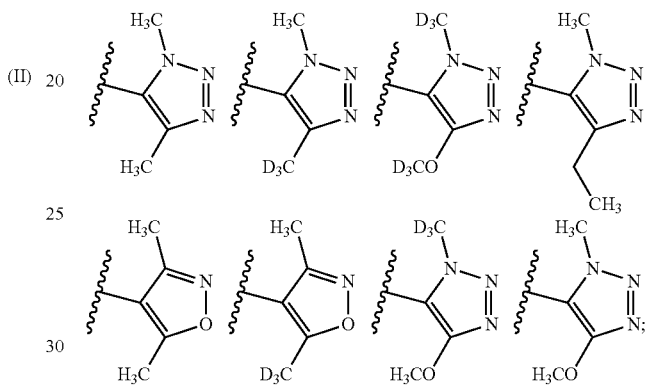

X and Y are independently selected from hydrogen, $(C_1-C_6)$alkyl, optionally substituted $(C_3-C_5)$cycloalkyl, optionally substituted aryl, optionally substituted heteroaryl or optionally substituted heterocyclo; wherein the substituents are one or more hydrogen, halogen, $CD_3$, $OCD_3$ or $(C_1-C_6)$alkyl;

Z is hydrogen, halogen, —OH, $(C_1-C_6)$alkyl or $(C_1-C_6)$alkoxy;

$R^1$ is optionally substituted heteroaryl or optionally substituted 5-8 membered heterocyclyl; wherein the substituents are one or more hydrogen, halogen, OH, $CF_3$, $CD_3$, $OCD_3$, $(C_1-C_4)$alkyl, $(C_1-C_3)$alkoxy, CO $(C_1-C_4)$alkyl, CON$(C_1-C_4)$alkyl, COO $(C_1-C_4)$alkyl, $SO_2$ $(C_1-C_4)$alkyl, $SO_2N$ $(C_1-C_4)$alkyl, $COCH_2OH$, $COCH_2OCOCH_3$ or $CH_2CONH_2$;

$R^2$ is hydrogen, halogen, $(C_1-C_6)$alkyl, —$SO_2$ $(C_1-C_6)$alkyl, $(C_1-C_6)$ alkoxy, aryl, $SO_2$ 5-8 membered heteroaryl or 5 8 membered heterocyclo;

or a pharmaceutically acceptable salt, tautomer or stereoisomer thereof.

5. A compound according to claim 4 of formula (II)

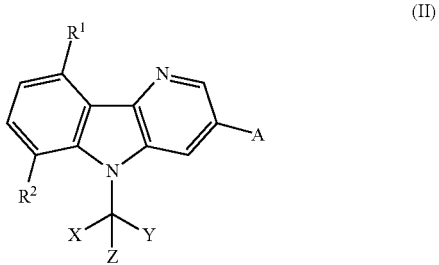

(II)

wherein:
A is

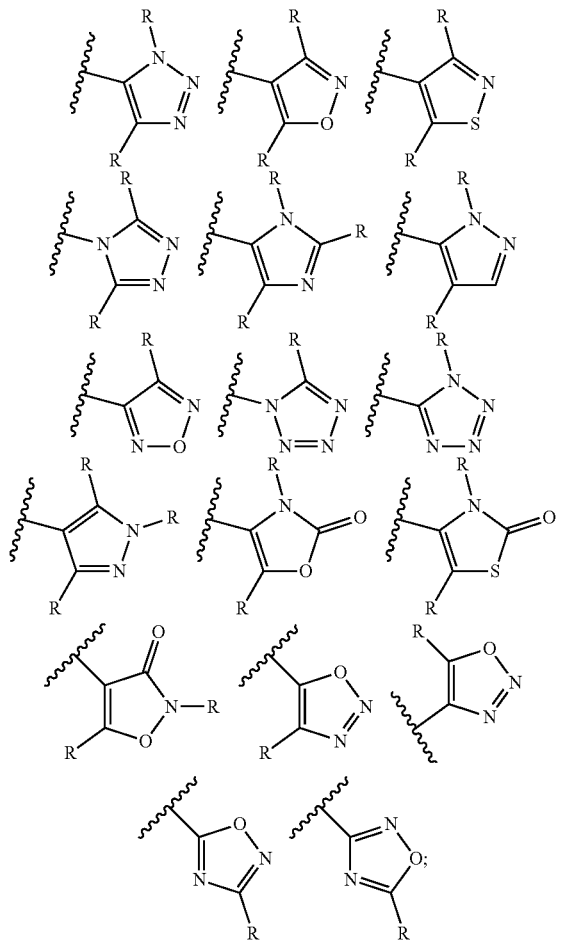

R is independently one or more hydrogen, CD₃, halogen, haloalkyl, hydroxyalkyl, CN, CF₃, CH₂F, CHF₂, (C₁-C₆)alkyl, (C₁-C₆)alkoxy, or (C₃-C₆)cycloalkyl;

X and Y are independently selected from hydrogen, (C₁-C₆)alkyl, optionally substituted (C₃-C₅)cycloalkyl, optionally substituted aryl, optionally substituted heteroaryl or optionally substituted heterocyclo; wherein the substituents are one or more hydrogen, halogen, CD₃, OCD₃ or (C₁-C₆)alkyl;

Z is hydrogen, halogen, —OH, (C₁-C₆)alkyl or (C₁-C₆)alkoxy;

R¹ is optionally substituted heteroaryl or optionally substituted 5-8 membered heterocyclyl; wherein the substituents are one or more hydrogen, halogen, OH, CF₃, CD₃, OCD₃, (C₁-C₄)alkyl, (C₁-C₃)alkoxy, CO (C₁-C₄)alkyl, CON(C₁-C₄)alkyl, COO (C₁-C₄)alkyl, SO₂ (C₁-C₄)alkyl, SO₂N (C₁-C₄)alkyl, COCH₂OH, COCH₂OCOCH₃ or CH₂CONH₄, R² is hydrogen, halogen, (C₁-C₆)alkyl, —SO₂ (C₁-C₆)alkyl, (C₁-C₆) alkoxy, aryl, SO₂ 5-8 membered heteroaryl or 5-8 membered heterocyclo;

or a pharmaceutically acceptable salt, tautomer or stereoisomer thereof.

6. A compound according to claim 5 of the formula

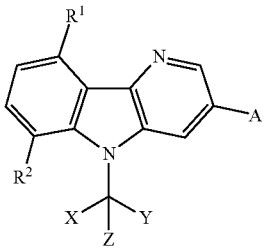

(II)

wherein
A is

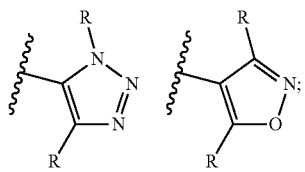

R is independently one or more hydrogen, CD₃, halogen, haloalkyl, hydroxyalkyl, CN, CF₃, CH₂F, CHF₂, (C₁-C₆)alkyl, (C₁-C₆)alkoxy, or (C₃-C₆)cycloalkyl;

X and Y are independently selected from hydrogen, (C₁-C₆)alkyl, optionally substituted (C₃-C₈)cycloalkyl, optionally substituted aryl, optionally substituted heteroaryl or optionally substituted heterocyclo; wherein the substituents are one or more hydrogen, halogen, CD₃, OCD₃ or (C₁-C₆)alkyl;

Z is hydrogen, halogen, —OH, (C₁-C₆)alkyl or (C₁-C₆)alkoxy;

R¹ is optionally substituted heteroaryl or optionally substituted 5-8 membered heterocyclyl; wherein the substituents are one or more hydrogen, halogen, OH, CF₃, CD₃, OCD₃, (C₁-C₄)alkyl, (C₁-C₃)alkoxy, CO (C₁-C₄)alkyl, CON(C₁-C₄)alkyl, COO (C₁-C₄)alkyl, SO₂ (C₁-C₄)alkyl, SO₂N (C₁-C₄)alkyl, COCH₂OH, COCH₂OCOCH₃ or CH₂CONH₂;

R² is hydrogen, halogen, (C₁-C₆)alkyl, —SO₂ (C₁-C₆)alkyl, (C₁-C₆) alkoxy, aryl, SO₂ 5-8 membered heteroaryl or 5-8 membered heterocyclo;

or a pharmaceutically acceptable salt, tautomer or stereoisomer thereof.

7. A compound according to claim 6 of the formula

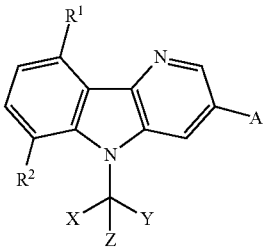

(II)

wherein:
A is

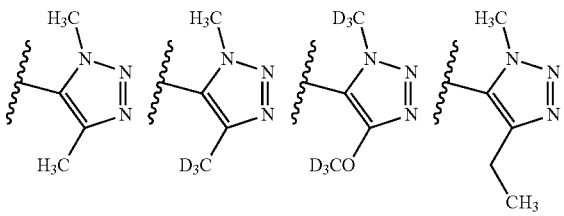

-continued

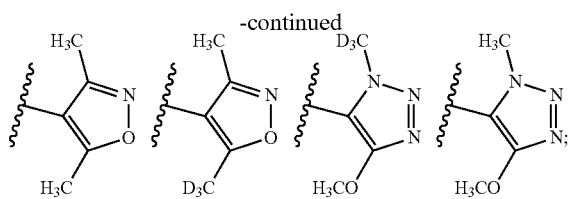

X and Y are independently selected from hydrogen, $(C_1-C_6)$alkyl, optionally substituted $(C_3-C_5)$cycloalkyl, optionally substituted aryl, optionally substituted heteroaryl or optionally substituted heterocyclo; wherein the substituents are one or more hydrogen, halogen, $CD_3$, $OCD_3$ or $(C_1-C_6)$alkyl;

Z is hydrogen, halogen, —OH, $(C_1-C_6)$alkyl or $(C_1-C_6)$alkoxy;

$R^1$ is optionally substituted heteroaryl or optionally substituted 5-8 membered heterocyclyl; wherein the substituents are one or more hydrogen, halogen, OH, $CF_3$, $CD_3$, $OCD_3$, $(C_1-C_4)$alkyl, $(C_1-C_3)$alkoxy, CO $(C_1-C_4)$alkyl, $CON(C_1-C_4)$alkyl, COO $(C_1-C_4)$alkyl, $SO_2$ $(C_1-C_4)$alkyl, $SO_2N$ $(C_1-C_4)$alkyl, $COCH_2OH$, $COCH_2OCOCH_3$ or $CH_2CONH_2$;

$R^2$ is hydrogen, halogen, $(C_1-C_6)$alkyl, —$SO_2$ $(C_1-C_6)$alkyl, $(C_1-C_6)$ alkoxy, aryl, $SO_2$ 5-8 membered heteroaryl or 5 8 membered heterocyclo;

or a pharmaceutically acceptable salt, tautomer or stereoisomer thereof.

8. A compound according to claim 2 of formula (III)

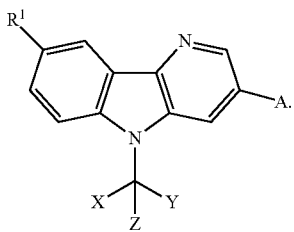

or a pharmaceutically acceptable salt, tautomer or stereoisomer thereof.

9. A compound according to claim 2 of formula (IV)

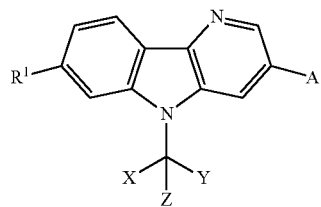

or a pharmaceutically acceptable salt, tautomer or stereoisomer thereof.

10. A compound selected from the following
1,4-dimethyl-5-[7-(1-methyl-1H-pyrazol-5-yl)-5-[(S)-oxan-4-yl(phenyl)methyl]-5H-pyrido[3,2-b]indol-3-yl]-1H-1,2,3-triazole,
1,4-dimethyl-5-{5-[(S)-oxan-4-yl(phenyl)methyl]-7-(1,2-oxazol-3-yl)-5H-pyrido[3,2-b]indol-3-yl}-1H-1,2,3-triazole,
(2R,6S)-4-[3-(dimethyl-1H-1,2,3-triazol-5-yl)-5-[(R)-oxan-4-yl(phenyl)methyl]-5H-pyrido[3,2-b]indol-8-yl]-2,6-dimethylmorpholine,
4-[3-(dimethyl-1H-1,2,3-triazol-5-yl)-5-[(S)-oxan-4-yl(phenyl)methyl]-5H-pyrido[3,2-b]indol-8-yl]piperidine,
tert-butyl 4-[3-(dimethyl-1H-1,2,3-triazol-5-yl)-5-[(S)-oxan-4-yl(phenyl)methyl]-5H-pyrido[3,2-b]indol-8-yl]piperidine-1-carboxylate,
1-{4-[3-(dimethyl-1,2-oxazol-4-yl)-5-[(S)-oxan-4-yl(phenyl)methyl]-5H-pyrido[3,2-b]indol-8-yl]piperidin-1-yl}-2-hydroxyethan-1-one,
1-{4-[3-(dimethyl-1,2-oxazol-4-yl)-5-[(S)-oxan-4-yl(phenyl)methyl]-5H-pyrido[3,2-b]indol-8-yl]piperidin-1-yl}ethan-1-one,
2-{4-[3-(dimethyl-1H-1,2,3-triazol-5-yl)-5-[(S)-oxan-4-yl(phenyl)methyl]-5H-pyrido[3,2-b]indol-8-yl]piperidin-1-yl}-2-oxoethyl acetate,
(5S)-5-[3-(dimethyl-1H-1,2,3-triazol-5-yl)-5-[(S)-oxan-4-yl(phenyl)methyl]-5H-pyrido[3,2-b]indol-7-yl]-5-methyl-1,3-oxazolidin-2-one,
(5R)-5-[3-(dimethyl-1H-1,2,3-triazol-5-yl)-5-[(S)-oxan-4-yl(phenyl)methyl]-5H-pyrido[3,2-b]indol-7-yl]-5-methyl-1,3-oxazolidin-2-one,
5-[3-(dimethyl-1H-1,2,3-triazol-5-yl)-5-[(S)-oxan-4-yl(phenyl)methyl]-5H-pyrido[3,2-b]indol-7-yl]-1H-1,2,3,4-tetrazole,
3-[3-(dimethyl-1H-1,2,3-triazol-5-yl)-5-[(S)-oxan-4-yl(phenyl)methyl]-5H-pyrido[3,2-b]indol-7-yl]-1,3-oxazinan-2-one,
1-[3-(dimethyl-1H-1,2,3-triazol-5-yl)-5-[(S)-oxan-4-yl(phenyl)methyl]-5H-pyrido[3,2-b]indol-8-yl]piperazine,
2-{4-[3-(dimethyl-1H-1,2,3-triazol-5-yl)-5-[(S)-oxan-4-yl(phenyl)methyl]-5H-pyrido[3,2-b]indol-8-yl]piperazin-1-yl}-2-oxoethyl acetate,
1-[3-(dimethyl-1H-1,2,3-triazol-5-yl)-5-[(S)-oxan-4-yl(phenyl)methyl]-5H-pyrido[3,2-b]indol-8-yl]-4-(oxetan-3-yl)piperazine,
1,4-dimethyl-5-{5-[(S)-oxan-4-yl(phenyl)methyl]-7-[1-(propan-2-yl)-1H-pyrazol-4-yl]-5H-pyrido[3,2-b]indol-3-yl}-1H-1,2,3-triazole,
5-[7-(3,5-dimethyl-1H-pyrazol-4-yl)-5-[(S)-oxan-4-yl(phenyl)methyl]-5H-pyrido[3,2-b]indol-3-yl]-1,4-dimethyl-1H-1,2,3-triazole,
5-[3-(dimethyl-1H-1,2,3-triazol-5-yl)-5-[(S)-oxan-4-yl(phenyl)methyl]-5H-pyrido[3,2-b]indol-7-yl]-4-($^2H_3$)methyl-1-methyl-1H-1,2,3-triazole,
2-[3-(dimethyl-1H-1,2,3-triazol-5-yl)-6-methanesulfonyl-5-[(S)-oxan-4-yl(phenyl)methyl]-5H-pyrido[3,2-b]indol-9-yl]-1$\lambda^6$,2-thiazolidine-1,1-dione,
2-[3-(dimethyl-1H-1,2,3-triazol-5-yl)-6-methanesulfonyl-5-[(S)-oxan-4-yl(phenyl)methyl]-5H-pyrido[3,2-b]indol-9-yl]-1$\lambda^6$,2-thiazinane-1,1-dione,
1-[3-(dimethyl-1H-1,2,3-triazol-5-yl)-6-methanesulfonyl-5-[(S)-oxan-4-yl(phenyl)methyl]-5H-pyrido[3,2-b]indol-9-yl]piperazine,
2-{4-[3-(dimethyl-1H-1,2,3-triazol-5-yl)-6-methanesulfonyl-5-[(S)-oxan-4-yl(phenyl)methyl]-5H-pyrido[3,2-b]indol-9-yl]piperazin-1-yl}acetamide,
1-[3-(dimethyl-1H-1,2,3-triazol-5-yl)-6-methanesulfonyl-5-[(S)-oxan-4-yl(phenyl)methyl]-5H-pyrido[3,2-b]indol-9-yl]-4-(oxetan-3-yl)piperazine,
4-{6-methanesulfonyl-3-[4-($^2H_3$)methyl-1-methyl-1H-1,2,3-triazol-5-yl]-5-[(S)-oxan-4-yl(phenyl)methyl]-5H-pyrido[3,2-b]indol-9-yl}-1$\lambda^6$,4-thiomorpholine-1,1-dione, tert-butyl 4-[3-(dimethyl-1H-1,2,3-triazol-5-yl)-6-methanesulfonyl-5-[(S)-oxan-4-yl(phenyl)methyl]-5H-pyrido[3,2-b]indol-9-yl]piperazine-1-carboxylate, 2-{6-methanesulfonyl-3-[4-($^2$H$_3$)methyl-1-methyl-1H-1,2,3-triazol-5-yl]-5-[(S)-oxan-4-yl(phenyl)methyl]-5H-pyrido[3,2-b]indol-9-yl}-1λ$^6$,2-thiazolidine-1,1-dione, 2-({3,7-bis[4-($^2$H$_3$)methyl-1-methyl-1H-1,2,3-triazol-5-yl]-5H-pyrido[3,2-b]indol-5-yl}(oxan-4-yl)methyl)-3-fluoropyridine, 2-({3,7-bis[4-($^2$H$_3$)methyl-1-methyl-1H-1,2,3-triazol-5-yl]-5H-pyrido[3,2-b]indol-5-yl}(oxan-4-yl)methyl)-3-fluoropyridine, 4-($^2$H$_3$)methoxy-5-{7-[4-($^2$H$_3$)methoxy-1-methyl-1H-1,2,3-triazol-5-yl]-5-[(S)-oxan-4-yl(phenyl)methyl]-5H-pyrido[3,2-b]indol-3-yl}-1-methyl-1H-1,2,3-triazole, 4-methoxy-5-{7-[4-methoxy-1-($^2$H$_3$)methyl-1H-1,2,3-triazol-5-yl]-5-[(S)-oxan-4-yl(phenyl)methyl]-5H-pyrido[3,2-b]indol-3-yl}-1-($^2$H$_3$)methyl-1H-1,2,3-triazole, 4-($^2$H$_3$)methyl-1-methyl-5-{7-[4-($^2$H$_3$)methyl-1-methyl-1H-1,2,3-triazol-5-yl]-5-[(S)-oxan-4-yl(phenyl)methyl]-5H-pyrido[3,2-b]indol-3-yl}-1H-1,2,3-triazole, 4-methoxy-5-[7-(4-methoxy-1-methyl-1H-1,2,3-triazol-5-yl)-5-[(S)-oxan-4-yl(phenyl)methyl]-5H-pyrido[3,2-b]indol-3-yl]-1-methyl-1H-1,2,3-triazole, 2-{5-[(S)-(4-fluorophenyl)(oxan-4-yl)methyl]-6-methanesulfonyl-3-[4-($^2$H$_3$)methyl-1-methyl-1H-1,2,3-triazol-5-yl]-5H-pyrido[3,2-b]indol-9-yl}-1λ$^6$,2-thiazolidine-1,1-dione, 2-{5-[(S)-(2-fluorophenyl)(oxan-4-yl)methyl]-6-methanesulfonyl-3-[4-($^2$H$_3$)methyl-1-methyl-1H-1,2,3-triazol-5-yl]-5H-pyrido[3,2-b]indol-9-yl}-1λ$^6$,2-thiazolidine-1,1-dione, 2-{5-[(3-fluoropyridin-2-yl)(oxan-4-yl)methyl]-6-methanesulfonyl-3-[4-($^2$H$_3$)methyl-1-methyl-1H-1,2,3-triazol-5-yl]-5H-pyrido[3,2-b]indol-9-yl}-1λ$^6$,2-thiazolidine-1,1-dione, 2-{5-[(3-fluoropyridin-2-yl)(oxan-4-yl)methyl]-6-methanesulfonyl-3-[4-($^2$H$_3$)methyl-1-methyl-1H-1,2,3-triazol-5-yl]-5H-pyrido[3,2-b]indol-9-yl}-1λ$^6$,2-thiazolidine-1,1-dione, 2-{5-[(S)-(2-fluorophenyl)(oxan-4-yl)($^2$H)methyl]-6-methanesulfonyl-3-[4-($^2$H$_3$)methyl-1-methyl-1H-1,2,3-triazol-5-yl]-5H-pyrido[3,2-b]indol-9-yl}-1λ$^6$,2-thiazolidine-1,1-dione, 2-{6-methanesulfonyl-3-[4-($^2$H$_3$)methyl-1-methyl-1H-1,2,3-triazol-5-yl]-5-[(S)-oxan-4-yl(phenyl)($^2$H)methyl]-5H-pyrido[3,2-b]indol-9-yl}-1λ$^6$,2-thiazolidine-1,1-dione, 4-{5-[(S)-(4-fluorophenyl)(oxan-4-yl)methyl]-3-[4-($^2$H$_3$)methyl-1-methyl-1H-1,2,3-triazol-5-yl]-5H-pyrido[3,2-b]indol-8-yl}-1λ$^6$,4-thiomorpholine-1,1-dione, 1-{5-[(S)-(4-fluorophenyl)(oxan-4-yl)methyl]-3-[4-($^2$H$_3$)methyl-1-methyl-1H-1,2,3-triazol-5-yl]-5H-pyrido[3,2-b]indol-8-yl}-4-methanesulfonylpiperazine, 4-{5-[(S)-(2-fluorophenyl)(oxan-4-yl)methyl]-3-[4-($^2$H$_3$)methyl-1-methyl-1H-1,2,3-triazol-5-yl]-5H-pyrido[3,2-b]indol-8-yl}-1λ$^6$,4-thiomorpholine-1,1-dione, 1-{5-[(S)-(2-fluorophenyl)(oxan-4-yl)methyl]-3-[4-($^2$H$_3$)methyl-1-methyl-1H-1,2,3-triazol-5-yl]-5H-pyrido[3,2-b]indol-8-yl}-4-methanesulfonylpiperazine, 2-{5-[(S)-(4-fluorophenyl)(oxan-4-yl)methyl]-3-[4-($^2$H$_3$)methyl-1-methyl-1H-1,2,3-triazol-5-yl]-5H-pyrido[3,2-b]indol-8-yl}-1,2,3,4-tetrahydroisoquinoline, 4-[3-(dimethyl-1H-1,2,3-triazol-5-yl)-5-[(S)-oxan-4-yl(phenyl)methyl]-5H-pyrido[3,2-b]indol-7-yl]-1λ$^6$,4-thiomorpholine-1,1-dione, 4-{3-[4-($^2$H$_3$)methyl-1-methyl-1H-1,2,3-triazol-5-yl]-5-[(S)-oxan-4-yl(phenyl)methyl]-5H-pyrido[3,2-b]indol-7-yl}-1λ$^6$,4-thiomorpholine-1,1-dione, 1-methanesulfonyl-4-{3-[4-($^2$H$_3$)methyl-1-methyl-1H-1,2,3-triazol-5-yl]-5-[(S)-oxan-4-yl(phenyl)methyl]-5H-pyrido[3,2-b]indol-7-yl}piperazine, 1-[3-(dimethyl-1H-1,2,3-triazol-5-yl)-5-[(S)-oxan-4-yl(phenyl)methyl]-5H-pyrido[3,2-b]indol-7-yl]-4-methylpiperazine, 1-[3-(dimethyl-1H-1,2,3-triazol-5-yl)-5-[(S)-oxan-4-yl(phenyl)methyl]-5H-pyrido[3,2-b]indol-7-yl]-4-(1-methylpiperidin-4-yl)piperazine, 4-[3-(dimethyl-1H-1,2,3-triazol-5-yl)-5-[(S)-oxan-4-yl(phenyl)methyl]-5H-pyrido[3,2-b]indol-7-yl]-N,N-dimethylpiperazine-1-carboxamide, 4-[3-(dimethyl-1H-1,2,3-triazol-5-yl)-5-[(S)-oxan-4-yl(phenyl)methyl]-5H-pyrido[3,2-b]indol-7-yl]-N,N-dimethylpiperazine-1-sulfonamide, (2R)-4-{5-[(S)-(2-fluorophenyl)(oxan-4-yl)methyl]-3-[4-($^2$H$_3$)methyl-1-methyl-1H-1,2,3-triazol-5-yl]-5H-pyrido[3,2-b]indol-8-yl}-2-methyl-1λ$^6$,4-thiomorpholine-1,1-dione, (2 S)-4-{5-[(S)-(2-fluorophenyl)(oxan-4-yl)methyl]-3-[4-($^2$H$_3$)methyl-1-methyl-1H-1,2,3-triazol-5-yl]-5H-pyrido[3,2-b]indol-8-yl}-2-methyl-1λ$^6$,4-thiomorpholine-1,1-dione, 4-{6-Fluoro-3-[4-($^2$H$_3$)methyl-1-methyl-1H-1,2,3-triazol-5-yl]-5-[(S)-oxan-4-yl(phenyl)methyl]-5H-pyrido[3,2-b]indol-7-yl}piperidin-4-ol, 4-{6-Fluoro-3-[4-($^2$H$_3$)methyl-1-methyl-1H-1,2,3-triazol-5-yl]-5-[(S)-oxan-4-yl(phenyl)methyl]-5H-pyrido[3,2-b]indol-7-yl}-1-methylpiperidin-4-ol, 4-{6-Fluoro-3-[4-($^2$H$_3$)methyl-1-methyl-1H-1,2,3-triazol-5-yl]-5-[(S)-oxan-4-yl(phenyl)methyl]-5H-pyrido[3,2-b]indol-7-yl}-4-methyl-1,3-oxazolidin-2-one, Diastereomer A, 4-{6-Fluoro-3-[4-($^2$H$_3$)methyl-1-methyl-1H-1,2,3-triazol-5-yl]-5-[(S)-oxan-4-yl(phenyl)methyl]-5H-pyrido[3,2-b]indol-7-yl}-4-methyl-1,3-oxazolidin-2-one, Diastereomer B, 1-{6-Fluoro-3-[4-($^2$H$_3$)methyl-1-methyl-1H-1,2,3-triazol-5-yl]-5-[(S)-oxan-4-yl(phenyl)methyl]-5H-pyrido[3,2-b]indol-7-yl}pyrrolidin-2-one, 2-{6-Fluoro-3-[4-($^2$H$_3$)methyl-1-methyl-1H-1,2,3-triazol-5-yl]-5-[(S)-oxan-4-yl(phenyl)methyl]-5H-pyrido[3,2-b]indol-7-yl}-1λ$^6$,2-thiazolidine-1,1-dione, 1-{6-Fluoro-3-[4-($^2$H$_3$)methyl-1-methyl-1H-1,2,3-triazol-5-yl]-5-[(S)-oxan-4-yl(phenyl)methyl]-5H-pyrido[3,2-b]indol-7-yl}imidazolidin-2-one, 3-{6-Fluoro-3-[4-($^2$H$_3$)methyl-1-methyl-1H-1,2,3-triazol-5-yl]-5-[(S)-oxan-4-yl(phenyl)methyl]-5H-pyrido[3,2-b]indol-7-yl}-1,3-oxazolidin-2-one, 2-{6-Fluoro-5-[(S)-(3-fluoropyridin-2-yl)(oxan-4-yl)methyl]-3-[4-($^2$H$_3$)methyl-1-methyl-1H-1,2,3-triazol-5-yl]-5H-pyrido[3,2-b]indol-7-yl}-1λ$^6$,2-thiazolidine-1,1-dione, 4-{6-Fluoro-3-[4-($^2$H$_3$)methyl-1-methyl-1H-1,2,3-triazol-5-yl]-5-[(S)-oxan-4-yl(phenyl)methyl]-5H-pyrido[3,2-b]indol-7-yl}oxan-4-ol, 3-{6-Fluoro-3-[4-($^2$H$_3$)methyl-1-methyl-1H-1,2,3-triazol-5-yl]-5-[(S)-oxan-4-yl(phenyl)methyl]-5H-pyrido[3,2-b]indol-7-yl}oxolan-3-ol, 2-{[7-(4,4-Difluoropiperidin-1-yl)-3-[4-($^2$H$_3$)methyl-1-methyl-1H-1,2,3-triazol-5-yl]-5H-pyrido[3,2-b]indol-5-yl](oxan-4-yl)methyl}-3-fluoropyridine, 4-{5-[(3-Fluoropyridin-2-yl)(oxan-4-yl)methyl]-3-[4-($^2$H$_3$)methyl-1-methyl-1H-1,2,3-triazol-5-yl]-5H-pyrido[3,2-b]indol-7-yl}-1λ$^6$,4-thiomorpholine-1,1-dione, 3-Fluoro-2-{[7-(4-methanesulfonylpiperidin-1-yl)-3-[4-($^2$H$_3$)methyl-1-methyl-1H-1,2,3-triazol-5-yl]-5H-pyrido[3,2-b]indol-5-yl](oxan-4-yl)methyl}pyridine, 1-[3-(Dimethyl-1H-1,2,3-triazol-5-yl)-5-[(S)-oxan-4-yl(phenyl)methyl]-5H-pyrido[3,2-b]indol-7-yl]-4,4-difluoropiperidine, 1-[3-(Dimethyl-1H-1,2,3-triazol-5-yl)-5-[(S)-oxan-4-yl(phenyl)methyl]-5H-pyrido[3,2-b]indol-7-yl]-4-(trifluoromethyl)piperidine, 1-{5-[(4,4-Difluorocyclohexyl)(phenyl)methyl]-6-methanesulfonyl-3-[4-($^2$H$_3$)methyl-1-methyl-1H-1,2,3-triazol-5-yl]-5H-pyrido[3,2-b]indol-9-yl}-4,4-difluoropiperidine, 1-{5-[(4,4-Difluorocyclohexyl)(phenyl)methyl]-3-(dimethyl-1H-1,2,3-triazol-5-yl)-5H-pyrido[3,2-b]indol-7-yl}-4,4-difluoropiperidine, or 1-{5-[(4,4-Difluorocyclohexyl)(phenyl)methyl]-3-(dimethyl-1H-1,2,3-triazol-5-yl)-5H-pyrido[3,2-b]indol-7-yl}-4-(trifluoromethyl)piperidine, or a pharmaceutically acceptable salt, tautomer or stereoisomer thereof.

11. A pharmaceutical composition which comprises a compound according to claim 1 or a pharmaceutically acceptable salt thereof and one or more pharmaceutically acceptable carriers, diluents or excipients.

12. A combination pharmaceutical product comprising a compound according to claim 1 or a pharmaceutically acceptable salt thereof together with one or more other therapeutically active agents.

13. A method of treating cancer wherein the cancer is small cell lung cancer, non-small cell lung cancer, colorectal cancer, multiple myeloma, acute myeloid leukemia (AML), acute lymphoblastic leukemia, (ALL), pancreatic cancer, liver cancer, hepatocellular cancer, neuroblastoma, other solid tumors or other hematological cancers comprising administering a therapeutically effective amount of one or more compounds according to claim 1 or a pharmaceutically acceptable salt thereof.

* * * * *

SEQUENCE LISTING

```
<160> NUMBER OF SEQ ID NOS: 3

<210> SEQ ID NO 1
<211> LENGTH: 21
<212> TYPE: PRT
<213> ORGANISM: Tobacco vein mottling virus

<400> SEQUENCE: 1

Met Gly Ser Ser His His His His His His Ser Ser Gly Glu Thr Val
1               5                   10                  15

Arg Phe Gln Ser Met
            20

<210> SEQ ID NO 2
<211> LENGTH: 39
<212> TYPE: PRT
<213> ORGANISM: Tobacco vein mottling virus

<400> SEQUENCE: 2

Met Gly Ser Ser His His His His His His Ser Ser Gly Glu Thr Val
1               5                   10                  15

Arg Phe Gln Gly Leu Asn Asp Ile Phe Glu Ala Gln Lys Ile Glu Trp
            20                  25                  30

His Glu Asp Thr Gly His Met
        35

<210> SEQ ID NO 3
<211> LENGTH: 21
<212> TYPE: PRT
<213> ORGANISM: Artificial Sequence
<220> FEATURE:
<223> OTHER INFORMATION: Biotinylated histone peptide
<220> FEATURE:
<221> NAME/KEY: MOD_RES
<222> LOCATION: (5)..(5)
<223> OTHER INFORMATION: ACETYLATION
<220> FEATURE:
<221> NAME/KEY: MOD_RES
<222> LOCATION: (8)..(8)
<223> OTHER INFORMATION: ACETYLATION
```

```
<220> FEATURE:
<221> NAME/KEY: MOD_RES
<222> LOCATION: (12)..(12)
<223> OTHER INFORMATION: ACETYLATION
<220> FEATURE:
<221> NAME/KEY: MOD_RES
<222> LOCATION: (16)..(16)
<223> OTHER INFORMATION: ACETYLATION

<400> SEQUENCE: 3

Ser Gly Arg Gly Lys Gly Gly Lys Gly Leu Gly Lys Gly Gly Ala Lys
1               5                   10                  15

Arg His Arg Lys Val
            20
```